(12) United States Patent
Watanabe et al.

(10) Patent No.: US 8,129,377 B2
(45) Date of Patent: Mar. 6, 2012

(54) 6-(PYRIDINYL)-4-PYRIMIDONE DERIVATES AS TAU PROTEIN KINASE 1 INHIBITORS

(75) Inventors: Kazutoshi Watanabe, Tokyo (JP); Kenji Fukunaga, Tokyo (JP); Toshiyuki Kohara, Tokyo (JP); Fumiaki Uehara, Tokyo (JP); Shinsuke Hiki, Tokyo (JP); Satoshi Yokoshima, Tokyo (JP)

(73) Assignees: Mitsubishi Tanabe Pharma Corporation, Osaka (JP); Sanofi-Aventis, Paris (FR)

( * ) Notice: Subject to any disclaimer, the term of this patent is extended or adjusted under 35 U.S.C. 154(b) by 1173 days.

(21) Appl. No.: 11/576,062

(22) PCT Filed: Sep. 29, 2005

(86) PCT No.: PCT/JP2005/018497
§ 371 (c)(1),
(2), (4) Date: Jul. 27, 2007

(87) PCT Pub. No.: WO2006/036015
PCT Pub. Date: Apr. 6, 2006

(65) Prior Publication Data
US 2009/0239864 A1 Sep. 24, 2009

(30) Foreign Application Priority Data
Sep. 29, 2004 (JP) .................. 2004-313115

(51) Int. Cl.
*A61K 31/535* (2006.01)
*A61K 31/505* (2006.01)
*A01N 43/54* (2006.01)
*C07D 413/00* (2006.01)

(52) U.S. Cl. ............ 514/235.8; 514/229.5; 514/229.8; 514/269; 544/121; 544/123

(58) Field of Classification Search ........... 514/235.8, 514/229.5, 229.8, 269; 544/121, 123
See application file for complete search history.

(56) References Cited

U.S. PATENT DOCUMENTS

| | | | |
|---|---|---|---|
| 6,844,335 B2 | 1/2005 | Almario Garcia et al. | |
| 7,256,199 B1 | 8/2007 | Watanabe et al. | |
| 7,427,615 B2 * | 9/2008 | Uehara et al. ............ | 514/229.5 |
| 2003/0187004 A1 | 10/2003 | Almario Garcia et al. | |
| 2005/0090490 A1 | 4/2005 | Uehara et al. | |
| 2005/0130967 A1 | 6/2005 | Uehara et al. | |
| 2006/0252768 A1 | 11/2006 | Watanabe et al. | |

FOREIGN PATENT DOCUMENTS

| | | |
|---|---|---|
| EP | 1136483 | 9/2001 |
| EP | 1454908 | 9/2004 |
| WO | 00/18758 | 4/2000 |
| WO | 01/70729 | 9/2001 |
| WO | 03/027080 | 4/2003 |
| WO | 03/037888 | 5/2003 |
| WO | 2004/085408 | 10/2004 |

OTHER PUBLICATIONS

G.G. Glenner et al.: Biochem. Biophys. Res. Comm., 1984, vol. 120, No. 3, pp. 885-890.
C.L. Masters et al.: EMBO J., 1985, vol. 4, No. 11, pp. 2757-2763.
C.L. Masters et al.: Proc. Natl. Acad. Sci. USA, 1985, vol. 82, pp. 4245-4249.
C.M. Wischik et al.: Proc. Natl. Acad. Sci. USA, 1988, vol. 85, pp. 4506-4510.
J. Kondo et al.: Neuron, 1988, vol. 1, pp. 827-834.
R. Sherington et al.: Nature, 1995, vol. 375, pp. 754-760.
E. Levy-Lahad et al.: Science, 1995, vol. 269, pp. 973-977.
E.I. Rogaev et al.: Nature, 1995, vol. 376, pp. 775-778.
D.R. Borchelt et al.: Neuron, 1996, vol. 17, pp. 1005-1013.
T. Tomita et al.: Proc. Natl. Acad. Sci. USA, 1997, vol. 94, pp. 2025-2030.
A. Willoughby et al: Society for Neuroscience Abstracts, 1991, vol. 17, p. 1445.
R. Siman et al.: The Journal of Neuroscience, 1990, vol. 10, No. 7, pp. 2400-2411.
Y. Ihara et al.: J. Biochem, 1986, vol. 99, pp. 1807-1810.
I. Grundke-Iqbal et al.: Proc. Natl. Acad. Sci. USA, 1986, vol. 83, pp. 4913-4917.
K. Ishiguro et al.: J. Biol. Chem., 1992, vol. 267, No. 15, pp. 10897-10901.
K. Ishiguro et al.: FEBS, 1993, vol. 325, No. 3, pp. 167-172.
B.A. Yankner et al.: Science, 1990, vol. 250, pp. 279-282.
A. Takashima et al.: Proc. Natl. Acad. Sci. USA, 1993, vol. 90, pp. 7789-7793.
Extended European Search Report dated Jan. 13, 2011 that issued with respect to counterpart European Patent Application No. 10010448.8.
Extended European Search Report dated Jan. 13, 2011 that issued with respect to counterpart European Patent Application No. 10010450.4.

* cited by examiner

*Primary Examiner* — Sreeni Padmanabhan
*Assistant Examiner* — Uma Ramachandran
(74) *Attorney, Agent, or Firm* — Greenblum & Bernstein, PLC

(57) ABSTRACT

A compound represented by the formula (I), an optically active isomer thereof, or a pharmaceutical acceptable salt thereof:

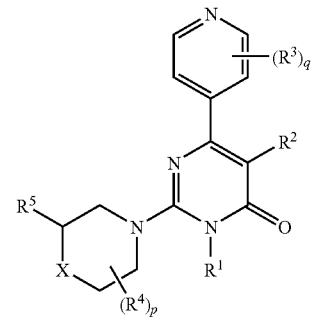

wherein $R^1$ represents a $C_1$-$C_{12}$ alkyl; $R^2$ represents a hydrogen atom or the like; $R^3$ represents a halogen or the like; q represents an integer of 1 to 7; $R^4$ represents a halogen or the like; p represents 0 or an integer of 1 to 5; $R^5$ represents a $C_6$-$C_{10}$ aryl, a heterocycle or the like; and X represents oxygen, NH, or the like, which is used for preventive and/or therapeutic treatment of a disease caused by tau protein kinase 1 hyperactivity such as a neurodegenerative diseases (e.g. Alzheimer disease).

7 Claims, No Drawings

6-(PYRIDINYL)-4-PYRIMIDONE DERIVATES AS TAU PROTEIN KINASE 1 INHIBITORS

TECHNICAL FIELD

The present invention relates to compounds that are useful as an active ingredient of a medicament for preventive and/or therapeutic treatment of diseases mainly caused by abnormal activity of tau protein kinase 1, such as neurodegenerative diseases (e.g. Alzheimer disease).

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and β amyloid protein has been elucidated as their main component (abbreviated as "Aβ" hereinafter in the specification: Biochem. Biophys. Res. Commun., 120, 885 (1984); EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature. 376, 775 (1995)), and it has been revealed that presence of mutants of presenilins 1 and 2 promotes the secretion of Aβ (Neuron, 17, 1005 (1996); Proc. Natl. Acad. Sci. USA, 94, 2025 (1997)). From these results, it is considered that, in Alzheimer disease, Aβ abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents.

It has been reported that kainic acid treatment that stimulates the AMPA receptor, one of glutamate receptor, increases mRNA of the amyloid precursor protein (abbreviated as "APP" hereinafter in the specification) as a precursor of Aβ (Society for Neuroscience Abstracts, 17, 1445 (1991)), and also promotes metabolism of APP (The Journal of Neuroscience, 10, 2400 (1990)). Therefore, it has been strongly suggested that the accumulation of Aβ is involved in cellular death due to ischemic cerebrovascular disorders. Other diseases in which abnormal accumulation and agglomeration of Aβ are observed include, for example, Down syndrome, cerebral bleeding due to solitary cerebral amyloid angiopathy, Lewy body disease and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like.

The tau protein is generally composed of a group of related proteins that forms several bands at molecular weights of 48-65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced. As a result, it has been revealed that the primary structure of the rat TPK1 corresponds to that of the enzyme known as rat GSK-3β (glycogen synthase kinase 3β, FEBS Lett., 325, 167 (1993)).

It has been reported that Aβ, the main component of senile plaques, is neurotoxic (Science, 250, 279 (1990)). However, various theories have been proposed as for the reason why Aβ causes the cell death, and any authentic theory has not yet been established. Takashima et al. observed that the cell death was caused by Aβ treatment of fetal rat hippocampus primary culture system, and then found that the TPK1 activity was increased by Aβ treatment and the cell death by Aβ was inhibited by antisense of TPK1 (Proc. Natl. Acad. Sci. USA, 90, 7789 (1993); EP616032).

In view of the foregoing, compounds which inhibit the TPK1 activity may possibly suppress the neurotoxicity of Aβ and the formation of PHF and inhibit the nerve cell death in the Alzheimer disease, thereby cease or defer the progress of the disease. The compounds may also be possibly used as a medicament for therapeutic treatment of ischemic cerebrovascular disorder, Down syndrome, cerebral amyloid angiopathy, cerebral bleeding due to Lewy body disease and the like by suppressing the cytotoxicity of Aβ. Furthermore, the compounds may possibly be used as a medicament for therapeutic treatment of neurodegenerative diseases such as progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration and frontotemporal dementia, vascular dementia, traumatic injuries, brain and spinal cord trauma, peripheral neuropathies, retinopathies and glaucoma, as well as other diseases such as non-insulin dependent diabetes, obesity, manic depressive illness, schizophrenia, alopecia, breast cancer, non-small cell lung carcinoma, thyroid cancer, T or B-cell leukemia, and several virus-induced tumors.

As structurally similar compounds to the compounds of the present invention represented by formula (I) described later, the compounds disclosed in the International Publication Nos. WO01/70729, WO03/037888 and WO03/027080 are known. However, these compounds are not enough as medicament in the pharmacokinetics and so on.

DISCLOSURE OF THE INVENTION

An object of the present invention is to provide compounds useful as an active ingredient of a medicament for preventive and/or therapeutic treatment of diseases such as Alzheimer disease. More specifically, the object is to provide novel compounds useful as an active ingredient of a medicament that enables radical prevention and/or treatment of the neurodegenerative diseases such as Alzheimer disease by inhibiting the TPK1 activity to suppress the neurotoxicity of Aβ and the formation of the PHF and by inhibiting the death of nerve cells.

In order to achieve the foregoing object, the inventors of the present invention conducted screenings of various compounds having inhibitory activity against the phosphorylation of TPK1. As a result, they found that compounds represented by the following formula (I) had the desired activity and were useful as an active ingredient of a medicament for preventive and/or therapeutic treatment of the aforementioned diseases. The present invention was achieved on the basis of these findings.

The present invention thus provides;

1. A compound represented by the formula (I), an optically active isomer thereof, or a pharmaceutically acceptable salt thereof:

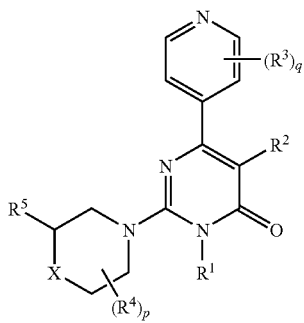

(I)

wherein each symbol is as defined below.
$R^1$ represents a $C_1$-$C_{12}$ alkyl which may be substituted;
$R^2$ represents hydrogen atom, a halogen or a $C_1$-$C_6$ alkyl which may be substituted;
$R^3$ may be the same or different and represents
hydroxyl,
a halogen,
nitro,
cyano,
a $C_1$-$C_6$ alkyl which may be substituted,
a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocycle which may be substituted,
a $C_1$-$C_6$ alkyloxy which may be substituted,
a $C_3$-$C_6$ alkenyloxy which may be substituted,
a $C_3$-$C_6$ alkynyloxy which may be substituted,
a $C_3$-$C_7$ cycloalkyloxy which may be substituted,
a $C_3$-$C_7$ cycloalkenyloxy which may be substituted,
a $C_6$-$C_{10}$ aryloxy which may be substituted,
a heterocycle-oxy group which may be substituted,
a $C_1$-$C_6$ alkylthio which may be substituted,
a $C_3$-$C_6$ alkenylthio which may be substituted,
a $C_3$-$C_6$ alkynylthio which may be substituted,
a $C_3$-$C_7$ cycloalkylthio which may be substituted,
a $C_3$-$C_7$ cycloalkenylthio which may be substituted,
a $C_6$-$C_{10}$ arylthio which may be substituted,
a heterocycle-thio group which may be substituted,
amino,
a $C_1$-$C_6$ alkylamino which may be substituted,
a $C_3$-$C_6$ alkenylamino which may be substituted,
a $C_3$-$C_6$ alkynylamino which may be substituted,
a $C_3$-$C_7$ cycloalkylamino which may be substituted,
a $C_3$-$C_7$ cycloalkenylamino which may be substituted,
an $C_6$-$C_{10}$ arylamino which may be substituted,
a heterocycle-amino which may be substituted,
a N,N-di-$C_1$-$C_6$ alkylamino which may be substituted,
a N—$C_1$-$C_6$ alkyl-N—$C_3$-$C_6$ alkenylamino which may be substituted,
a N—$C_1$-$C_6$ alkyl-N—$C_3$-$C_6$ alkynylamino which may be substituted,
a N—$C_1$-$C_6$ alkyl-N—$C_3$-$C_7$ cycloalkylamino which may be substituted,
a N—$C_1$-$C_6$ alkyl-N—$C_3$-$C_7$ cycloalkenylamino which may be substituted,
a N—$C_1$-$C_6$ alkyl-N—$C_6$-$C_{10}$ arylamino which may be substituted,
a N—$C_1$-$C_6$ alkyl-N-heterocycle-amino which may be substituted,
a N,N-di-$C_3$-$C_6$ alkenylamino which may be substituted,
a N—$C_3$-$C_6$ alkenyl-N—$C_3$-$C_6$ alkynylamino which may be substituted,
a N—$C_3$-$C_6$ alkenyl-N—$C_3$-$C_7$ cycloalkylamino which may be substituted,
a N—$C_3$-$C_6$ alkenyl-N—$C_3$-$C_7$ cycloalkenylamino which may be substituted,
a N—$C_3$-$C_6$ alkenyl-N—$C_6$-$C_{10}$ arylamino which may be substituted,
a N—$C_8$-$C_6$ alkenyl-N-heterocycle-amino which may be substituted,
a N,N-di-$C_3$-$C_6$ alkynylamino which may be substituted,
a N—$C_3$-$C_6$ alkynyl-N—$C_3$-$C_7$ cycloalkylamino which may be substituted,
a N—$C_3$-$C_6$ alkynyl-N—$C_3$-$C_7$ cycloalkenylamino which may be substituted,
a N—$C_3$-$C_6$ alkynyl-N—$C_6$-$C_{10}$ arylamino which may be substituted,
a N—$C_3$-$C_6$ alkynyl-N-heterocycle-amino which may be substituted,
a N,N-di-$C_3$-$C_7$ cycloalkylamino which may be substituted,
a N—$C_3$-$C_7$ cycloalkyl-N—$C_3$-$C_7$ cycloalkenylamino which may be substituted,
a N—$C_3$-$C_7$ cycloalkyl-N—$C_6$-$C_{10}$ arylamino which may be substituted,
a N—$C_3$-$C_7$ cycloalkyl-N-heterocycle-amino which may be substituted,
a N,N-di-$C_3$-$C_7$ cycloalkenylamino which may be substituted,
a N—$C_3$-$C_7$ cycloalkenyl-N—$C_6$-$C_{10}$ arylamino which may be substituted,
a N—$C_3$-$C_7$ cycloalkenyl-N-heterocycle-amino which may be substituted,
a N,N-di-$C_6$-$C_{10}$ arylamino which may be substituted,
a N—$C_6$-$C_{10}$ aryl-N-heterocycle-amino which may be substituted, or
a N,N-diheterocycle-amino which may be substituted,
or any two of $R^3$ may combine to each other to form a ring;
q represents an integer of 1 to 4;
$R^4$ may be the same or different and represents
hydroxyl,
a halogen,
nitro,
cyano,
a $C_1$-$C_6$ alkyl which may be substituted, a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocycle which may be substituted,
a $C_1$-$C_6$ alkyloxy which may be substituted,
a $C_3$-$C_6$ alkenyloxy which may be substituted,
a $C_3$-$C_6$; alkynyloxy which may be substituted,
a $C_3$-$C_7$ cycloalkyloxy which may be substituted,
a $C_3$-$C_7$ cycloalkenyloxy which may be substituted,
a $C_6$-$C_{10}$ aryloxy which may be substituted,
a heterocycle-oxy group which may be substituted,
a $C_1$-$C_6$ alkylcarbonyl which may be substituted,
a $C_2$-$C_6$ alkenylcarbonyl which may be substituted,
a $C_2$-$C_6$ alkynylcarbonyl which may be substituted,
a $C_3$-$C_7$ cycloalkylcarbonyl which may be substituted,
a $C_3$-$C_7$ cycloalkenylcarbonyl which may be substituted,
a $C_6$-$C_{10}$ arylcarbonyl which may be substituted,
a heterocycle-carbonyl which may be substituted,
carboxyl,
a $C_1$-$C_6$ alkyloxycarbonyl which may be substituted,
a $C_3$-$C_6$ alkenyloxycarbonyl which may be substituted,
a $C_3$-$C_6$ alkynyloxycarbonyl which may be substituted,
a $C_3$-$C_7$ cycloalkyloxycarbonyl which may be substituted,
a $C_3$-$C_7$ cycloalkenyloxycarbonyl which may be substituted,
a $C_6$-$C_{10}$ aryloxycarbonyl which may be substituted,
a heterocycle-oxycarbonyl which may be substituted,
aminocarbonyl,
a $C_1$-$C_6$ alkylaminocarbonyl which may be substituted,
a $C_3$-$C_6$ alkenylaminocarbonyl which may be substituted,
a $C_3$-$C_6$ alkynylaminocarbonyl which may be substituted,
a $C_3$-$C_7$ cycloalkylaminocarbonyl which may be substituted,
a $C_3$-$C_7$ cycloalkenylaminocarbonyl which may be substituted,
a $C_6$-$C_{10}$ arylaminocarbonyl which may be substituted,
a heterocycle-aminocarbonyl which may be substituted,
a N,N-di-$C_1$-$C_6$ alkylaminocarbonyl which may be substituted,
a N—$C_1$-$C_6$ alkyl-N—$C_3$-$C_7$ alkenylaminocarbonyl which may be substituted,
a N—$C_1$-$C_6$ alkyl-N—$C_3$-$C_7$ alkynylaminocarbonyl which may be substituted,
a N—$C_1$-$C_6$ alkyl-N—$C_3$-$C_7$ cycloalkylaminocarbonyl which may be substituted,
a N—$C_1$-$C_6$ alkyl-N—$C_3$-$C_7$ cycloalkenylaminocarbonyl which may be substituted,
a N—$C_1$-$C_6$ alkyl-N—$C_6$-$C_{10}$ arylaminocarbonyl which may be substituted,
a N—$C_1$-$C_6$ alkyl-N-heterocycle-aminocarbonyl which may be substituted,
a N,N-di-$C_3$-$C_6$ alkenylaminocarbonyl which may be substituted,
a N—$C_3$-$C_6$ alkenyl-N—$C_3$-$C_6$ alkynylaminocarbonyl which may be substituted,
a N—$C_3$-$C_6$ alkenyl-N—$C_3$-$C_7$ cycloalkylaminocarbonyl which may be substituted,
a N—$C_3$-$C_6$ alkenyl-N—$C_3$-$C_7$ cycloalkenylaminocarbonyl which may be substituted,
a N—$C_3$-$C_6$ alkenyl-N—$C_6$-$C_{10}$ arylaminocarbonyl which may be substituted,
a N—$C_3$-$C_6$ alkenyl-N-heterocycle-aminocarbonyl which may be substituted,
a N,N-di-$C_3$-$C_6$ alkynylaminocarbonyl which may be substituted,
a N—$C_3$-$C_6$ alkynyl-N—$C_3$-$C_7$ cycloalkylaminocarbonyl which may be substituted,
a N—$C_3$-$C_6$ alkynyl-N—$C_3$-$C_7$ cycloalkenylaminocarbonyl which may be substituted,
a N—$C_3$-$C_6$ alkynyl-N—$C_6$-$C_{10}$ arylaminocarbonyl which may be substituted,
a N—$C_3$-$C_6$ alkynyl-N-heterocycle-aminocarbonyl which may be substituted,
a N,N-di-$C_3$-$C_7$ cycloalkylaminocarbonyl which may be substituted,
a N—$C_3$-$C_7$ cycloalkyl-N—$C_3$-$C_7$ cycloalkenylaminocarbonyl which may be substituted,
a N—$C_3$-$C_7$ cycloalkyl-N—$C_6$-$C_{10}$ arylaminocarbonyl which may be substituted,
a N—$C_3$-$C_7$ cycloalkyl-N-heterocycle-aminocarbonyl which may be substituted,
a N,N-di-$C_3$-$C_7$ cycloalkenylaminocarbonyl which may be substituted,
a N—$C_3$-$C_7$ cycloalkenyl-N—$C_6$-$C_{10}$ arylaminocarbonyl which may be substituted,
a N—$C_3$-$C_7$ cycloalkenyl-N-heterocycle-aminocarbonyl which may be substituted,
a N,N-di-$C_6$-$C_{10}$ arylaminocarbonyl which may be substituted,
a N—$C_6$-$C_{10}$ aryl-N-heterocycle-aminocarbonyl which may be substituted, or
a N,N-di-heterocycle-aminocarbonyl which may be substituted, or
any two of $R^4$ may combine to each other to form oxo group;
p represents 0 or an integer of 1 to 7;
$R^5$ represents
hydrogen atom, or
a group represented by the following formula (II):

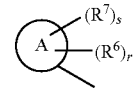

(II)

wherein A represents a $C_6$-$C_{10}$ aryl or heterocycle;
$R^6$ may be the same or different and represents
hydrogen atom,
hydroxyl,
a halogen,
nitro,
cyano
a $C_1$-$C_6$ alkyl which may be substituted,
a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocycle which may be substituted,
a $C_1$-$C_6$ alkyloxy which may be substituted,
a $C_3$-$C_6$ alkenyloxy which may be substituted,
a $C_3$-$C_6$ alkynyloxy which may be substituted,
a $C_3$-$C_7$ cycloalkyloxy which may be substituted,
a $C_3$-$C_7$ cycloalkenyloxy which may be substituted,
a $C_6$-$C_{10}$ aryloxy which may be substituted,
a heterocycle-oxy group which may be substituted,
mercapto,
a $C_1$-$C_6$ alkylthio which may be substituted,
a $C_3$-$C_6$ alkenylthio which may be substituted,
a $C_3$-$C_6$ alkynylthio which may be substituted,
a $C_3$-$C_7$ cycloalkylthio which may be substituted,
a $C_3$-$C_7$ cycloalkenylthio which may be substituted,
a $C_6$-$C_{10}$ arylthio which may be substituted, a heterocycle-thio group which may be substituted,
amino,
a $C_1$-$C_6$ alkylamino which may be substituted,
a $C_3$-$C_6$ alkenylamino which may be substituted,
a $C_3$-$C_6$ alkynylamino which may be substituted,
a $C_3$-$C_7$ cycloalkylamino which may be substituted,
a $C_3$-$C_7$ cycloalkenylamino which may be substituted,
an $C_6$-$C_{10}$ arylamino which may be substituted,
a heterocycle-amino which may be substituted,
a N,N-di-$C_1$-$C_6$ alkylamino which may be substituted,
a N—$C_1$-$C_6$ alkyl-N—$C_3$-$C_6$ alkenylamino which may be substituted,
a N—$C_1$-$C_6$ alkyl-N—$C_3$-$C_6$ alkynylamino which may be substituted,
a N—$C_1$-$C_6$ alkyl-N—$C_3$-$C_7$ cycloalkylamino which may be substituted,
a N—$C_1$-$C_6$ alkyl-N—$C_3$-$C_7$ cycloalkenylamino which may be substituted,
a N—$C_1$-$C_6$ alkyl-N—$C_6$-$C_{10}$ arylamino which may be substituted,
a N—$C_1$-$C_6$ alkyl-N-heterocycle-amino which may be substituted,
a N,N-di-$C_3$-$C_6$ alkenylamino which may be substituted,
a N—$C_3$-$C_6$ alkenyl-N—$C_3$-$C_6$ alkynylamino which may be substituted,
a N—$C_3$-$C_6$ alkenyl-N—$C_3$-$C_7$ cycloalkylamino which may be substituted,
a N—$C_3$-$C_6$ alkenyl-N—$C_3$-$C_7$ cycloalkenylamino which may be substituted,
a N—$C_3$-$C_6$ alkenyl-N—$C_6$-$C_{10}$ arylamino which may be substituted,
a N—$C_3$-$C_6$ alkenyl-N-heterocycle-amino which may be substituted,
a N,N-di-$C_3$-$C_6$ alkynylamino which may be substituted,
a N—$C_3$-$C_6$ alkynyl-N—$C_3$-$C_7$ cycloalkylamino which may be substituted,
a N—$C_3$-$C_6$ alkynyl-N—$C_3$-$C_7$ cycloalkenylamino which may be substituted,
a N—$C_3$-$C_6$ alkynyl-N—$C_6$-$C_{10}$ arylamino which may be substituted,
a N—$C_3$-$C_6$ alkynyl-N-heterocycle-amino which may be substituted,
a N,N-di-$C_3$-$C_7$ cycloalkylamino which may be substituted,
a N—$C_3$-$C_7$ cycloalkyl-N—$C_3$-$C_7$ cycloalkenylamino which may be substituted,
a N—$C_3$-$C_7$ cycloalkyl-N—$C_6$-$C_{10}$ arylamino which may be substituted,
a N—$C_3$-$C_7$ cycloalkyl-N-heterocycle-amino which may be substituted,
a N,N-di-$C_3$-$C_7$ cycloalkenylamino which may be substituted,
a N—$C_3$-$C_7$ cycloalkenyl-N—$C_6$-$C_{10}$ arylamino which may be substituted,
a N—$C_3$-$C_7$ cycloalkenyl-N-heterocycle-amino which may be substituted,
a N,N-di-$C_6$-$C_{10}$ arylamino which may be substituted,
a N—$C_6$-$C_{10}$ aryl-N-heterocycle-amino which may be substituted,
a N,N-diheterocycle-amino which may be substituted,
a $C_1$-$C_6$ alkylcarbonyl which may be substituted,
a $C_2$-$C_6$ alkenylcarbonyl which may be substituted,
a $C_2$-$C_6$ alkynylcarbonyl which may be substituted,
a $C_3$-$C_7$ cycloalkylcarbonyl which may be substituted,
a $C_3$-$C_7$ cycloalkenylcarbonyl which may be substituted,
a $C_6$-$C_{10}$ arylcarbonyl which may be substituted,
a heterocycle-carbonyl which may be substituted,
a $C_1$-$C_6$ alkylsulfonyl which may be substituted,
a $C_3$-$C_6$ alkenylsulfonyl which may be substituted,
a $C_3$-$C_6$ alkynylsulfonyl which may be substituted,
a $C_3$-$C_7$ cycloalkylsulfonyl which may be substituted,
a $C_3$-$C_7$ cycloalkenylsulfonyl which may be substituted,
a $C_6$-$C_{10}$ arylsulfonyl which may be substituted,
a heterocycle-sulfonyl which may be substituted,
carboxyl,
a $C_1$-$C_6$ alkyloxycarbonyl which may be substituted,
a $C_3$-$C_6$ alkenyloxycarbonyl which may be substituted,
a $C_3$-$C_6$ alkynyloxycarbonyl which may be substituted,
a $C_3$-$C_7$ cycloalkyloxycarbonyl which may be substituted,
a $C_3$-$C_7$ cycloalkenyloxycarbonyl which may be substituted,
a $C_6$-$C_{10}$ aryloxycarbonyl which may be substituted,
a heterocycle-oxycarbonyl which may be substituted,
aminocarbonyl,
a $C_1$-$C_6$ alkylaminocarbonyl which may be substituted,
a $C_3$-$C_6$ alkenylaminocarbonyl which may be substituted,
a $C_3$-$C_6$ alkynylaminocarbonyl which may be substituted,
a $C_3$-$C_7$ cycloalkylaminocarbonyl which may be substituted,
a $C_3$-$C_7$ cycloalkenylaminocarbonyl which may be substituted,
a $C_6$-$C_{10}$ arylaminocarbonyl which may be substituted,
a heterocycle-aminocarbonyl which may be substituted,
a N,N-di-$C_1$-$C_6$ alkylaminocarbonyl which may be substituted,
a N—$C_1$-$C_6$ alkyl-N—$C_3$-$C_7$ alkenylaminocarbonyl which may be substituted,
a N—$C_1$-$C_6$ alkyl-N—$C_3$-$C_7$ alkynylaminocarbonyl which may be substituted,
a N—$C_1$-$C_6$ alkyl-N—$C_3$-$C_7$ cycloalkylaminocarbonyl which may be substituted,
a N—$C_1$-$C_6$ alkyl-N—$C_3$-$C_7$ cycloalkenylaminocarbonyl which may be substituted,
a N—$C_1$-$C_6$ alkyl-N—$C_6$-$C_{10}$ arylaminocarbonyl which may be substituted,
a N—$C_1$-$C_6$ alkyl-N-heterocycle-aminocarbonyl which may be substituted,
a N,N-di-$C_3$-$C_6$ alkenylaminocarbonyl which may be substituted,
a N—$C_3$-$C_6$ alkenyl-N—$C_3$-$C_6$ alkynylaminocarbonyl which may be substituted,
a N—$C_3$-$C_6$ alkenyl-N—$C_3$-$C_7$ cycloalkylaminocarbonyl which may be substituted,
a N—$C_3$-$C_6$ alkenyl-N—$C_3$-$C_7$ cycloalkenylaminocarbonyl which may be substituted,
a N—$C_3$-$C_6$ alkenyl-N—$C_6$-$C_{10}$ arylaminocarbonyl which may be substituted,
a N—$C_3$-$C_6$ alkenyl-N-heterocycle-aminocarbonyl which may be substituted,
a N,N-di-$C_3$-$C_6$ alkynylaminocarbonyl which may be substituted,
a N—$C_3$-$C_6$ alkynyl-N—$C_3$-$C_7$ cycloalkylaminocarbonyl which may be substituted,
a N—$C_3$-$C_6$ alkynyl-N—$C_3$-$C_7$ cycloalkenylaminocarbonyl which may be substituted,
a N—$C_3$-$C_6$ alkynyl-N—$C_6$-$C_{10}$ arylaminocarbonyl which may be substituted,
a N—$C_3$-$C_6$ alkynyl-N-heterocycle-aminocarbonyl which may be substituted,
a N,N-di-$C_3$-$C_7$ cycloalkylaminocarbonyl which may be substituted,
a N—$C_3$-$C_7$ cycloalkyl-N—$C_3$-$C_7$ cycloalkenylaminocarbonyl which may be substituted,
a N—$C_3$-$C_7$ cycloalkyl-N—$C_6$-$C_{10}$ arylaminocarbonyl which may be substituted,
a N—$C_3$-$C_7$ cycloalkyl-N-heterocycle-aminocarbonyl which may be substituted, a N,N-di-$C_3$-$C_7$ cycloalkenylaminocarbonyl which may be substituted,
a N—$C_3$-$C_7$ cycloalkenyl-N—$C_6$-$C_{10}$ arylaminocarbonyl which may be substituted,
a N—$C_3$-$C_7$ cycloalkenyl-N-heterocycle-aminocarbonyl which may be substituted,
a N,N-di-$C_6$-$C_{10}$ arylaminocarbonyl which may be substituted,
a N—$C_6$-$C_{10}$ aryl-N-heterocycle-aminocarbonyl which may be substituted, or
a N,N-di-heterocycle-aminocarbonyl which may be substituted,
aminothiocarbonyl,
a $C_1$-$C_6$ alkylaminothiocarbonyl which may be substituted,
a $C_3$-$C_6$ alkenylaminothiocarbonyl which may be substituted,
a $C_3$-$C_6$ alkynylaminothiocarbonyl which may be substituted,
a $C_3$-$C_7$ cycloalkylaminothiocarbonyl which may be substituted,
a $C_3$-$C_7$ cycloalkenylaminothiocarbonyl which may be substituted,
a $C_6$-$C_{10}$ arylaminothiocarbonyl which may be substituted,
a heterocycle-aminothiocarbonyl which may be substituted,
a N,N-di-$C_1$-$C_6$ alkylaminothiocarbonyl which may be substituted,
a N—$C_1$-$C_6$ alkyl-N—$C_3$-$C_7$ alkenylaminothiocarbonyl which may be substituted,
a N—$C_1$-$C_6$ alkyl-N—$C_3$-$C_7$ alkynylaminothiocarbonyl which may be substituted,
a N—$C_1$-$C_6$ alkyl-N—$C_3$-$C_7$ cycloalkylaminothiocarbonyl which may be substituted,
a N—$C_1$-$C_6$ alkyl-N—$C_3$-$C_7$ cycloalkenylaminothiocarbonyl which may be substituted,
a N—$C_1$-$C_6$ alkyl-N—$C_6$-$C_{10}$ arylaminothiocarbonyl which may be substituted,
a N—$C_1$-$C_6$ alkyl-N-heterocycle-aminothiocarbonyl which may be substituted,
a N,N-di-$C_3$-$C_6$ alkenylaminothiocarbonyl which may be substituted,
a N—$C_3$-$C_6$ alkenyl-N—$C_3$-$C_7$ alkynylaminothiocarbonyl which may be substituted,
a N—$C_3$-$C_6$ alkenyl-N—$C_3$-$C_7$ cycloalkylaminothiocarbonyl which may be substituted,
a N—$C_3$-$C_6$ alkenyl-N—$C_3$-$C_7$ cycloalkenylaminothiocarbonyl which may be substituted,
a N—$C_3$-$C_6$ alkenyl-N—$C_6$-$C_{10}$ arylaminothiocarbonyl which may be substituted,
a N—$C_3$-$C_6$ alkenyl-N-heterocycle-aminothiocarbonyl which may be substituted,
a N,N-di-$C_3$-$C_6$ alkynylaminothiocarbonyl which may be substituted,
a N—$C_3$-$C_6$ alkynyl-N—$C_3$-$C_7$ cycloalkylaminothiocarbonyl which may be substituted,
a N—$C_3$-$C_6$ alkynyl-N—$C_3$-$C_7$ cycloalkenylaminothiocarbonyl which may be substituted,
a N—$C_3$-$C_6$ alkynyl-N—$C_6$-$C_{10}$ arylaminothiocarbonyl which may be substituted,
a N—$C_3$-$C_6$ alkynyl-N-heterocycle-aminothiocarbonyl which may be substituted,
a N,N-di-$C_3$-$C_7$ cycloalkylaminothiocarbonyl which may be substituted,
a N—$C_3$-$C_7$ cycloalkyl-N—$C_3$-$C_7$ cycloalkenylaminothiocarbonyl which may be substituted,
a N—$C_3$-$C_7$ cycloalkyl-N—$C_6$-$C_{10}$ arylaminothiocarbonyl which may be substituted,
a N—$C_3$-$C_7$ cycloalkyl-N-heterocycle-aminothiocarbonyl which may be substituted,
a N,N-di-$C_3$-$C_7$ cycloalkenylaminothiocarbonyl which may be substituted,
a N—$C_3$-$C_7$ cycloalkenyl-N—$C_6$-$C_{10}$ arylaminothiocarbonyl which may be substituted,
a N—$C_3$-$C_7$ cycloalkenyl-N-heterocycle-aminothiocarbonyl which may be substituted,
a N,N-di-$C_6$-$C_{10}$ arylaminothiocarbonyl which may be substituted,
a N—$C_6$-$C_{10}$ aryl-N-heterocycle-aminothiocarbonyl which may be substituted, or
a N,N-di-heterocycle-aminothiocarbonyl which may be substituted,
$R^7$ represents hydrogen atom, or
a group represented by the following formula (III):

$$-Z-N\begin{matrix}R^8\\R^9\end{matrix} \quad (III)$$

wherein Z represents a bond, carbonyl or sulfonyl,
$R^8$ and $R^9$ each independently represents
hydrogen atom,
a $C_1$-$C_6$ alkyl which may be substituted,
a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocycle which may be substituted,
a $C_1$-$C_6$ alkylcarbonyl which may be substituted,
a $C_2$-$C_6$ alkenylcarbonyl which may be substituted,
a $C_2$-$C_6$ alkynylcarbonyl which may be substituted,
a $C_3$-$C_7$ cycloalkylcarbonyl which may be substituted,
a $C_3$-$C_7$ cycloalkenylcarbonyl which may be substituted,
a $C_6$-$C_{10}$ arylcarbonyl which may be substituted,
a heterocycle-carbonyl which may be substituted,
a $C_1$-$C_6$ alkylsulfonyl which may be substituted,
a $C_3$-$C_6$ alkenylsulfonyl which may be substituted,
a $C_3$-$C_6$ alkynylsulfonyl which may be substituted,
a $C_3$-$C_7$ cycloalkylsulfonyl which may be substituted,
a $C_3$-$C_7$ cycloalkenylsulfonyl which may be substituted,
a $C_6$-$C_{10}$ arylsulfonyl which may be substituted,
a heterocycle-sulfonyl which may be substituted,
carboxyl,
a $C_1$-$C_6$ alkyloxycarbonyl which may be substituted,
a $C_3$-$C_6$ alkenyloxycarbonyl which may be substituted,
a $C_3$-$C_6$ alkynyloxycarbonyl which may be substituted,
a $C_3$-$C_7$ cycloalkyloxycarbonyl which may be substituted,
a $C_3$-$C_7$ cycloalkenyloxycarbonyl which may be substituted,
a $C_6$-$C_{10}$ aryloxycarbonyl which may be substituted,
a heterocycle-oxycarbonyl which may be substituted,
aminocarbonyl,
a $C_1$-$C_6$ alkylaminocarbonyl which may be substituted,
a $C_3$-$C_6$ alkenylaminocarbonyl which may be substituted,
a $C_3$-$C_6$ alkynylaminocarbonyl which may be substituted,
a $C_3$-$C_7$ cycloalkylaminocarbonyl which may be substituted,
a $C_3$-$C_7$ cycloalkenylaminocarbonyl which may be substituted,
a $C_6$-$C_{10}$ arylaminocarbonyl which may be substituted,
a heterocycle-aminocarbonyl which may be substituted,
a N,N-di-$C_1$-$C_6$ alkylaminocarbonyl which may be substituted,
a N—$C_1$-$C_6$ alkyl-N—$C_5$-$C_7$ alkenylaminocarbonyl which may be substituted, a N—$C_1$-$C_6$ alkyl-N—$C_3$-$C_7$ alkynylaminocarbonyl which may be substituted,
a N—$C_1$-$C_6$ alkyl-N—$C_3$-$C_7$ cycloalkylaminocarbonyl which may be substituted,
a N—$C_1$-$C_6$ alkyl-N—$C_3$-$C_7$ cycloalkenylaminocarbonyl which may be substituted,
a N—$C_1$-$C_6$ alkyl-N—$C_6$-$C_{10}$ arylaminocarbonyl which may be substituted,
a N—$C_3$-$C_6$ alkyl-N-heterocycle-aminocarbonyl which may be substituted,
a N,N-di-$C_3$-$C_6$ alkenylaminocarbonyl which may be substituted,
a N—$C_3$-$C_6$ alkenyl-N—$C_3$-$C_6$ alkynylaminocarbonyl which may be substituted,
a N—$C_3$-$C_6$ alkenyl-N—$C_3$-$C_7$ cycloalkylaminocarbonyl which may be substituted,
a N—$C_3$-$C_6$ alkenyl-N—$C_3$-$C_7$ cycloalkenylaminocarbonyl which may be substituted,
a N—$C_3$-$C_6$ alkenyl-N—$C_6$-$C_{10}$ arylaminocarbonyl which may be substituted,
a N—$C_3$-$C_6$ alkenyl-N-heterocycle-aminocarbonyl which may be substituted,
a N,N-di-$C_3$-$C_6$ alkynylaminocarbonyl which may be substituted,
a N—$C_3$-$C_6$ alkynyl-N—$C_3$-$C_7$ cycloalkylaminocarbonyl which may be substituted,
a N—$C_3$-$C_7$ alkynyl-N—$C_3$-$C_7$ cycloalkenylaminocarbonyl which may be substituted,
a N—$C_3$-$C_6$ alkynyl-N—$C_5$-$C_{10}$ arylaminocarbonyl which may be substituted,
a N—$C_3$-$C_6$ alkynyl-N-heterocycle-aminocarbonyl which may be substituted,
a N,N-di-$C_3$-$C_7$ cycloalkylaminocarbonyl which may be substituted,
a N—$C_3$-$C_7$ cycloalkyl-N—$C_3$-$C_7$ cycloalkenylaminocarbonyl which may be substituted,
a N—$C_3$-$C_7$ cycloalkyl-N—$C_6$-$C_{10}$ arylaminocarbonyl which may be substituted,
a N—$C_3$-$C_7$ cycloalkyl-N-heterocycle-aminocarbonyl which may be substituted,
a N,N-di-$C_3$-$C_7$ cycloalkenylaminocarbonyl which may be substituted,
a N—$C_3$-$C_7$ cycloalkenyl-N—$C_6$-$C_{10}$ arylaminocarbonyl which may be substituted,
a N—$C_3$-$C_7$ cycloalkenyl-N-heterocycle-aminocarbonyl which may be substituted,
a N,N-di-$C_6$-$C_{10}$ arylaminocarbonyl which may be substituted,
a N—$C_6$-$C_{10}$ aryl-N-heterocycle-aminocarbonyl which may be substituted, or
a N,N-di-heterocycle-aminocarbonyl which may be substituted,
aminothiocarbonyl,
a $C_1$-$C_6$ alkylaminothiocarbonyl which may be substituted,
a $C_3$-$C_6$ alkenylaminothiocarbonyl which may be substituted,
a $C_3$-$C_6$ alkynylaminothiocarbonyl which may be substituted,
a $C_3$-$C_7$ cycloalkylaminothiocarbonyl which may be substituted,
a $C_3$-$C_7$ cycloalkenylaminothiocarbonyl which may be substituted,
a $C_6$-$C_{10}$ arylaminothiocarbonyl which may be substituted,
a heterocycle-aminothiocarbonyl which may be substituted,
a N,N-di-$C_1$-$C_6$ alkylaminothiocarbonyl which may be substituted,
a N—$C_1$-$C_6$ alkyl-N—$C_3$-$C_7$ alkenylaminothiocarbonyl which may be substituted,
a N—$C_1$-$C_6$ alkyl-N—$C_3$-$C_7$ alkynylaminothiocarbonyl which may be substituted,
a N—$C_1$-$C_6$ alkyl-N—$C_3$-$C_7$ cycloalkylaminothiocarbonyl which may be substituted,
a N—$C_1$-$C_6$ alkyl-N—$C_3$-$C_7$ cycloalkenylaminothiocarbonyl which may be substituted,
a N—$C_3$-$C_6$ alkyl-N—$C_6$-$C_{10}$ arylaminothiocarbonyl which may be substituted,
a N—$C_1$-$C_6$ alkyl-N-heterocycle-aminothiocarbonyl which may be substituted,
a N,N-di-$C_3$-$C_6$ alkenylaminothiocarbonyl which may be substituted,
a N—$C_3$-$C_6$ alkenyl-N—$C_3$-$C_6$ alkynylaminothiocarbonyl which may be substituted,
a N—$C_3$-$C_6$ alkenyl-N—$C_3$-$C_7$ cycloalkylaminothiocarbonyl which may be substituted,
a N—$C_3$-$C_6$ alkenyl-N—$C_3$-$C_7$ cycloalkenylaminothiocarbonyl which may be substituted,
a N—$C_3$-$C_6$ alkenyl-N—$C_6$-$C_{10}$ arylaminothiocarbonyl which may be substituted,
a N—$C_3$-$C_6$ alkenyl-N-heterocycle-aminothiocarbonyl which may be substituted,
a N,N-di-$C_3$-$C_6$ alkynylaminothiocarbonyl which may be substituted,
a N—$C_3$-$C_6$ alkynyl-N—$C_3$-$C_7$ cycloalkylaminothiocarbonyl which may be substituted,
a N—$C_3$-$C_6$ alkynyl-N—$C_3$-$C_7$ cycloalkenylaminothiocarbonyl which may be substituted,
a N—$C_3$-$C_6$ alkynyl-N—$C_6$-$C_{10}$ arylaminothiocarbonyl which may be substituted,
a N—$C_3$-$C_6$ alkynyl-N-heterocycle-aminothiocarbonyl which may be substituted,
a N,N-di-$C_3$-$C_7$ cycloalkylaminothiocarbonyl which may be substituted,
a N—$C_3$-$C_7$ cycloalkyl-N—$C_3$-$C_7$ cycloalkenylaminothiocarbonyl which may be substituted,
a N—$C_3$-$C_7$ cycloalkyl-N—$C_6$-$C_{10}$ arylaminothiocarbonyl which may be substituted,
a N—$C_3$-$C_7$ cycloalkyl-N-heterocycle-aminothiocarbonyl which may be substituted,
a N,N-di-$C_3$-$C_7$ cycloalkenylaminothiocarbonyl which may be substituted,
a N—$C_3$-$C_7$ cycloalkenyl-N—$C_6$-$C_{10}$ arylaminothiocarbonyl which may be substituted,
a N—$C_3$-$C_7$ cycloalkenyl-N-heterocycle-aminothiocarbonyl which may be substituted,
a N,N-di-$C_6$-$C_{10}$ arylaminothiocarbonyl which may be substituted,
a N—$C_6$-$C_{10}$ aryl-N-heterocycle-aminothiocarbonyl which may be substituted, or
a N,N-di-heterocycle-aminothiocarbonyl which may be substituted, or
$R^8$ and $R^9$ may combine to each other to form a 3 to 7-membered nitrogen-containing heterocyclic ring which may further contain oxygen and/or sulfur atom and may be substituted, or
$R^8$ and $R^6$ may combine to each other to form a 5 to 7-membered nitrogen-containing heterocyclic ring which may further contain oxygen and/or sulfur atom and may be substituted,
each of r and s represents 0 or an integer of 1 to 5, provided that sum of r and s is 5 or less;
X represents oxygen atom, S(=O)m (m represents 0, 1 or 2), a group represented by the following formula (IV):

(IV)

wherein $R^{10}$ represents
hydrogen atom,
a $C_1$-$C_6$ alkyl which may be substituted,
a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocycle which may be substituted,
a $C_1$-$C_6$ alkylcarbonyl which may be substituted,
a $C_2$-$C_6$ alkenylcarbonyl which may be substituted,
a $C_2$-$C_6$ alkynylcarbonyl which may be substituted,
a $C_3$-$C_7$ cycloalkylcarbonyl which may be substituted,
a $C_3$-$C_7$ cycloalkenylcarbonyl which may be substituted,
a $C_6$-$C_{10}$ arylcarbonyl which may be substituted,
a heterocycle-carbonyl which may be substituted,
a $C_1$-$C_6$ alkylthiocarbonyl which may be substituted,
a $C_2$-$C_6$ alkenylthiocarbonyl which may be substituted,
a $C_2$-$C_6$ alkynylthiocarbonyl which may be substituted,
a $C_3$-$C_7$ cycloalkylthiocarbonyl which may be substituted,
a $C_3$-$C_7$ cycloalkenylthiocarbonyl which may be substituted,
a $C_6$-$C_{10}$ arylthiocarbonyl which may be substituted,
a heterocycle-thiocarbonyl which may be substituted,
a $C_1$-$C_6$ alkylsulfonyl which may be substituted,
a $C_8$-$C_6$ alkenylsulfonyl which may be substituted,
a $C_3$-$C_6$ alkynylsulfonyl which may be substituted,
a $C_3$-$C_7$ cycloalkylsulfonyl which may be substituted,
a $C_3$-$C_7$ cycloalkenylsulfonyl which may be substituted
a $C_6$-$C_{10}$ arylsulfonyl which may be substituted,
a heterocycle-sulfonyl which may be substituted,
carboxyl,
a $C_1$-$C_6$ alkyloxycarbonyl which may be substituted,
a $C_3$-$C_6$ alkenyloxycarbonyl which may be substituted,
a $C_3$-$C_6$ alkynyloxycarbonyl which may be substituted,
a $C_3$-$C_7$ cycloalkyloxycarbonyl which may be substituted,
a $C_3$-$C_7$ cycloalkenyloxycarbonyl which may be substituted,
a $C_6$-$C_{10}$ aryloxycarbonyl which may be substituted,
a heterocycle-oxycarbonyl which may be substituted,
aminocarbonyl,
a $C_1$-$C_6$ alkylaminocarbonyl which may be substituted,
a $C_3$-$C_6$ alkenylaminocarbonyl which may be substituted,
a $C_3$-$C_6$ alkynylaminocarbonyl which may be substituted,
a $C_3$-$C_7$ cycloalkylaminocarbonyl which may be substituted,
a $C_3$-$C_7$ cycloalkenylaminocarbonyl which may be substituted,
a $C_6$-$C_{10}$ arylaminocarbonyl which may be substituted,
a heterocycle-aminocarbonyl which may be substituted,
a N,N-di-$C_1$-$C_6$ alkylaminocarbonyl which may be substituted,
a N—$C_1$-$C_6$ alkyl-N—$C_3$-$C_7$ alkenylaminocarbonyl which may be substituted,
a N—$C_1$-$C_6$ alkyl-N—$C_3$-$C_7$ alkynylaminocarbonyl which may be substituted,
a N—$C_1$-$C_6$ alkyl-N—$C_3$-$C_7$ cycloalkylaminocarbonyl which may be substituted,
a N—$C_1$-$C_6$ alkyl-N—$C_3$-$C_7$ cycloalkenylaminocarbonyl which may be substituted,
a N—$C_1$-$C_6$ alkyl-N—$C_6$-$C_{10}$ arylaminocarbonyl which may be substituted,
a N—$C_1$-$C_6$ alkyl-N-heterocycle-aminocarbonyl which may be substituted,
a N,N-di-$C_9$-$C_6$ alkenylaminocarbonyl which may be substituted,
a N—$C_3$-$C_6$ alkenyl-N—$C_3$-$C_6$ alkynylaminocarbonyl which may be substituted,
a N—$C_3$-$C_6$ alkenyl-N—$C_3$-$C_7$ cycloalkylaminocarbonyl which may be substituted,
a N—$C_3$-$C_6$ alkenyl-N—$C_3$-$C_7$ cycloalkenylaminocarbonyl which may be substituted,
a N—$C_3$-$C_6$ alkenyl-N—$C_6$-$C_{10}$ arylaminocarbonyl which may be substituted,
a N—$C_3$-$C_6$ alkenyl-N-heterocycle-aminocarbonyl which may be substituted,
a N,N-di-$C_3$-$C_6$ alkynylaminocarbonyl which may be substituted,
a N—$C_3$-$C_6$ alkynyl-N—$C_3$-$C_7$ cycloalkylaminocarbonyl which may be substituted,
a N—$C_3$-$C_6$ alkynyl-N—$C_3$-$C_7$ cycloalkenylaminocarbonyl which may be substituted,
a N—$C_3$-$C_6$ alkynyl-N—$C_6$-$C_{10}$ arylaminocarbonyl which may be substituted,
a N—$C_3$-$C_6$ alkynyl-N-heterocycle-aminocarbonyl which may be substituted,
a N,N-di-$C_3$-$C_7$ cycloalkylaminocarbonyl which may be substituted,
a N—$C_3$-$C_7$ cycloalkyl-N—$C_3$-$C_7$ cycloalkenylaminocarbonyl which may be substituted,
a N—$C_3$-$C_7$ cycloalkyl-N—$C_6$-$C_{10}$ arylaminocarbonyl which may be substituted,
a N—$C_3$-$C_7$ cycloalkyl-N-heterocycle-aminocarbonyl which may be substituted,
a N,N-di-$C_3$-$C_7$ cycloalkenylaminocarbonyl which may be substituted,
a N—$C_3$-$C_7$ cycloalkenyl-N—$C_6$-$C_{10}$ arylaminocarbonyl which may be substituted,
a N—$C_3$-$C_7$ cycloalkenyl-N-heterocycle-aminocarbonyl which may be substituted,
a N,N-di-$C_6$-$C_{10}$ arylaminocarbonyl which may be substituted,
a N—$C_6$-$C_{10}$ aryl-N-heterocycle-aminocarbonyl which may be substituted,
a N,N-di-heterocycle-aminocarbonyl which may be substituted,
aminothiocarbonyl,
a $C_1$-$C_6$ alkylaminothiocarbonyl which may be substituted,
a $C_3$-$C_6$ alkenylaminothiocarbonyl which may be substituted,
a $C_3$-$C_6$ alkynylaminothiocarbonyl which may be substituted,
a $C_3$-$C_7$ cycloalkylaminothiocarbonyl which may be substituted,
a $C_3$-$C_7$ cycloalkenylaminothiocarbonyl which may be substituted,
a $C_6$-$C_{10}$ arylaminothiocarbonyl which may be substituted,
a heterocycle-aminothiocarbonyl which may be substituted,
a N,N-di-$C_1$-$C_6$ alkylaminothiocarbonyl which may be substituted,
a N—$C_1$-$C_6$ alkyl-N—$C_3$-$C_7$ alkenylaminothiocarbonyl which may be substituted,
a N—$C_1$-$C_6$ alkyl-N—$C_3$-$C_7$ alkynylaminothiocarbonyl which may be substituted,
a N—$C_1$-$C_6$ alkyl-N—$C_3$-$C_7$ cycloalkylaminothiocarbonyl which may be substituted,
a N—$C_1$-$C_6$ alkyl-N—$C_3$-$C_7$ cycloalkenylaminothiocarbonyl which may be substituted,
a N—$C_1$-$C_6$ alkyl-N—$C_6$-$C_{10}$ arylaminothiocarbonyl which may be substituted, a N—$C_1$-$C_6$ alkyl-N-heterocycle-aminothiocarbonyl which may be substituted,
a N,N-di-$C_3$-$C_6$ alkenylaminothiocarbonyl which may be substituted,
a N—$C_3$-$C_6$ alkenyl-N—$C_3$-$C_6$ alkynylaminothiocarbonyl which may be substituted,
a N—$C_3$-$C_6$ alkenyl-N—$C_3$-$C_7$ cycloalkylaminothiocarbonyl which may be substituted,
a N—$C_3$-$C_6$ alkenyl-N—$C_3$-$C_7$ cycloalkenylaminothiocarbonyl which may be substituted,
a N—$C_3$-$C_6$ alkenyl-N—$C_6$-$C_{10}$ arylaminothiocarbonyl which may be substituted,
a N—$C_3$-$C_6$ alkenyl-N-heterocycle-aminothiocarbonyl which may be substituted,
a N,N-di-$C_3$-$C_6$ alkynylaminothiocarbonyl which may be substituted,
a N—$C_3$-$C_6$ alkynyl-N—$C_3$-$C_7$ cycloalkylaminothiocarbonyl which may be substituted,
a N—$C_3$-$C_7$ alkynyl-N—$C_3$-$C_7$ cycloalkenylaminothiocarbonyl which may be substituted,
a N—$C_3$-$C_6$ alkynyl-N—$C_6$-$C_{10}$ arylaminothiocarbonyl which may be substituted,
a N—$C_3$-$C_6$ alkynyl-N-heterocycle-aminothiocarbonyl which may be substituted,
a N,N-di-$C_3$-$C_7$ cycloalkylaminothiocarbonyl which may be substituted,
a N—$C_3$-$C_7$ cycloalkyl-N—$C_3$-$C_7$ cycloalkenylaminothiocarbonyl which may be substituted,
a N—$C_3$-$C_7$ cycloalkyl-N—$C_6$-$C_{10}$ arylaminothiocarbonyl which may be substituted,
a N—$C_3$-$C_7$ cycloalkyl-N-heterocycle-aminothiocarbonyl which may be substituted,
a N,N-di-$C_3$-$C_7$ cycloalkenylaminothiocarbonyl which may be substituted,
a N—$C_3$-$C_7$ cycloalkenyl-N—$C_6$-$C_{10}$ arylaminothiocarbonyl which may be substituted,
a N—$C_3$-$C_{17}$ cycloalkenyl-N-heterocycle-aminothiocarbonyl which may be substituted,
a N,N-di-$C_6$-$C_{10}$ arylaminothiocarbonyl which may be substituted,
a N—$C_6$-$C_{10}$ aryl-N-heterocycle-aminothiocarbonyl which may be substituted, or
a N,N-di-heterocycle-aminothiocarbonyl which may be substituted, or
$R^{10}$ may combine with $R^6$ to form a 5 to 7 membered ring which may have nitrogen atom, oxygen atom and/or sulfur atom in the ring which may be substituted, or
a group represented by the following formula (V):

(V)

wherein $R^{11}$ and $R^{12}$ each independently represents
hydrogen atom,
hydroxyl,
a halogen,
nitro,
cyano
a $C_1$-$C_6$ alkyl which may be substituted,
a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocycle which may be substituted,
a $C_1$-$C_6$ alkyloxy which may be substituted,
a $C_3$-$C_6$ alkenyloxy which may be substituted,
a $C_3$-$C_6$ alkynyloxy which may be substituted,
a $C_3$-$C_7$ cycloalkyloxy which may be substituted,
a $C_3$-$C_7$ cycloalkenyloxy which may be substituted,
a $C_6$-$C_{10}$ aryloxy which may be substituted,
a heterocycle-oxy group which may be substituted,
a $C_1$-$C_6$ alkylthio which may be substituted,
a $C_3$-$C_6$ alkenylthio which may be substituted,
a $C_3$-$C_6$ alkynylthio which may be substituted,
a $C_3$-$C_7$ cycloalkylthio which may be substituted,
a $C_3$-$C_7$ cycloalkenylthio which may be substituted,
a $C_6$-$C_{10}$ arylthio which may be substituted,
a heterocycle-thio group which may be substituted,
amino,
a $C_1$-$C_6$ alkylamino which may be substituted,
a $C_3$-$C_6$ alkenylamino which may be substituted,
a $C_3$-$C_6$ alkynylamino which may be substituted,
a $C_3$-$C_7$ cycloalkylamino which may be substituted,
a $C_3$-$C_7$ cycloalkenylamino which may be substituted,
an $C_6$-$C_{10}$ arylamino which may be substituted,
a heterocycle-amino which may be substituted,
a N,N-di-$C_1$-$C_6$ alkylamino which may be substituted,
a N—$C_1$-$C_6$ alkyl-N—$C_3$-$C_6$ alkenylamino which may be substituted,
a N—$C_1$-$C_6$ alkyl-N—$C_3$-$C_6$ alkynylamino which may be substituted,
a N—$C_1$-$C_6$ alkyl-N—$C_3$-$C_7$ cycloalkylamino which may be substituted,
a N—$C_1$-$C_6$ alkyl-N—$C_3$-$C_7$ cycloalkenylamino which may be substituted,
a N—$C_1$-$C_6$ alkyl-N—$C_6$-$C_{10}$ arylamino which may be substituted,
a N—$C_1$-$C_6$ alkyl-N-heterocycle-amino which may be substituted,
a N,N-di-$C_3$-$C_6$ alkenylamino which may be substituted,
a N—$C_3$-$C_6$ alkenyl-N—$C_3$-$C_6$ alkynylamino which may be substituted,
a N—$C_3$-$C_6$ alkenyl-N—$C_3$-$C_7$ cycloalkylamino which may be substituted,
a N—$C_3$-$C_6$ alkenyl-N—$C_3$-$C_7$ cycloalkenylamino which may be substituted,
a N—$C_3$-$C_6$ alkenyl-N—$C_6$-$C_{10}$ arylamino which may be substituted,
a N—$C_3$-$C_6$ alkenyl-N-heterocycle-amino which may be substituted,
a N,N-di-$C_3$-$C_6$ alkynylamino which may be substituted,
a N—$C_3$-$C_6$ alkynyl-N—$C_3$-$C_7$ cycloalkylamino which may be substituted,
a N—$C_3$-$C_6$ alkynyl-N—$C_3$-$C_7$ cycloalkenylamino which may be substituted,
a N—$C_3$-$C_6$ alkynyl-N—$C_6$-$C_{10}$ arylamino which may be substituted,
a N—$C_3$-$C_6$ alkynyl-N-heterocycle-amino which may be substituted,
a N,N-di-$C_3$-$C_7$ cycloalkylamino which may be substituted,
a N—$C_3$-$C_7$ cycloalkyl-N—$C_3$-$C_7$ cycloalkenylamino which may be substituted,
a N—$C_3$-$C_7$ cycloalkyl-N—$C_6$-$C_{10}$ arylamino which may be substituted,
a N—$C_3$-$C_7$ cycloalkyl-N-heterocycle-amino which may be substituted,
a N,N-di-$C_3$-$C_7$ cycloalkenylamino which may be substituted, a N—$C_3$-$C_7$ cycloalkenyl-N—$C_6$-$C_{10}$ arylamino which may be substituted,
a N—$C_3$-$C_{17}$ cycloalkenyl-N-heterocycle-amino which may be substituted,
a N,N-di-$C_6$-$C_{10}$ arylamino which may be substituted,
a N—$C_6$-$C_{10}$ aryl-N-heterocycle-amino which may be substituted,
a N,N-diheterocycle-amino which may be substituted,
a $C_1$-$C_6$ alkylcarbonyl which may be substituted,
a $C_2$-$C_6$ alkenylcarbonyl which may be substituted,
a $C_2$-$C_6$ alkynylcarbonyl which may be substituted,
a $C_3$-$C_7$ cycloalkylcarbonyl which may be substituted,
a $C_3$-$C_7$ cycloalkenylcarbonyl which may be substituted,
a $C_6$-$C_{10}$ arylcarbonyl which may be substituted,
a heterocycle-carbonyl which may be substituted,
a $C_1$-$C_6$ alkylsulfonyl which may be substituted,
a $C_3$-$C_6$ alkenylsulfonyl which may be substituted,
a $C_3$-$C_6$ alkynylsulfonyl which may be substituted,
a $C_3$-$C_7$ cycloalkylsulfonyl which may be substituted,
a $C_3$-$C_7$ cycloalkenylsulfonyl which may be substituted,
a $C_6$-$C_{10}$ arylsulfonyl which may be substituted,
a heterocycle-sulfonyl which may be substituted,
carboxyl,
a $C_1$-$C_6$ alkyloxycarbonyl which may be substituted,
a $C_3$-$C_6$ alkenyloxycarbonyl which may be substituted,
a $C_3$-$C_6$ alkynyloxycarbonyl which may be substituted,
a $C_3$-$C_7$ cycloalkyloxycarbonyl which may be substituted,
a $C_3$-$C_7$ cycloalkenyloxycarbonyl which may be substituted,
a $C_6$-$C_{10}$ aryloxycarbonyl which may be substituted,
a heterocycle-oxycarbonyl which may be substituted,
aminocarbonyl,
a $C_1$-$C_6$ alkylaminocarbonyl which may be substituted,
a $C_3$-$C_6$ alkenylaminocarbonyl which may be substituted,
a $C_3$-$C_6$ alkynylaminocarbonyl which may be substituted,
a $C_3$-$C_7$ cycloalkylaminocarbonyl which may be substituted,
a $C_3$-$C_7$ cycloalkenylaminocarbonyl which may be substituted,
a $C_6$-$C_{10}$ arylaminocarbonyl which may be substituted,
a heterocycle-aminocarbonyl which may be substituted,
a N,N-di-$C_1$-$C_6$ alkylaminocarbonyl which may be substituted,
a N—$C_1$-$C_6$ alkyl-N—$C_3$-$C_7$ alkenylaminocarbonyl which may be substituted,
a N—$C_1$-$C_6$ alkyl-N—$C_3$-$C_7$ alkynylaminocarbonyl which may be substituted,
a N—$C_1$-$C_6$ alkyl-N—$C_3$-$C_7$ cycloalkylaminocarbonyl which may be substituted,
a N—$C_1$-$C_6$ alkyl-N—$C_3$-$C_7$ cycloalkenylaminocarbonyl which may be substituted,
a N—$C_1$-$C_6$ alkyl-N—$C_6$-$C_{10}$ arylaminocarbonyl which may be substituted,
a N—$C_1$-$C_6$ alkyl-N-heterocycle-aminocarbonyl which may be substituted,
a N,N-di-$C_3$-$C_6$ alkenylaminocarbonyl which may be substituted,
a N—$C_3$-$C_6$ alkenyl-N—$C_3$-$C_6$ alkynylaminocarbonyl which may be substituted,
a N—$C_3$-$C_6$ alkenyl-N—$C_3$-$C_7$ cycloalkylaminocarbonyl which may be substituted,
a N—$C_3$-$C_6$ alkenyl-N—$C_3$-$C_7$ cycloalkenylaminocarbonyl which may be substituted,
a N—$C_3$-$C_6$ alkenyl-N—$C_6$-$C_{10}$ arylaminocarbonyl which may be substituted,
a N—$C_3$-$C_6$ alkenyl-N-heterocycle-aminocarbonyl which may be substituted,
a N,N-di-$C_3$-$C_6$ alkynylaminocarbonyl which may be substituted,
a N—$C_3$-$C_6$ alkynyl-N—$C_3$-$C_7$ cycloalkylaminocarbonyl which may be substituted,
a N—$C_3$-$C_6$ alkynyl-N—$C_3$-$C_7$ cycloalkenylaminocarbonyl which may be substituted,
a N—$C_3$-$C_6$ alkynyl-N—$C_6$-$C_{10}$ arylaminocarbonyl which may be substituted,
a N—$C_3$-$C_6$ alkynyl-N-heterocycle-aminocarbonyl which may be substituted,
a N,N-di-$C_3$-$C_7$ cycloalkylaminocarbonyl which may be substituted,
a N—$C_3$-$C_7$ cycloalkyl-N—$C_3$-$C_7$ cycloalkenylaminocarbonyl which may be substituted,
a N—$C_3$-$C_7$ cycloalkyl-N—$C_6$-$C_{10}$ arylaminocarbonyl which may be substituted,
a N—$C_3$-$C_7$ cycloalkyl-N-heterocycle-aminocarbonyl which may be substituted,
a N,N-di-$C_3$-$C_7$ cycloalkenylaminocarbonyl which may be substituted,
a N—$C_3$-$C_7$ cycloalkenyl-N—$C_6$-$C_{10}$ arylaminocarbonyl which may be substituted,
a N—$C_3$-$C_7$ cycloalkenyl-N-heterocycle-aminocarbonyl which may be substituted,
a N,N-di-$C_6$-$C_{10}$ arylaminocarbonyl which may be substituted,
a N—$C_6$-$C_{10}$ aryl-N-heterocycle-aminocarbonyl which may be substituted, or
a N,N-di-heterocycle-aminocarbonyl which may be substituted, or
$R^{11}$ and $R^{12}$ may combine to each other to form oxo group or a spiro ring which may have nitrogen atom, oxygen atom and/or sulfur atom in the ring which may be substituted.

2. The compound, an optically active isomer thereof, or a pharmaceutically acceptable salt thereof according to the above 1, wherein $R^2$ is hydrogen atom or a halogen.

3. The compound, an optically active isomer thereof, or a pharmaceutically acceptable salt thereof according to the above 1, wherein $R^2$ is hydrogen atom.

4. The compound, an optically active isomer thereof, or a pharmaceutically acceptable salt thereof according to the above 1, wherein $R^1$ is a $C_1$-$C_6$ alkyl which may be substituted.

5. The compound, an optically active isomer thereof, or a pharmaceutically acceptable salt thereof according to the above 1, wherein $R^1$ is methyl group.

6. The compound, an optically active isomer thereof, or a pharmaceutically acceptable salt thereof according to the above 1, wherein $R^3$ is
hydroxyl, a halogen, nitro, cyano,
a $C_1$-$C_6$ alkyl which may be substituted,
a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocycle which may be substituted,
a $C_1$-$C_6$ alkyloxy which may be substituted,
a $C_8$-$C_6$ alkenyloxy which may be substituted,
a $C_3$-$C_6$ alkynyloxy which may be substituted,
a $C_3$-$C_7$ cycloalkyloxy which may be substituted,
a $C_3$-$C_7$ cycloalkenyloxy which may be substituted,
a $C_6$-$C_{10}$ aryloxy which may be substituted,
a heterocycle-oxy group which may be substituted,
amino,
a $C_1$-$C_6$ alkylamino which may be substituted,
a $C_3$-$C_6$ alkenylamino which may be substituted,
a $C_3$-$C_6$ alkynylamino which may be substituted,
a $C_3$-$C_7$ cycloalkylamino which may be substituted, a $C_3$-$C_7$ cycloalkenylamino which may be substituted,
an $C_6$-$C_{10}$ arylamino which may be substituted,
a heterocycle-amino which may be substituted,
a N,N-di-$C_1$-$C_6$ alkylamino which may be substituted,
a N—$C_1$-$C_6$ alkyl-N—$C_3$-$C_6$ alkenylamino which may be substituted,
a N—$C_1$-$C_6$ alkyl-N—$C_3$-$C_6$ alkynylamino which may be substituted,
a N—$C_1$-$C_6$ alkyl-N—$C_3$-$C_7$ cycloalkylamino which may be substituted,
a N—$C_1$-$C_6$ alkyl-N—$C_3$-$C_7$ cycloalkenylamino which may be substituted,
a N—$C_1$-$C_6$ alkyl-N—$C_6$-$C_{10}$ arylamino which may be substituted,
a N—$C_1$-$C_6$ alkyl-N-heterocycle-amino which may be substituted,
a N,N-di-$C_3$-$C_6$ alkenylamino which may be substituted,
a N—$C_3$-$C_6$ alkenyl-N—$C_3$-$C_6$ alkynylamino which may be substituted,
a N—$C_3$-$C_6$ alkenyl-N—$C_3$-$C_7$ cycloalkylamino which may be substituted,
a N—$C_3$-$C_6$ alkenyl-N—$C_3$-$C_7$ cycloalkenylamino which may be substituted,
a N—$C_3$-$C_6$ alkenyl-N—$C_6$-$C_{10}$ arylamino which may be substituted,
a N—$C_3$-$C_6$ alkenyl-N-heterocycle-amino which may be substituted,
a N,N-di-$C_3$-$C_6$ alkynylamino which may be substituted,
a N—$C_3$-$C_6$ alkynyl-N—$C_3$-$C_7$ cycloalkylamino which may be substituted,
a N—$C_3$-$C_6$ alkynyl-N—$C_3$-$C_7$ cycloalkenylamino which may be substituted,
a N—$C_3$-$C_6$ alkynyl-N—$C_6$-$C_{10}$ arylamino which may be substituted,
a N—$C_3$-$C_6$ alkynyl-N-heterocycle-amino which may be substituted,
a N,N-di-$C_3$-$C_7$ cycloalkylamino which may be substituted,
a N—$C_3$-$C_7$ cycloalkyl-N—$C_3$-$C_7$ cycloalkenylamino which may be substituted,
a N—$C_3$-$C_7$ cycloalkyl-N—$C_6$-$C_{10}$ arylamino which may be substituted,
a N—$C_3$-$C_7$ cycloalkyl-N-heterocycle-amino which may be substituted,
a N,N-di-$C_3$-$C_7$ cycloalkenylamino which may be substituted,
a N—$C_3$-$C_7$ cycloalkenyl-N—$C_6$-$C_{10}$ arylamino which may be substituted,
a N—$C_3$-$C_7$ cycloalkenyl-N-heterocycle-amino which may be substituted,
a N,N-di-$C_6$-$C_{10}$ arylamino which may be substituted,
a N—$C_6$-$C_{10}$ aryl-N-heterocycle-amino which may be substituted, or
a N,N-diheterocycle-amino which may be substituted.

7. The compound, an optically active isomer thereof, or a pharmaceutically acceptable salt thereof according to the above 1, wherein $R^3$ is a halogen, a $C_1$-$C_6$ alkyl which may be substituted, a $C_6$-$C_{10}$ aryl which may be substituted, a $C_1$-$C_6$ alkyloxy which may be substituted, amino, or a $C_1$-$C_6$ alkylamino which may be substituted.

8. The compound, an optically active isomer thereof, or a pharmaceutically acceptable salt thereof according to the above 1, wherein $R^3$ is a halogen, a $C_1$-$C_6$ alkyl which may be substituted, a $C_6$-$C_{10}$ aryl which may be substituted, or a $C_1$-$C_6$ alkyloxy which may be substituted.

9. The compound, an optically active isomer thereof, or a pharmaceutically acceptable salt thereof according to the above 1, wherein $R^3$ is a halogen.

10. The compound, an optically active isomer thereof, or a pharmaceutically acceptable salt thereof according to the above 1, wherein A is phenyl group.

11. The compound, an optically active isomer thereof, or a pharmaceutically acceptable salt thereof according to the above 1, wherein q is 1 and $R^3$ is fluorine atom substituting on 3-position of the pyridine group.

12. The compound, an optically active isomer thereof, or a pharmaceutically acceptable salt thereof according to the above 1, wherein X is oxygen atom.

13. The compound, an optically active isomer thereof, or a pharmaceutically acceptable salt thereof according to the above 1, wherein X is a group represented by the formula (IV).

14. The compound, an optically active isomer thereof, or a pharmaceutically acceptable salt thereof according to the above 1, wherein X is a group represented by the formula (V).

15. A compound according to the above 1 selected from the group consisting of:
6-(3-Fluoro-pyridin-4-yl)-3-methyl-2-((3S)-3-(4-morpholin-4-yl-phenyl)-piperazin-1-yl)-3H-pyrimidin-4-one;
2-((2S)-2-(4-((3R)-3-Dimethylamino-pyrrolidin-1-yl)-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((3S)-3-(4-piperidin-1-yl-phenyl)-piperazin-1-yl)-3H-pyrimidin-4-one;
6-(3-Fluoro-pyridin-4-yl)-3-methyl-2-((2S)-2-(4-(4-pyrrolidin-1-yl-piperidin-1-yl)-phenyl(-morpholin-4-yl)-3H-pyrimidin-4-one;
2-((2S)-2-(4-(4-Dimethylamino-piperidin-1-yl)-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((3S)-3-(4-(4-methyl-piperazin-1-yl)-phenyl)-piperazin-1-yl)-3H-pyrimidin-4-one;
6-(3-Fluoro-pyridin-4-yl)-2-(3S)-3-(4-(4-hydroxy-piperidin-1-yl)-phenyl)-piperazin-1-yl)-3-methyl-3H-pyrimidin-4-one;
6-(3-Fluoro-pyridin-4-yl)-2-((3S)-3-(4-((3R)-3-hydroxy-pyrrolidin-1-yl)-phenyl)-piperazin-1-yl)-3-methyl-3H-pyrimidin-4-one;
2-((2S)-2-(4-((3S,5R)-3,5-Dimethyl-piperazin-1-yl)-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((2S)-2-(4-(4-methyl-piperazin-1-yl)-phenyl)-morpholin-4-yl)-3H-pyrimidin-4-one;
2-((2S)-2-(4-((3S)-3-Dimethylamino-pyrrolidin-1-yl)-phenyl)-morpholin-4-yl)-6-(3-fluoro-pyridin-4-yl)-3-methyl-3H-pyrimidin-4-one;
6-(3-Fluoro-pyridin-4-yl)-2-((2S)-2-(4-(4-isopropyl-piperazin-1-yl)-phenyl)-morpholin-4-yl)-3-methyl-3H-pyrimidin-4-one;
6-(3-Fluoro-pyridin-4-yl)-2-((2S)-2-(4-(4-(2-hydroxy-ethyl)-piperazin-1-yl)-phenyl)-morpholin-4-yl)-3-methyl-3H-pyrimidin-4-one;
6-(3-Fluoro-pyridin-4-yl)-3-methyl-2-((3S)-3-(4-((3S)-3-(pyrrolidin-1-yl)-pyrrolidin-1-yl)-phenyl)-piperazin-1-yl)-3H-pyrimidin-4-one;
6-(3-Fluoro-pyridin-4-yl)-3-methyl-2-((3S)-3-(4-(5-methyl-(1,2,4)oxadiazol-3-yl)-phenyl)-piperazin-1-yl)-3H-pyrimidin-4-one;
6-(3-Fluoro-pyridin-4-yl)-3-methyl-2-[3-(4-morpholin-4-yl-phenyl)-piperidin-1-yl]-3H-pyrimidin-4-one;
2-((2S)-2-(4-Cyclopentylamino-phenyl)-morpholin-4-yl)-6-(3-fluoro-pyridin-4-yl)-3-methyl-3H-pyrimidin-4-one;

6-(3-Fluoro-pyridin-4-yl)-2-((2S)-2-(4-(3-hydroxy-azetidin-1-yl)-phenyl)-morpholin-4-yl)-3-methyl-3H-pyrimidin-4-one;

N-(4-((2S)-4-((4-(3-Fluoro-pyridin-4-yl)-1-methyl-6-oxo-1,6-dihydro-pyrimidin-2-yl)-morpholin-2-yl)-phenyl)-acetamide 2-((2S)-2-(4-Cyclopentyloxy-phenyl)-morpholin-4-yl)-6-(3-fluoro-pyridin-4-yl)-3-methyl-3H-pyrimidin-4-one;

2-((2S)-2-(4-Cyclopropylmethoxy-phenyl)-morpholin-4-yl)-6-(3-fluoro-pyridin-4-yl)-3-methyl-3H-pyrimidin-4-one;

2-((2S)-2-(4-(2-Dimethylamino-ethoxy)-phenyl)-morpholin-4-yl)-6-(3-fluoro-pyridin-4-yl)-3-methyl-3H-pyrimidin-4-one;

2-((2S)-2-(4-Amino-phenyl)-morpholin-4-yl)-6-(3-fluoro-pyridin-4-yl)-3-methyl-3H-pyrimidin-4-one;

Cyclopropanecarboxylic acid (4-((2S)-4-(4-(3-fluoro-pyridin-4-yl)-1-methyl-6-oxo-1,6-dihydro-pyrimidin-2-yl)-morpholin-2-yl)-phenyl)-amide;

N-(4-((2S)-4-(4-(3-Fluoro-pyridin-4-yl)-1-methyl-6-oxo-1,6-dihydro-pyrimidin-2-yl)-morpholin-2-yl)-phenyl)-2,2-dimethyl-propionamide;

6-(3-Fluoro-pyridin-4-yl)-3-methyl-2-((2S)-2-(4-(methyl-((3R)-tetrahydro-furan-3-yl)-amino)-phenyl)-morpholin-4-yl)-3H-pyrimidin-4-one;

6-(3-Fluoro-pyridin-4-yl)-3-methyl-2-((2S)-2-[4-(2-pyrrolidin-1-yl-ethoxy)-phenyl]-morpholin-4-yl)-3H-pyrimidin-4-one;

6-(3-Fluoro-pyridin-4-yl)-2-((2S)-2-(4-hydroxy-phenyl)-morpholin-4-yl)-3-methyl-3H-pyrimidin-4-one;

2-((2S)-2-(4-(2-Diethylamino-ethoxy)-phenyl)-morpholin-4-yl)-6-(3-fluoro-pyridin-4-yl)-3-methyl-3H-pyrimidin-4-one;

6-(3-Fluoro-pyridin-4-yl)-3-methyl-2-((2S)-2-(4-(2-piperidin-1-yl-ethoxy)-phenyl)-morpholin-4-yl)-3H-pyrimidin-4-one;

6-(3-Fluoro-pyridin-4-yl)-3-methyl-2-((2S)-2-(4-(2-(4-methyl-piperazin-1-yl)-ethoxy)-phenyl)-morpholin-4-yl)-3H-pyrimidin-4-one;

$N^2,N^2$-Dimethyl-$N^1$-(4-((2S)-4-(3-methyl-4-oxo-3,4-dihydro-6-(3-fluoropyridin-4-yl)pyrimidin-2-yl)morpholin-2-yl)phenyl)glycinamide;

Methyl (4-((2S)-4-(6-(3-fluoropyridin-4-yl)-3-methyl-4-oxo-3H-pyrimidin-2-yl)morpholin-2-yl)phenyl)carbamate;

N'-(4-((2S)-4-(6-(3-Fluoropyridin-4-yl)-3-methyl-4-oxo-3H-pyrimidin-2-yl)morpholin-2-yl)phenyl)-N,N-dimethylurea;

6-{4-[4-(3-Fluoropyridin-4-yl)-1-methyl-6-oxo-1,6-dihydropyrimidin-2-yl]morpholin-2-yl}-3,4-dihydroquinolin-2(1H)-one;

6-(3-Fluoro-pyridin-4-yl)-3-methyl-2-{(2S)-2-[4-morpholine-4-carbonyl]-phenyl}-morpholin-4-yl}-3H-pyrimidin-4-one;

N-(3-{(2S)-4-[4-(3-Fluoropyridin-4-yl)-1-methyl-6-oxo-1,6-dihydropyrimidin-2-yl]-morpholin-2-yl}-4-methoxyphenyl)acetamide;

N-(3-{(2S)-4-[4-(3-Fluoropyridin-4-yl)-1-methyl-6-oxo-1,6-dihydropyrimidin-2-yl]-morpholin-2-yl}phenyl)acetamide; and 6-(3-Fluoropyridin-4-yl)-3-methyl-2-((3S)-3-(4-([1,2,4]oxadiazol-3-yl)phenyl)piperazin-1-yl)-3H-pyrimidin-4-one, an optically active isomer thereof, or a pharmaceutically acceptable salt thereof.

16. A medicament comprising as an active ingredient a substance selected from the group consisting of the compound represented by the formula (I) and an optically active isomer thereof, or a pharmaceutically acceptable salt thereof according to the above 1.

17. A tau protein kinase 1 inhibitor selected from the group consisting of the compound represented by the formula (I) and an optically active isomer thereof, or a pharmaceutically acceptable salt thereof according to the above 1.

18. The medicament according to the above 16 which is used for preventive and/or therapeutic treatment of a disease caused by tau protein kinase 1 hyperactivity.

19. The medicament according to the above 16 which is used for preventive and/or therapeutic treatment of a neurodegenerative disease.

20. The medicament according to the above 19, wherein the disease is selected from the group consisting of Alzheimer disease, ischemic cerebrovascular accidents, Down syndrome, cerebral bleeding due to cerebral amyloid angiopathy, progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration, frontotemporal dementia, vascular dementia, traumatic injuries, brain and spinal cord trauma, peripheral neuropathies, retinopathies and glaucoma.

21. The medicament according to the above 16, which is used for preventive and/or therapeutic treatment of a disease selected from the group consisting of non-insulin dependent diabetes, obesity, manic depressive illness, schizophrenia, alopecia, breast cancer, non-small cell lung carcinoma, thyroid cancer, T or B-cell leukemia, and a virus-induced tumor.

MODE FOR CARRYING OUT THE INVENTION

Unless otherwise indicated, the following definitions are set forth to illustrate and defined the meaning and scope of the various terms used to describe the invention herein.

The term "$C_1$-$C_{12}$ alkyl" means alkyl group having 1 to 12 carbon atoms which may be either linear or branched, for example, methyl, ethyl, n-propyl, isopropyl, n-butyl, isobutyl, sec-butyl, tert-butyl, n-pentyl, isopentyl, neopentyl, 1,1-dimethylpropyl, n-hexyl, isohexyl, heptyl, octyl, nonyl, decyl, undecyl or dodecyl.

The term "$C_1$-$C_6$ alkyl" means alkyl group having 1 to 6 carbon atoms which may be either linear or branched, for example, methyl, ethyl, n-propyl, isopropyl, n-butyl, isobutyl, sec-butyl, tert-butyl, n-pentyl, isopentyl, neopentyl, 1,1-dimethylpropyl, n-hexyl, isohexyl (a $C_1$-$C_6$ alkyl moiety of substituents containing a $C_1$-$C_6$ alkyl moiety mentioned in the specification has the same meaning).

The term "$C_2$-$C_6$ alkenyl" means alkenyl group having 2 to 6 carbon atoms, for example, vinyl, propenyl, butenyl, pentenyl, hexenyl (a $C_2$-$C_6$ alkenyl moiety of substituents containing a $C_2$-$C_6$ alkenyl moiety mentioned in the specification has the same meaning).

The term "$C_3$-$C_6$ alkenyl" means alkenyl group having 3 to 6 carbon atoms, for example, propenyl, butenyl, pentenyl, hexenyl (a $C_3$-$C_6$ alkenyl moiety of substituents containing a $C_3$-$C_6$ alkenyl moiety mentioned in the specification has the same meaning).

The term "$C_2$-$C_6$ alkynyl" means alkynyl group having 2 to 6 carbon atoms, for example, ethynyl, propynyl, butynyl, pentynyl, hexynyl (a $C_2$-$C_6$ alkynyl moiety of substituents containing a $C_2$-$C_6$ alkynyl moiety mentioned in the specification has the same meaning).

The term "$C_3$-$C_6$ alkynyl" means alkynyl group having 3 to 6 carbon atoms, for example, propynyl, butynyl, pentynyl, hexynyl (a $C_3$-$C_6$ alkynyl moiety of substituents containing a $C_3$-$C_6$ alkynyl moiety mentioned in the specification has the same meaning).

The term "$C_3$-$C_7$ cycloalkyl" means cycloalkyl having 3 to 7 carbon atoms, for example, cyclopropyl, cyclobutyl, cyclopentyl, cyclohexyl, cycloheptyl (a $C_3$-$C_7$ cycloalkyl moiety of substituents containing a $C_3$-$C_7$ cycloalkyl moiety mentioned in the specification has the same meaning).

The term "$C_3$-$C_7$ cycloalkenyl" means cycloalkenyl group having 3 to 7 carbon atoms, for example, cyclopropenyl cyclobutenyl, cyclopentenyl, cyclohexenyl, cycloheptenyl (a $C_3$-$C_7$ cycloalkenyl moiety of substituents containing a $C_3$-$C_7$ cycloalkenyl moiety mentioned in the specification has the same meaning).

The term "$C_6$-$C_{10}$ aryl" means a group having 6 to 10 carbon atoms derived from, for example, benzene, naphthalene, indane, indene, tetrahydronaphthalene (a $C_6$-$C_{10}$ aryl moiety of substituents containing a $C_6$-$C_{10}$ aryl moiety mentioned in the specification has the same meaning). The bond position in the cycle is not limited.

The term "heterocycle" means cyclic group derived from, for example, furan, dihydrofuran, tetrahydrofuran, pyran, dihydropyran, tetrahydropyran, benzofuran, dihydrobenzofuran, isobenzofuran, chromene, chroman, isochroman, thiophene, benzothiophene, pyrrole, pyrroline, pyrrolidine, imidazole, imidazoline, imidazolidine, pyrazole, pyrazoline, pyrazolidine, triazole, tetrazole, pyridine, pyridine oxide, piperidine, pyrazine, piperazine, pyrimidine, pyridazine, indole, indoline, isoindole, isoindoline, indazole, benzimidazole, benzotriazole, tetrahydroisoquinoline, benzothiazolinone, benzoxazolinone, purine, quinolizine, quinoline, phthalazine, naphthyridine, quinoxaline, quinazoline, cinnoline, pteridine, oxazole, oxazolidine, isoxazole, isoxazolidine, oxadiazole, thiazole, benzothiazole, thiazylidine, isothiazole, isothiazolidine, benzodioxole, dioxane, benzodioxane, dithian, morpholine, thiomorpholine, phthalimide homopiperidinyl, homopiperazinyl(a heterocycle moiety of substituents containing a heterocycle moiety mentioned in the specification has the same meaning). The bond position in the cycle is not limited.

The term "halogen" means chlorine, bromine, fluorine, or iodine.

In the specification, when a functional group is defined as "which may be substituted", the number of substituents as well as their types and substituting positions are not particularly limited, and when two or more substituents are present, they may be the same or different. Examples of the substituent include, for example, a $C_1$-$C_6$ alkyl, a $C_2$-$C_6$ alkenyl, a $C_2$-$C_6$ alkynyl, a $C_3$-$C_7$ cycloalkyl, a $C_3$-$C_7$ cycloalkenyl, a $C_6$-$C_{10}$ aryl, a heterocycle, a $C_1$-$C_6$ alkyloxy, a $C_3$-$C_6$ alkenyloxy, a $C_3$-$C_6$ alkynyloxy, a $C_3$-$C_7$ cycloalkyloxy, a $C_3$-$C_7$ cycloalkenyloxy, a $C_6$-$C_{10}$ aryloxy, a heterocycloxy, a halogen, nitro, cyano, hydroxyl, oxo group, a $C_1$-$C_6$ alkylcarbonyl, a $C_2$-$C_6$ alkenylcarbonyl, a $C_2$-$C_6$ alkynylcarbonyl, a $C_3$-$C_7$ cycloalkylcarbonyl, a $C_3$-$C_7$ cycloalkenylcarbonyl, a $C_6$-$C_{10}$ arylcarbonyl, a heterocyclecarbonyl, a $C_1$-$C_6$ alkylsulfonyl, a $C_2$-$C_6$ alkenylsulfonyl, a $C_2$-$C_6$ alkynylsulfonyl, a $C_3$-$C_7$ cycloalkylsulfonyl, a $C_3$-$C_7$ cycloalkenylsulfonyl, a $C_6$-$C_{10}$ arylsulfonyl, a heterocyclesulfonyl, a $C_1$-$C_6$ alkyloxycarbonyl, a $C_3$-$C_6$ alkenyloxycarbonyl, a $C_3$-$C_6$ alkynyloxycarbonyl, a $C_3$-$C_7$ cycloalkyloxycarbonyl, a $C_3$-$C_7$ cycloalkenyloxycarbonyl, a $C_6$-$C_{10}$ aryloxycarbonyl, a heterocycleoxycarbonyl, amino, a $C_1$-$C_6$ alkylamino, a $C_2$-$C_6$ alkenylamino, a $C_2$-$C_6$ alkynylamino, a $C_3$-$C_7$ cycloalkylamino, a $C_3$-$C_7$ cycloalkenylamino, a $C_6$-$C_{10}$ arylamino, a heterocycle-amino, a N,N-di-$C_1$-$C_6$ alkylamino, aminocarbonyl, a $C_1$-$C_6$ alkylaminocarbonyl, a $C_3$-$C_6$ alkenylaminocarbonyl, a $C_3$-$C_6$ alkynylaminocarbonyl, a $C_3$-$C_7$ cycloalkylaminocarbonyl, a $C_3$-$C_7$ cycloalkenylaminocarbonyl, a $C_6$-$C_{10}$ arylaminocarbonyl, a heterocycle-aminocarbonyl, a N,N-di-$C_1$-$C_6$ alkylaminocarbonyl. In the above substituents, every term expressed by "$C_1$-$C_6$ alkyl, $C_2$-$C_6$ alkenyl, $C_3$-$C_6$ alkenyl, $C_2$-$C_6$ alkynyl, $C_3$-$C_6$ alkynyl, $C_3$-$C_7$ cycloalkyl, $C_3$-$C_7$ cycloalkenyl, $C_6$-$C_{10}$ aryl, heterocycle" represents the same meaning as defined above. These substituents are also substituted by the substituents described above.

When two $R^3$ combine to each other to form a ring, together with the carbon atoms to which $R^3$ bind, the ring may be, for example, cyclobutenyl ring, cyclopentenyl ring, cyclohexenyl ring, cycloheptenyl ring, benzene ring.

When $R^8$ and $R^9$ combine to each other to form a nitrogen containing 3- to 7-membered heterocyclic ring together with the adjacent nitrogen atom, the ring may be, for example, azetidinyl, pyrrolidinyl, piperidinyl, morpholino, thiomorpholino, piperazinyl, or homopiperazinyl. The ring may be substituted by the substituents described above.

When $R^8$ and $R^6$ combine to each other to form a nitrogen containing 5- to 7-membered heterocyclic ring together with the nitrogen atom adjacent to $R^8$, Z, the carbon atom to which Z bind, and the carbon atom to which $R^6$ bind, the ring may be, for example, pyrrolidinyl, piperidinyl, morpholino, thiomorpholino, piperazinyl, or homopiperazinyl. The ring may be substituted by the substituents described above.

When $R^{10}$ and $R^6$ combine to each other to form a ring, the ring may be 5 to 7 membered ring which may have nitrogen atom, oxygen atom and/or sulfur atom in the ring which may be substituted.

When $R^{11}$ and $R^{12}$ combine to each other to form a ring, the ring may be a spiro ring which may have nitrogen atom, oxygen atom and/or sulfur atom in the ring which may be substituted.

$R^1$ may preferably be a $C_1$-$C_6$ alkyl group, more preferably be a methyl group.

$R^2$ may preferably be hydrogen atom.

q may preferably be 1.

$R^3$ may preferably be hydroxyl, a halogen, nitro, cyano,
a $C_1$-$C_6$ alkyl which may be substituted,
a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocycle which may be substituted,
a $C_1$-$C_6$ alkyloxy which may be substituted,
a $C_2$-$C_6$ alkenyloxy which may be substituted,
a $C_2$-$C_6$ alkynyloxy which may be substituted,
a $C_3$-$C_7$ cycloalkyloxy which may be substituted,
a $C_3$-$C_7$ cycloalkenyloxy which may be substituted,
a $C_6$-$C_{10}$ aryloxy which may be substituted,
a heterocycle-oxy group which may be substituted,
amino,
a $C_1$-$C_6$ alkylamino which may be substituted,
a $C_2$-$C_6$ alkenylamino which may be substituted,
a $C_2$-$C_6$ alkynylamino which may be substituted,
a $C_3$-$C_7$ cycloalkylamino which may be substituted,
a $C_3$-$C_7$ cycloalkenylamino which may be substituted,
an $C_6$-$C_{10}$ arylamino which may be substituted,
a heterocycle-amino which may be substituted,
a N,N-di-$C_1$-$C_6$ alkylamino which may be substituted,
a N—$C_1$-$C_6$ alkyl-N—$C_2$-$C_6$ alkenylamino which may be substituted,
a N—$C_1$-$C_6$ alkyl-N—$C_2$-$C_6$ alkynylamino which may be substituted, a N—$C_1$-$C_6$ alkyl-N—$C_3$-$C_7$ cycloalkylamino which may be substituted, a N—$C_1$-$C_6$ alkyl-N—$C_3$-$C_7$ cycloalkenylamino which may be substituted, a N—$C_1$-$C_6$ alkyl-N—$C_6$-$C_{10}$ arylamino which may be substituted, a N—$C_1$-$C_6$ alkyl-N-heterocycle-amino which may be substituted, a N,N-di-$C_2$-$C_6$ alkenylamino which may be substituted, a N—$C_2$-$C_6$ alkenyl-N—$C_2$-$C_6$ alkynylamino which may be substituted, a N—$C_2$-$C_6$ alkenyl-N—$C_3$-$C_7$ cycloalkylamino which may be substituted, a N—$C_2$-$C_6$ alkenyl-N—$C_3$-$C_7$ cycloalkenylamino which may be substituted, a N—$C_2$-$C_6$ alkenyl-N—$C_6$-$C_{10}$ arylamino which may be substituted, a N—$C_2$-$C_6$ alkenyl-N-heterocycle-amino which may be substituted, a N,N-di-$C_2$-$C_6$ alkynylamino which may be substituted, a N—$C_2$-$C_6$ alkynyl-N—$C_3$-$C_7$ cycloalkylamino which may be substituted, a N—$C_2$-$C_6$ alkynyl-N—$C_3$-$C_7$ cycloalkenylamino which may be substituted, a N—$C_2$-$C_6$ alkynyl-N—$C_6$-$C_{10}$ arylamino which may be substituted, a N—$C_2$-$C_6$ alkynyl-N-heterocycle-amino which may be substituted, a N,N-di-$C_3$-$C_7$ cycloalkylamino which may be substituted, a N—$C_3$-$C_7$ cycloalkyl-N—$C_3$-$C_7$ cycloalkenylamino which may be substituted, a N—$C_3$-$C_7$ cycloalkyl-N—$C_6$-$C_{10}$ arylamino which may be substituted, a N—$C_3$-$C_7$ cycloalkyl-N-heterocycle-amino which may be substituted, a N,N-di-$C_3$-$C_7$ cycloalkenylamino which may be substituted, a N—$C_3$-$C_7$ cycloalkenyl-N—$C_6$-$C_{10}$ arylamino which may be substituted, a N—$C_3$-$C_7$ cycloalkenyl-N-heterocycle-amino which may be substituted, a N,N-di-$C_6$-$C_{10}$ arylamino which may be substituted, a N—$C_6$-$C_{10}$ aryl-N-heterocycle-amino which may be substituted, or a N,N-diheterocycle-amino which may be substituted.

$R^3$ may more preferably be a halogen, a $C_1$-$C_6$ alkyl which may be substituted, a $C_6$-$C_{10}$ aryl which may be substituted, a $C_1$-$C_6$ alkyloxy which may be substituted, amino, or a $C_1$-$C_6$ alkylamino which may be substituted.

$R^3$ may further more preferably be a halogen, a $C_1$-$C_6$ alkyl which may be substituted, a $C_6$-$C_{10}$ aryl which may be substituted, a $C_1$-$C_6$ alkyloxy which may be substituted.

$R^3$ may further more preferably be a halogen.

$R^3$ may most preferably be fluorine atom substituting on 3-position of the pyridine group.

p may preferably be 0.

$R^5$ may preferably be the group represented by formula (II). In formula (II), A may preferably be phenyl group, sum of r and s preferably be 1, and $R^6$ or $R^7$ may preferably substitute on 4-position of phenyl group.

X may preferably be oxygen atom, a group represented by the formula (IV), or a group represented by the formula (V). X may more preferably be oxygen atom, or a group represented by the formula (IV) wherein $R^{10}$ is hydrogen atom.

The pharmaceutically acceptable salt of the compound represented by the aforementioned formula (I) may include the salt with inorganic acid such as hydrochloric acid, hydrobromic acid and the like and the salt with organic acid such as acetic acid, propionic acid, tartaric acid, fumaric acid, maleic acid, malic acid, oxalic acid, succinic acid, citric acid, benzoic acid and the like.

In addition to the compound represented by the aforementioned formula (I), an optically active isomer thereof, or a pharmaceutically acceptable salt thereof, their solvates and hydrates also fall within the scope of the present invention. The compound represented by the formula (I) may have one or more asymmetric carbon atoms. As for the stereochemistry of such asymmetric carbon atoms, they may independently be in either of (R) and (S) configuration, and the pyrimidone derivative may exist as stereoisomers such as optical isomers, or diastereoisomers. Any stereoisomers of pure form, any mixtures of stereoisomers, racemates and the like fall within the scope of the present invention Examples of preferred compounds of the present invention are shown in the tables set out below. However, the scope of the present invention is not limited by the following compounds.

TABLE 1

| Compound No. | STRUCTURE |
| --- | --- |
| 1 | 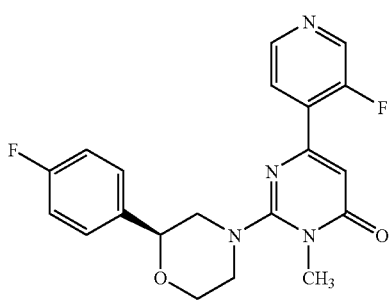 |

TABLE 1-continued
| Compound No. | STRUCTURE |
|---|---|
| 2 | 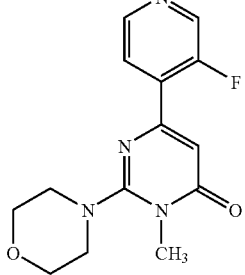 |
| 3 | 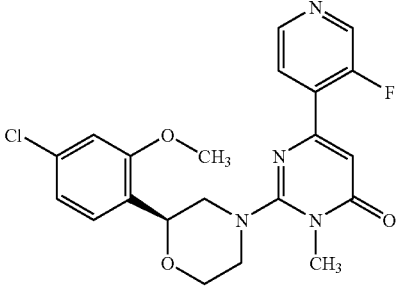 |
| 4 | 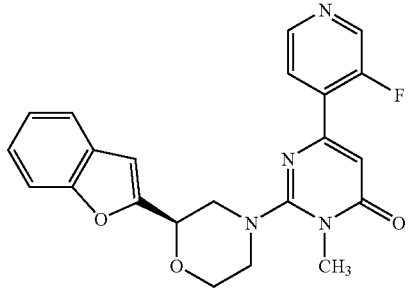 |
| 5 | 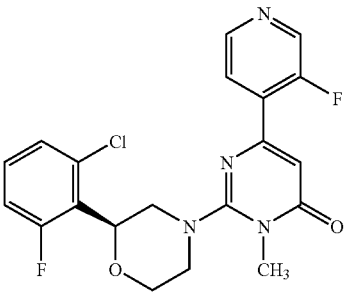 |
| 6 | 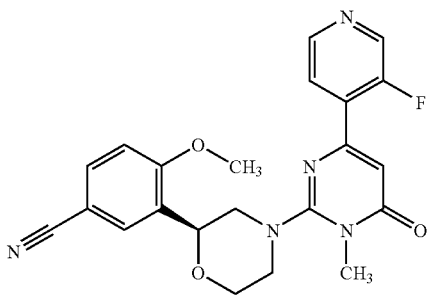 |

TABLE 1-continued

| Compound No. | STRUCTURE |
|---|---|
| 7 | 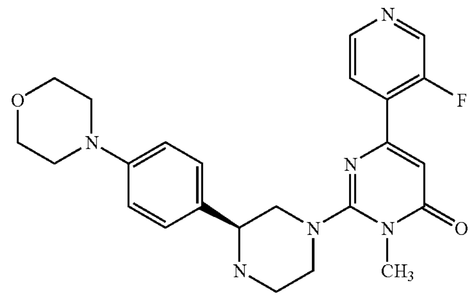 |
| 8 | 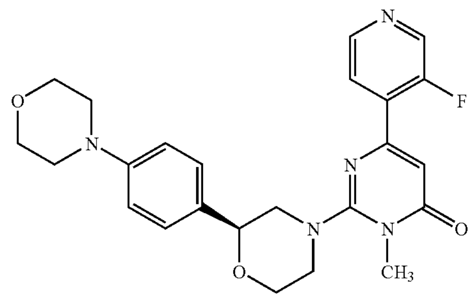 |
| 9 | 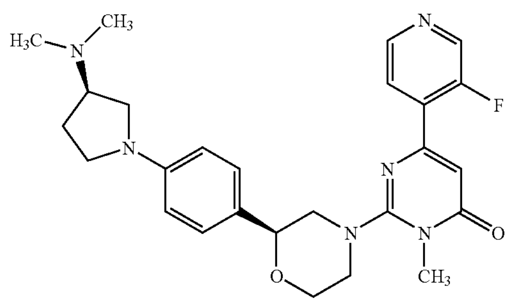 |
| 10 | 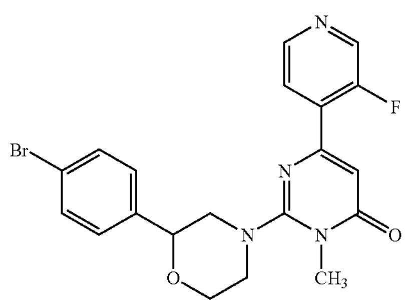 |
| 11 | 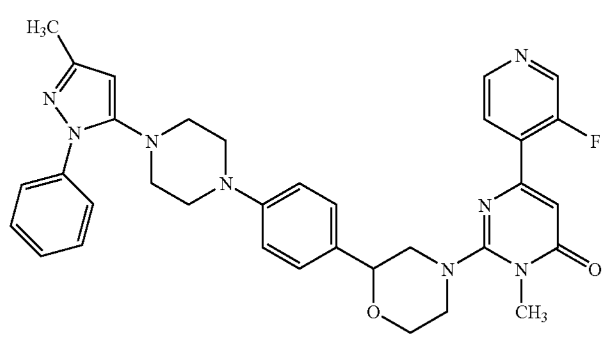 |

TABLE 1-continued

| Compound No. | STRUCTURE |
|---|---|
| 12 | 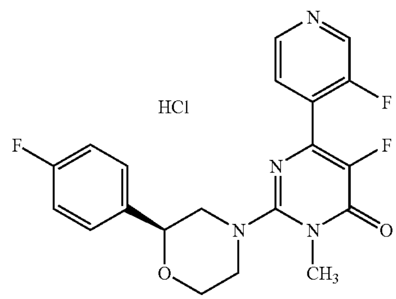 |
| 13 | 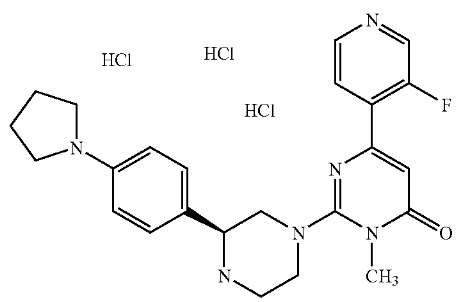 |
| 14 | 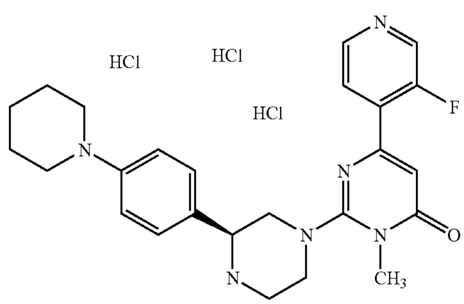 |
| 15 | 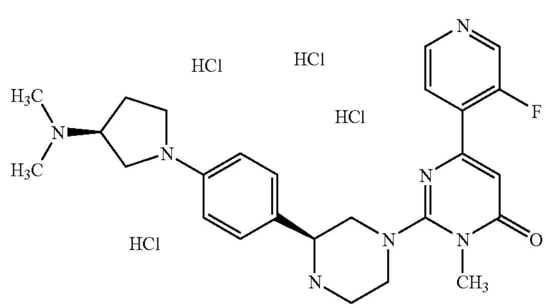 |
| 16 | 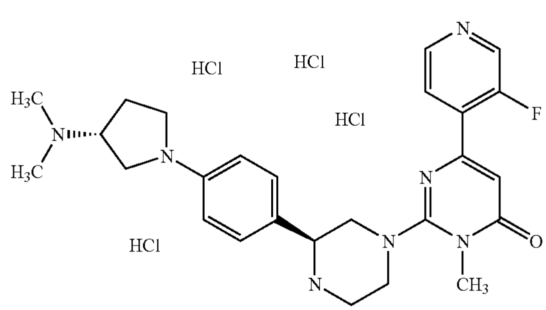 |

TABLE 1-continued

| Compound No. | STRUCTURE |
|---|---|
| 17 | 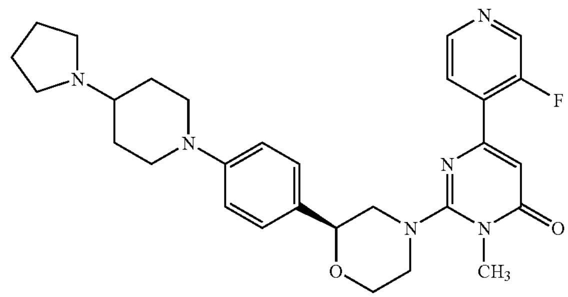 |
| 18 | 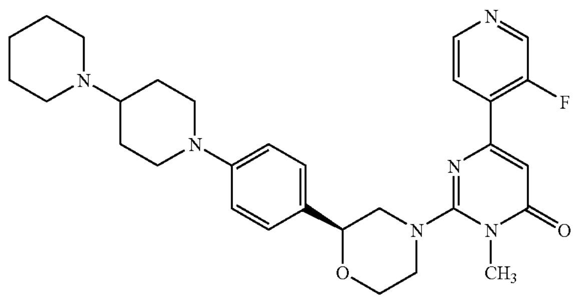 |
| 19 | 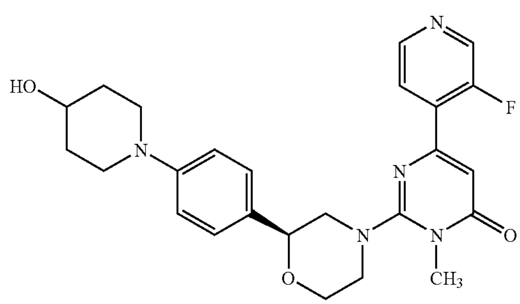 |
| 20 | 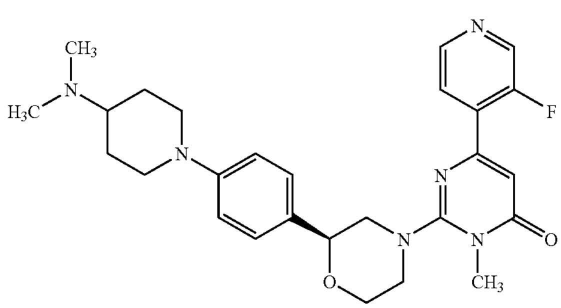 |
| 21 | 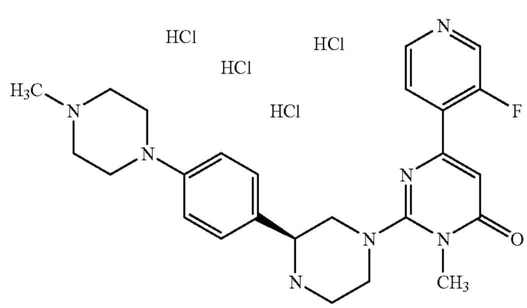 |

TABLE 1-continued

| Compound No. | STRUCTURE |
|---|---|
| 22 | 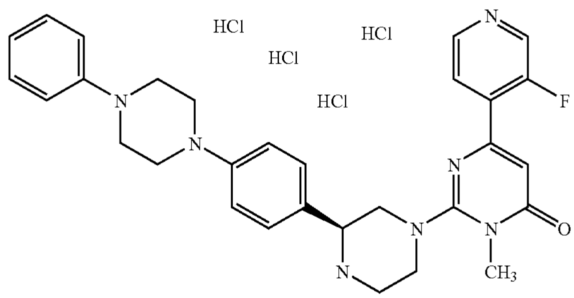 |
| 23 | 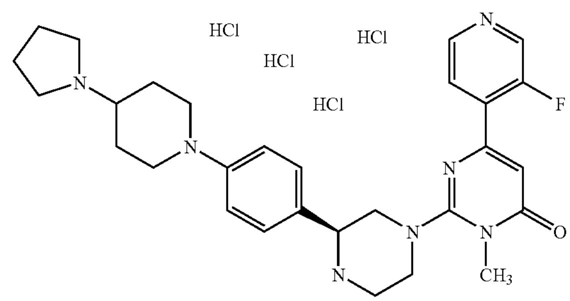 |
| 24 | 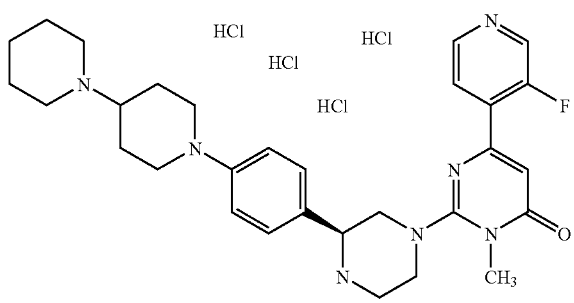 |
| 25 | 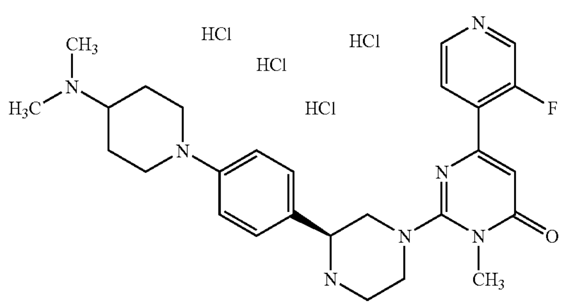 |
| 26 | 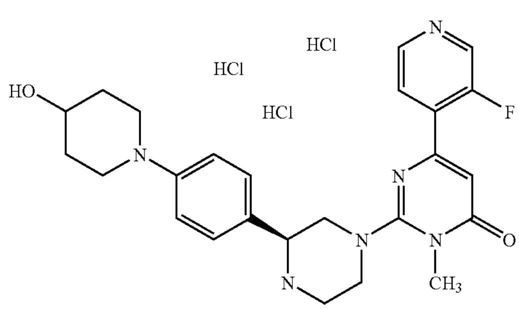 |

TABLE 1-continued
| Compound No. | STRUCTURE |
|---|---|
| 27 | 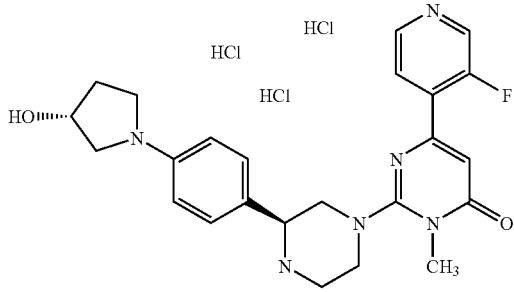 |
| 28 | 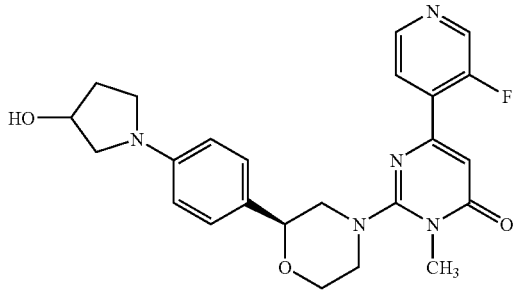 |
| 29 | 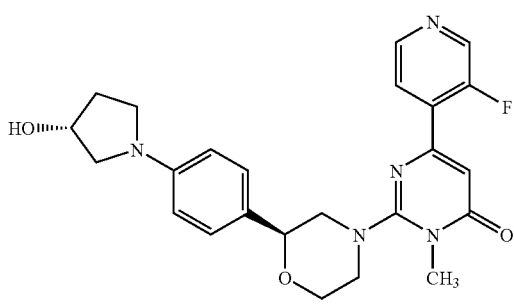 |
| 30 | 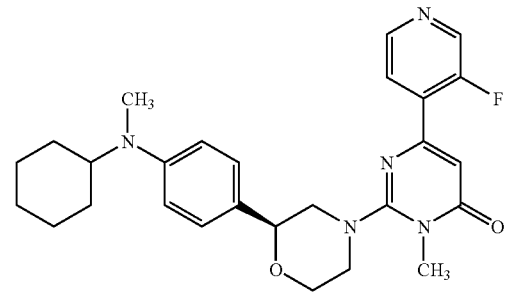 |
| 31 | 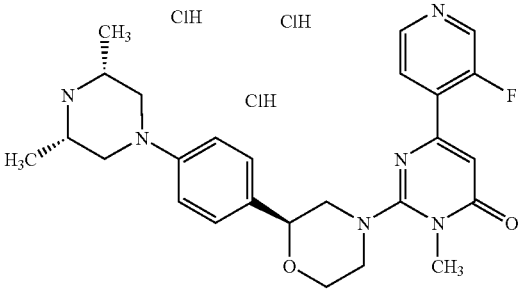 |

TABLE 1-continued

| Compound No. | STRUCTURE |
|---|---|
| 32 | 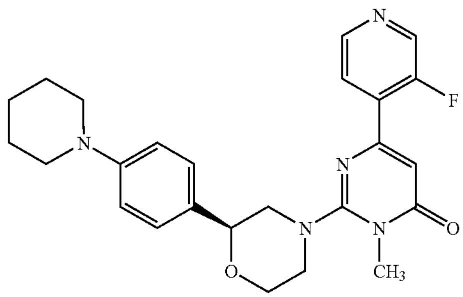 |
| 33 | 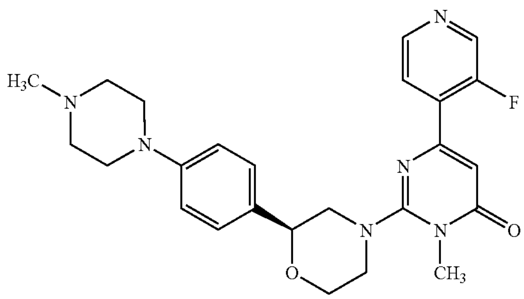 |
| 34 | 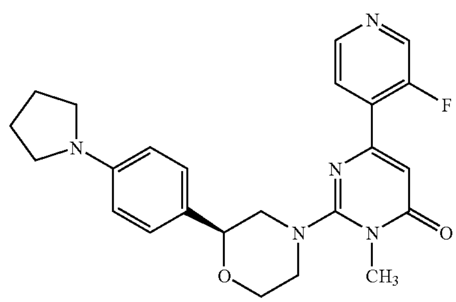 |
| 35 | 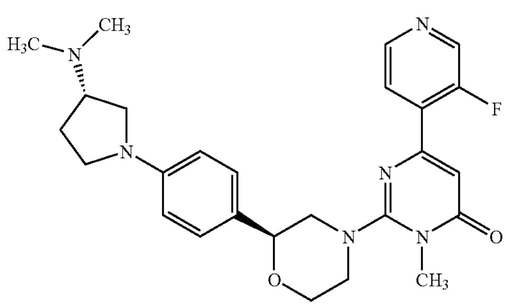 |
| 36 | 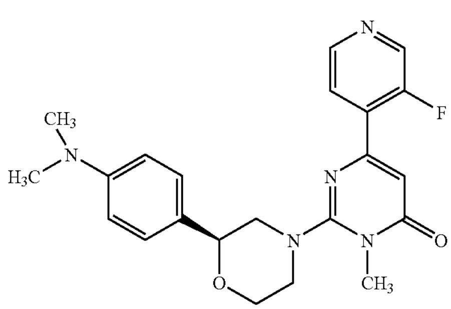 |

TABLE 1-continued

| Compound No. | STRUCTURE |
|---|---|
| 37 | 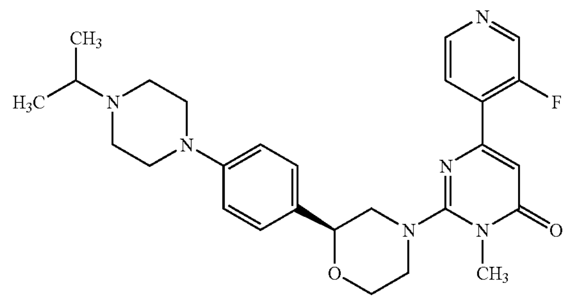 |
| 38 | 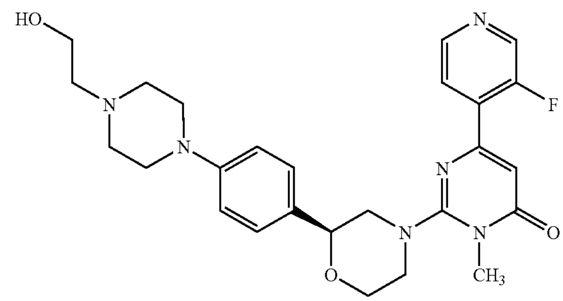 |
| 39 | 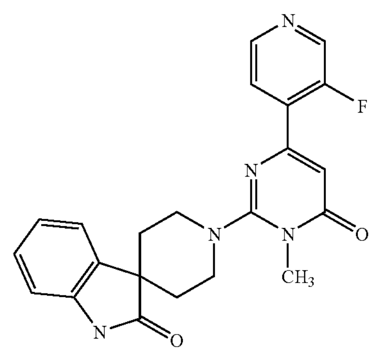 |
| 40 | 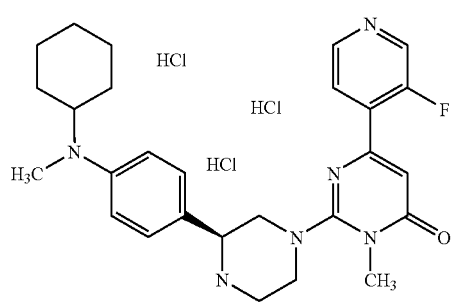 |
| 41 | 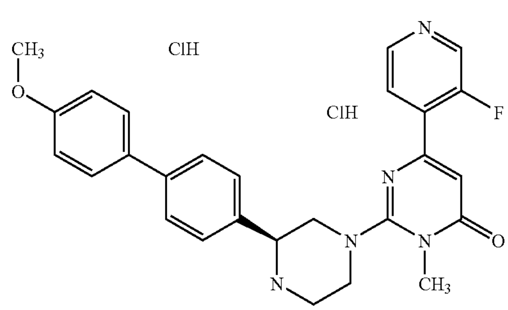 |

TABLE 1-continued

| Compound No. | STRUCTURE |
|---|---|
| 42 | 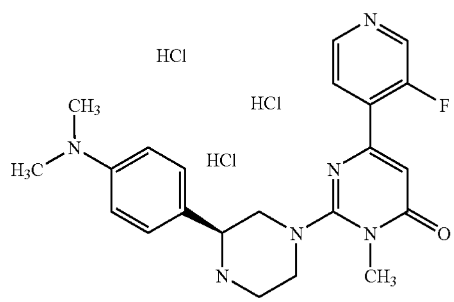 |
| 43 | 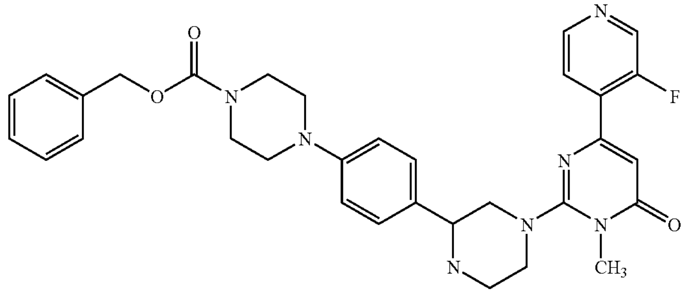 |
| 44 | 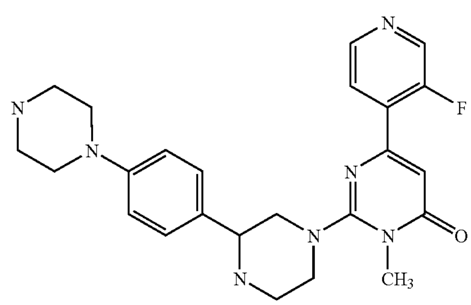 |
| 45 | 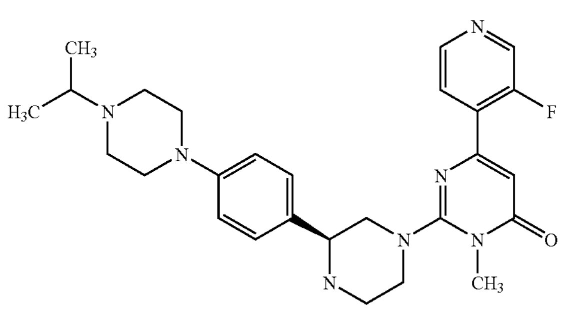 |
| 46 | 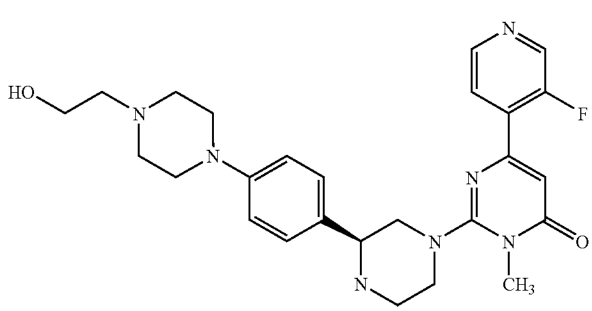 |

TABLE 1-continued
| Compound No. | STRUCTURE |
|---|---|
| 47 | 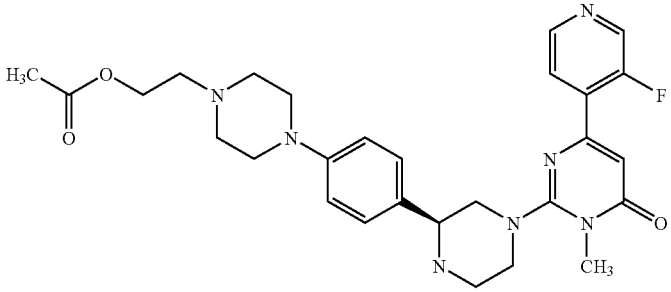 |
| 48 | 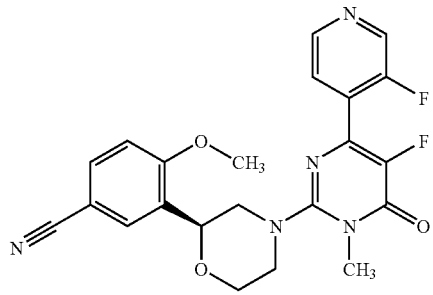 |
| 49 | 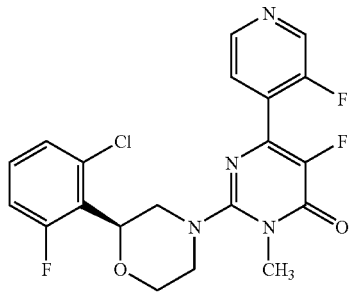 |
| 50 | 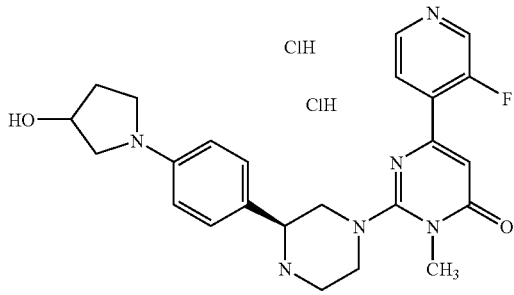 |
| 51 | 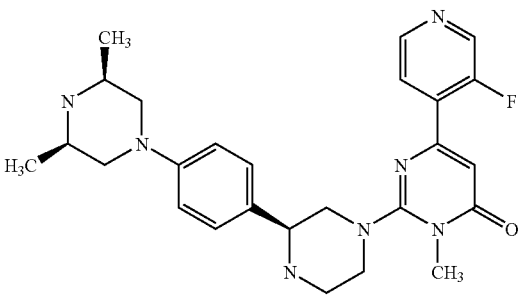 |

TABLE 1-continued
| Compound No. | STRUCTURE |
|---|---|
| 52 | 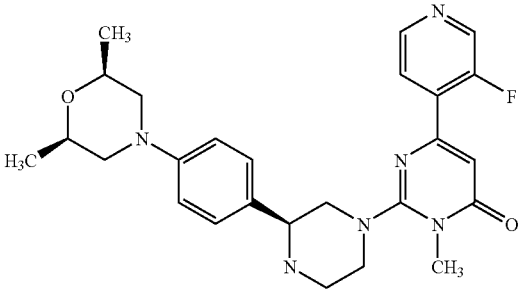 |
| 53 | 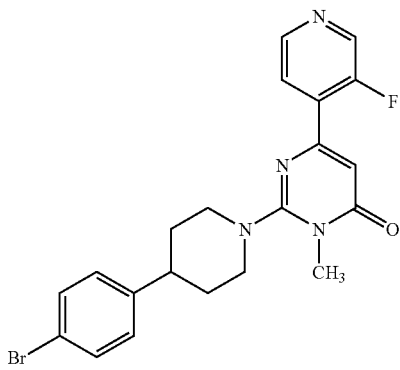 |
| 54 | 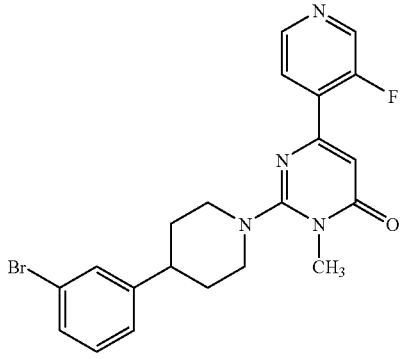 |
| 55 | 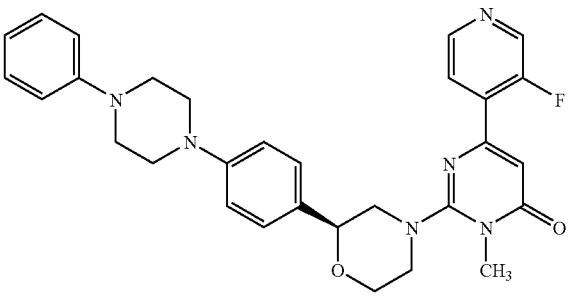 |

TABLE 1-continued
| Compound No. | STRUCTURE |
|---|---|
| 56 | 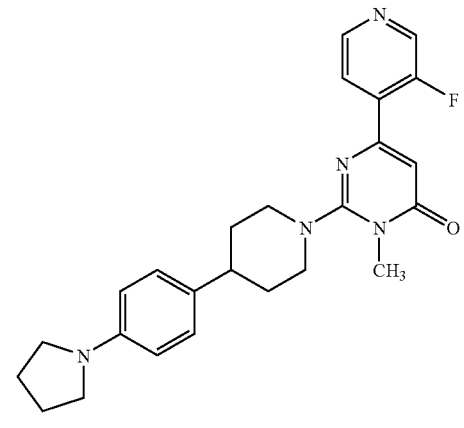 |
| 57 | 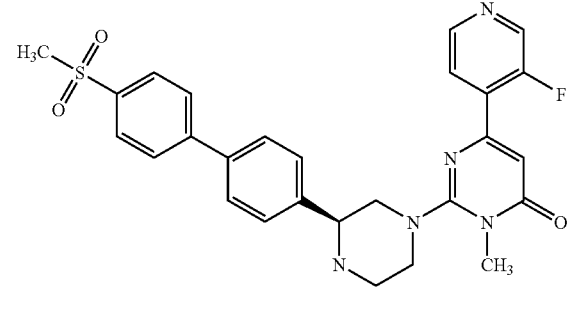 |
| 58 | 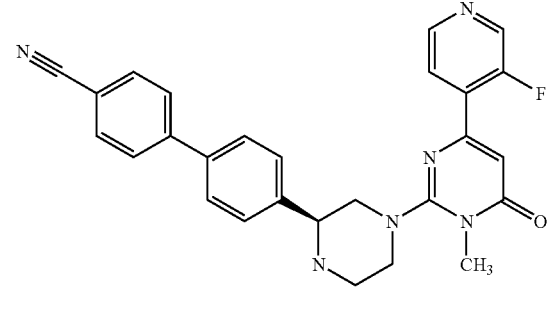 |
| 59 | 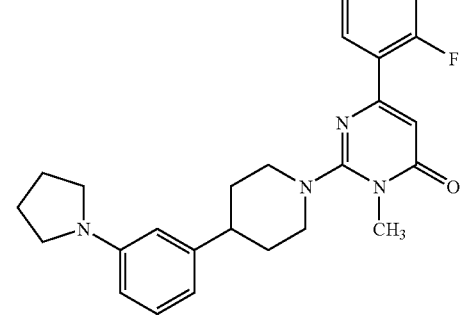 |

TABLE 1-continued

| Compound No. | STRUCTURE |
|---|---|
| 60 | 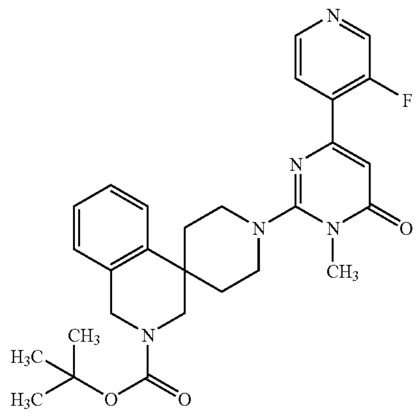 |
| 61 | 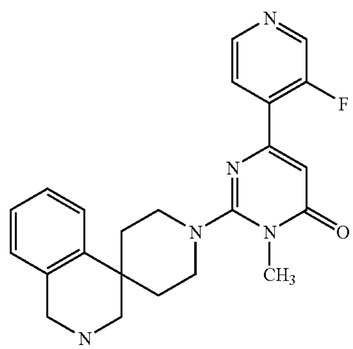 |
| 62 | 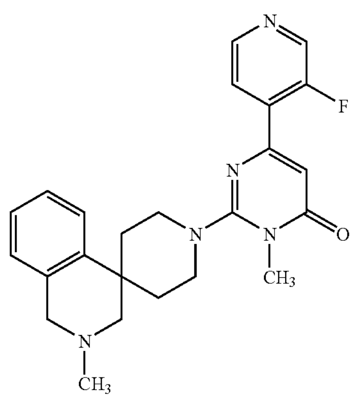 |
| 63 | 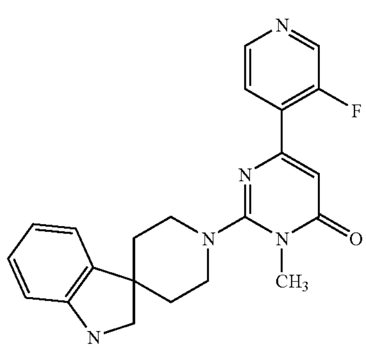 |

TABLE 1-continued

| Compound No. | STRUCTURE |
| --- | --- |
| 64 | 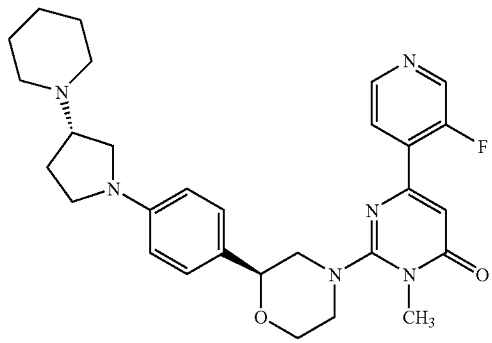 |
| 65 | 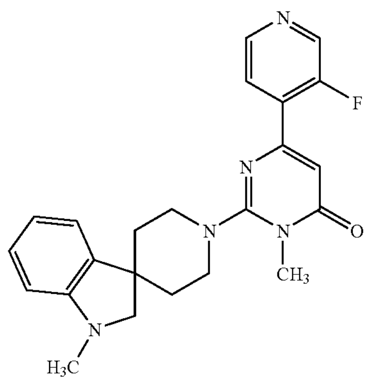 |
| 66 | 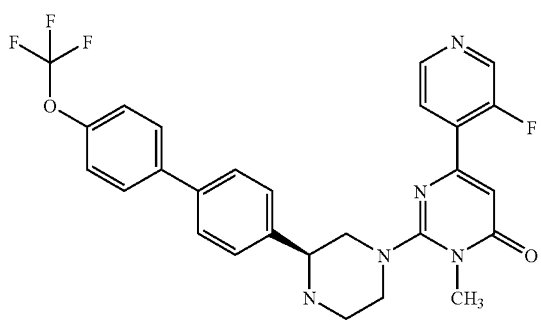 |
| 67 | 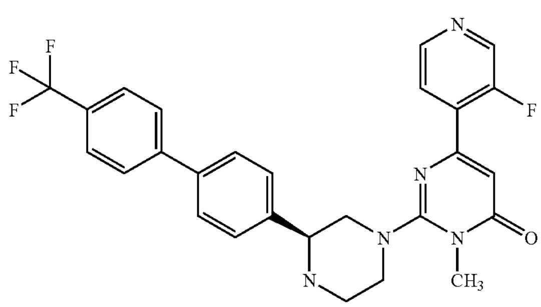 |

TABLE 1-continued
| Compound No. | STRUCTURE |
|---|---|
| 68 | 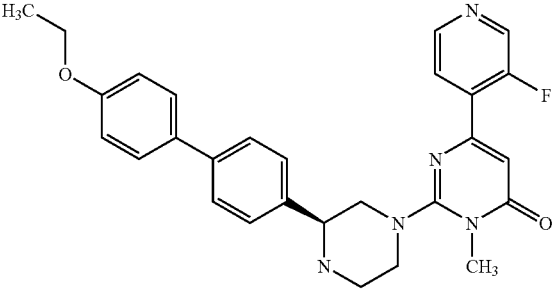 |
| 69 | 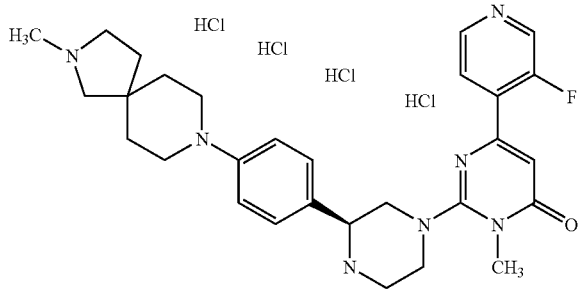 |
| 70 | 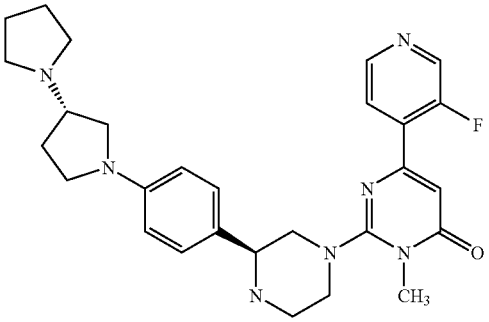 |
| 71 | 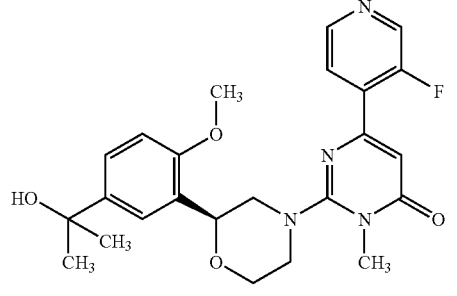 |
| 72 | 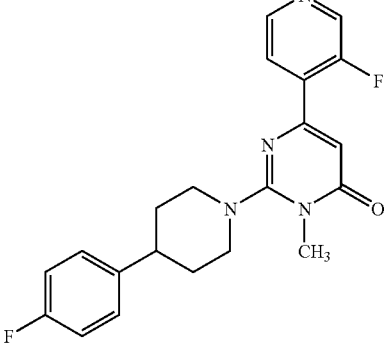 |

TABLE 1-continued

| Compound No. | STRUCTURE |
|---|---|
| 73 | 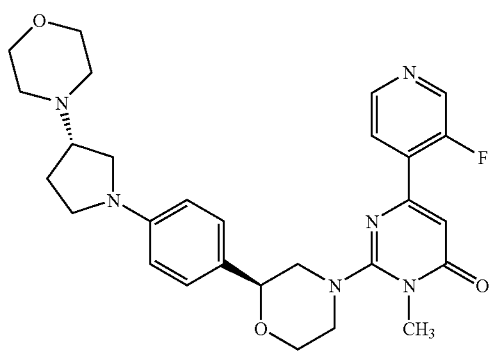 |
| 74 | 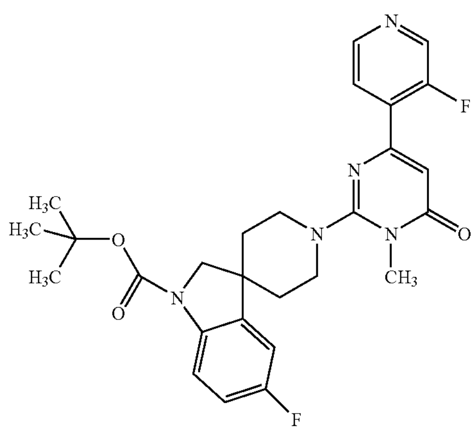 |
| 75 | 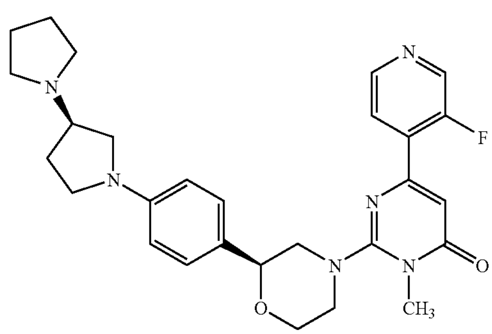 |
| 76 | 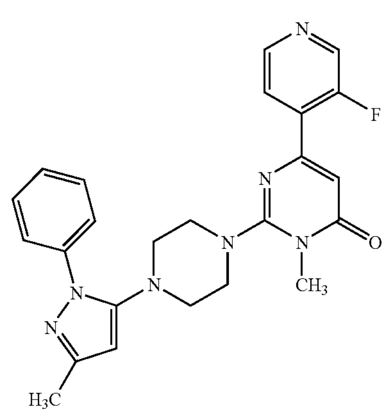 |

TABLE 1-continued

| Compound No. | STRUCTURE |
|---|---|
| 77 | 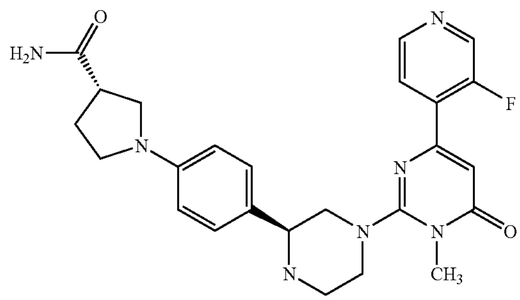 |
| 78 | 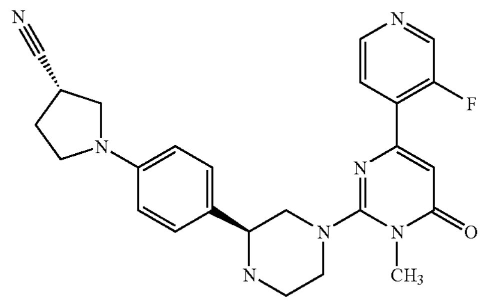 |
| 79 | 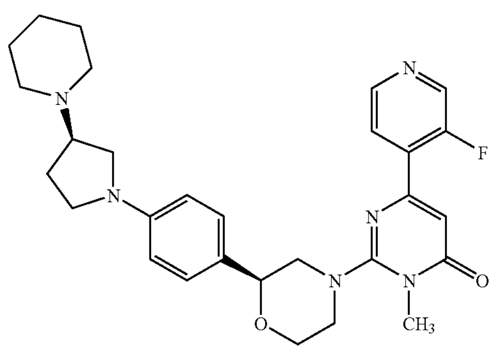 |
| 80 | 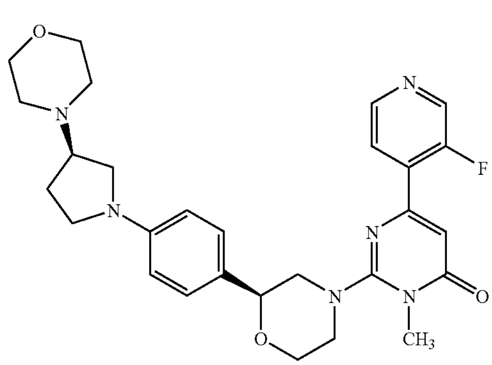 |

TABLE 1-continued
| Compound No. | STRUCTURE |
|---|---|
| 81 | 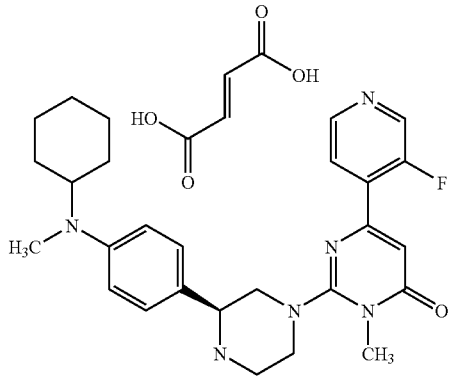 |
| 82 | 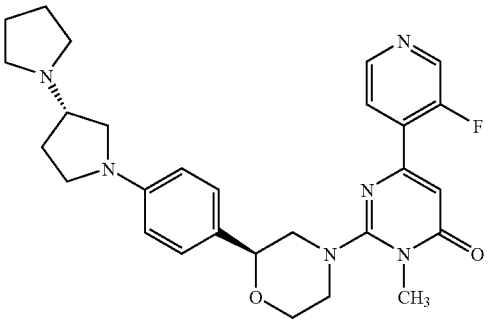 |
| 83 | 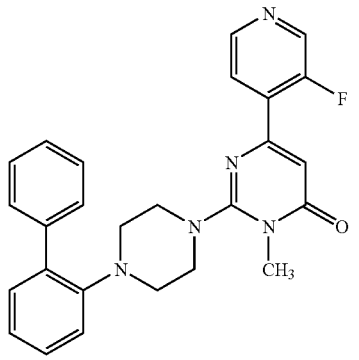 |
| 84 | 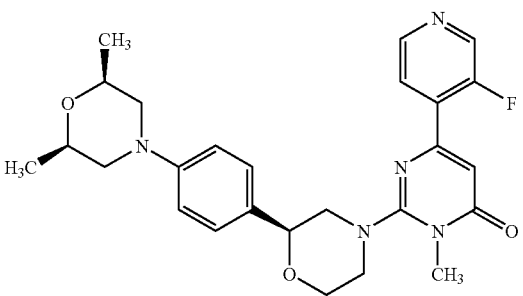 |

TABLE 1-continued
| Compound No. | STRUCTURE |
|---|---|
| 85 | 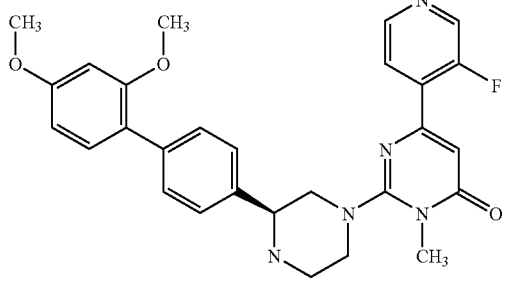 |
| 86 | 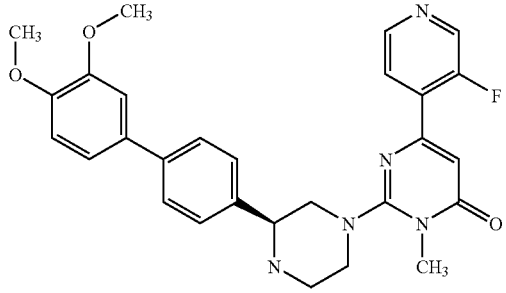 |
| 87 | 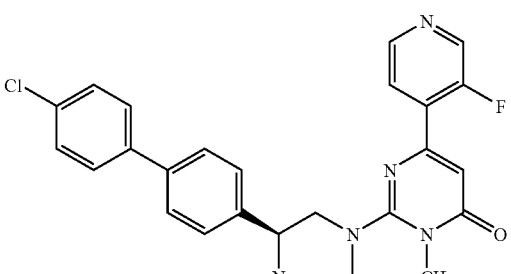 |
| 88 | 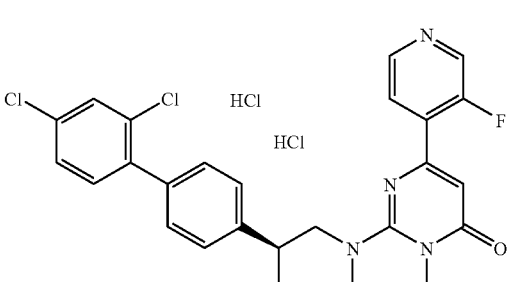 |
| 89 | 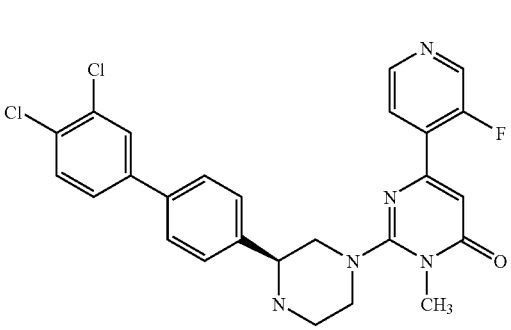 |

TABLE 1-continued
| Compound No. | STRUCTURE |
|---|---|
| 90 | 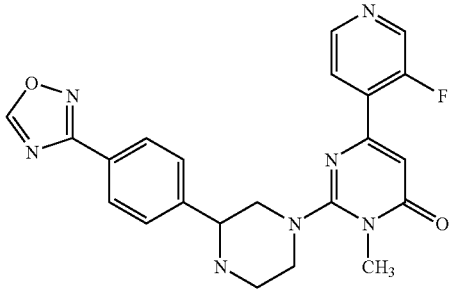 |
| 91 | 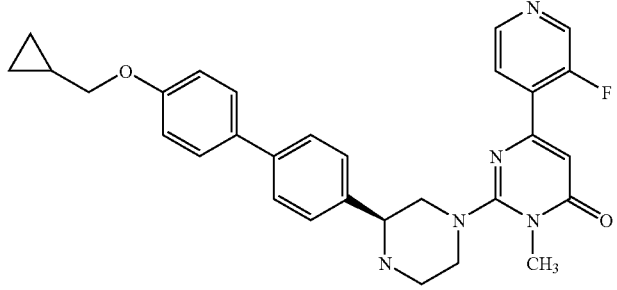 |
| 92 | 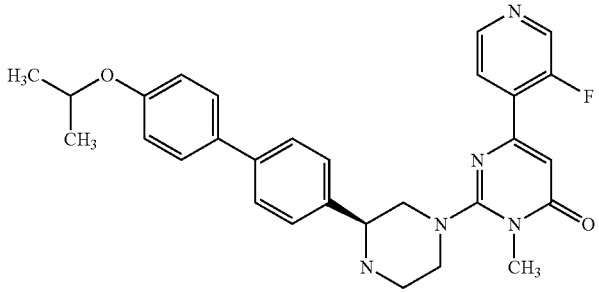 |
| 93 | 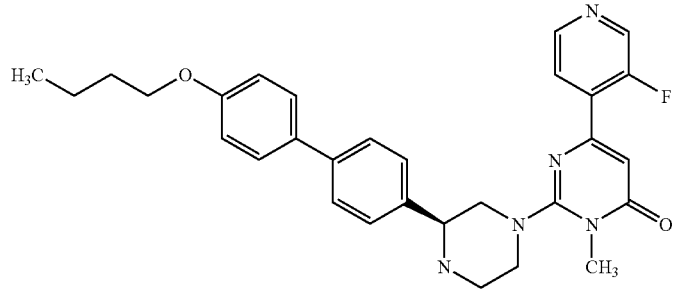 |

TABLE 1-continued
| Compound No. | STRUCTURE |
|---|---|
| 94 | 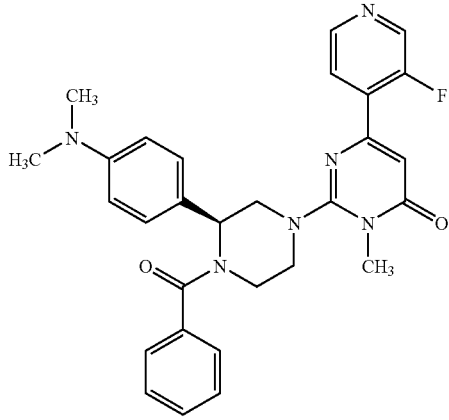 |
| 95 | 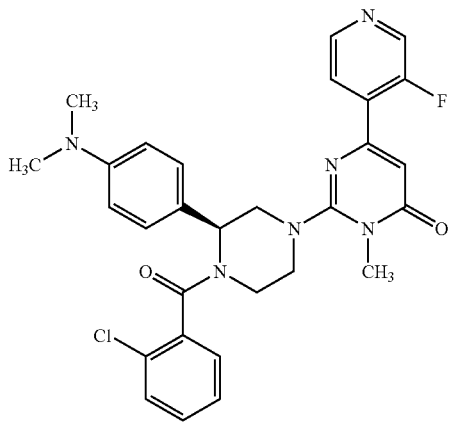 |
| 96 | 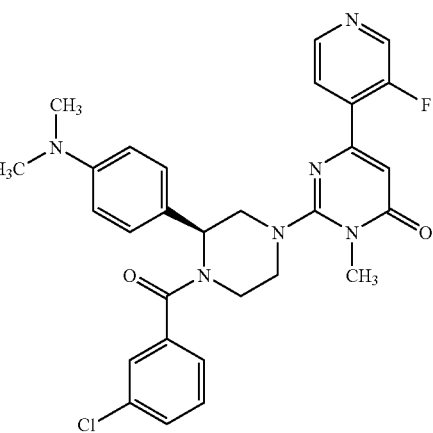 |

TABLE 1-continued
| Compound No. | STRUCTURE |
|---|---|
| 97 | 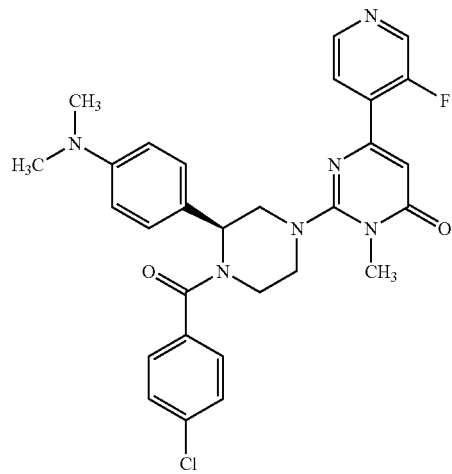 |
| 98 | 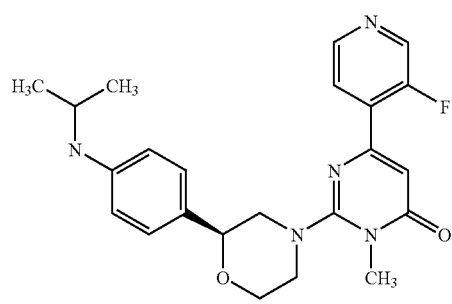 |
| 99 | 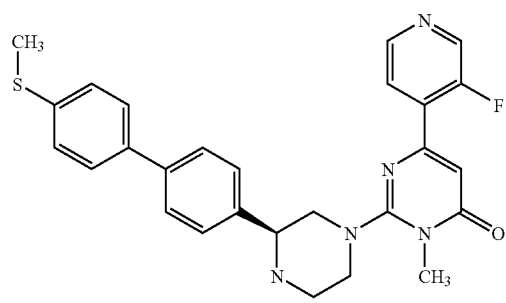 |
| 100 | 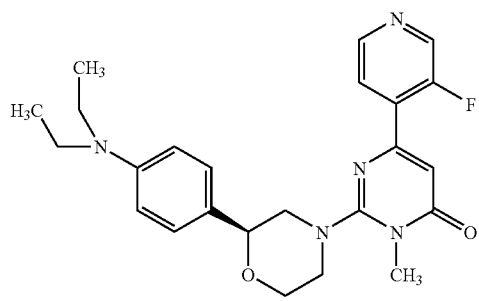 |

TABLE 1-continued
| Compound No. | STRUCTURE |
|---|---|
| 101 | 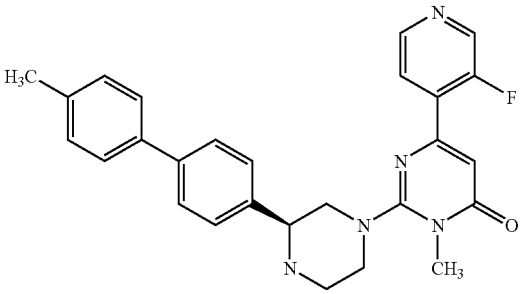 |
| 102 | 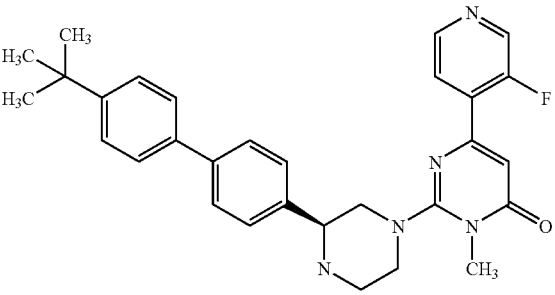 |
| 103 | 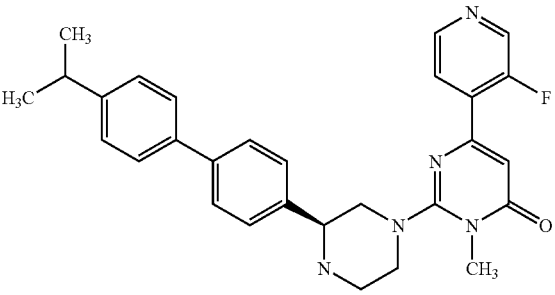 |
| 104 | 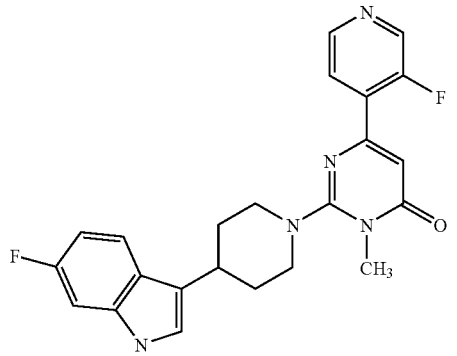 |
| 105 | 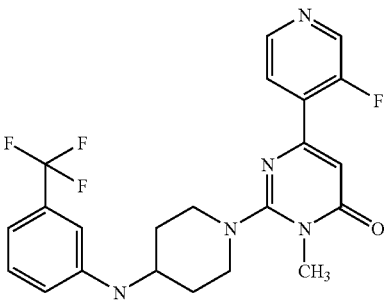 |

TABLE 1-continued
| Compound No. | STRUCTURE |
|---|---|
| 106 | 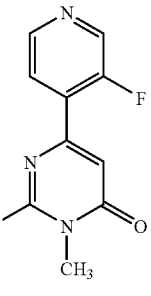 |
| 107 | 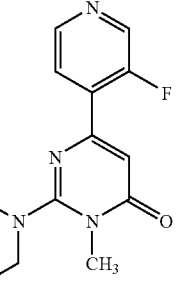 |
| 108 | 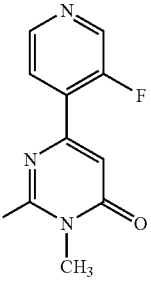 |
| 109 | 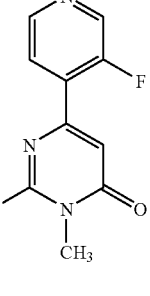 |
| 110 | 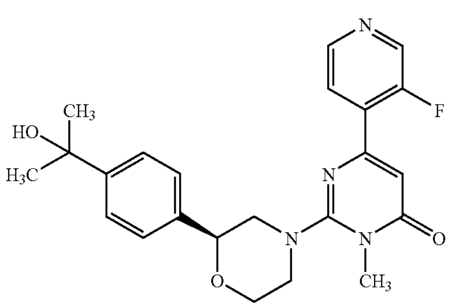 |

TABLE 1-continued
| Compound No. | STRUCTURE |
|---|---|
| 111 | 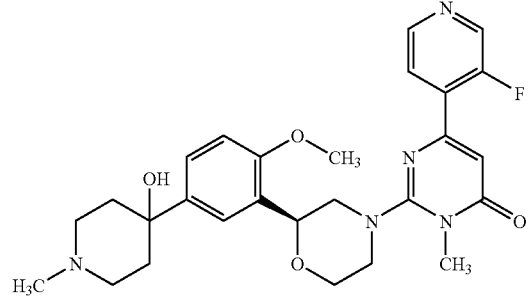 |
| 112 | 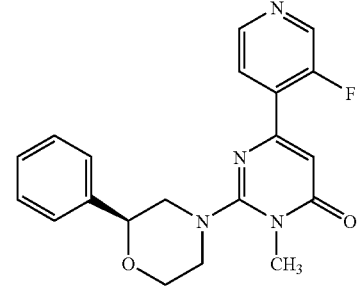 |
| 113 | 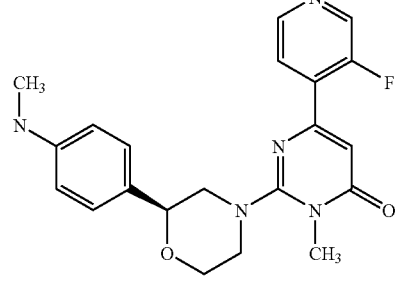 |
| 114 | 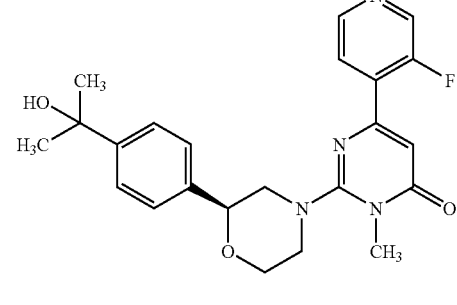 |
| 115 | 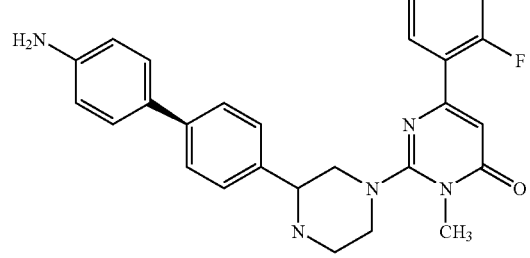 |

TABLE 1-continued
| Compound No. | STRUCTURE |
|---|---|
| 116 | 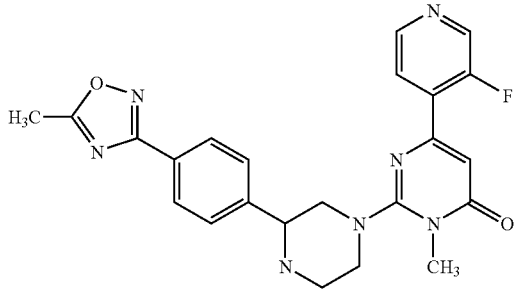 |
| 117 | 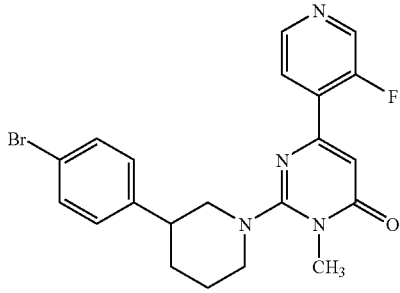 |
| 118 | 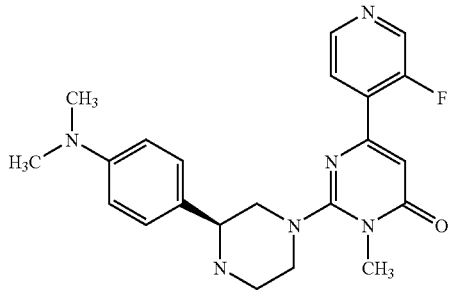 |
| 119 | 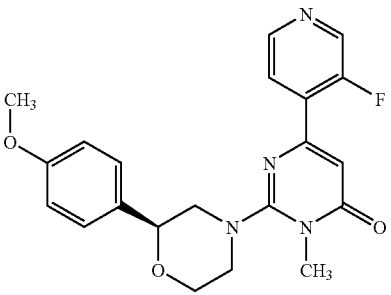 |
| 120 | 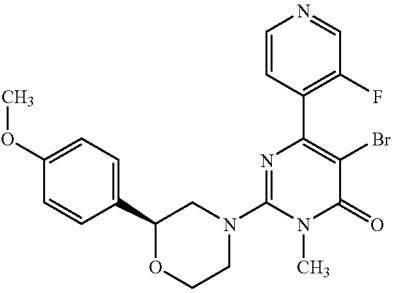 |

TABLE 1-continued

| Compound No. | STRUCTURE |
|---|---|
| 121 | 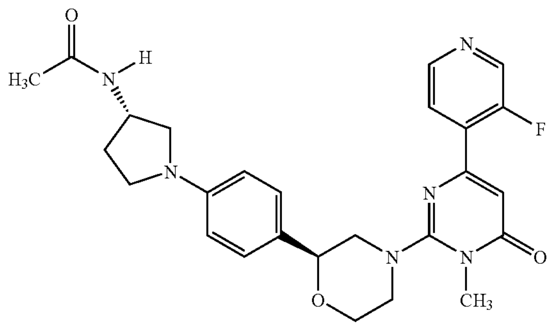 |
| 122 | 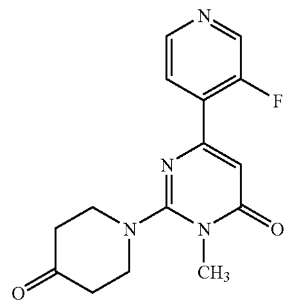 |
| 123 | 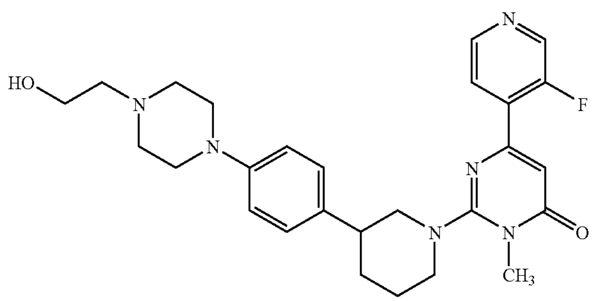 |
| 124 | 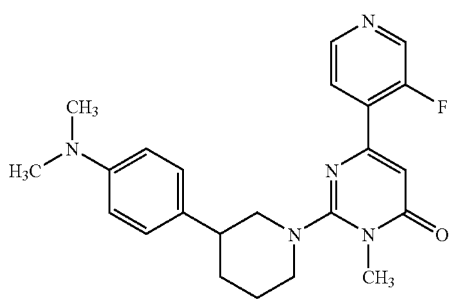 |
| 125 | 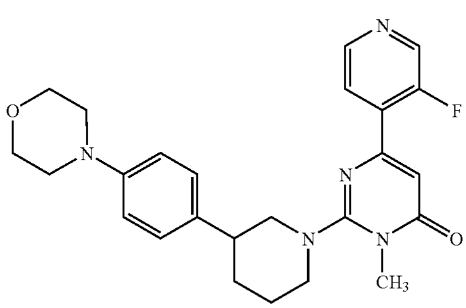 |

TABLE 1-continued
| Compound No. | STRUCTURE |
|---|---|
| 126 | 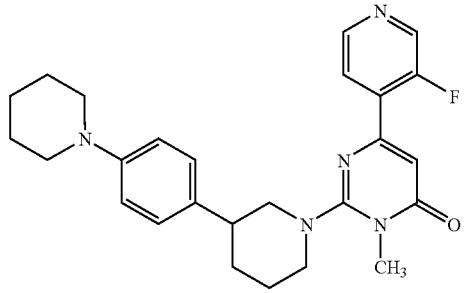 |
| 127 | 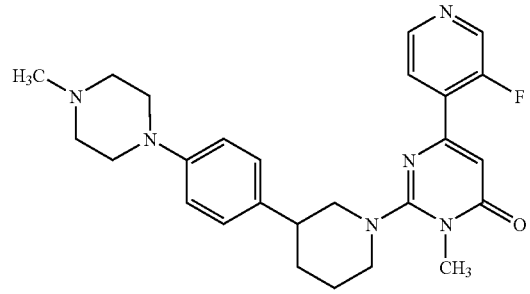 |
| 128 | 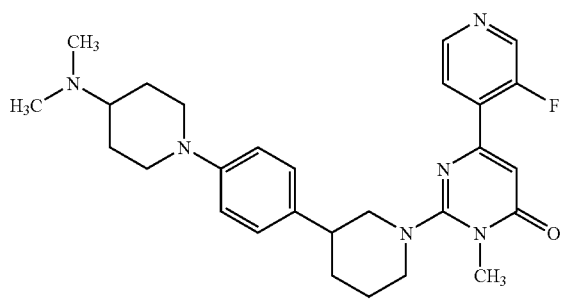 |
| 129 | 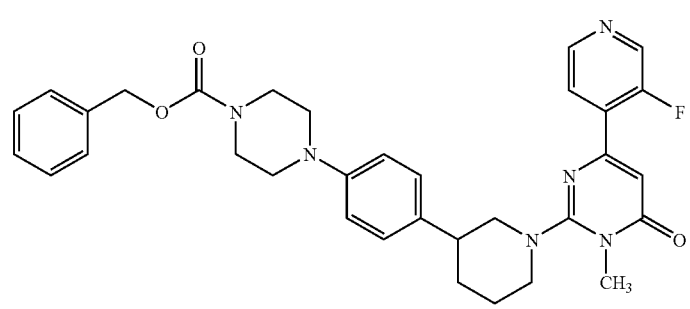 |
| 130 | 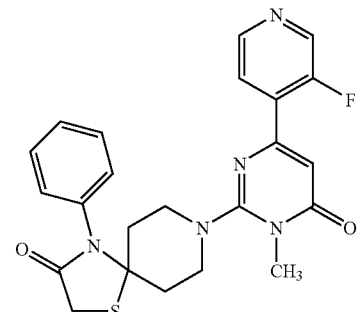 |

TABLE 1-continued
| Compound No. | STRUCTURE |
|---|---|
| 131 | 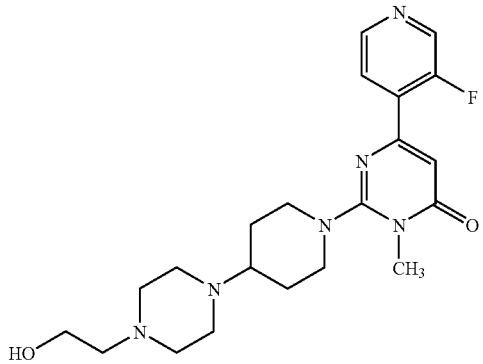 |
| 132 | 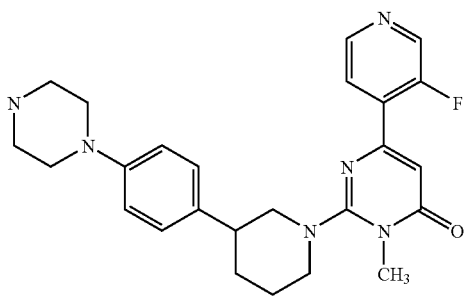 |
| 133 | 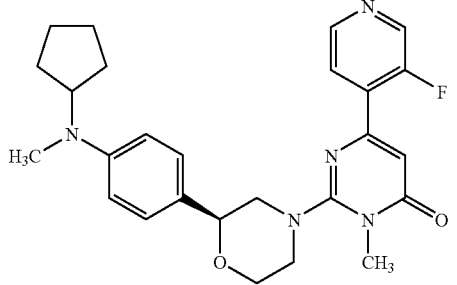 |
| 134 | 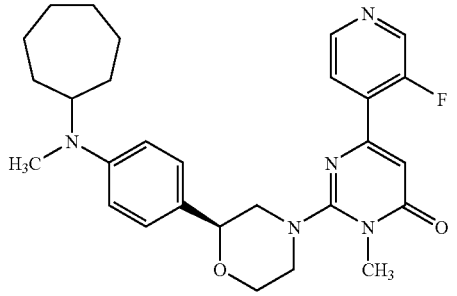 |
| 135 | 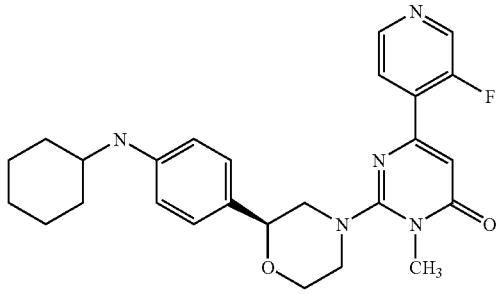 |

TABLE 1-continued
| Compound No. | STRUCTURE |
|---|---|
| 136 | 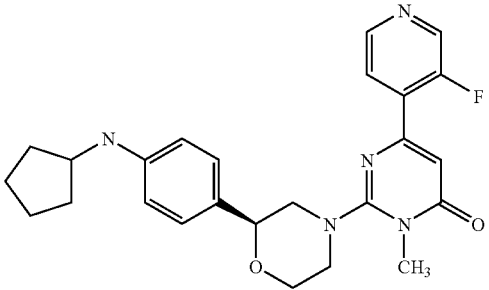 |
| 137 | 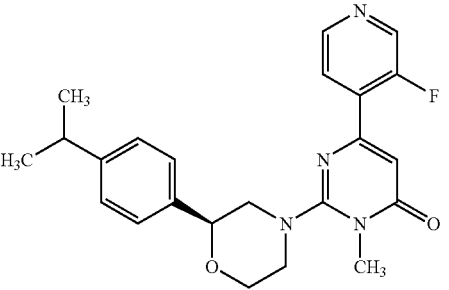 |
| 138 | 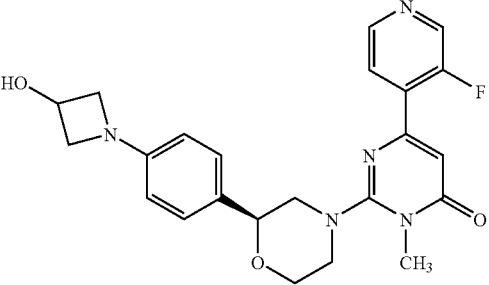 |
| 139 | 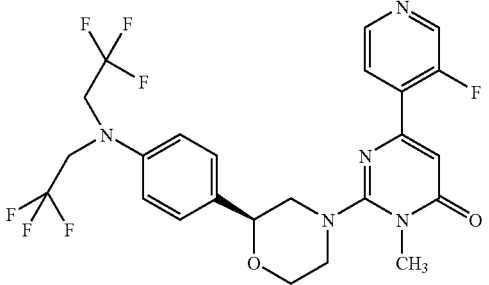 |
| 140 | 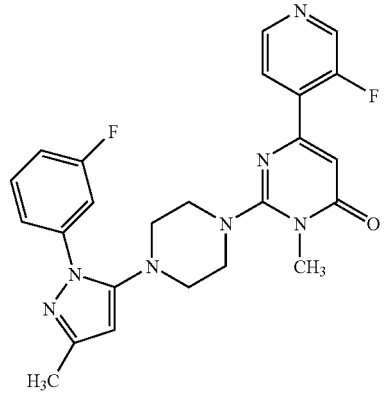 |

TABLE 1-continued
| Compound No. | STRUCTURE |
|---|---|
| 141 | 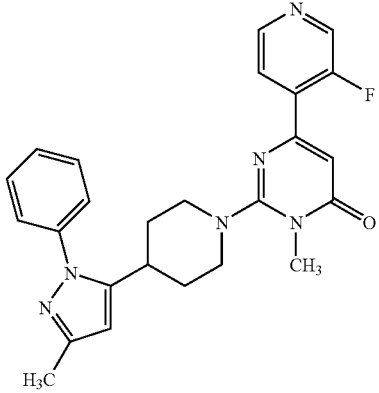 |
| 142 | 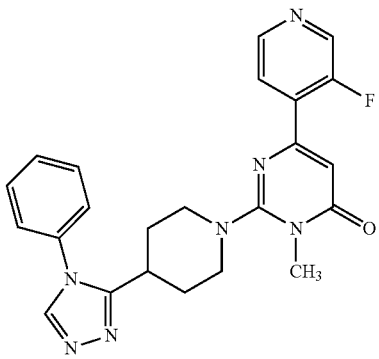 |
| 143 | 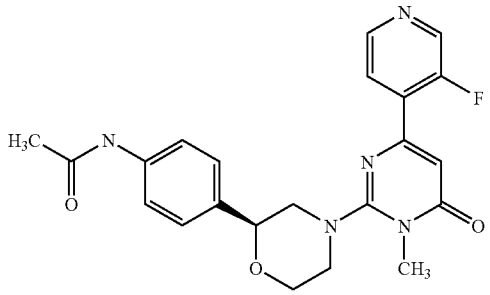 |
| 144 | 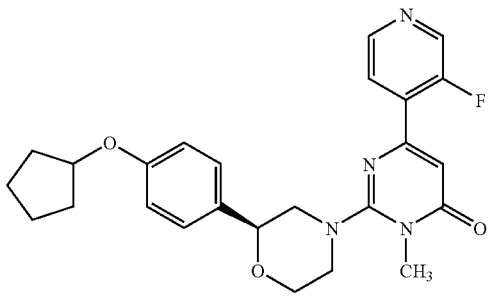 |

TABLE 1-continued
| Compound No. | STRUCTURE |
|---|---|
| 145 | 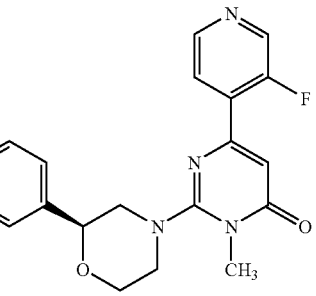 |
| 146 | 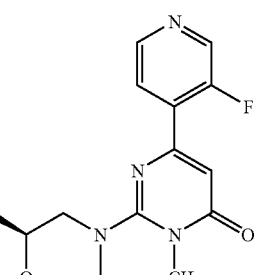 |
| 147 | 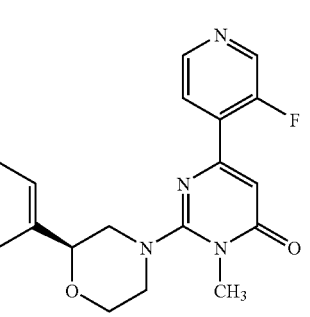 |
| 148 | 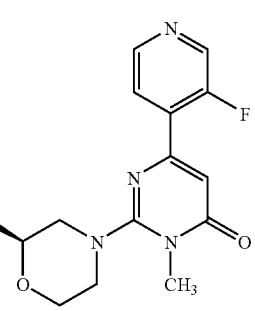 |
| 149 | 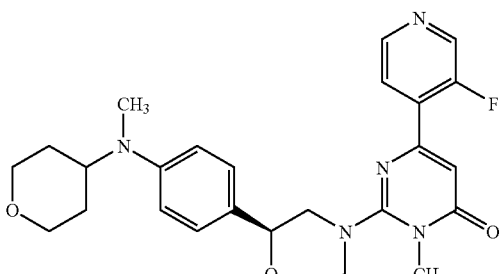 |

TABLE 1-continued
| Compound No. | STRUCTURE |
|---|---|
| 150 | 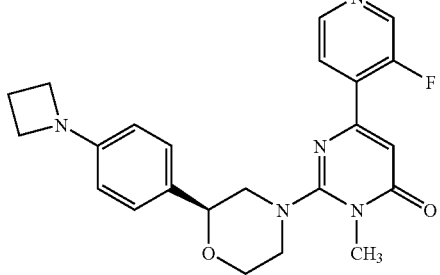 |
| 151 | 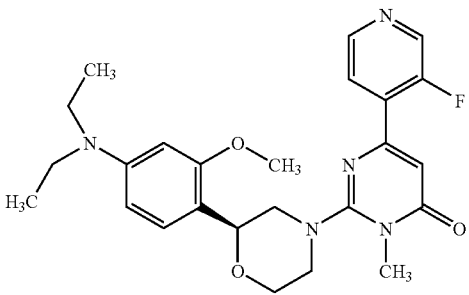 |
| 152 | 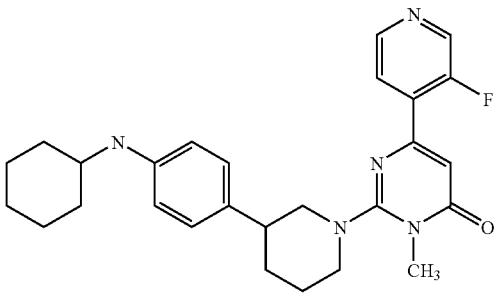 |
| 153 | 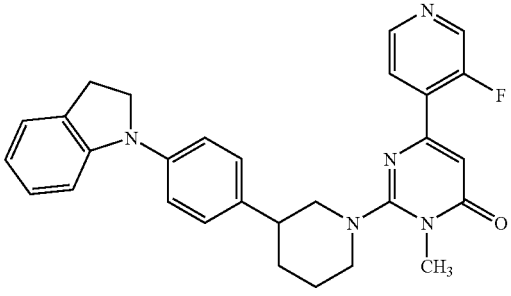 |
| 154 | 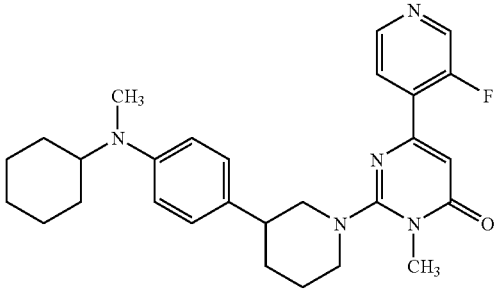 |

TABLE 1-continued

| Compound No. | STRUCTURE |
| --- | --- |
| 155 | 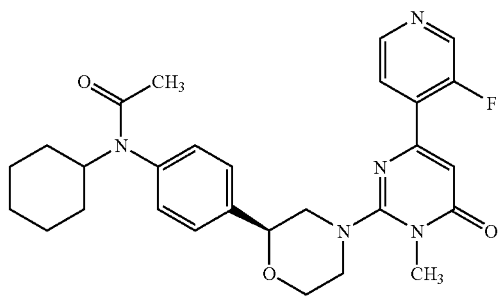 |
| 156 | 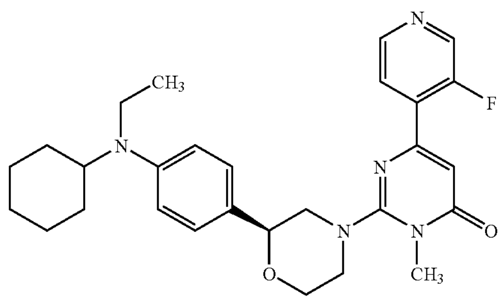 |
| 157 | 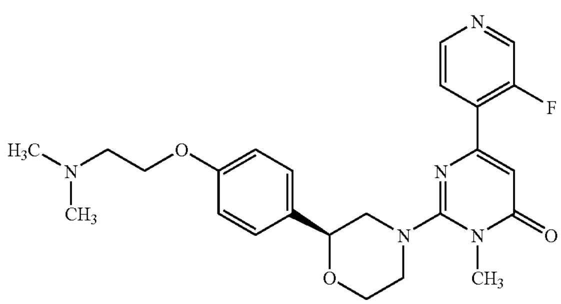 |
| 158 | 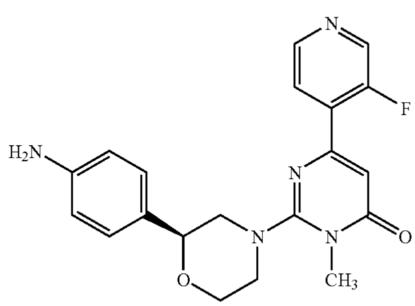 |
| 159 | 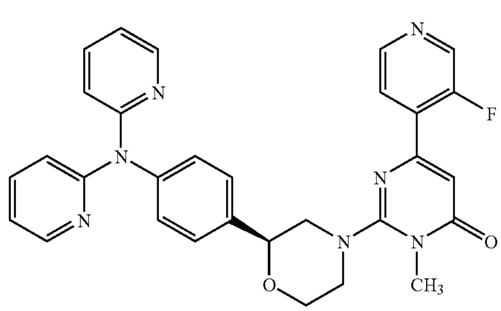 |

TABLE 1-continued

| Compound No. | STRUCTURE |
|---|---|
| 160 | 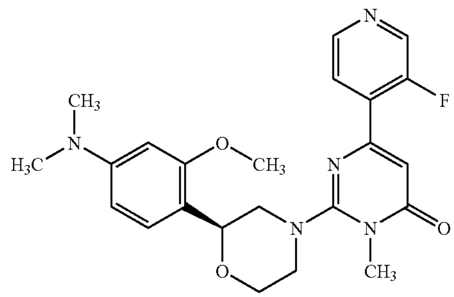 |
| 161 | 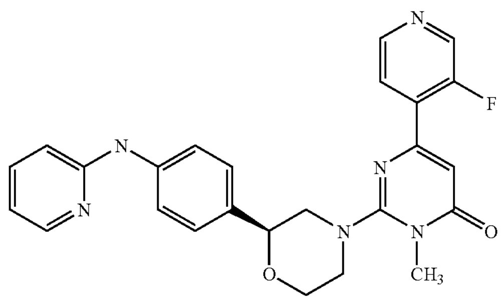 |
| 162 | 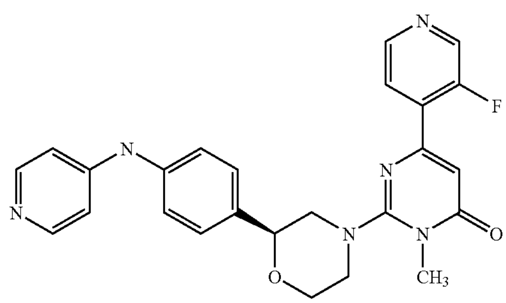 |
| 163 | 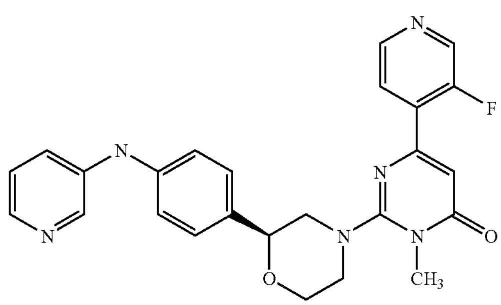 |
| 164 | 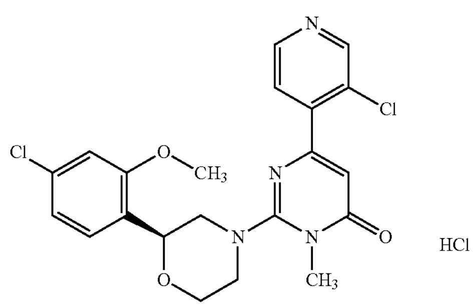 |

TABLE 1-continued
| Compound No. | STRUCTURE |
|---|---|
| 165 | 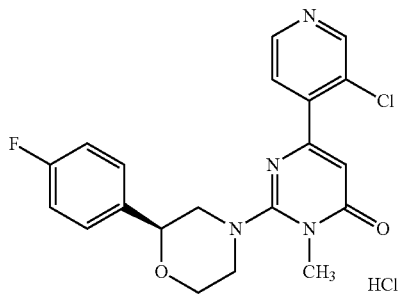 HCl |
| 166 | 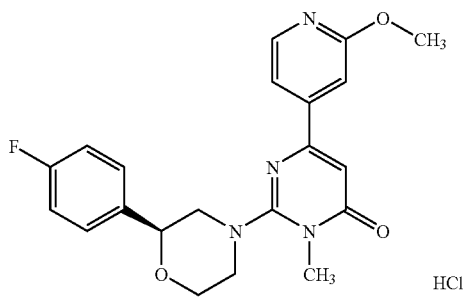 HCl |
| 167 | 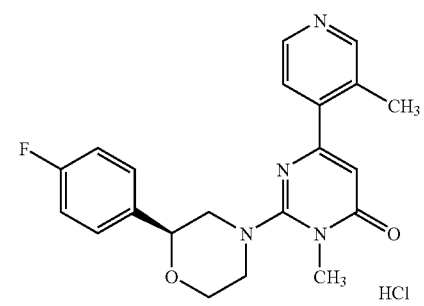 HCl |
| 168 | 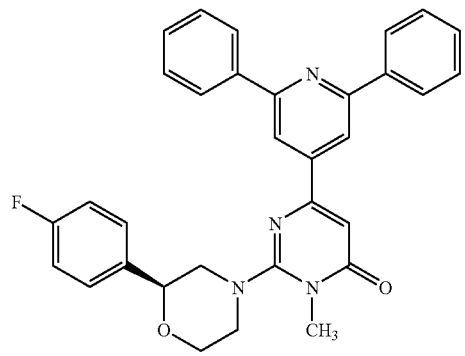 |
| 169 | 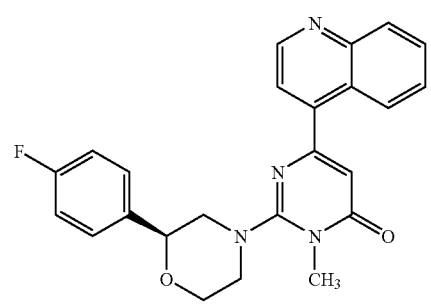 |

TABLE 1-continued

| Compound No. | STRUCTURE |
|---|---|
| 170 | 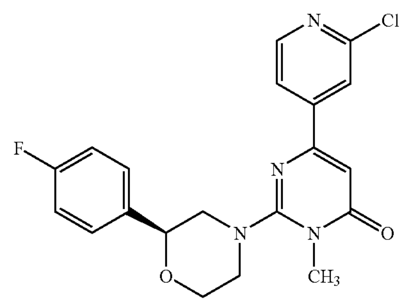 |
| 171 | 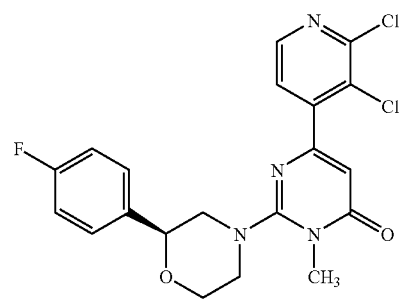 |
| 172 | 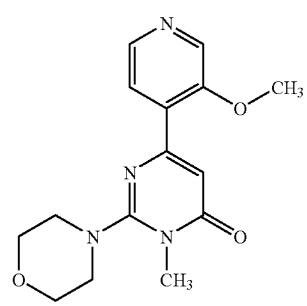 |
| 173 | 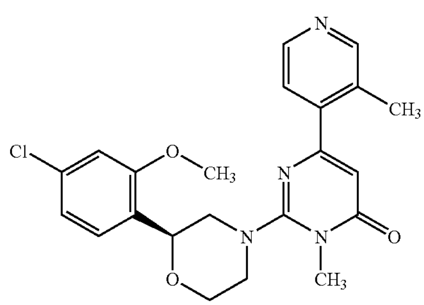 |
| 174 | 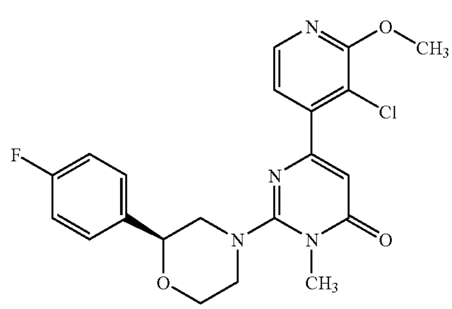 |

TABLE 1-continued
| Compound No. | STRUCTURE |
|---|---|
| 175 | 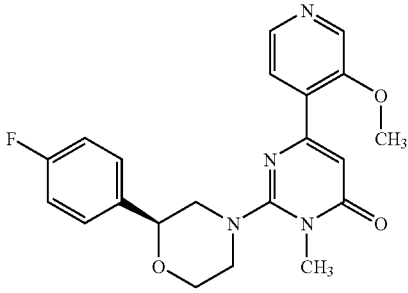 |
| 176 | 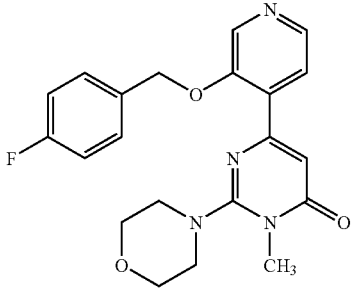 |
| 177 | 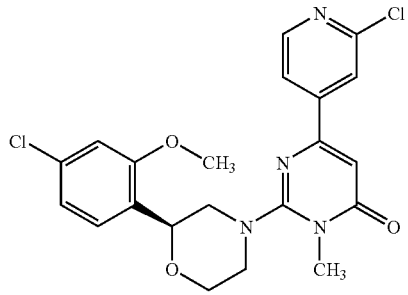 |
| 178 | 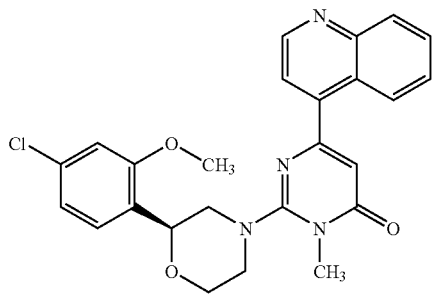 |
| 179 | 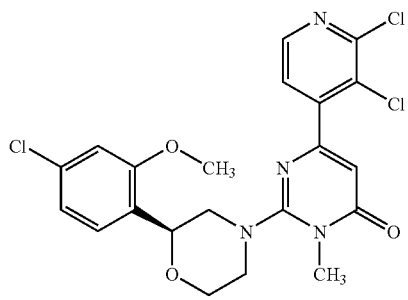 |

TABLE 1-continued
| Compound No. | STRUCTURE |
|---|---|
| 180 | 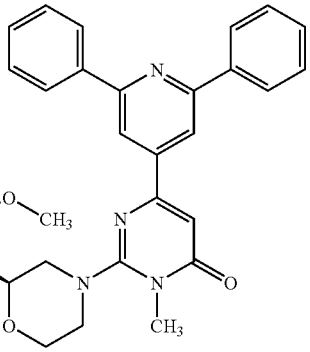 |
| 181 | 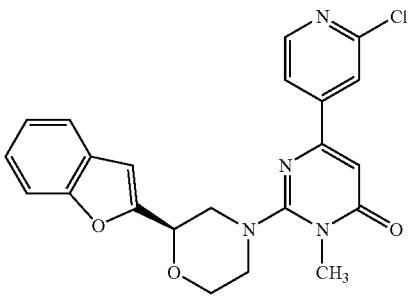 |
| 182 | 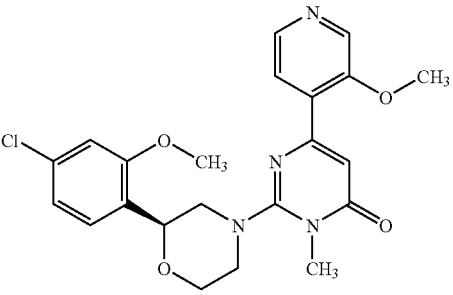 |
| 183 | 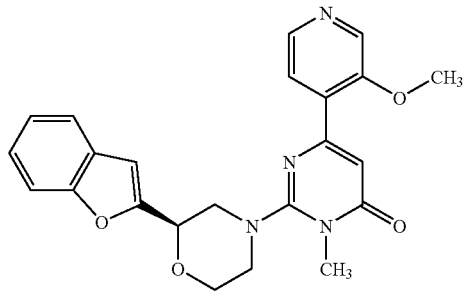 |
| 184 | 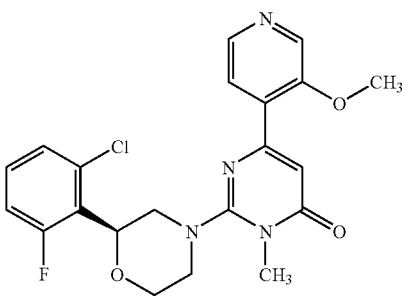 |

TABLE 1-continued
| Compound No. | STRUCTURE |
|---|---|
| 185 | 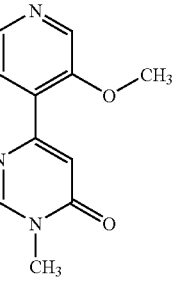 |
| 186 | 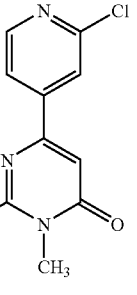 |
| 187 | 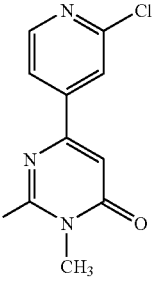 |
| 188 | 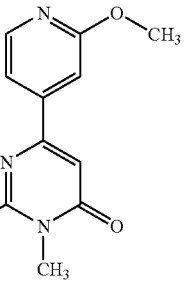 |
| 189 | 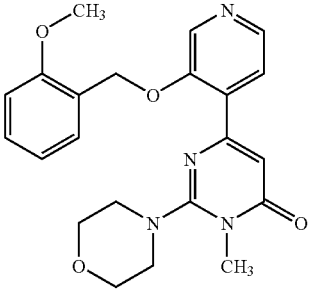 |

TABLE 1-continued

| Compound No. | STRUCTURE |
|---|---|
| 190 | 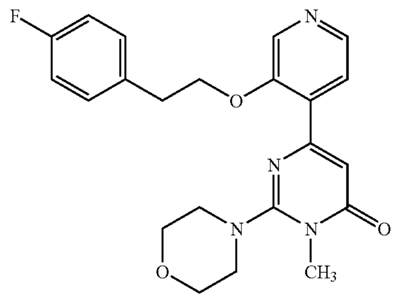 |
| 191 | 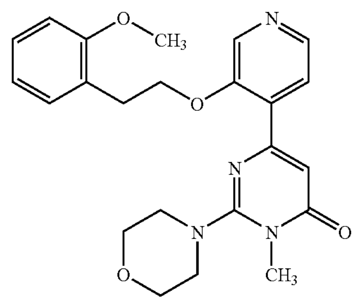 |
| 192 | 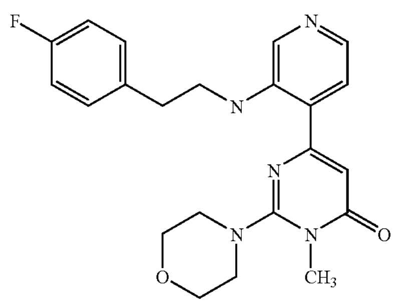 |
| 193 | 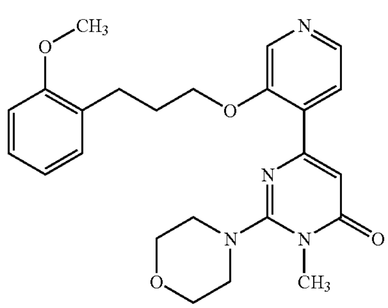 |
| 194 | 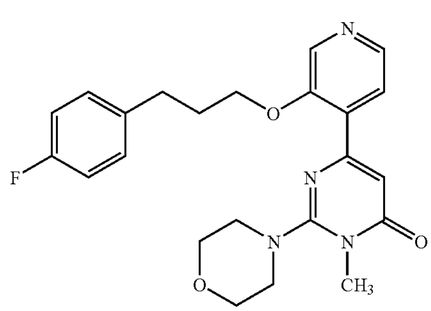 |

TABLE 1-continued
| Compound No. | STRUCTURE |
|---|---|
| 195 | 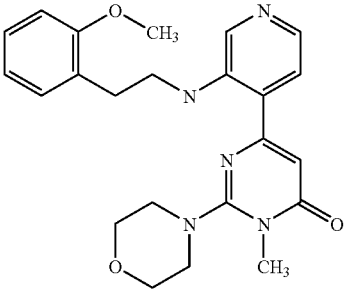 |
| 196 | 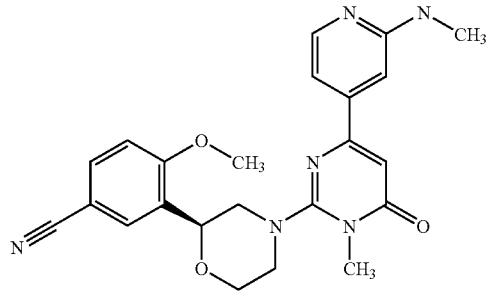 |
| 197 | 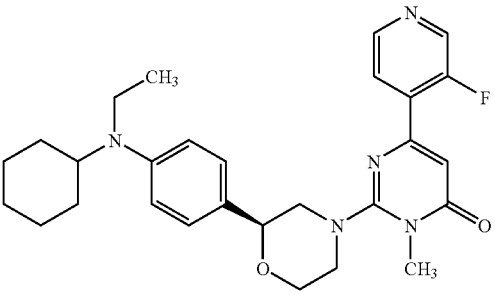 |
| 198 | 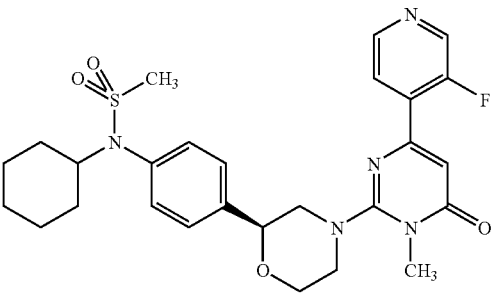 |
| 199 | 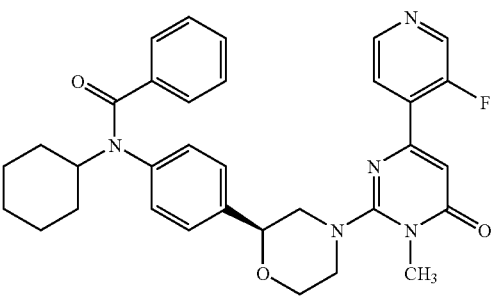 |

TABLE 1-continued

| Compound No. | STRUCTURE |
|---|---|
| 200 | 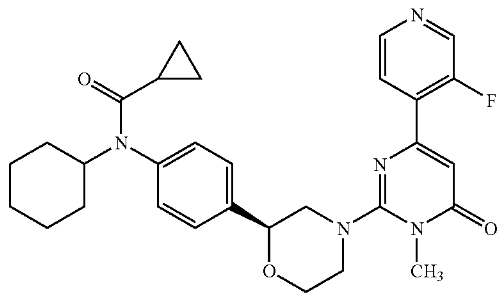 |
| 201 | 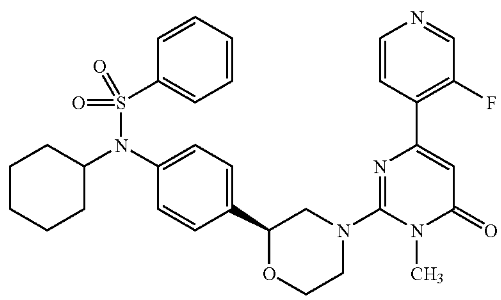 |
| 202 | 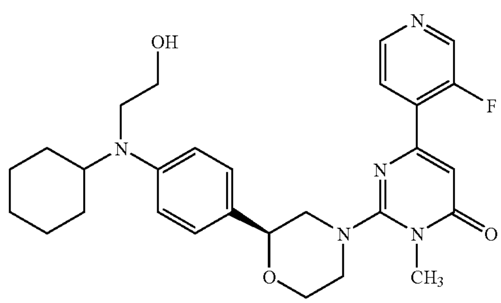 |
| 203 | 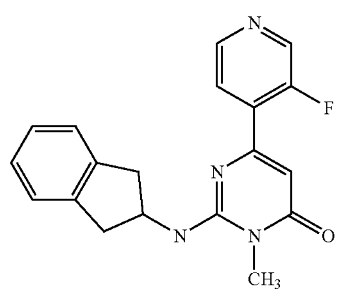 |
| 204 | 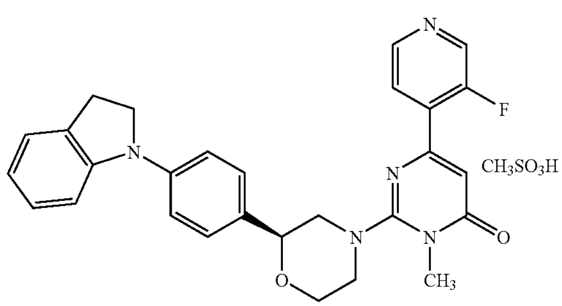 |

TABLE 1-continued
| Compound No. | STRUCTURE |
|---|---|
| 205 | 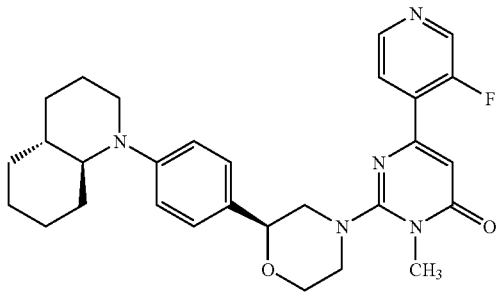 |
| 206 | 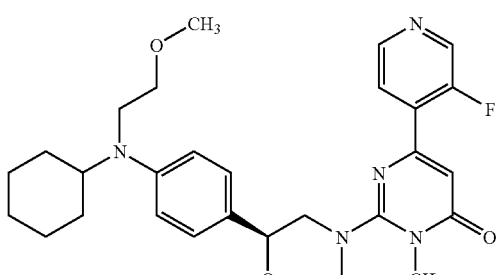 |
| 207 | 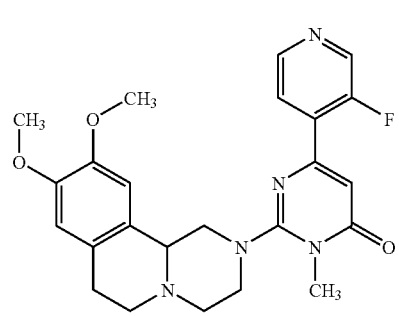 |
| 208 | 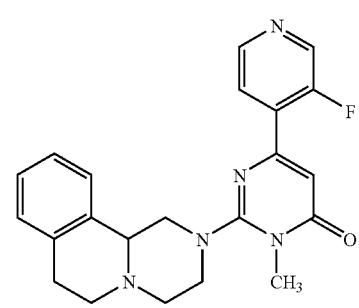 |
| 209 | 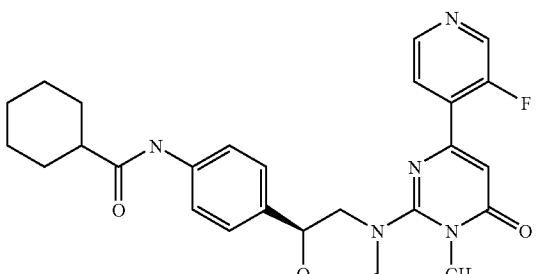 |

TABLE 1-continued
| Compound No. | STRUCTURE |
|---|---|
| 210 | 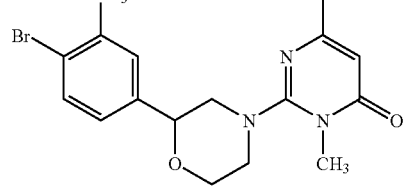 |
| 211 | 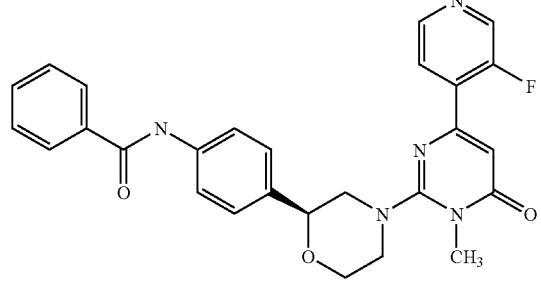 |
| 212 | 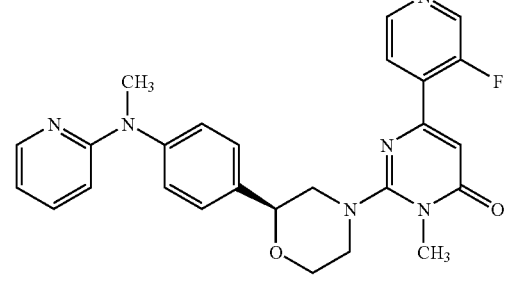 |
| 213 | 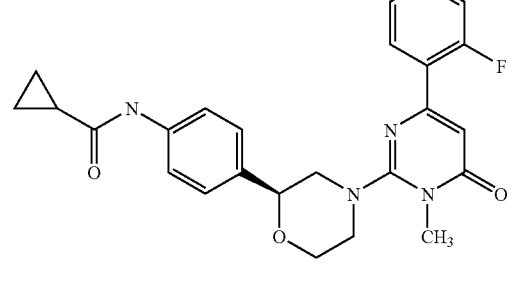 |
| 214 | 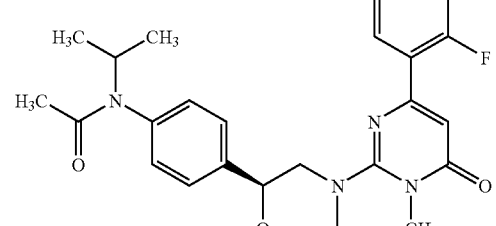 |

US 8,129,377 B2
TABLE 1-continued
| Compound No. | STRUCTURE |
|---|---|
| 215 | 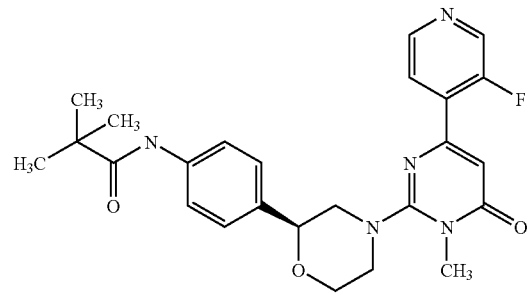 |
| 216 | 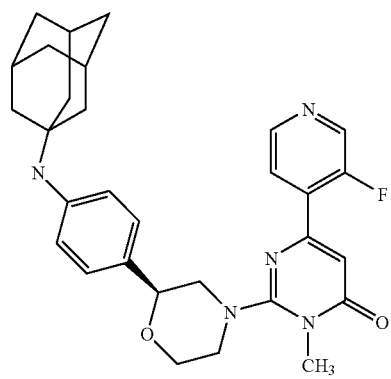 |
| 217 | 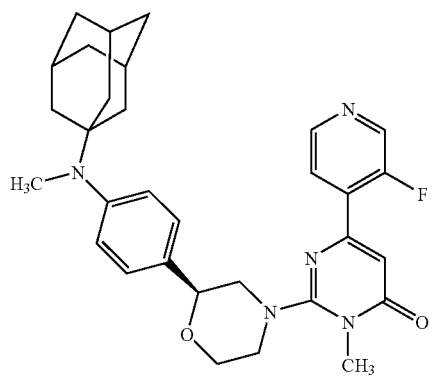 |
| 218 | 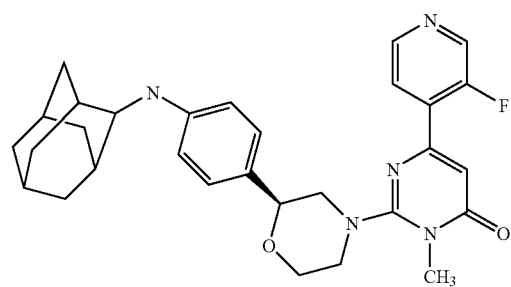 |

TABLE 1-continued
| Compound No. | STRUCTURE |
|---|---|
| 219 | 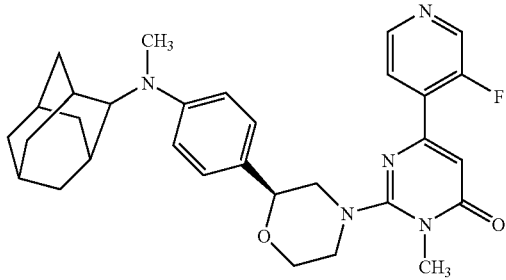 |
| 220 | 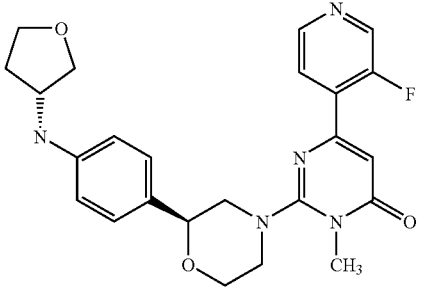 |
| 221 | 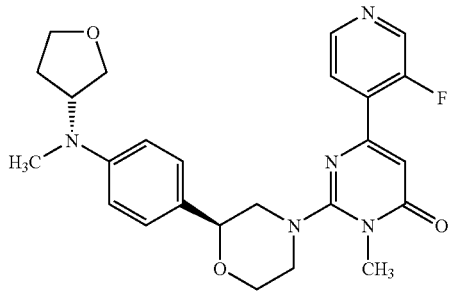 |
| 222 | 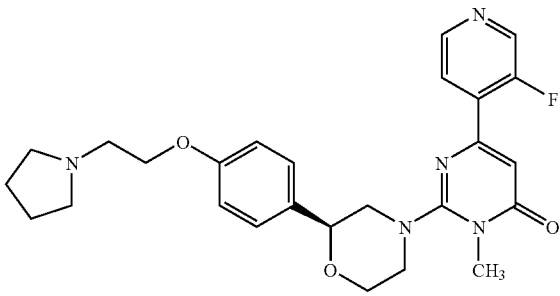 |
| 223 | 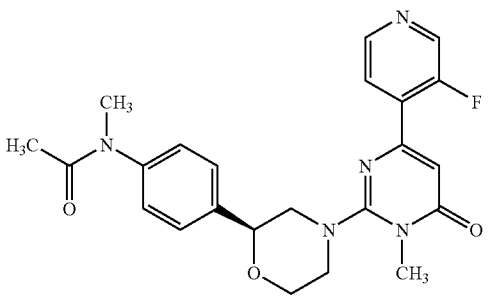 |

US 8,129,377 B2
TABLE 1-continued
| Compound No. | STRUCTURE |
|---|---|
| 224 | 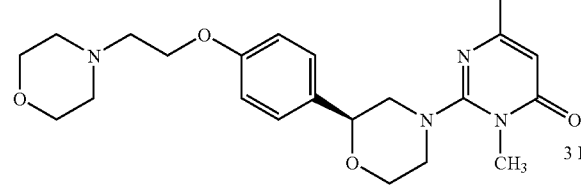 3 HCl |
| 225 | 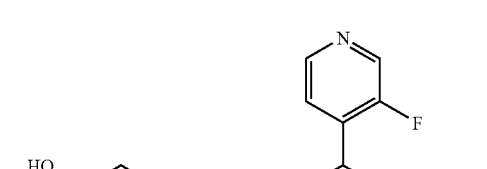 |
| 226 | 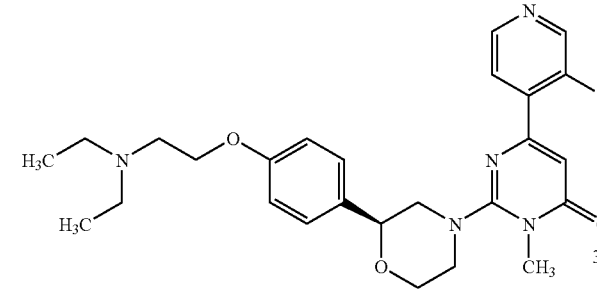 3 HCl |
| 227 | 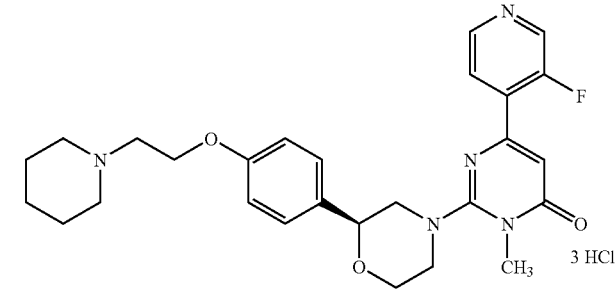 3 HCl |
| 228 | 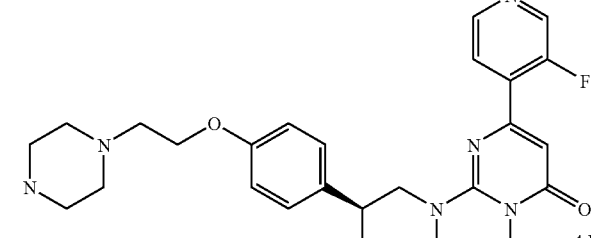 4 HCl |

TABLE 1-continued

| Compound No. | STRUCTURE |
| --- | --- |
| 229 | 4 HCl |
| 230 | 3 HCl |
| 231 | 3 HCl |
| 232 | 3 HCl |
| 233 | 3 HCl |

TABLE 1-continued
| Compound No. | STRUCTURE |
|---|---|
| 234 | 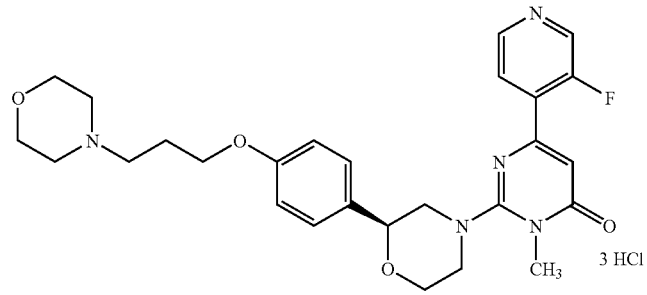 3 HCl |
| 235 | 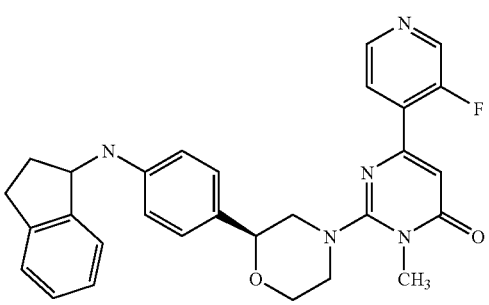 |
| 236 | 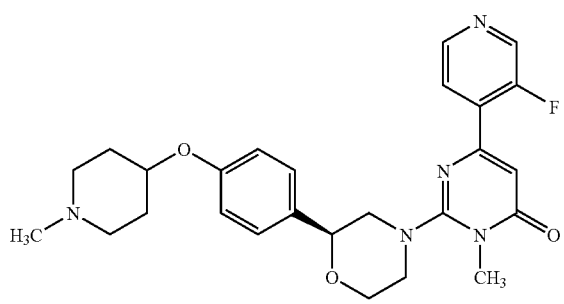 |
| 237 | 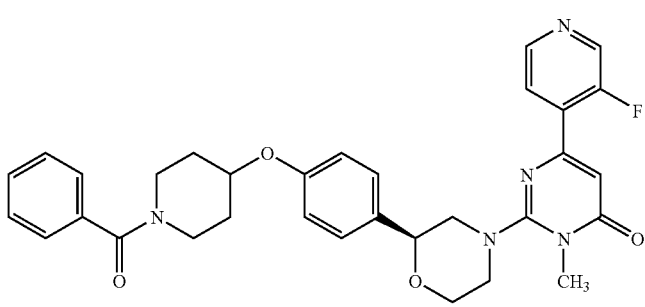 |
| 238 | 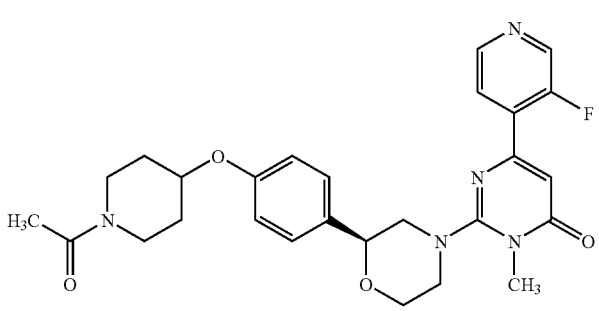 |

TABLE 1-continued

| Compound No. | STRUCTURE |
|---|---|
| 239 | 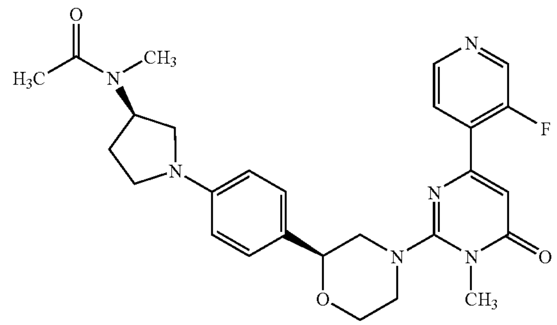 |
| 240 | 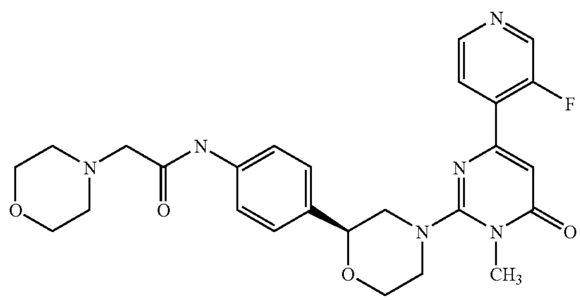 |
| 241 | 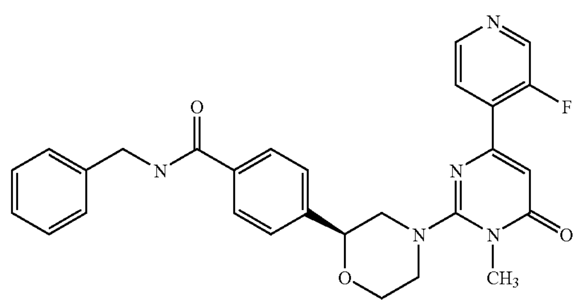 |
| 242 | 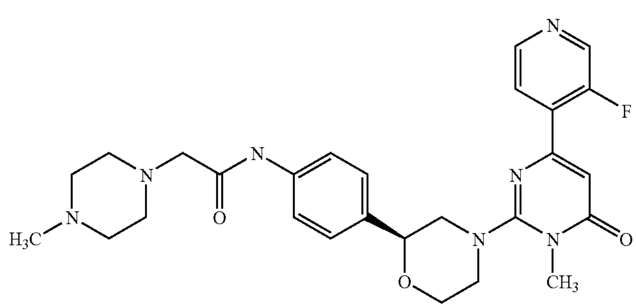 |
| 243 | 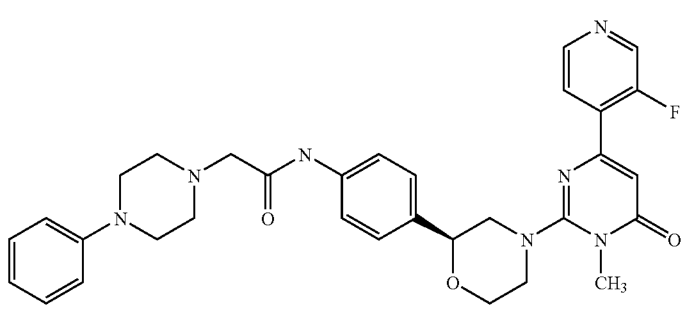 |

TABLE 1-continued
| Compound No. | STRUCTURE |
|---|---|
| 244 | 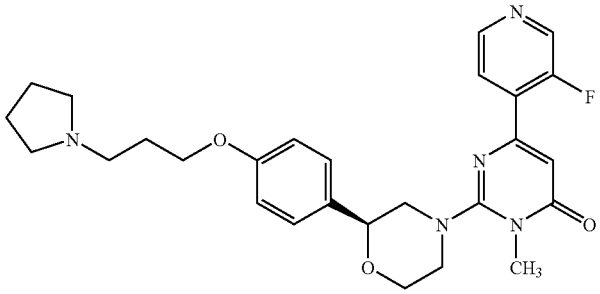 |
| 245 | 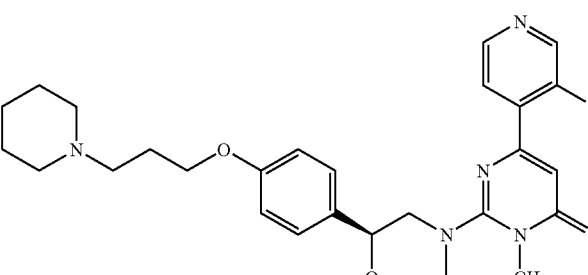 |
| 246 | 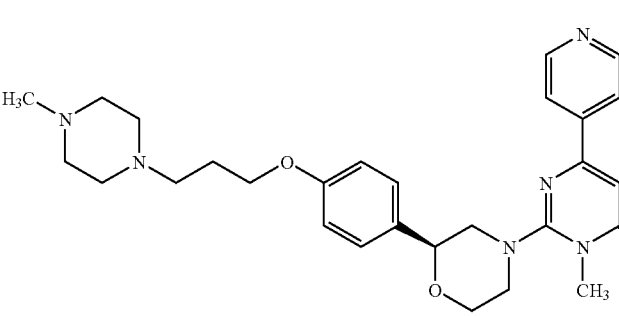 |
| 247 | 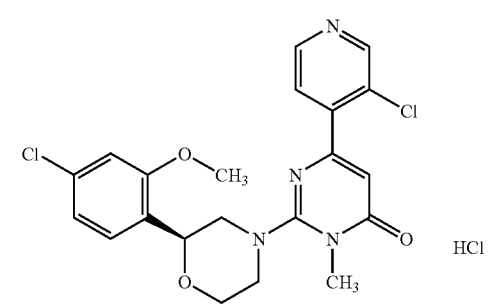 HCl |
| 248 | 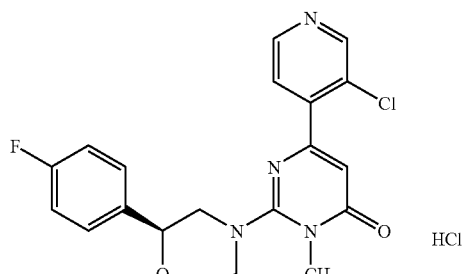 HCl |

TABLE 1-continued
| Compound No. | STRUCTURE |
|---|---|
| 249 | 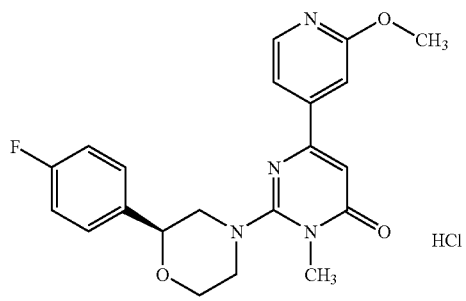 HCl |
| 250 | 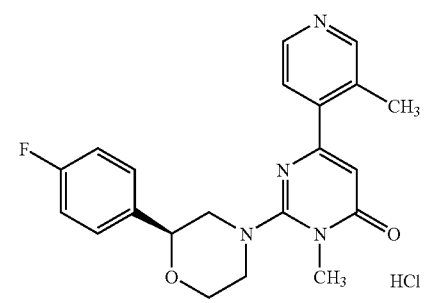 HCl |
| 251 | 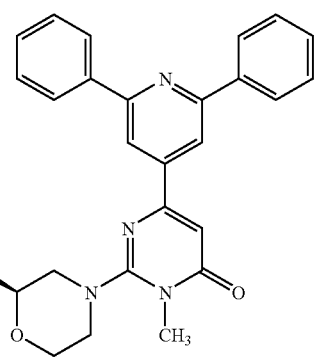 |
| 252 | 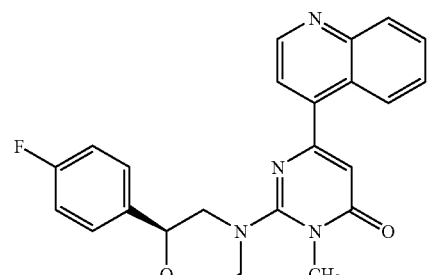 |
| 253 | 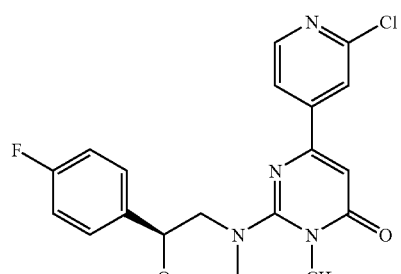 |

TABLE 1-continued

| Compound No. | STRUCTURE |
|---|---|
| 254 | 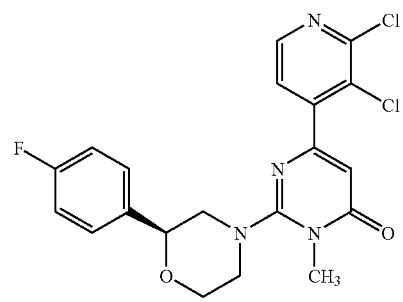 |
| 255 | 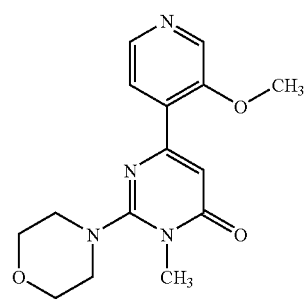 |
| 256 | 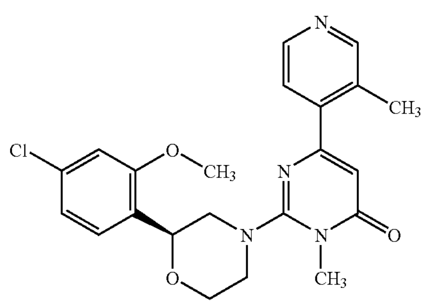 |
| 257 | 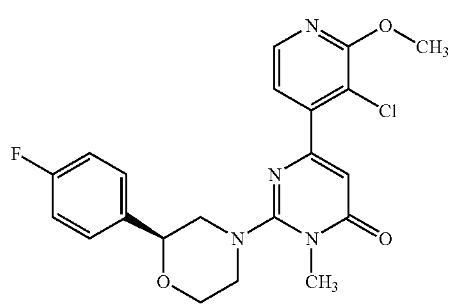 |
| 258 | 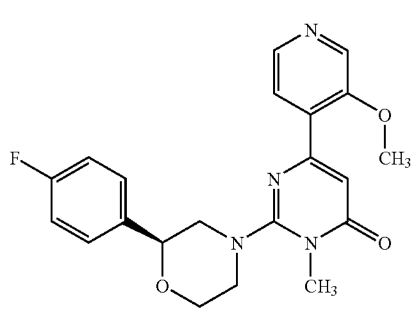 |

TABLE 1-continued

| Compound No. | STRUCTURE |
|---|---|
| 259 | 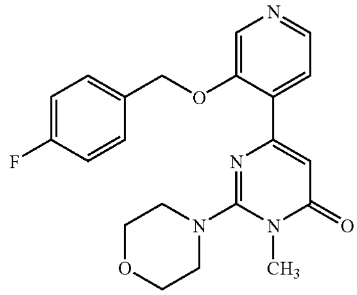 |
| 260 | 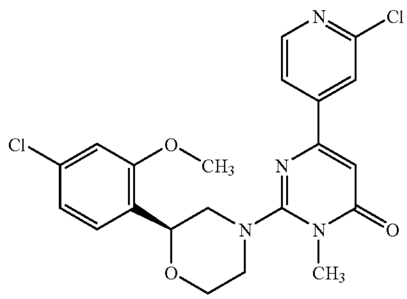 |
| 261 | 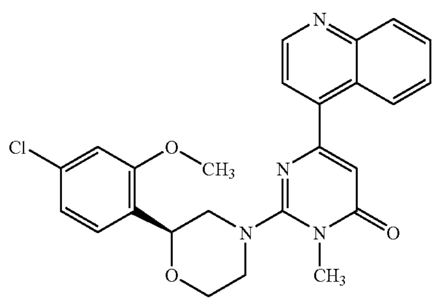 |
| 262 | 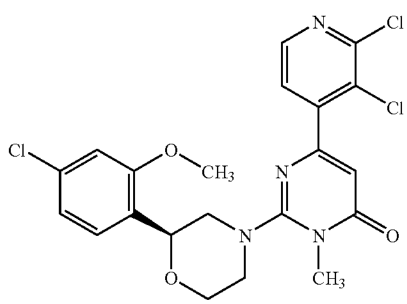 |
| 263 | 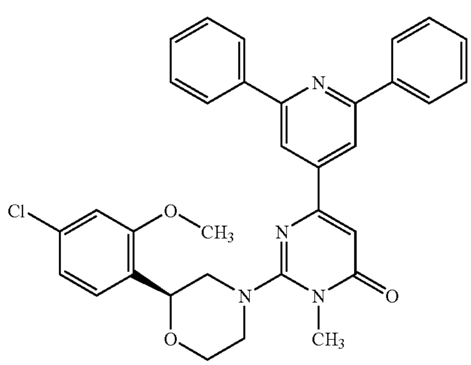 |

TABLE 1-continued
| Compound No. | STRUCTURE |
|---|---|
| 264 | 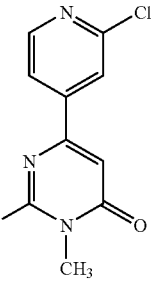 |
| 265 | 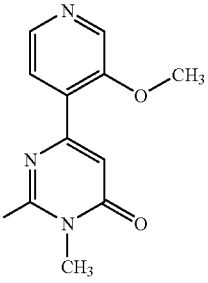 |
| 266 | 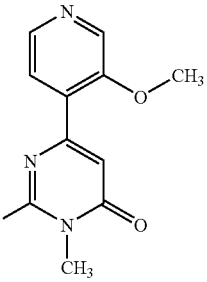 |
| 267 | 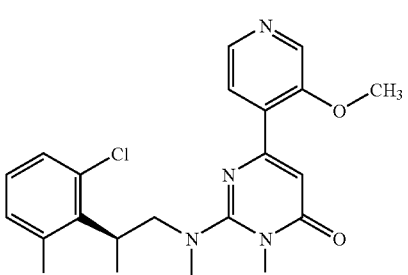 |
| 268 | 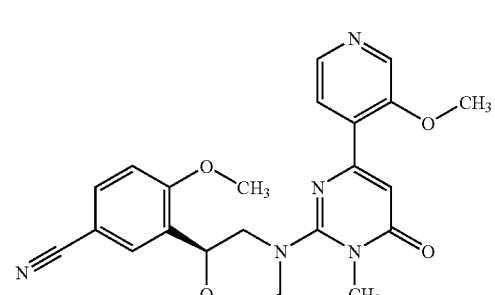 |

TABLE 1-continued

| Compound No. | STRUCTURE |
|---|---|
| 269 | 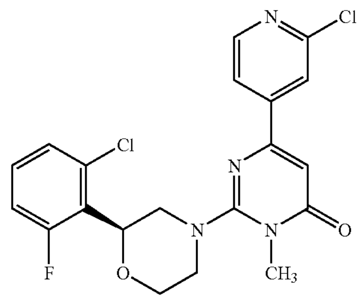 |
| 270 | 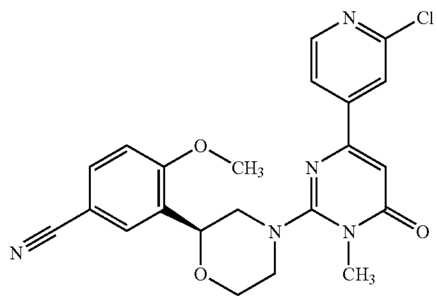 |
| 271 | 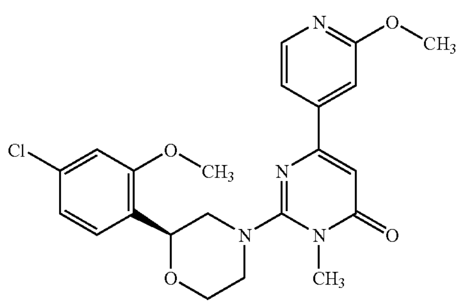 |
| 272 | 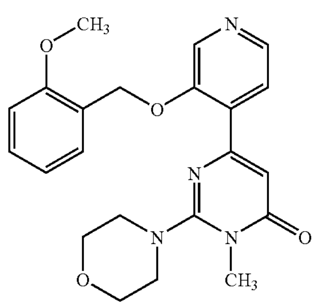 |
| 273 | 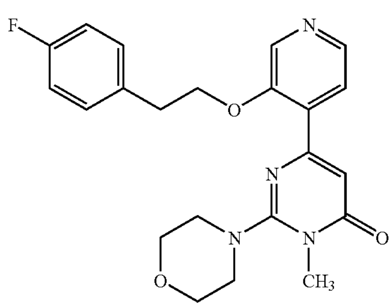 |

TABLE 1-continued
| Compound No. | STRUCTURE |
|---|---|
| 274 | 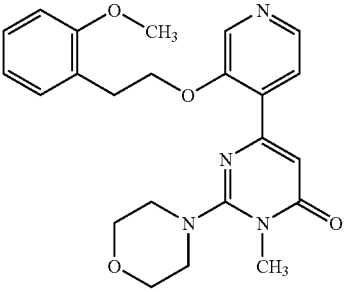 |
| 275 | 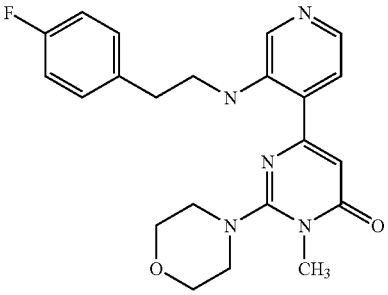 |
| 276 | 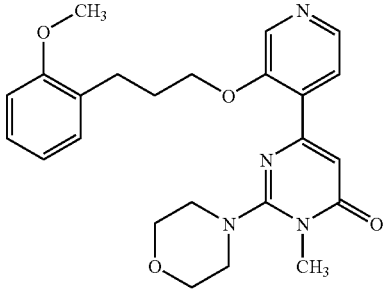 |
| 277 | 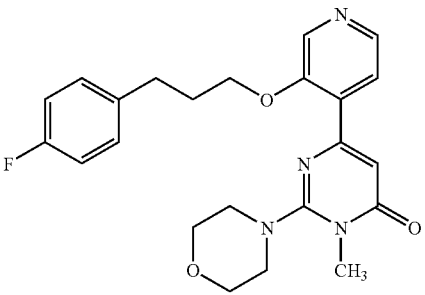 |
| 278 | 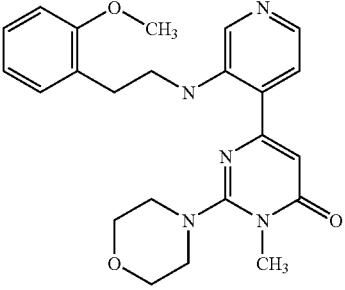 |

TABLE 1-continued

| Compound No. | STRUCTURE |
|---|---|
| 279 | 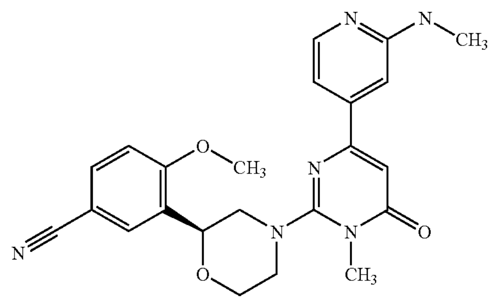 |
| 280 | 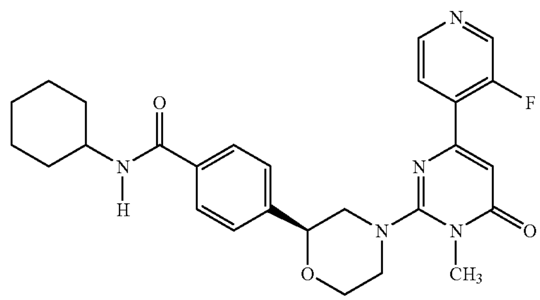 |
| 281 | 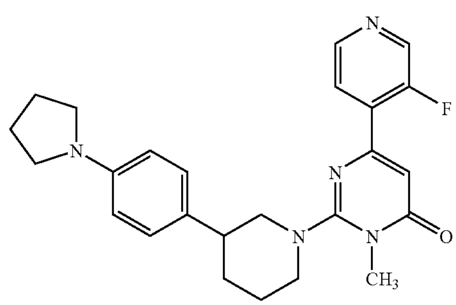 |
| 282 | 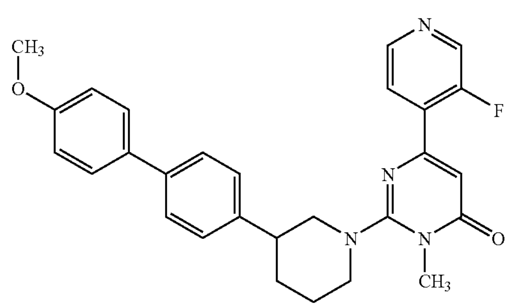 |
| 283 | 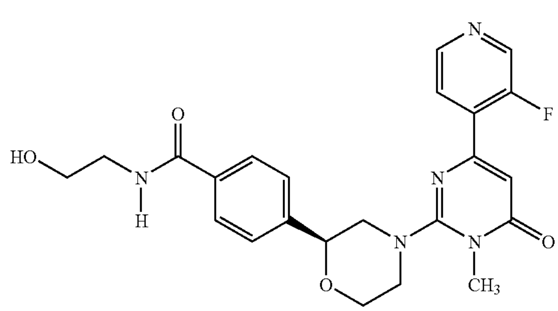 |

TABLE 1-continued
| Compound No. | STRUCTURE |
|---|---|
| 284 | 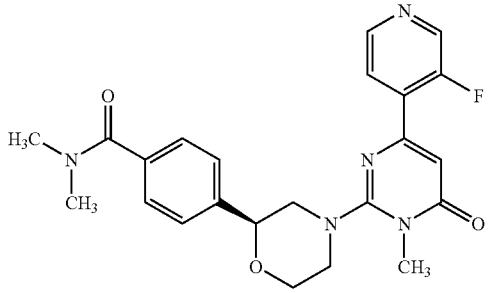 |
| 285 | 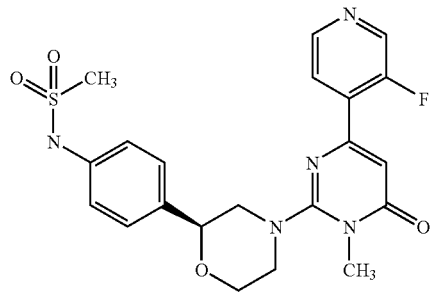 |
| 286 | 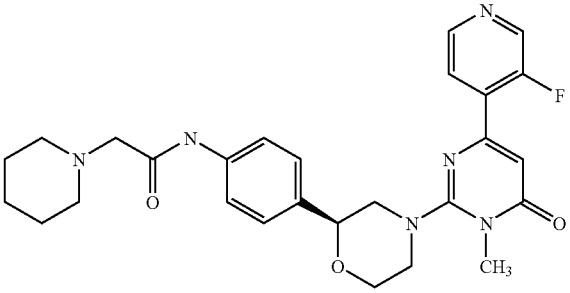 |
| 287 | 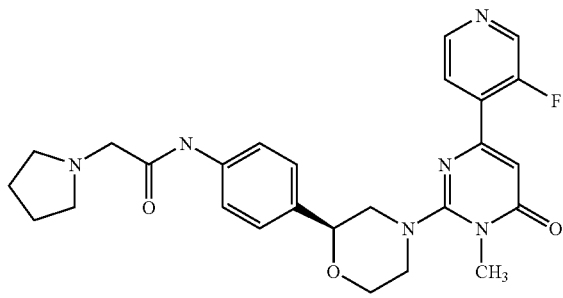 |
| 288 | 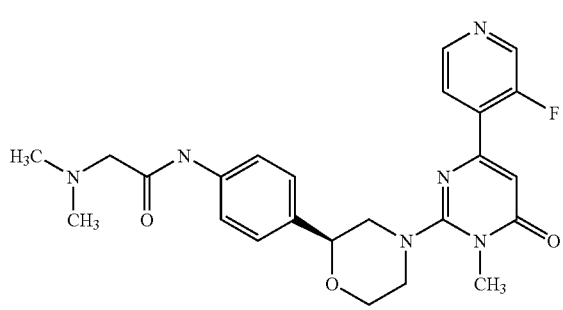 |

TABLE 1-continued

| Compound No. | STRUCTURE |
|---|---|
| 289 | 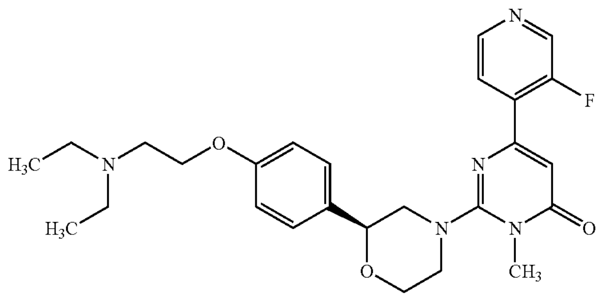 |
| 290 | 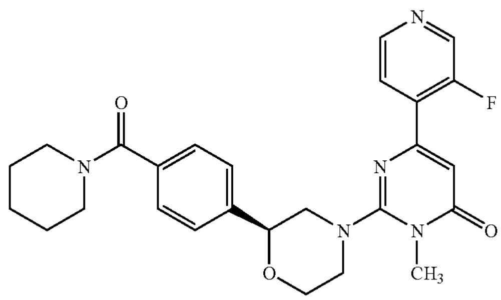 |
| 291 | 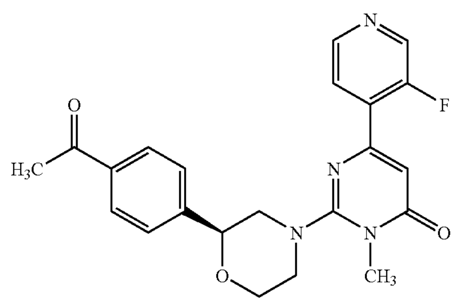 |
| 292 | 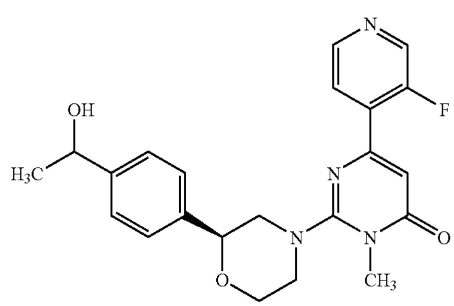 |
| 293 | 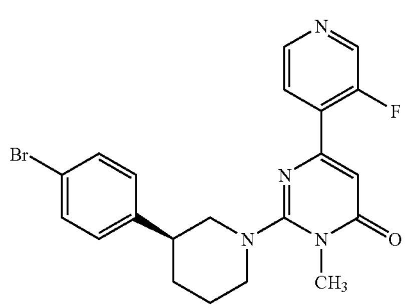 |

TABLE 1-continued

| Compound No. | STRUCTURE |
|---|---|
| 294 | 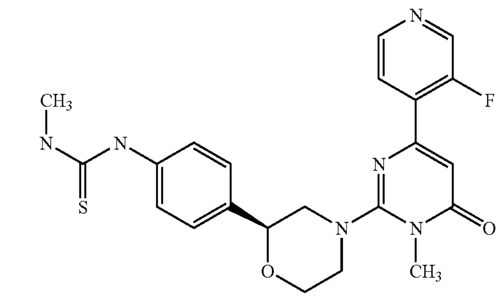 |
| 295 | 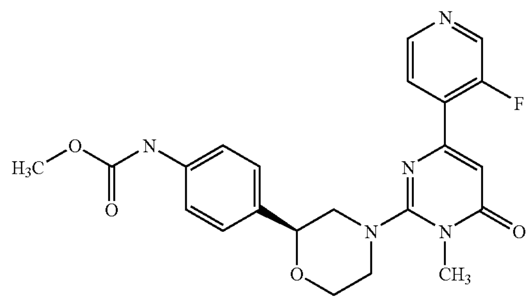 |
| 296 | 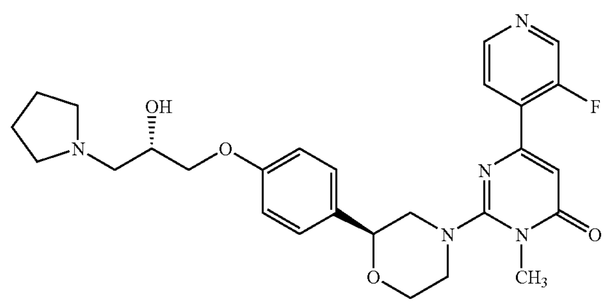 |
| 297 | 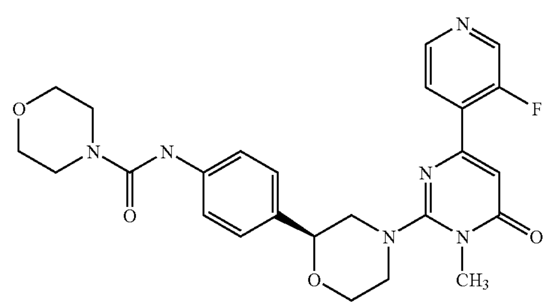 |
| 298 | 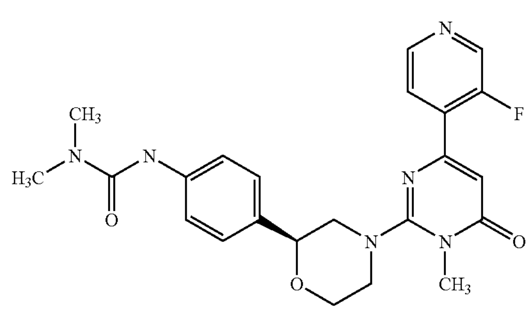 |

TABLE 1-continued
| Compound No. | STRUCTURE |
|---|---|
| 299 | 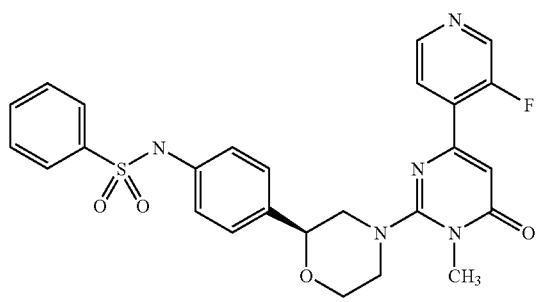 |
| 300 | 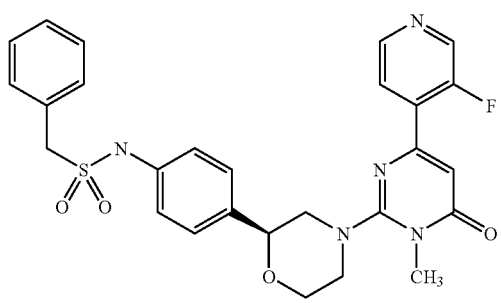 |
| 301 | 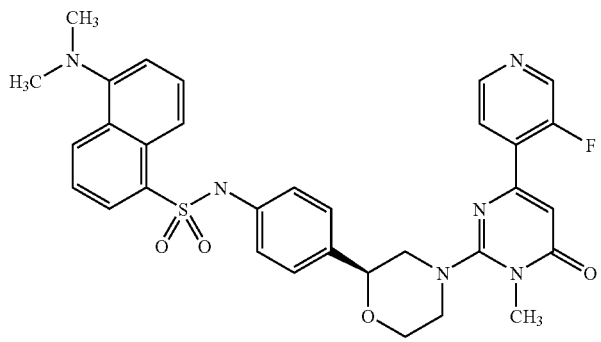 |
| 302 | 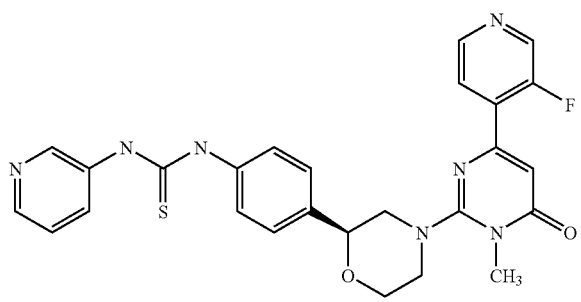 |
| 303 | 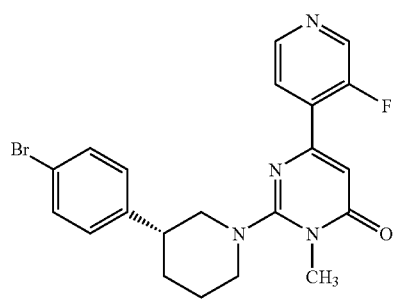 |

US 8,129,377 B2
TABLE 1-continued
| Compound No. | STRUCTURE |
|---|---|
| 304 | 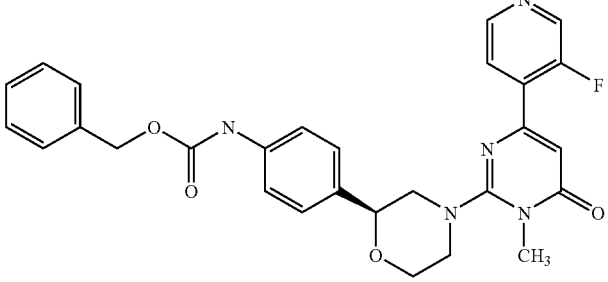 |
| 305 | 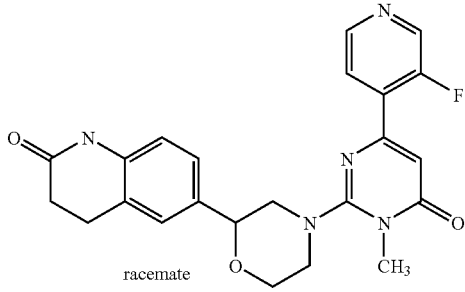 racemate |
| 306 | 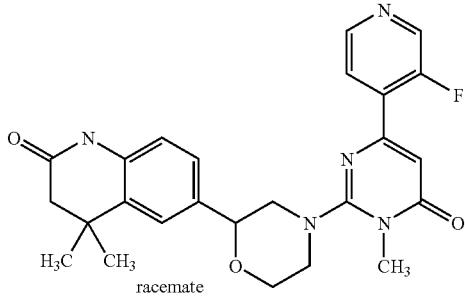 racemate |
| 307 | 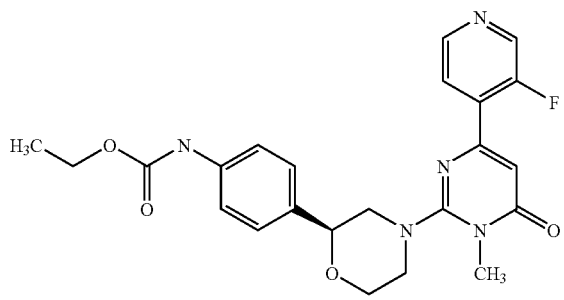 |
| 308 | 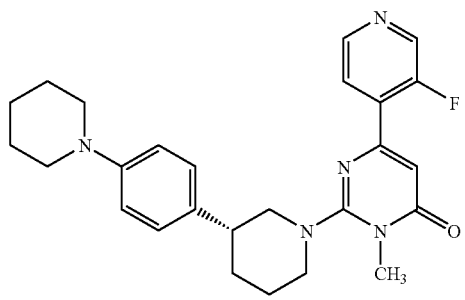 |

TABLE 1-continued

| Compound No. | STRUCTURE |
|---|---|
| 309 | 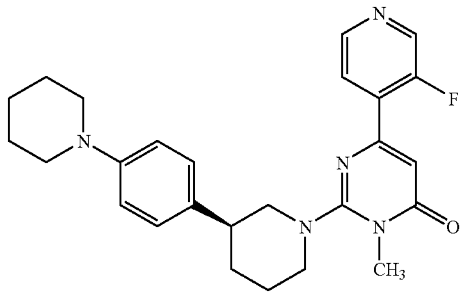 |
| 310 | 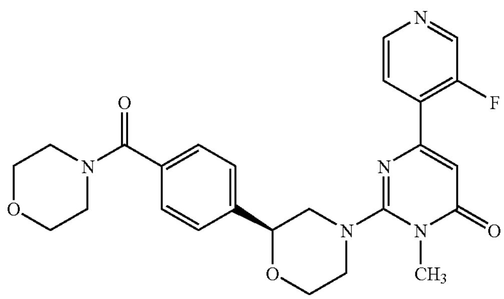 |
| 311 | 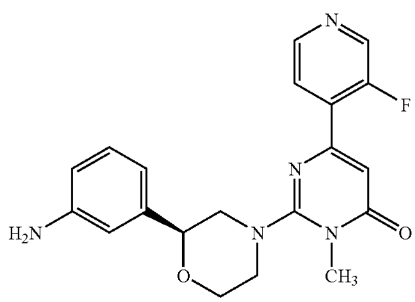 |
| 312 | 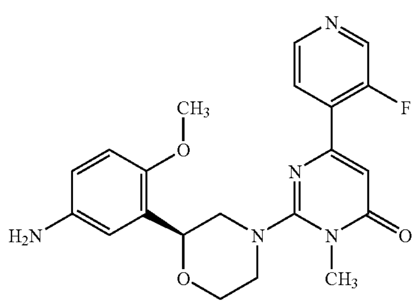 |
| 313 | 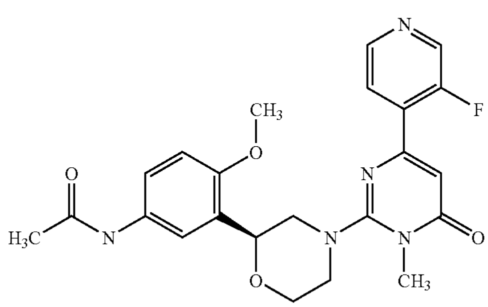 |

TABLE 1-continued

| Compound No. | STRUCTURE |
|---|---|
| 314 | 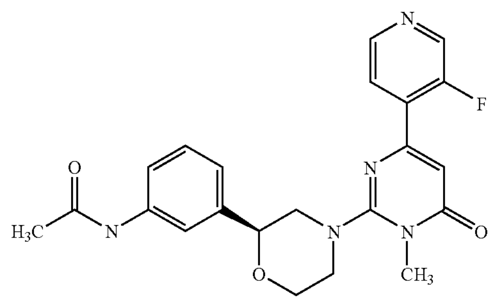 |
| 315 | 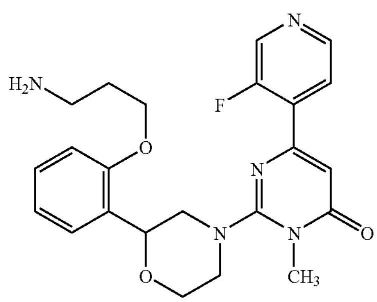 |
| 316 | 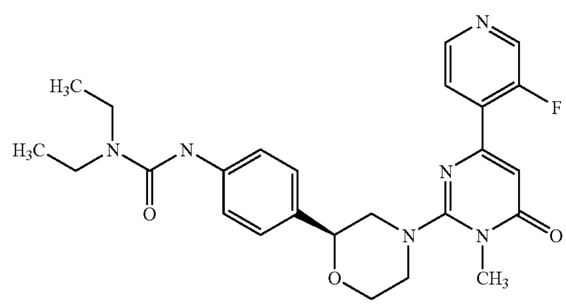 |
| 317 | racemate |
| 318 | 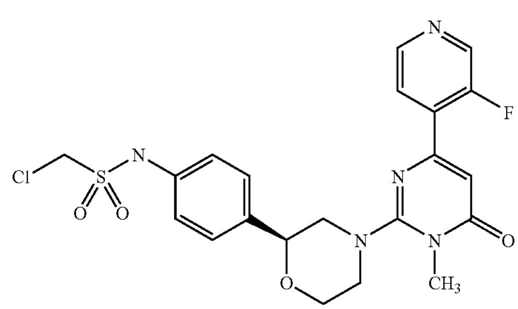 |

TABLE 1-continued

| Compound No. | STRUCTURE |
|---|---|
| 319 | 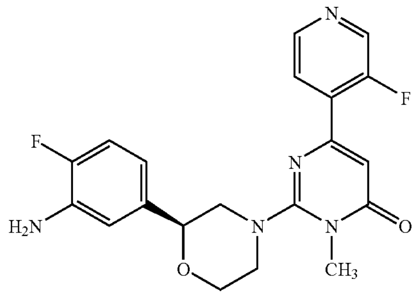 |
| 320 | 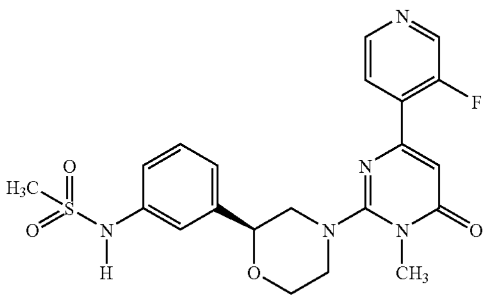 |
| 321 | racemate |
| 322 | 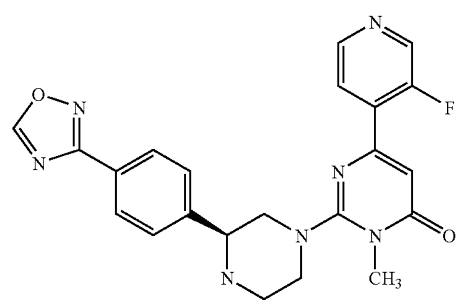 |
| 323 | 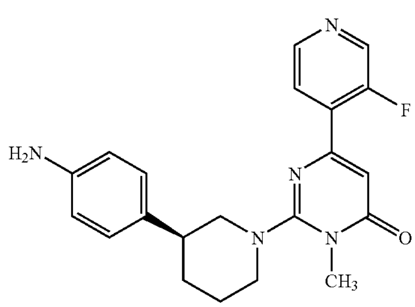 |

TABLE 1-continued

| Compound No. | STRUCTURE |
|---|---|
| 324 | 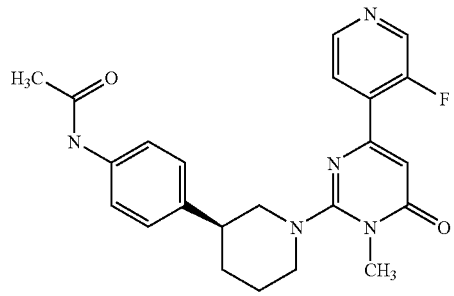 |
| 325 | 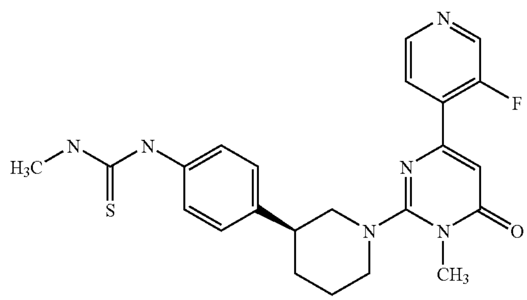 |
| 326 | 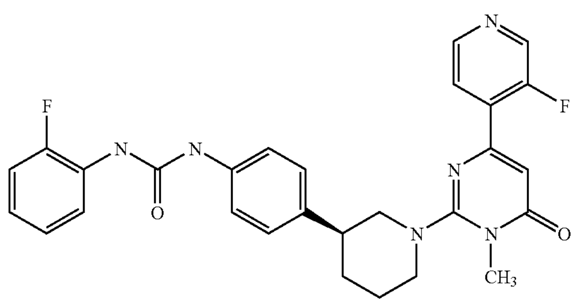 |
| 327 | 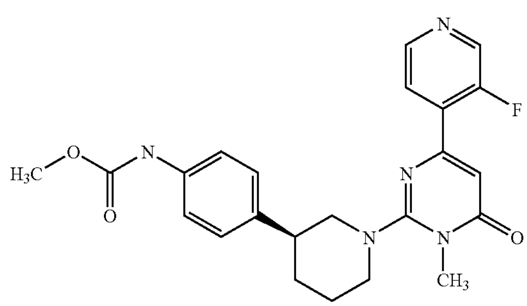 |
| 328 | 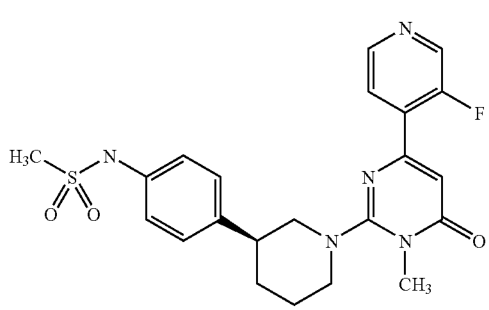 |

TABLE 1-continued

| Compound No. | STRUCTURE |
|---|---|
| 329 | 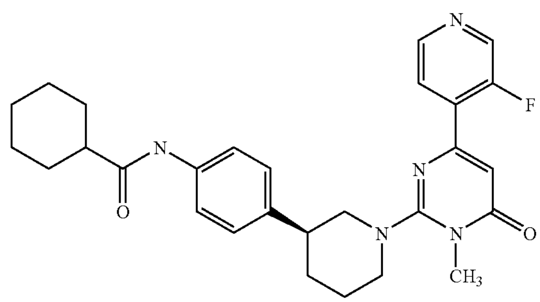 |
| 330 | 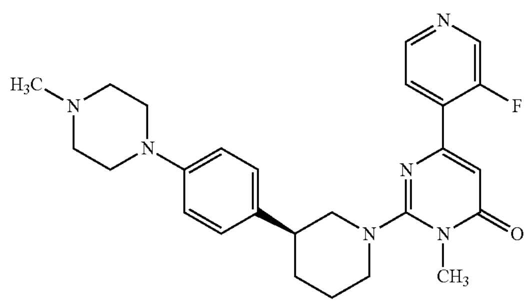 |
| 331 | 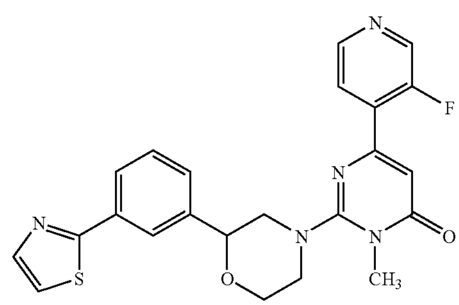 |
| 332 | 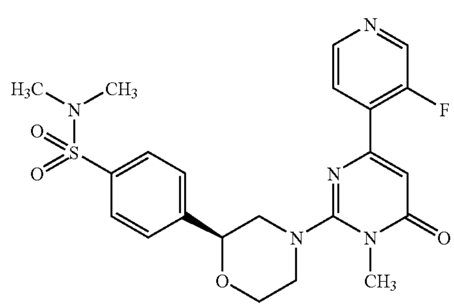 |
| 333 | 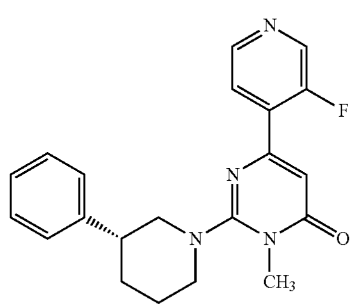 |

TABLE 1-continued
| Compound No. | STRUCTURE |
|---|---|
| 334 | 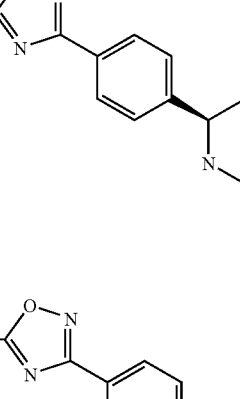 |
| 335 | 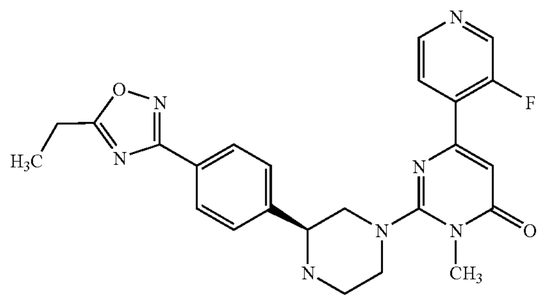 |
| 336 | 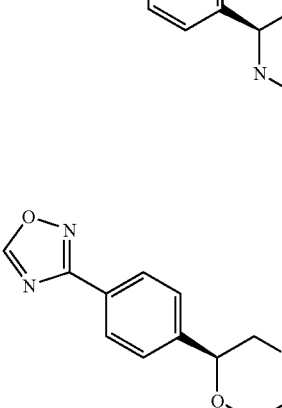 |
| 337 | 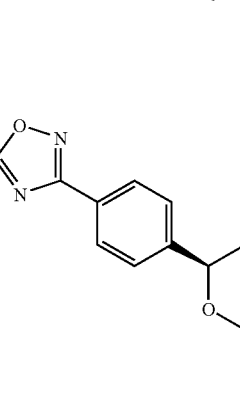 |
| 338 | 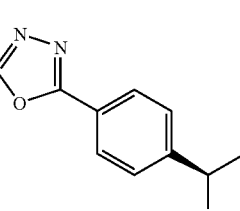 |

TABLE 1-continued

| Compound No. | STRUCTURE |
|---|---|
| 339 | 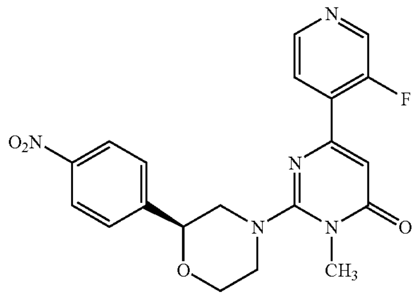 |
| 340 | 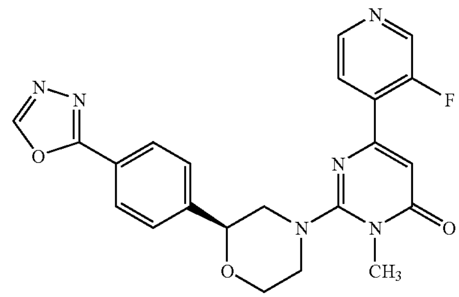 |
| 341 | 2 HCl |
| 342 | 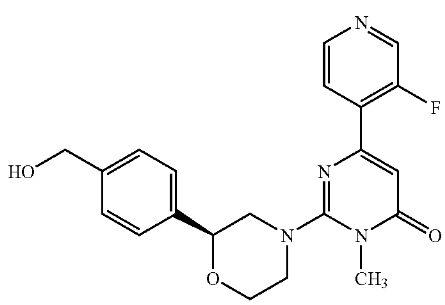 |
| 343 | 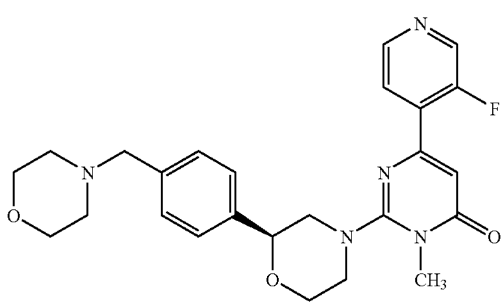 |

TABLE 1-continued
| Compound No. | STRUCTURE |
|---|---|
| 344 | 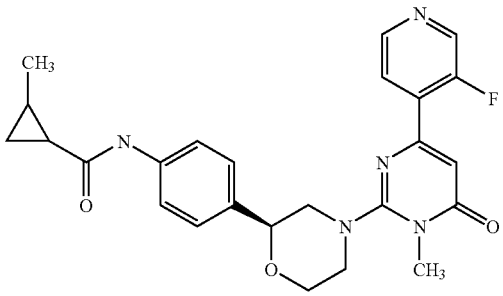 |
| 345 | 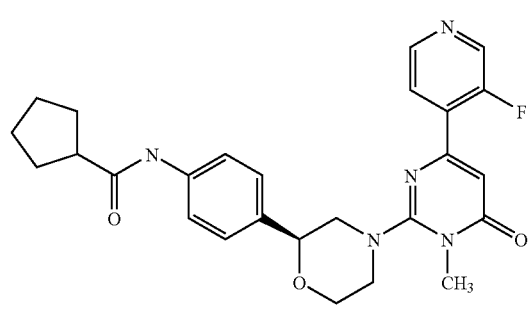 |
| 346 | 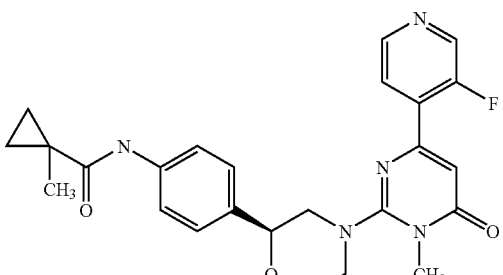 |
| 347 | 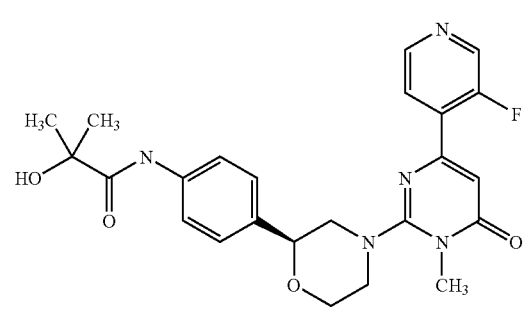 |
| 348 | 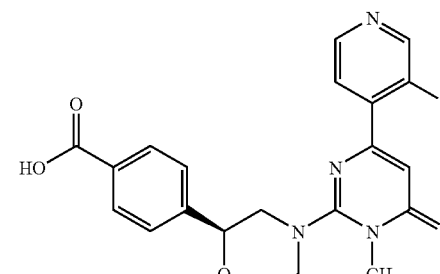 |

TABLE 1-continued

| Compound No. | STRUCTURE |
|---|---|
| 349 | 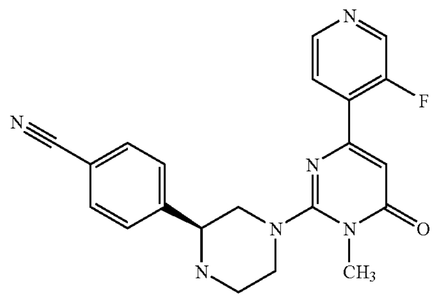 |
| 350 | 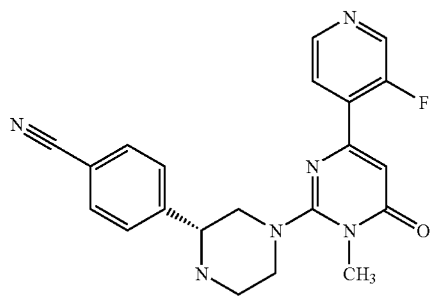 |
| 351 | 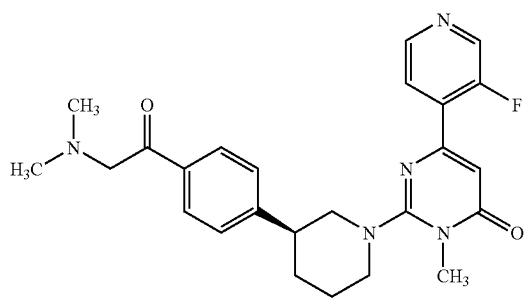 |
| 352 | 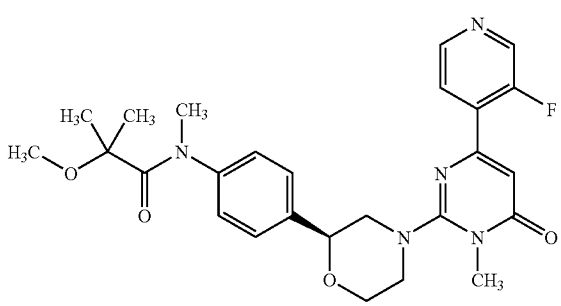 |
| 353 | 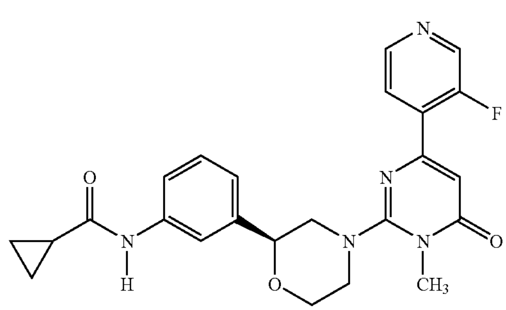 |

TABLE 1-continued
| Compound No. | STRUCTURE |
|---|---|
| 354 | 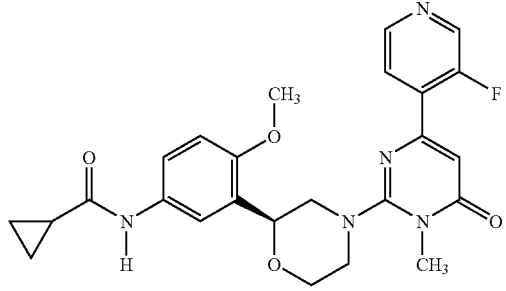 |
| 355 | 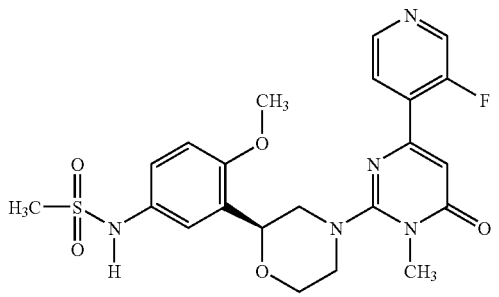 |
| 356 | 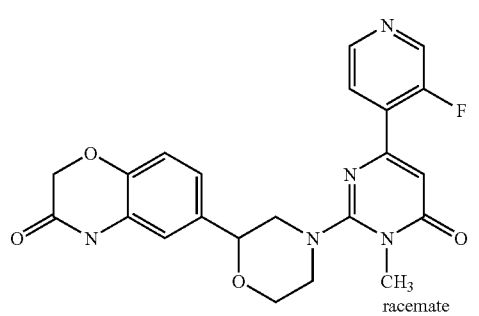 racemate |
| 357 | 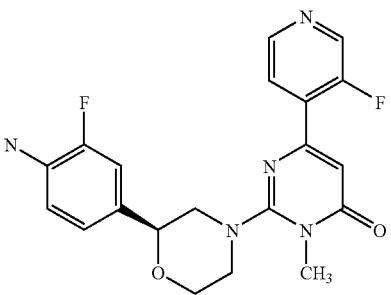 |
| 358 | 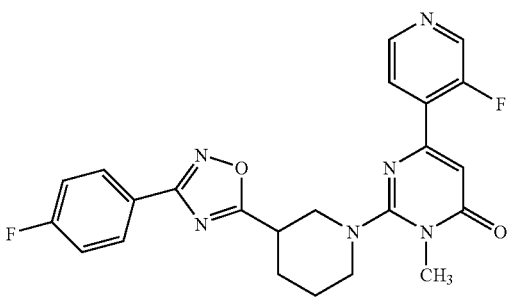 |

US 8,129,377 B2
TABLE 1-continued
| Compound No. | STRUCTURE |
|---|---|
| 359 | 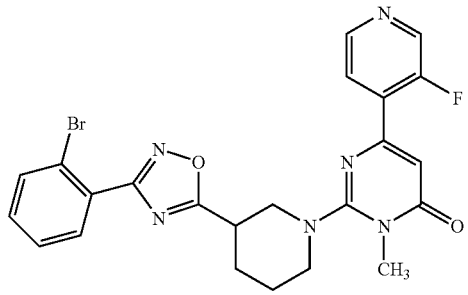 |
| 360 | 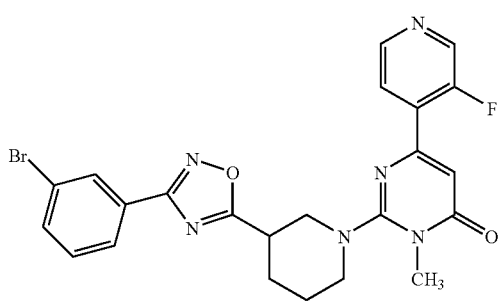 |
| 361 | 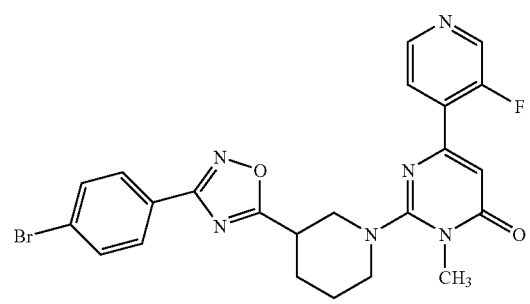 |
| 362 | 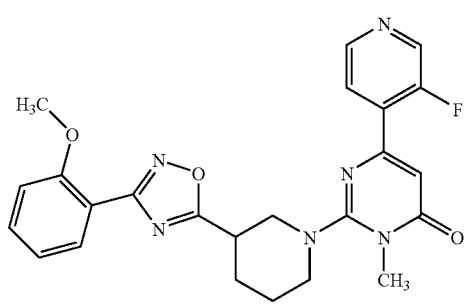 |
| 363 | 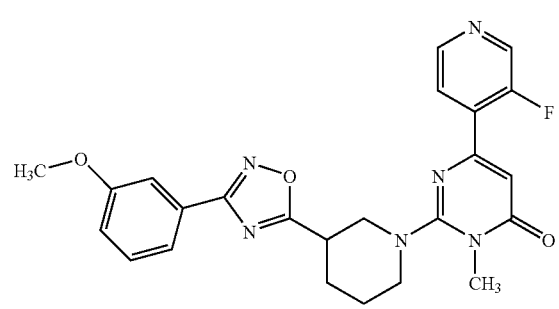 |

TABLE 1-continued

| Compound No. | STRUCTURE |
| --- | --- |
| 364 | 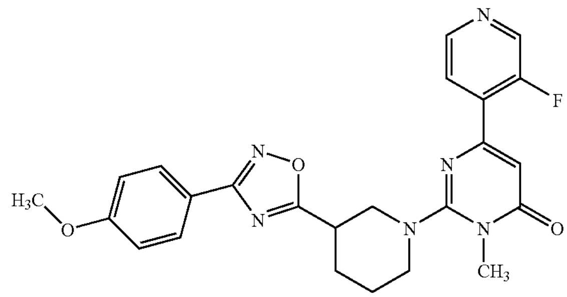 |
| 365 | 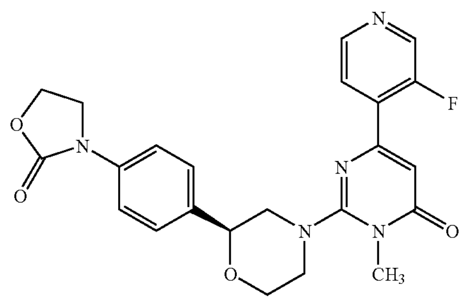 |
| 366 | 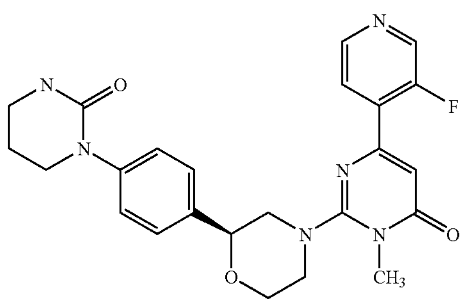 |
| 367 | 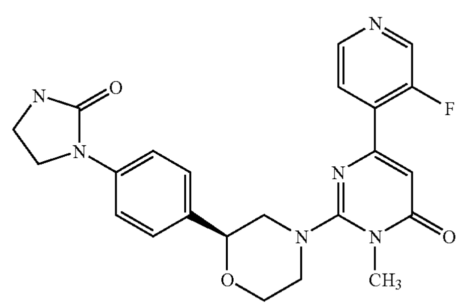 |
| 368 | 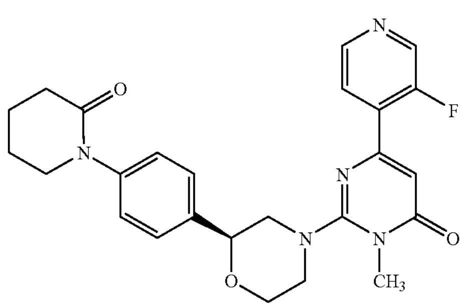 |

TABLE 1-continued

| Compound No. | STRUCTURE |
|---|---|
| 369 | 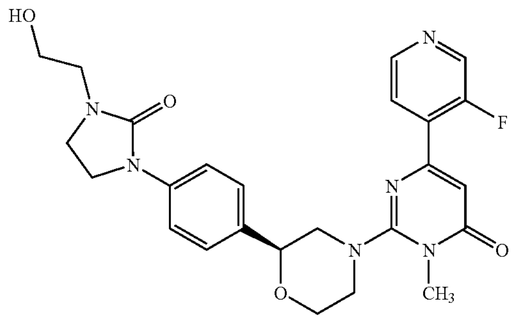 |
| 370 | 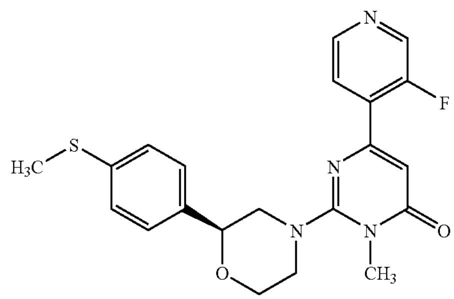 |

Particularly preferred compounds of the present invention represented by formula (I) include:
6-(3-Fluoro-pyridin-4-yl)-3-methyl-2-((3S)-3-(4-morpholin-4-yl-phenyl)-piperazin-1-yl)-3H-pyrimidin-4-one;
2-((2S)-2-(4-((3R)-3-Dimethylamino-pyrrolidin-1-yl)-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((3S)-3-(4-piperidin-1-yl-phenyl)-piperazin-1-yl)-3H-pyrimidin-4-one;
6-(3-Fluoro-pyridin-4-yl)-3-methyl-2-((2S)-2-(4-(4-pyrrolidin-1-yl-piperidin-1-yl)-phenyl(-morpholin-4-yl)-3H-pyrimidin-4-one;
2-((2S)-2-(4-(4-Dimethylamino-piperidin-1-yl)-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((3S)-3-(4-(4-methyl-piperazin-1-yl)-phenyl)-piperazin-1-yl)-3H-pyrimidin-4-one;
6-(3-Fluoro-pyridin-4-yl)-2-(3S)-3-(4-(4-hydroxy-piperidin-1-yl)-phenyl)-piperazin-1-yl)-3-methyl-3H-pyrimidin-4-one;
6-(3-Fluoro-pyridin-4-yl)-2-((3S)-3-(4-((3R)-3-hydroxy-pyrrolidin-1-yl)-phenyl)-piperazin-1-yl)-3-methyl-3H-pyrimidin-4-one;
2-((2S)-2-(4-((3S,5R)-3,5-Dimethyl-piperazin-1-yl)-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((2S)-2-(4-(4-methyl-piperazin-1-yl)-phenyl)-morpholin-4-yl)-3H-pyrimidin-4-one;
2-((2S)-2-(4-((3S)-3-Dimethylamino-pyrrolidin-1-yl)-phenyl)-morpholin-4-yl)-6-(3-fluoro-pyridin-4-yl)-3-methyl-3H-pyrimidin-4-one;
6-(3-Fluoro-pyridin-4-yl)-2-((2S)-2-(4-(4-isopropyl-piperazin-1-yl)-phenyl)-morpholin-4-yl)-3-methyl-3H-pyrimidin-4-one;
6-(3-Fluoro-pyridin-4-yl)-2-((2S)-2-(4-(4-(2-hydroxy-ethyl)-piperazin-1-yl)-phenyl)-morpholin-4-yl)-3-methyl-3H-pyrimidin-4-one;
6-(3-fluoro-pyridin-4-yl)-3-methyl-2-((3S)-3-(4-((3S)-3-(pyrrolidin-1-yl)-pyrrolidin-1-yl)-phenyl)-piperazin-1-yl)-3H-pyrimidin-4-one;
6-(3-Fluoro-pyridin-4-yl)-3-methyl-2-((3S)-3-(4-(5-methyl-(1,2,4)oxadiazol-3-yl)-phenyl)-piperazin-1-yl)-3H-pyrimidin-4-one;
6-(3-Fluoro-pyridin-4-yl)-3-methyl-2-[3-(4-morpholin-4-yl-phenyl)-piperidin-1-yl]-3H-pyrimidin-4-one;
2-((2S)-2-(4-Cyclopentylamino-phenyl)-morpholin-4-yl)-6-(3-fluoro-pyridin-4-yl)-3-methyl-3H-pyrimidin-4-one;
6-(3-Fluoro-pyridin-4-yl)-2-((2S)-2-(4-(3-hydroxy-azetidin-1-yl)-phenyl)-morpholin-4-yl)-3-methyl-3H-pyrimidin-4-one;
N-(4-((2S)-4-((4-(3-Fluoro-pyridin-4-yl)-1-methyl-6-oxo-1,6-dihydro-pyrimidin-2-yl)-morpholin-2-yl)-phenyl)-acetamide
2-((2S)-2-(4-Cyclopentyloxy-phenyl)-morpholin-4-yl)-6-(3-fluoro-pyridin-4-yl)-3-methyl-3H-pyrimidin-4-one;
2-((2S)-2-(4-Cyclopropylmethoxy-phenyl)-morpholin-4-yl)-6-(3-fluoro-pyridin-4-yl)-3-methyl-3H-pyrimidin-4-one;
2-((2S)-2-(4-(2-Dimethylamino-ethoxy)-phenyl)-morpholin-4-yl)-6-(3-fluoro-pyridin-4-yl)-3-methyl-3H-pyrimidin-4-one;
2-((2S)-2-(4-Amino-phenyl)-morpholin-4-yl)-6-(3-fluoro-pyridin-4-yl)-3-methyl-3H-pyrimidin-4-one;
Cyclopropanecarboxylic acid (4-((2S)-4-(4-(3-fluoro-pyridin-4-yl)-1-methyl-6-oxo-1,6-dihydro-pyrimidin-2-yl)-morpholin-2-yl)-phenyl)-amide;
N-(4-((2S)-4-(4-(3-Fluoro-pyridin-4-yl)-1-methyl-6-oxo-1,6-dihydro-pyrimidin-2-yl)-morpholin-2-yl)-phenyl)-2,2-dimethyl-propionamide;
6-(3-Fluoro-pyridin-4-yl)-3-methyl-2-((2S)-2-(4-(methyl-((3R)-tetrahydro-furan-3-yl)-amino)-phenyl)-morpholin-4-yl)-3H-pyrimidin-4-one;

6-(3-Fluoro-pyridin-4-yl)-3-methyl-2-((2S)-2-[4-(2-pyrrolidin-1-yl-ethoxy)-phenyl]-morpholin-4-yl)-3H-pyrimidin-4-one;
6-(3-Fluoro-pyridin-4-yl)-2-((2S)-2-(4-hydroxy-phenyl)-morpholin-4-yl)-3-methyl-3H-pyrimidin-4-one;
2-((2S)-2-(4-(2-Diethylamino-ethoxy)-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((2S)-2-(4-(2-piperidin-1-yl-ethoxy)-phenyl)-morpholin-4-yl)-3H-pyrimidin-4-one;
6-(3-Fluoro-pyridin-4-yl)-3-methyl-2-((2S)-2-(4-(2-(4-methyl-piperazin-1-yl)-ethoxy)-phenyl)-morpholin-4-yl)-3H-pyrimidin-4-one;
$N^2,N^2$-Dimethyl-$N^1$-(4-((2S)-4-(3-methyl-4-oxo-3,4-dihydro-6-(3-fluoropyridin-4-yl)pyrimidin-2-yl)morpholin-2-yl)phenyl)glycinamide;
Methyl (4-((2S)-4-(6-(3-fluoropyridin-4-yl)-3-methyl-4-oxo-3H-pyrimidin-2-yl)morpholin-2-yl)phenyl)carbamate;
N'-(4-((2S)-4-(6-(3-Fluoropyridin-4-yl)-3-methyl-4-oxo-3H-pyrimidin-2-yl)morpholin-2-yl)phenyl)-N,N-dimethylurea;
6-{4-[4-(3-Fluoropyridin-4-yl)-1-methyl-6-oxo-1,6-dihydropyrimidin-2-yl]morpholin-2-yl}-3,4-dihydroquinolin-2(1H)-one;
6-(3-Fluoro-pyridin-4-yl)-3-methyl-2-{(2S)-2-[4-morpholine-4-carbonyl]-phenyl}-morpholin-4-yl}-3H-pyrimidin-4-one;
N-(3-{(2S)-4-[4-(3-Fluoropyridin-4-yl)-1-methyl-6-oxo-1,6-dihydropyrimidin-2-yl]-morpholin-2-yl}-4-methoxyphenyl)acetamide;
N-(3-{(2S)-4-[4-(3-Fluoropyridin-4-yl)-1-methyl-6-oxo-1,6-dihydropyrimidin-2-yl]-morpholin-2-yl}phenyl)acetamide; and
6-(3-Fluoropyridin-4-yl)-3-methyl-2-((3S)-3-(4-([1,2,4]oxadiazol-3-yl)phenyl)piperazin-1-yl)-3H-pyrimidin-4-one,
an optically active isomer thereof, or a pharmaceutically acceptable salt thereof.

Additionally, compounds represented by formula (I) also include: 2-((2S)-2-(4-((3R)-3-Dimethylamino-pyrrolidin-1-yl)-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((2S)-2-(4-(4-pyrrolidin-1-yl-piperidin-1-yl)-phenyl(-morpholin-4-yl)-3H-pyrimidin-4-one;
2-((2S)-2-(4-(4-Dimethylamino-piperidin-1-yl)-phenyl)-morpholin-4-yl)-6-(3-fluoro-pyridin-4-yl)-3-methyl-3H-pyrimidin-4-one;
2-((2S)-2-(4-((3S,5R)-3,5-Dimethyl-piperazin-1-yl)-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((2S)-2-(4-(4-methyl-piperazin-1-yl)-phenyl)-morpholin-4-yl)-3H-pyrimidin-4-one;
2-((2S)-2-(4-((3S)-3-Dimethylamino-pyrrolidin-1-yl)-phenyl)-morpholin-4-yl)-6-(3-fluoro-pyridin-4-yl)-3-methyl-3H-pyrimidin-4-one;
6-(3-Fluoro-pyridin-4-yl)-2-((2S)-2-(4-(4-isopropyl-piperazin-1-yl)-phenyl)-morpholin-4-yl)-3-methyl-3H-pyrimidin-4-one;
6-(3-Fluoro-pyridin-4-yl)-2-((2S)-2-(4-(4-(2-hydroxy-ethyl)-piperazin-1-yl)-phenyl)-morpholin-4-yl)-3-methyl-3H-pyrimidin-4-one;
2-((2S)-2-(4-Cyclopentylamino-phenyl)-morpholin-4-yl)-6-(3-fluoro-pyridin-4-yl)-3-methyl-3H-pyrimidin-4-one;
6-(3-Fluoro-pyridin-4-yl)-2-((2S)-2-(4-(3-hydroxy-azetidin-1-yl)-phenyl)-morpholin-4-yl)-3-methyl-3H-pyrimidin-4-one;
2-((2S)-2-(4-Cyclopentyloxy-phenyl)-morpholin-4-yl)-6-(3-fluoro-pyridin-4-yl)-3-methyl-3H-pyrimidin-4-one;
2-((2S)-2-(4-Cyclopropylmethoxy-phenyl)-morpholin-4-yl)-6-(3-fluoro-pyridin-4-yl)-3-methyl-3H-pyrimidin-4-one;
2-((2S)-2-(4-(2-Dimethylamino-ethoxy)-phenyl)-morpholin-4-yl)-6-(3-fluoro-pyridin-4-yl)-3-methyl-3H-pyrimidin-4-one;
2-((2S)-2-(4-Amino-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((2S)-2-(4-(methyl-((3R)-tetrahydro-furan-3-yl)-amino)-phenyl)-morpholin-4-yl)-3H-pyrimidin-4-one;
6-(3-Fluoro-pyridin-4-yl)-3-methyl-2-((2S)-2-[4-(2-pyrrolidin-1-yl-ethoxy)-phenyl]-morpholin-4-yl)-3H-pyrimidin-4-one;
6-(3-Fluoro-pyridin-4-yl)-2-((2S)-2-(4-hydroxy-phenyl)-morpholin-4-yl)-3-methyl-3H-pyrimidin-4-one;
2-((2S)-2-(4-(2-Diethylamino-ethoxy)-phenyl)-morpholin-4-yl)-6-(3-fluoro-pyridin-4-yl)-3-methyl-3H-pyrimidin-4-one;
6-(3-Fluoro-pyridin-4-yl)-3-methyl-2-((2S)-2-(4-(2-piperidin-1-yl-ethoxy)-phenyl)-morpholin-4-yl)-3H-pyrimidin-4-one;
6-(3-Fluoro-pyridin-4-yl)-3-methyl-2-((2S)-2-(4-(2-(4-methyl-piperazin-1-yl)-ethoxy)-phenyl)-morpholin-4-yl)-3H-pyrimidin-4-one;
6-(3-Fluoro-pyridin-4-yl)-3-methyl-2-{(2S)-2-[4-morpholine-4-carbonyl]-phenyl }-morpholin-4-yl }-3H-pyrimidin-4-one;
2-[(2S)-2-(4-fluorophenyl)morpholin-4-yl]-6-(3-fluoropyridin-4-yl)-3-methyl-3H-pyrimidien-4-one;
(S)-6-(3-fluoropyridin-4-yl)-2-(2-(4-isopropoxyphenyl)morpholino)-3-methylpyrimidin-4(3H)-one;
(S)-2-(2-(4-(cyclopropylmethoxy)phenyl)morpholino-6-(3-fluoropyridin-4-yl)-3-methylpyrimidin-4(3H)-one;
(S)-2-(2-(4-(1,2,4-oxadiazol-3-yl)phenyl)morpholino)-6-(3-fluoropyridin-4-yl)-3-methylpyrimidin-4(3H)-one;
(S)-6-(3-fluoropyridin-4-yl)-3-methyl-2-(2-(4-(5-methyl-1,2,4-oxadiazol-3-yl)phenyl)morpholino)pyrimidin-4(3H)-one;
2-[(2S)-2-(2-chloro-6-fluorophenyl)morpholin-4-yl]-6-(3-fluoropyridin-4-yl)-3-methylpyrimidin-4(3H)-one;
2-[(2S)-2-(4-bromo-3-methylphenyl)morpholin-4-yl]-6-(3-fluoropyridin-4-yl)-3-methylpyrimidin-4(3H)-one;
6-(3-fluoropyridin-4-yl)-3-methyl-2-((2S)-2-{4-[methyl(pyridin-2-yl)amino]phenyl}morpholin-4-yl)pyrimidin-4(3H)-one;
6-(3-fluoropyridin-4-yl)-3-methyl-2-((2S)-2-{4-[(3R)-tetrahydrofuran-3-ylamino]phenyl}morpholin-4-yl)pyrimidin-4(3H)-one;
6-(3-fluoropyridin-4-yl)-3-methyl-2-{(2S)-2-[4-(2-morpholin-4-ylethoxy)phenyl]morpholin-4-yl}pyrimidin-4(3H)-one trihydrochloride; and
2-((2S)-2-{4-[(1-acetylpiperidin-4-yl)oxy]phenyl}morpholin-4-yl)-6-(3-fluoropyridin-4-yl)-3-methylpyrimidin-4(3H)-one;
an optically active isomer thereof, or a pharmaceutically acceptable salt thereof.

Salts of the aforementioned preferred compound, and solvates or hydrates of the aforementioned compounds and salts thereof are also preferred.

The compounds represented by the aforementioned formula (I) can be prepared, for example, according to the method explained below.

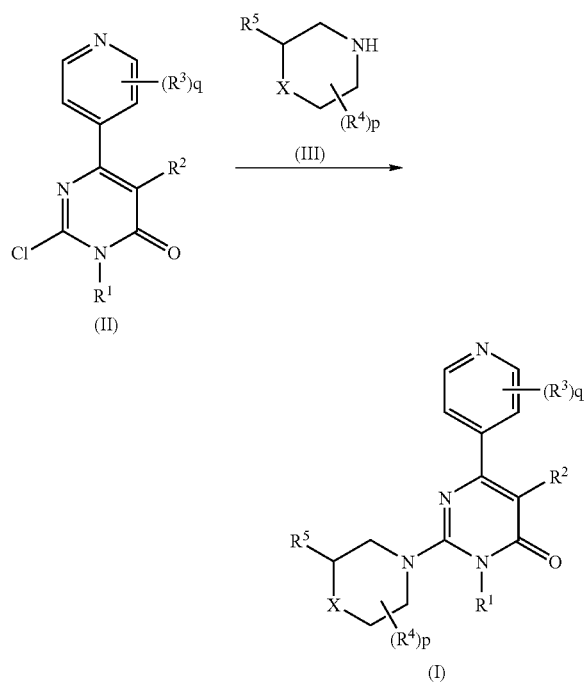

(In the above scheme, definitions of each symbol are the same as those already described.)

The 2-chloropyrimidone represented by the above formula (II) is prepared easily by the method described in the specification of WO2003/027080 and WO2003/037888.

Then the chloride derivative (II) is allowed to react with the amine (III) or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, and 1,8-diazabicyclo[5,4,0]undec-7-en for 1 to 100 hours at a suitable temperature ranging from 0° C. to 200° C. under nitrogen or argon atmosphere or under ordinary air to afford the desired compound (I).

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The compounds of the present invention have inhibitory activity against TPK1, and they inhibit TPK1 activity in neurodegenerative diseases such as Alzheimer disease, thereby suppress the neurotoxicity of Aβ and the formation of PHF and inhibit the nerve cell death. Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitis, postencephalitic parkinsonism, pugilistic encephalosis, Guam parkinsonism-dementia complex, Lewy body disease, Pick's disease, corticobasal degeneration frontotemporal dementia, vascular dementia, traumatic injuries, brain and spinal cord trauma, peripheral neuropathies, retinopathies and glaucoma, non-insulin dependent diabetes, obesity, manic depressive illness, schizophrenia, alopecia, breast cancer, non-small cell lung carcinoma, thyroid cancer, T or B-cell leukemia, and several virus-induced tumors. As the compound of the present invention has good pharmacological activities, good safety and good pharmacokinetics, the compound has preferable characteristics as a medicament.

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 3000 mg (the weight of an active ingredient) to an adult.

EXAMPLES

The present invention will be explained more specifically with reference to examples. However, the scope of the present invention is not limited to the following examples. The compound numbers in the examples correspond to those in the table above.

Reference Example 1

Synthesis of 2-chloro-6-(3-fluoropyridin-4-yl)-3-methyl-3H-pyrimidin-4-one

3-Fluoroisonicotinic Acid

3-Fluoropyridine (25 g, 257 mmol) was added to a solution of butyllithium (270 mmol) and diisopropylamine (27.4 g, 271 mmol) in tetrahydrofuran (600 mL) at −78° C. After stirring for one hour, crushed dry ice was added to the solution and the solution was warmed to room temperature during one hour. Aqueous hydrogen chloride was added to the solution to acidify the solution to pH 5. The resulting precipitate was filtered and dried. The title compound (25.2 g, 179 mmol, 70%) was obtained as colorless crystal.

3-(3-Fluoro-pyridin-4-yl)-3-oxo-propionic Acid Ethyl Ester

Carbonyl diimidazole (30.5 g, 188 mmol) was added to a solution of 3-fluoroisonicotinic acid (25.2 g, 179 mmol) in tetrahydrofuran, and the mixture was refluxed for 1 hour. After cooled to room temperature, the solution was added with potassium monoethylmalonate (33.6 g, 197 mmol) and magnesium chloride (20.5 g, 215 mmol), and the mixture was heated at 60° C. After cooled to room temperature, the solution was added with aqueous hydrogen chloride for acidification to pH 5, and then extracted with ethyl acetate. The extract was dried over magnesium sulfate and the solvent was removed under reduced pressure. The residue was purified by silica gel column chromatography (eluent; ethyl acetate/hexane=1/2) to give desired keto-ester (25.0 g, 118 mmol, 66%) as colorless crystal.

6-(3-Fluoropyridin-4-yl)-2-mercapto-3-methyl-3H-pyrimidin-4-one

A suspension of 3-(3-fluoropyridin-4-yl)-3-oxo-propionic acid ethyl ester (60.3 g, 286 mmol), N-methylthiourea (88 g, 976 mmol) and 1,8-diazabicyclo[5,4,0]undec-7-ene (48 g, 315 mmol) in toluene (600 ml) was heated at 100° C. for 5 hour. After addition of water (2000 ml) and methanesulfonic acid (30.3 g, 315 mmol) at room temperature and stirring for one hour, resulting precipitate was collected by filtration and dried to afford 6-(3-fluoropyridin-4-yl)-2-mercapto-3-methyl-3H-pyrimidin-4-one (46.3 g, 195 mmol, 68%) as white crystals.

2-Chloro 6-(3-fluoropyridin-4-yl)-3-methyl-3H-pyrimidin-4-one

After one hour stirring of a solution of phosphorus oxychloride (45 g, 293 mmol) in dimethylformamide (450 ml) at room temperature, 6-(3-fluoropyridin-4-yl)-2-mercapto-3-methyl-3H-pyrimidin-4-one (46.3 g, 195 mmol) was added and heated at 60° C. for 2 hours. The resulting suspension was partitioned between ethyl acetate and saturated aqueous sodium bicarbonate. The aqueous layer was extracted with ethyl acetate and the combined organic layer was washed with brine, dried over magnesium sulfate, and concentrated in vacuo. The residue was washed by hexane to furnish 2-chloro-6-(3-fluoropyridin-4-yl)-3-methyl-3H-pyrimidin-4-one (34.2 g, 143 mmol, 73%) as white crystals.

Reference Example 2

Synthesis of 2-Chloro-6-(2,3-dichloropyridin-4-yl)-3-methyl-3H-pyrimidin-4-one

2,3-Dichloroisonicotinic Acid

To a solution of diisopropylamine (21.6 g, 213 mmol) and n-butyllithium in hexane (137 ml, 214 mmol) in tetrahydrofuran (600 ml) was added 2,3-dichloropyridine (30.0 g, 203 mmol) in tetrahydrofuran at −78° C. After 2 hour stirring, dry ice (100 g) was added and the solution was further stirred for one hour. Resulting white precipitate formed by acidification to pH 1 with 6N hydrochloric acid was collected by filtration and dried to afford 2,3-dichloroisonicotinic acid (32.5 g, 169 mmol, 83%) as white crystals.

3-((2,3-Dichloropyridin)-4-yl)-3-oxo-propionic acid ethyl ester

A solution of 2,3-dichloroisonicotinic acid (25.3 g, 132 mmol) and 1,1'-carbonyldiimidazole (22.5 g, 139 mmol) in tetrahydrofuran (500 ml) was heated at 90° C. for 2 hours. Malonic acid monoethyl ester potassium salt (24.7 g, 145 mmol) and magnesium chloride (15.1 g, 159 mmol) was added and heated at 60° C. for 3 hours. The resulting suspension was acidified and extracted with ethyl acetate. The combined organic layer was washed with brine, dried over magnesium sulfate, and concentrated in vacuo. The residue was purified by silica gel chromatography eluting 20-50% of ethyl acetate in hexane to afford 3-((2,3-dichloropyridin)-4-yl)-3-oxo-propionic acid ethyl ester (22.0 g, 83.9 mmol, 64%) as white crystals.

6-(2,3-Dichloropyridin-4-yl)-2-mercapto-3-methyl-3H-pyrimidin-4-one

A suspension of 3-((2,3-dichloropyridin)-4-yl)-3-oxo-propionic acid ethyl ester (22.0 g, 83.9 mmol), N-methylthiourea (25.8 g, 286 mmol) and 1,8-diazabicyclo[5,4,0]undec-7-ene (14.1 g, 92.6 mmol) in toluene (450 ml) was heated at 100° C. for 5 hours. After the suspension was added with water (1000 ml) and methanesulfonic acid (8.9 g, 92.0 mmol) at room temperature and stirred for one hour, the precipitate was collected by filtration and dried to afford 6-(2,3-dichloropyridin-4-yl)-2-mercapto-3-methyl-3H-pyrimidin-4-one (3.58 g, 12.4 mmol, 15%) as white crystal.

2-Chloro-6-(2,3-dichloropyridin-4-yl)-3-methyl-3H-pyrimidin-4-one

After one hour stirring of a solution of phosphorus oxychloride (2.9 g, 18.9 mmol) in dimethylformamide (30 ml) at room temperature, 6-(2,3-dichloropyridin-4-yl)-2-mercapto-3-methyl-3H-pyrimidin-4-one (3.58 g, 12.4 mmol) was added and heated at 60° C. for 2 hours. The resulting suspension was partitioned between ethyl acetate and saturated aqueous sodium bicarbonate and the aqueous layer was extracted with ethyl acetate. The combined organic layer was washed with brine, dried over magnesium sulfate, and concentrated in vacuo. The residue was washed by hexane to furnish 2-chloro-6-(2,3-dichloropyridin-4-yl)-3-methyl-3H-pyrimidin-4-one (2.6 g, 8.95 mmol, 72%) as white crystals.

Reference Example 3

Synthesis of (2S)-2-(4-Piperidin-1-yl-phenyl)-piperazine Trihydrochloride (2S)-2-(4-Bromophenyl)-piperazine-1,4-dicarboxylic acid di-tert-butyl ester (2S)-2-(4-Bromophenyl)-piperazine-1,4-dicarboxylic acid di-tert-butyl ester was prepared from 4-bromophenacyl bromide by the same route as (2S)-2-(4-chlorophenyl)-piperazine-1,4-dicarboxylic acid di-tert-butyl ester in WO2004/085408.

(2S)-2-(4-Piperidin-1-yl-phenyl)-piperazine-1,4-dicarboxylic acid di-tert-butyl ester A solution of (2S)-2-(4-bromophenyl)-piperazine-1,4-dicarboxylic acid di-tert-butyl ester (1.06 g, 2.40 mmol), piperidine (0.29 ml, 2.88 mmol), palladium acetate (22.0 mg, 0.096 mmol), sodium tert-butoxide (323 mg, 3.36 mmol) and 2-(di-t-butylphosphino)biphenyl (57.0 mg, 0.192 mmol) in toluene (16 ml) was stirred at 80° C. for 6 hours. Water and ethyl acetate were added to the solution and the solution was passed through Celite column. The whole was extracted with ethyl acetate and the organic lawyer was washed with brine, dried over anhydrous sodium sulfate and concentrated under reduced pressure. The resulting residue was purified by silica gel column chromatography (hexane/ethyl acetate) to give (2S)-2-(4-piperidin-1-yl-phenyl)-piperazine-1,4-dicarboxylic acid di-tert-butyl ester (455 mg, 43%) as white crystals.

(2S)-2-(4-Piperidin-1-yl-phenyl)-piperazine trihydrochloride

Hydrogen chloride (4N, 1.5 ml) in ethyl acetate was added to a solution of (2S)-2-(4-piperidin-1-yl-phenyl)-piperazine-1,4-dicarboxylic acid di-tert-butyl ester (455 g, 1.02 mmol) in dichloromethane (10 ml) and the solution was stirred for 2 hours. Filtration and washing with ethyl acetate of the precipitant gave (2S)-2-(4-piperidin-1-yl-phenyl)-piperazine trihydrochloride (353 mg, 98%) as white crystals.
$^1$H-NMR (DMSO-d6) δ: 1.65(2H,m), 1.81-1.91(4H, m), 3.39-3.53(10H,m), 4.68(1H, m), 7.71(4H,m), 10.0(3H,m), 10.68(1H,m).

Reference Example 4

Synthesis of N-(4-((2S)-morpholin-2-yl)phenyl)acetamide

2-Bromo-(1S)-1-(4-bromophenyl)ethanol

A borane-tetrahydrofuran complex (1.0 M solution in tetrahydrofuran, 270 ml, 270 mmol) was added to the solution of (S)—CBS ((S)-2-methyl-CBS-oxazaborolidine, 50 ml, 1.0M solution in toluene) at −30° C. over 15 minutes and the solution was stirred for 15 minutes. 4-Bromophenacyl bromide (75.0 g, 270 mmol) in dichloromethane (350 ml) was dropped over 70 minutes keeping the temperature −32 to −28° C. After one hour stirring, the solution was warmed to room temperature, and methanol (10 ml) was added slowly and then 0.5 M hydrochloric acid (300 ml) was dropped over 10 minutes. The solution was filtered after 40 minutes stirring and filtrate was extracted with dichloromethane. The combined organic layer was washed with 0.5 M hydrochloric acid, 0.1M aqueous sodium hydroxide and brine and dried over anhydrous sodium sulfate. Concentration of the organic layer yielded 2-bromo-(1S)-1-(4-bromophenyl)ethanol (77 g) as a pale brown oil.

(2S)-2-(4-Bromophenyl) oxirane

Aqueous sodium hydroxide (1M, 400 ml) was added to 2-bromo-(1S)-1-(4-bromophenyl)ethanol (77.0 g) in diethyl ether (400 ml) and stirred at room temperature for 5 hours. The organic layer was separated and aqueous layer was extracted with ether. The combined organic layer was washed with brine and dried over anhydrous sodium sulfate. Removal of the solvent yielded (2S)-2-(4-bromophenyl) oxirane (55.0 g) as a pale brown oil.

(1S)-1-(4-Bromophenyl)-2-((1R)-1-phenylethylamino)ethanol

A mixture of (2S)-2-(4-bromophenyl)oxirane (55.0 g) and (R)-1-phenylethylamine (98.2 g, 810 mmol) was heated at 80° C. for 6 hours. Addition of isopropyl ether (200 ml) to the residue after distillation of excess phenethylamine and successive filtration yielded (1S)-1-(4-bromophenyl)-2-((1R)-1-phenylethylamino) ethanol (57.0 g) as white crystals. Further crystallization was performed by the concentration of the filtrate in vacuo and cooling the residue in refrigerator. Filtration of the crystal with isopropyl ether (30 ml) yielded additional title compound (5.60 g) as crystals (72.4% yield, 3 steps).

(6S)-6-(4-Bromophenyl)-4-((1R)-1-phenyethyl)morpholin-3-one

A solution of chloroacetyl chloride (24.3 g, 215 mmol) in dichloromethane (100 ml) was dropped into the ice-cooled solution of (1S)-1-(4-bromophenyl)-2-((1R)-1-phenylethylamino)ethanol (62.6 g, 215 mmol) and triethylamine (21.8 g, 215 mmol) in dichloromethane (600 ml) over 30 minutes and the mixture was stirred for one hour at the same temperature. Resulting solution was washed with 0.5 M hydrochloric acid, saturated sodium hydrogen carbonate, brine and dried over anhydrous magnesium sulfate. The solvents were removed under reduced pressure and potassium hydroxide (85%, 16.1 g, 244 mmol) was added to a solution of resulting pale brown oil in isopropyl alcohol (600 ml) and stirred for 16 hours. The solvent was removed in vacuo and the residue was partitioned between water and ethyl acetate. The organic layer was washed with 0.5 M hydrochloric acid, saturated sodium hydrogen carbonate, brine and dried over anhydrous magnesium sulfate. Removal of the solvent under reduced pressure furnished (6S)-6-(4-bromophenyl)-4-((1R)-1-phenyethyl) morpholin-3-one (70.2 g) as a brown oil.

(2S)-2-(4-Bromophenyl)-4-((1R)-1-phenylethyl) morpholine

A borane-tetrahydrofuran complex (1.0M solution in tetrahydrofuran, 510 ml, 510 mm) was added to the ice-cooled solution of (6S)-6-(4-bromophenyl)-4-((1R)-1-phenyethyl)-morpholin-3-one (70.2 g) in tetrahydrofuran (500 ml) over 45 minutes and the solution was stirred at the same temperature for one hour and room temperature for 30 minutes. After careful addition of methanol (60 ml) to the ice-cooled solution, the solvent was removed under reduced pressure and the residue in methanol (750 ml) and 1M aqueous sodium hydroxide (280 ml) was stirred at 80° C. for one hour with addition of 1M aqueous sodium hydroxide (70 ml) in every 15 minutes. The solvent was removed under reduced pressure and the residue was partitioned between water and ethyl acetate. The organic layer was washed with water and brine and dried over anhydrous magnesium sulfate. Removal of the solvent yielded (2S)-2-(4-bromophenyl)-4-((1R)-1-phenylethyl)morpholine (65.0 g, 96.3% yield, 2 steps) as white crystals.

Melting point; 85-87° C.
IR: 1487, 1449, 1117, 1098, 809, 758, 699, 550 cm$^{-1}$
$^1$H-NMR (CDCl$_3$) δ: 1.35(3H,d), 2.10(2H,m), 2.60(1H, m), 3.05(1H,m), 3.35(1H,q), 3.75(1H,m), 3.89(1H,m), 4.55 (1H,m), 7.25(7H,m), 7.46(2H,d)

(2S)-2-(4-Aminophenyl)-4-((1R)-1-phenylethyl) morpholine

A solution of (2S)-2-(4-bromophenyl)-4-((1R)-1-phenylethyl)morpholine (15.6 g, 45 mmol), benzophenone imine (9 g, 50 mmol), tris(dibenzylideneacetone)-dipalladium(0)-chloroform adduct (0.93 g, 0.9 mmol), sodium tert-butoxide (6.0 g, 63 mmol) and 2-(di-t-butylphosphino)biphenyl (0.53 g, 1.8 mmol) in toluene (135 ml) was stirred at 95° C. for 4 hours. The solvent was removed in vacuo and the residue was partitioned between water and ethyl acetate. The organic layer was dried over anhydrous sodium sulfate and the solvent was removed under reduced pressure. To a solution of the resulting residue in tetrahydrofuran (180 ml) was added 6N hydrochloric acid (180 ml) and the mixture was stirred at room temperature for one hour. The solvent was removed in vacuo and the residue was partitioned between water and ethyl acetate. The organic layer was dried over anhydrous sodium sulfate and the solvent was evaporated. The resulting residue was purified by column chromatography on silica gel (hexane-AcOEt, 2:1) to give (2S)-2-(4-aminophenyl)-4-((1R)-1-phenylethyl)morpholine (12.2 g, 96%) as an oil.

N-(4-((2S)-4-((1R)-1-Phenylethyl)morpholin-2-yl) phenyl)acetamide

To a solution of (2S)-2-(4-aminophenyl)-4-((1R)-1-phenylethyl)morpholine (7.9 g, 28 mmol) and triethylamine (8.5 g, 84 mmol) in tetrahydrofuran (180 ml) was added acetyl chloride (4.4 g, 56 mmol). The mixture was stirred at room temperature for 2 hours and partitioned between water and chloroform. The organic extract was washed with brine and dried over anhydrous sodium sulfate. The solvent was removed under reduced pressure and the precipitated crystals were collected by filtration, washed with isopropyl ether to give N-(4-((2S)-4-((1R)-1-phenylethyl)morpholin-2-yl)phenyl)-acetamide (6.47 g, 71%) as yellow crystals.

N-(4-((2S)-Morpholin-2-yl)phenyl)acetamide

To a solution of N-(4-((2S)-4-((1R)-1-phenylethyl)morpholin-2-yl)phenyl)acetamide (6.47 g, 20 mmol) and ammonium formate (6.3 g, 100 mmol) in mixture of tetrahydrofuran (136 ml), methanol (270 ml) and water (70 ml) was added 10% palladium on carbon (wet, 270 mg) and the solution was stirred at 95° C. for 3 hours. After filtration, the solvent was removed in vacuo and the residue was partitioned between water and dichloromethane. The organic layer was dried over anhydrous sodium sulfate and the solvent was evaporated under reduced pressure to give N-(4-((2S)-morpholin-2-yl) phenyl)acetamide (5.78 g, quant.) as an yellow oil.

Reference Example 5

Synthesis of (2S)-2-(5-Cyano-2-methoxyphenyl)-morpholine hydrochloride

(2S)-2-Bromo-1-(5-bromo-2-methoxyphenyl)-ethanol

To a solution of (S)-2-methyl-CBS-oxazaborolidine (39.5 ml, 1.0 M solution in toluene, 39.5 mmol) was added borane-tetrahydrofuran complex (237 ml, 1.0 M solution in tetrahydrofuran, 237 mmol) at −40° C. To the resulting solution was added a solution of 5'-bromo-2'-methoxyphenacyl bromide (60.8 g, 197.4 mmol) in tetrahydrofuran (400 ml) through dropping funnel over one hour. After stirring for 3 hours below 0° C., methanol (ca. 50 ml) was added dropwise. After stirring the resulting solution for another 30 minutes at room temperature, the solvents were removed in vacuo. The residue was partitioned between ethyl acetate and 1N hydrochloric acid. The organic layer was washed with hydrochloric acid and brine, dried over anhydrous sodium sulfate, and concentrated under reduced pressure. The residue was used for the next reaction without further purification.

(2S)-2-(5-Bromo-2-methoxyphenyl)-oxirane

A mixture of (2S)-2-bromo-1-(5-bromo-2-methoxyphenyl)-ethanol in diethyl ether (250 ml) and potassium hydroxide (26.3 g, 395 mmol) in water (250 ml) was stirred vigorously until the consumption of the starting material. The organic layer was washed with brine, dried over anhydrous sodium sulfate, filtered, and concentrated under reduced pressure. The residue was used for the next reaction without further purification.

(2S)-2-Benzylamino-1-(5-bromo-2-methoxyphenyl)-ethanol

A mixture of (2S)-2-(5-bromo-2-methoxyphenyl)-oxirane and benzylamine (147 ml, 1.34 mol) was heated at 80° C. for 4.5 hours. The excess benzylamine was distilled off under reduced pressure. Washing of the residue with diethyl ether/hexane afforded (2S)-2-benzylamino-1-(5-bromo-2-methoxyphenyl)-ethanol (104.5 g, 70%, 3 steps) as white crystals.

(6S)-4-Benzyl-6-(5-bromo-2-methoxyphenyl)-morpholin-3-one

A solution of chloroacetyl chloride (24.3 g, 215 mmol) in dichloromethane (100 ml) was dropped into a mixture of (2S)-2-benzylamino-1-(5-bromo-2-methoxyphenyl)-ethanol (101.8 g, 302.7 mmol) in dichloromethane (600 ml) and 1N aqueous sodium hydroxide at 0° C. and stirred for one hour. The resulting solution was partitioned between water and dichloromethane. The organic layer was dried over anhydrous sodium sulfate, filtered, and concentrated under reduced pressure. Potassium hydroxide (34.0 g, 605 mmol) was added to a solution of the residue in 2-propanol (600 ml) and the solution was stirred for 16 hours. The solvent was removed in vacuo and the residue was partitioned between water and ethyl acetate. The organic layer was washed with brine and dried over anhydrous sodium sulfate. Removal of the solvent under reduced pressure gave (6S)-4-benzyl-6-(5-bromo-2-methoxyphenyl)-morpholin-3-one (108.7 g, 95%, 2 steps) as a pale yellow oil.

(2S)-4-Benzyl-2-(5-bromo-2-methoxyphenyl)-morpholine

A solution of (6S)-4-benzyl-6-(5-bromo-2-methoxyphenyl)-morpholin-3-one (67.2 g, 179 mmol) in tetrahydrofuran (200 ml) was added to an ice-cooled mixture of lithium borohydride (8.55 g, 393 mmol) and chlorotrimethylsilane (99.7 ml, 785 mmol) in tetrahydrofuran (500 ml) over 45 minutes and the solution was stirred at same temperature for one hour and then at room temperature for 5 hours. After careful addition of methanol (60 ml) to the ice-cooled solution, solvent was removed under reduced pressure and the residue in 10% aqueous sodium hydroxide (280 ml) was stirred at 90° C. for 3 hours. The solvents were removed under reduced pressure and the residue was partitioned between water and diethyl ether. The organic layer was washed with water and brine, dried over anhydrous sodium sulfate and concentrated in vacuo. Purification of the residue by silica gel column chromatography (hexane/ethyl acetate) gave (2S)-4-benzyl-2-(5-bromo-2-methoxyphenyl)-morpholine (46.1 g, 71%, 2 steps) as a yellow oil.

(2S)-4-Benzyl-2-(5-cyano-2-methoxyphenyl)-morpholine

A solution of (2S)-4-benzyl-2-(5-bromo-2-methoxyphenyl)-morpholine (17.1 g, 47.2 mmol) and copper cyanide (6.35 g, 70.9 mmol) in 1-methyl-2-pyrrolidinone (140 ml) was stirred at 160° C. for 9 hours. Diethyl ether and 1N aqueous sodium hydroxide were added to the reaction mixture, and the solution was passed through Celite column. The whole was extracted with diethyl ether. The organic layer was washed with brine, dried over anhydrous sodium sulfate and concentrated under reduced pressure. The resulting residue was purified by silica gel column chromatography (hexane/ethyl acetate) to give (2S)-4-benzyl-2-(5-cyano-2-methoxyphenyl)-morpholine (10.1 mg, 69%) as a yellow oil.

(2S)-2-(5-Cyano-2-methoxyphenyl)-morpholine hydrochloride

To a solution of (2S)-4-benzyl-2-(5-cyano-2-methoxyphenyl)-morpholine (10.8 g, 35.0 mmol) in 1,2-dichloroethane (80 ml) was added 1-chloroethyl chloroformate (5.73 ml, 52.5 mmol) at room temperature. Upon disappearance of the starting material, the reaction mixture was concentrated under reduced pressure. The residue was then dissolved in methanol (100 ml) and refluxed for 30 minutes. The solvents were removed in vacuo and the residue was filtered and washed with ethyl acetate to afford (2S)-2-(5-cyano-2-methoxyphenyl)-morpholine hydrochloride (8.08 g, 91%) as white solids.

$^1$H-NMR (DMSO-d6) δ: 2.91-3.36(4H,m), 3.91(3H, s), 3.95(1H, m), 4.13(1H, dd, J=12.3, 3.3 Hz), 5.06(1H, dd, J=11.1, 2.1 Hz), 7.25(1H, d, J=5.7 Hz), 7.77(1H, d, J=2.1 Hz), 7.86 (1H, dd, J=5.7, 2.1 Hz), 9.57(2H, m).

Reference Example 6

Synthesis of (2S)-2-(4-(N-methyl-N-((3R)-tetrahydrofuran-3-yl)amino)phenyl)-morpholine hydrochloride 4-((1R)-1-phenylethyl)-(2S)-2-(4-(N-((3R)-tetrahydrofuran-3-yl)amino)phenyl)-morpholine (R)-(+)-3-Aminotetrahydrofuran toluene-4-sulfonate (2.0 g, 7.7 mmol) was added to a suspension of (2S)-2-(4-bromophenyl)-4-((1R)-1-phenylethyl)morpholine (2.4 g, 6.9 mmol), palladium acetate (65 mg, 0.29 mmol), 2-(di-t-butylphosphino)biphenyl (170 mg, 0.57 mmol), and sodium tert-butoxide (3.4 g, 35.4 mmol) in tert-butanol (50 ml) at room temperature. After heating at 90° C. for 6 hours, the resulting suspension was passed through a Celite column. The filtrate was concentrated under reduced pressure, and the residue was purified by silica gel chromatography eluting 5-10% methanol in chloroform to afford 4-((1R)-1-phenylethyl)-(2S)-2-(4-(N-((3R)-tetrahydrofuran-3-yl)amino)phenyl)morpholine (1.3 g, 53%) as white crystals.

$^1$H-NMR (CDCl$_3$) δ: 1.35 (3H, d, J=6.8 Hz), 2.04-2.16 (4H, m), 2.55-2.62 (1H, m), 3.08-3.12 (1H, m), 3.33-3.38 (1H, m), 3.67-3.93 (5H, m), 3.98-4.02 (1H,m), 4.46-4.58 (2H,m), 6.57 (2H, d, J=7.2 Hz), 6.83 (1H, d, J=9.0 Hz), 7.21-7.33 (7H, m)

(2S)-2-(4-(N-methyl-N-((3R)-tetrahydrofuran-3-yl)amino)phenyl)-4-((1R)-1-phenylethyl)morpholine Sodium triacetoxyborohydride (2.4 g, 11.3 mmol) was added to a solution of 4-((1R)-1-phenylethyl)-(2S)-2-(4-(N-((3R)-tetrahydrofuran-3yl)amino)phenyl)-morpholine (1.3 g, 3.69 mmol) and formalin (35%, 1.6 g, 18.6 mmol) in dichloroethane (50 mL) at room temperature. After stirring for 2 hours, the resulting suspension was partitioned between ethyl acetate and 1 N sodium hydroxide. The aqueous layer was extracted with ethyl acetate. The combined organic layer was washed with brine, dried over magnesium sulfate, and concentrated in vacuo. The residue was purified by silica gel chromatography eluting 5-10% methanol in chloroform to furnish (2S)-2-(4-(N-methyl-N-((3R)-tetrahydrofuran-3-yl)amino)phenyl)-4-((1R)-1-phenylethyl)morpholine (1.35 g, 100%) as a pale yellow oil.

$^1$H-NMR (CDCl$_3$) δ: 1.33 (3H, d, J=6.8 Hz), 2.02-2.13(4H, m), 2.53-2.60 (1H, m), 3.00 (3H, s), 3.08-3.12 (1H, m), 3.30-3.34 (1H, m), 3.70-3.98 (5H, m), 4.00-4.06 (1H, m), 4.46-4.58 (2H, m), 6.60 (2H, d, J=7.2 Hz), 7.28-7.37 (7H, m)

(2S)-2-(4-(N-methyl-N-((3R)-tetrahydrofuran-3-yl)amino)phenyl)morpholine hydrochloride A solution of 10% palladium on carbon (1.0 g) and ((2S)-2-(4-(N-methyl-N-((3R)-tetrahydrofuran-3yl)amino)phenyl)-4-((1R)-1-phenylethyl)morpholine (3.69 mmol) in methanol (10 ml) was stirred under hydrogen atmosphere vigorously at 50° C. for 10 hours. The catalyst was filtered off with a Celite pad, and the filtrate was concentrated under reduced pressure. The residue was treated by 4N hydrogen chloride in ethyl acetate and concentrated under reduced pressure to give a pale yellow solid, which was recrystallized from ethanol to afford (2S)-2-(4-(N-methyl-N-((3R)-tetrahydrofuran-3yl)amino)phenyl)morpholine hydrochloride (0.9 g, 73%) as white crystals.

$^1$H-NMR (CDCl$_3$) δ: 2.99 (3H, s), 3.00-3.12 (2H, m), 3.23-3.28 (1H, m), 3.61-4.02 (9H, m), 4.51-4.53 (1H, m), 4.79 (1H, d, J=10.1 Hz), 7.42-7.48 (4H,m), 9.63 (2H, br)

Reference Example 7

Synthesis of (2S)-2-(4-(N-((3R)-tetrahydrofuran-3-yl)amino)phenyl)morpholine

To a solution of 4-((1R)-1-phenylethyl)-(2S)-2-(4-[N-{(3R)-tetrahydrofuran-3-yl}amino]phenyl)morpholine (0.40 g, 1.09 mmol) and ammonium formate (0.69 g, 10.9 mmol) in mixture of tetrahydrofuran (50 ml), methanol (100 ml) and water (16 ml) was added 10% palladium on carbon (wet, 150 mg) and stirred at 95° C. for one hour. After filtration, the solvent was removed in vacuo and the residue was partitioned between water and dichloromethane. The organic layer was dried over anhydrous sodium sulfate and the solvent was evaporated under reduced pressure to give (2S)-2-[4-{N-((3R)-tetrahydrofuran-3-yl)amino}phenyl]morpholine (0.28 g, quant.) as a colorless oil.

$^1$H-NMR (CDCl$_3$) δ: 1.90 (1H, m), 2.21 (1H, m), 2.80-2.98 (4H, m), 3.67-4.20 (9H, m), 4.36 (1H, d, J=10.2 Hz), 6.56 (2H, d, J=3.4 Hz), 7.18 (2H, d, J=3.4 Hz)

Reference Example 8

Synthesis of (2S)-2-(4-(1-acetylpiperidin-4-yloxy)phenyl)morpholine hydrochloride 2-Bromo-1-(4-hydroxyphenyl)-ethan-1-one Phenyltrimethylammonium tribromide (276 g, 734 mmol) was added to a suspension of 4-hydroxyacetophenone (100 g, 734 mmol) in tetrahydrofuran (1000 ml) at room temperature. After stirring for 3 hours, the resulting suspension was filtered, and the filtrate was concentrated under reduced pressure. The residue was washed with diisopropyl ether to afford 2-bromo-1-(4-hydroxyphenyl)-ethan-1-one (85 g, 54%) as white crystals.

$^1$H-NMR (CDCl$_3$) δ: 3.84 (1H, br), 4.40 (2H, s), 6.98 (2H, d, J=7.2 Hz), 7.91 (2H, d, J=7.2 Hz)

4-(2-Bromoacetyl)phenyl methanesulfonate

Methanesulfonyl chloride (50 g, 436 mmol) was added to a solution of 2-bromo-1-(4-hydroxyphenyl)-ethan-1-one (85 g, 395 mmol) and triethylamine (48 g, 474 mmol) in tetrahydrofuran (1000 ml) at 0° C. and the mixture was stirred for 30 minutes at room temperature. The mixture was partitioned between water and ethyl acetate, and the organic layer was washed with brine, dried over magnesium sulfate. The solvent was evaporated under reduced pressure and the residue was washed with diisopropyl ether to afford 4-(2-bromoacetyl)phenyl methanesulfonate (96 g, 83%) as white crystals.

$^1$H-NMR (CDCl$_3$) δ: 3.22 (3H, s), 4.41 (2H, s), 7.41 (2H, d, J=7.2 Hz), 8.06 (2H, d, J=7.2 Hz)

4-((2S)-2-Bromo-1-hydroxyethyl)phenyl Methanesulfonate

Borane-tetrahydrofuran complex (1.0 M solution in tetrahydrofuran, 330 ml) was added to a solution of (S)—CBS ((S)-2-methyl-CBS-oxazaborolidine, 50 ml, 1.0 M solution in toluene) at −30° C. over 15 minutes and stirred for 30 minutes. 4-(2-Bromoacetyl)phenyl methanesulfonate (96 g, 328 mmol) in tetrahydrofuran (500 ml) was dropped over 70 minutes keeping the temperature −32 to −28° C. After one hour stirring, the solution was warmed to room temperature, and methanol (10 ml) was added slowly and then 0.5 M hydrochloric acid (300 ml) was dropped over 10 minutes. The solution was filtered after 40 minutes stirring and filtrate was extracted with ethyl acetate. The combined organic layer was washed with 0.5 M hydrochloric acid, 0.1M aqueous sodium hydroxide and brine and dried over anhydrous sodium sulfate. Concentration of the organic layer yielded 4-((2S)-2-bromo-1-hydroxyethyl)phenyl methanesulfonate as a pale brown oil.

$^1$H-NMR (CDCl$_3$) δ: 2.72 (1H, d, J=1.2 Hz), 3.10 (3H, s), 3.44-3.58 (2H, m), 4.93-4.97 (1H, m), 7.30 (2H, d, J=7.2 Hz), 7.46 (2H, d, J=7.2 Hz)

4-((S)-Oxiranyl)phenyl methanesulfonate

Aqueous sodium hydroxide (1M, 600 ml) was added to 4-((2S)-2-bromo-1-hydroxyethyl)phenyl methanesulfonate (328 mmol) in diethyl ether (400 ml) and stirred at room temperature for 5 hours. The organic layer was separated and aqueous layer was extracted with ethyl acetate. The combined organic layer was washed with brine and dried over anhydrous sodium sulfate. The solvent was evaporated under reduced pressure and the residue was washed with diisopropyl ether to afford 4-((S)-oxiranyl)phenyl methanesulfonate (69 g, 98%) as white crystals.

$^1$H-NMR (CDCl$_3$) δ: 2.75 (1H, dd, J=1.2 Hz, 6.8 Hz), 3.14-3.16 (4H, m), 3.88 (1H, dd, J=1.2 Hz, 7.2 Hz), 7.28 (2H, d, J=7.2 Hz), 7.42 (2H, d, J=7.2 Hz)

4-((1S)-2-benzylamino-1-hydroxyethyl)phenyl methanesulfonate

A mixture of 4-((S)-oxiranyl)phenyl methanesulfonate (69 g, 322 mmol) and benzylamine (104 g, 971 mmol) was heated at 80° C. for 3 hours. An excess benzylamine was evaporated under reduced pressure and the residue was washed with diisopropyl ether to afford 4-((1S)-2-benzylamino-1-hydroxyethyl)phenyl methanesulfonate (71.0 g, 69%) as white crystals.

$^1$H-NMR (CDCl$_3$) δ: 2.68-2.72 (1H, m), 2.96 (1H, dd, J=4.8 Hz, 10.2 Hz), 3.12 (3H, s), 3.84 (2H, d, J=1.2 Hz), 4.72 (1H, dd, J=1.2 Hz, 10.2 Hz), 7.23-7.43 (9H, m)

4-((2S)-4-Benzyl-5-oxo-morpholin-2-yl)phenyl methanesulfonate

Chloroacetyl chloride (27.5 g, 243 mmol) was dropped to a solution of 4-((1S)-2-benzylamino-1-hydroxyethyl)phenyl methanesulfonate (71 g, 221 mmol) in 1N aqueous sodium hydroxide (330 ml) and stirred for one hour at room temperature. Resulting solution was extracted with chloroform, and dried over anhydrous sodium sulfate. The solvent was removed under reduced pressure and potassium hydroxide (85%, 17.5 g, 265 mmol) was added to a solution of resulting pale brown oil in 2-propanol (600 ml) and stirred for 10 hours. The solvent was removed in vacuo and the residue was partitioned between water and chloroform. The organic layer was washed with 0.5 M hydrochloric acid, saturated sodium hydrogen carbonate, brine and dried over anhydrous magnesium sulfate. Removal of the solvent under reduced pressure furnished 4-((2S)-4-benzyl-5-oxo-morpholin-2-yl)phenyl methanesulfonate (79.8 g, 100%) as a brown oil.

$^1$H-NMR (CDCl$_3$) δ: 3.13 (3H, s), 3.29-3.36 (2H, m), 4.36-4.46 (4H, m), 4.81 (1H, dd, J=1.2 Hz, 10 Hz), 7.24-7.42 (9H, m)

(2S)-4-Benzyl-2-(4-hydroxyphenyl)morpholine

Chlorotrimethylsilane (96 g, 884 mmol) was added to a solution of lithium borohydride (9.6 g, 441 mmol) in tetrahydrofuran (500 ml) and the solution was stirred for one hour at room temperature. A solution of 4-((2S)-4-benzyl-5-oxo-morpholin-2-yl)phenyl methanesulfonate (79.8 g, 221 mmol) in tetrahydrofuran (200 ml) was added to the solution and stirred at room temperature for one hour. After careful addition of methanol (60 ml) under ice-cooling, the solvent was removed under reduced pressure. Potassium hydroxide (145 g, 2.2 mol) was added to a solution of the residue in ethanol (300 ml) and water (300 ml) and the solution was stirred at 80° C. for 2 hours. The solvents were removed under reduced pressure and the residue was extracted with ethyl acetate and dried over anhydrous magnesium sulfate. Removal of the solvent yielded (2S)-4-benzyl-2-(4-hydroxyphenyl)morpholine (39.8 g, 67%) as white crystals.

$^1$H-NMR (CDCl$_3$) δ: 2.05-2.31 (2H, m), 2.72-2.89 (2H, m), 3.54 (2H, s), 3.81-3.86 (1H, m), 3.96-4.00 (1H, m), 4.50 (1H, dd, J=1.2 Hz, 10.2 Hz), 5.12 (1H, br), 6.75 (2H, d, J=7.2 Hz), 7.19-1.32 (7H, m)

(2S)-2-(4-(1-Acetylpiperidin-4-yloxy)phenyl)-4-benzylmorpholine

Diisopropylazodicarboxylate (40% in toluene, 5.7 g, 11.3 mmol) was added to a solution of (2S)-2-(4-hydroxyphenyl)-4-benzylmorpholine (2.0 g, 7.43 mmol), triphenylphosphine (3.0 g, 11.4 mmol) and 1-acetyl-4-hydroxypiperidin (1.6 g, 11.2 mmol) in tetrahydrofuran (40 ml) at room temperature and the mixture stirred for 10 hours. The mixture was partitioned between ethyl acetate and water. The organic layer was washed with brine, dried over magnesium sulfate, and concentrated in vacuo. The solvent was evaporated under reduced pressure, and the residue was purified by silica gel column chromatography eluting 10-50% ethyl acetate in hexane to furnish (2S)-2-(4-(1-acetylpiperidin-4-yloxy)phenyl)-4-benzylmorpholine (1.68 g, 57%) as colorless oil.

$^1$H-NMR (CDCl$_3$) δ: 1.68-1.89 (4H, m), 2.11 (9H, s), 2.11-2.15 (1H, m), 2.24-2.31 (1H, m), 2.73-2.89 (2H, m), 3.33-3.40 (1H, m), 3.54 (2H, s), 3.65-3.85 (4H, m), 3.97-4.01 (1H, m), 4.89-4.53 (2H, m), 6.85 (2H, d, J=6.8 Hz), 7.24-7.33 (7H, m) (CDCl$_3$)

(2S)-2-(4-(1-acetylpiperidin-4-yloxy)phenyl)morpholine hydrochloride

1-Chloroethyl chloroformate (0.92 g, 6.43 mmol) was added to a solution of (2S)-2-(4-(1-acetylpiperidin-4-yloxy)phenyl)-4-benzylmorpholine (1.68 g, 4.26 mmol) in dichloroethane (30 ml). The reaction mixture was stirred vigorously at room temperature for 10 hours. The solvent was evaporated under reduced pressure and methanol (40 ml) was added to the residue. The mixture was heated at 80° C. for one hour, and then the solvent was evaporated under reduced pressure to give a white solid, which was recrystallized from ethanol to afford (2S)-2-(4-(1-acetylpiperidin-4-yloxy)phenyl)morpholine hydrochloride (1.3 g, 100%) as white crystals.

$^1$H-NMR (CDCl$_3$) δ: 1.45-1.61 (2H, m), 11.80-1.95 (2H, m), 2.01 (3H, s), 2.84-3.42 (6H, m), 3.67-3.92 (4H, m), 4.61-4.63 (1H, m), 4.72 (1H, dd, J=1.2 Hz 10.2 Hz), 7.00 (2H, d, J=6.8 Hz), 7.23 (2H, d, J=6.8 Hz), 9.78 (2H, br) (DMSO-d$_6$)

Reference Example 9

Synthesis of 4-((2S)-morpholin-2-yl)phenylamine

To a solution of (2S)-2-(4-aminophenyl)-4-((1R)-1-phenylethyl)morpholine (17.45 g, 61.8 mmol) and ammonium formate (11.7 g, 185.4 mmol) in a mixture of tetrahydrofuran (180 ml), methanol (180 ml) and water (45 ml) was added 10% palladium on carbon (wet, 1.8 g) and the solution was stirred at 95° C. for 3 hours. After filtration, the solvent was removed in vacuo and the residue was partitioned between water and dichloromethane. The organic layer was dried over anhydrous sodium sulfate and the solvent was evaporated under reduced pressure to give 4-((2S)-morpholin-2-yl)phenylamine (10.45 g, 95%) as pale yellow crystals.

$^1$H-NMR (CDCl$_3$) δ: 2.46-2.50 (2H, m), 2.68 (2H, d, J=5.8 Hz), 2.76 (1H, d, J=12.2 Hz), 3.52 (1H, m), 3.79 (1H, d, J=10.9 Hz), 4.13 (1H, d, J=9.7 Hz), 4.95 (2H, br.s), 6.49 (2H, d, J=8.1 Hz), 6.94 (2H, d, J=8.1 Hz).

Reference Example 10

Synthesis of (2S)-2-(4-([1,2,4]oxadiazol-3-yl)phenyl)piperazine dihydrochloride (2S)-1,4-Dibenzyl-2-(4-bromophenyl)piperazine Hydrogen chloride in ethyl acetate solution (4N) was added to a solution of di-tert-butyl (2S)-2-(4-bromophenyl)piperazine-1,4-dicarboxylate (10 g, 22.7 mmol) in methanol (50 ml). The mixture was stirred for one hour at room temperature and the solvent was evaporated under reduced pressure to give white solid. The mixture was partitioned between saturated aqueous sodium bicarbonate and chloroform. The organic layer was washed with brine, dried over magnesium sulfate and concentrated in vacuo to afford (2S)-2-(4-bromophenyl)piperazine as white crystals. Benzylbromide (9.7 g, 56.7 mmol) was added to a solution of sodium hydride (60% in oil, 2.0 g, 50 mmol) and (2S)-2-(4-bromophenyl)piperazine in tetrahydrofuran (50 ml) at room temperature and the mixture was stirred for one hour. The mixture was partitioned between water and chloroform. The organic layer was washed with brine, dried over magnesium sulfate and concentrated in vacuo. The residue was purified by silica gel column chromatography eluting 5-10% methanol in chloroform to furnish (2S)-1,4-Dibenzyl-2-(4-bromophenyl)piperazine (6.1 g, 64%) as a colorless oil.

$^1$H-NMR (CDCl$_3$) δ: 2.48-2.70 (6H, m), 3.48 (2H, s), 3.60 (2H, s), 4.24 (1H, d, J=10.0 Hz), 7.05-7.20 (10H, m), 7.28 (2H, d, J=7.2 Hz), 7.43(2H, d, J=7.2 Hz).

4-((2S)-1,4-Dibenzylpiperazin-2-yl)benzaldehyde n-Butyllithium (1.56M in hexane, 14 ml, 21.8 mmol) was added to a solution of (2S)-1,4-dibenzyl-2-(4-bromophenyl)piperazine (6.1 g, 14.5 mmol) in tetrahydrofuran (60 ml) at −78° C. After one hour stirring, dimethylformamide (1.6 g, 21.9 mmol) was added and the solution was stirred for one hour. The mixture was partitioned between water and chloroform. The organic layer was washed with brine, dried over magnesium sulfate and concentrated in vacuo. The residue was purified by silica gel column chromatography eluting 5-10% methanol in chloroform to furnish 4-((2S)-1,4-dibenzylpiperazin-2-yl)benzaldehyde (1.6 g, 41%) as a colorless oil.

$^1$H-NMR (CDCl$_3$) δ: 2.48-2.72 (6H, m), 3.58 (2H, s), 3.68 (2H, s), 4.32 (1H, d, J=10.0 Hz), 7.10-7.24 (10H, m), 7.28 (2H, d, J=7.2 Hz), 7.46(2H, d, J=7.2 Hz), 9.98 (1H, s).

4-((2S)-1,4-Dibenzylpiperazin-2-yl)benzonitrile

Hydroxylamine hydrochloride (0.5 g, 7.75 mmol) was added to a solution of 4-((2S)-1,4-dibenzylpiperazin-2-yl)benzaldehyde (2.2 g, 5.94 mmol) in 1N aqueous sodium hydroxide (10 ml) and ethanol (10 ml) at room temperature and stirred for 2 hours. The mixture was partitioned between water and chloroform. The organic layer was washed with brine, dried over magnesium sulfate and concentrated in vacuo. The residue was dissolved in acetic acid (10 ml) and was stirred at 80° C. for 6 hours. The solvent was removed under reduced pressure and the residue was partitioned between saturated aqueous sodium bicarbonate and chloroform. The organic layer was washed with brine, dried over magnesium sulfate and concentrated in vacuo. The residue was purified by silica gel column chromatography eluting 5-10% methanol in chloroform to furnish 4-((2S)-1,4-dibenzylpiperazin-2-yl)benzonitrile (1.4 g, 64%) as a colorless oil.

$^1$H-NMR (CDCl$_3$) δ: 2.45-2.68 (6H, m), 3.54 (2H, s), 3.62 (2H, s), 4.26 (1H, d, J=10.0 Hz), 7.07-7.14 (10H, m), 7.30 (2H, d, J=7.2 Hz), 7.46(2H, d, J=7.2 Hz).

Di-tert-butyl (2S)-2-(4-cyanophenyl)piperazine-1,4-dicarboxylate

1-Chloroethyl chloroformate (2.7 g, 18.9 mmol) was added to a solution of 4-((2S)-1,4-dibenzylpiperazin-2-yl)benzonitrile (1.4 g, 3.81 mmol) in dichloroethane (30 ml). The reaction mixture was vigorously stirred at room temperature for 10 hours. The solvent was evaporated under reduced pressure and methanol (40 ml) was added to the residue. The mixture was heated at 80° C. for one hour and the solvent was evaporated under reduced pressure to afford (2S)-2-(4-cyanophenyl)piperazine as white crystals. Di-tert-butyl di-carbonate (1.9 g, 8.71 mmol) was added to a solution of triethylamine (1.2 g, 11.9 mmol) and (2S)-2-(4-cyanophenyl)piperazine in tetrahydrofuran (50 ml) at room temperature and the mixture was stirred at 50° C. for one hour. The mixture was partitioned between water and ethyl acetate. The organic layer was washed with brine, dried over magnesium sulfate and concentrated in vacuo. The residue was purified by silica gel column chromatography eluting 10-20% ethyl acetate in hexane to furnish di-tert-butyl (2S)-2-(4-cyanophenyl)piperazine-1,4-dicarboxylate (1.2 g, 81%) as white crystals.

$^1$H-NMR (CDCl$_3$) δ: 1.41 (9H, s), 1.45 (9H, s), 2.91-2.98 (2H, m), 3.34-3.40 (1H, m), 3.86-3.98 (2H, m), 4.39-4.44 (1H, m), 5.52 (1H, br), 7.42 (2H, d, J=7.2 Hz), 7.66 (2H, d, J=7.2 Hz).

(2S)-2-(4-([1,2,4]Oxadiazol-3-yl)phenyl)piperazine dihydrochloride

Hydroxylamine hydrochloride (1.3 g, 20.2 mmol) and sodium carbonate (3.4 g, 32.1 mmol) were added to a solution of di-tert-butyl (2S)-2-(4-cyanophenyl)piperazine-1,4-dicarboxylate (2.5 g, 6.45 mmol) in ethanol (15 ml) and water (15 ml) at the room temperature and the solution was stirred at 80° C. for 2 hours. The mixture was partitioned between water and chloroform. The organic layer was washed with brine, dried over magnesium sulfate and concentrated in vacuo. Triethyl orthoformate (9.6 g, 64.8 mmol) and p-toluenesulfonic acid monohydrate (0.12 g, 0.63 mmol) were added to a solution of the residue in toluene (25 ml) and stirred at 90° C. for 2 hours. The mixture was partitioned between water and ethyl acetate. The organic layer was washed with brine, dried over magnesium sulfate and concentrated in vacuo. The residue was purified by silica gel column chromatography eluting 10-20% ethyl acetate in hexane to furnish di-tert-butyl (2S)-2-(4-([1,2,4]oxadiazol-3-yl)phenyl)-piperazine-1,4-dicarboxylate (1.94 g, 70%) as a colorless oil. Hydrogen chloride in ethyl acetate (4N) was added to a solution of di-tert-butyl (2S)-2-(4-([1,2,4]oxadiazol-3-yl)phenyl)piperazine-1,4-dicarboxylate (1.94 g, 4.51 mmol) in methanol and the mixture was stirred at room temperature for one hour. The solvent was evaporated under reduced pressure to give white solid, which was washed with ethyl acetate to afford (2S)-2-(4-([1,2,4]oxadiazol-3-yl)phenyl)piperazine dihydrochloride (1.3 g, 95%) as white crystals.

1H-NMR (DMSO) δ: 3.43-3.72 (6H, m), 4.82 (1H, d=10.2 Hz), 7.89 (2H, d, J=7.0 Hz), 8.15 (2H, d, J=7.0 Hz), 9.79 (1H, s), 10.21 (4H, br).

Reference Example 11

Synthesis of (2S)-2-(4-(5-methyl-[1,2,4]oxadiazol-3-yl)phenyl)piperazine dihydrochloride Hydroxylamine hydrochloride (1.3 g, 20.2 mmol) and sodium carbonate (3.4 g, 32.1 mmol) were added to a solution of di-tert-butyl (2S)-2-(4-cyanophenyl)piperazine-1,4-dicarboxylate (2.5 g, 6.45 mmol) in ethanol (15 ml) and water (15 ml) at room temperature and the solution was stirred at 80° C. for 2 hours. The mixture was partitioned between water and chloroform. The organic layer was washed with brine, dried over magnesium sulfate and concentrated in vacuo. Triethyl orthoacetate (10.5 g, 64.7 mmol) and p-toluenesulfonic acid monohydrate (0.12 g, 0.63 mmol) were added to the solution of the residue in toluene (25 ml) and the solution was stirred at 90° C. for 2 hours. The mixture was partitioned between water and ethyl acetate. The organic layer was washed with brine, dried over magnesium sulfate and concentrated in vacuo. The residue was purified by silica gel column chromatography eluting 10-20% ethyl acetate in hexane to furnish (2S)-2-(4-(5-methyl-[1,2,4]oxadiazol-3-yl)phenyl)piperazine-1,4-dicarboxylate (1.0 g, 35%) as a colorless oil. Hydrogen chloride in ethyl acetate (4N) was added to a solution of (2S)-2-(4-(5-methyl-[1,2,4]oxadiazol-3-yl)phenyl)piperazine-1,4-dicarboxylate (1.0 g, 2.25 mmol) in methanol and the mixture stirred at room temperature for one hour. The solvent was evaporated under reduced pressure to give a white solid, which was washed with ethyl acetate to afford (2S)-2-(4-(5-Methyl-[1,2,4]oxadiazol-3-yl)phenyl)piperazine dihydrochloride (0.64 g, 100%) as white crystals.

$^1$H-NMR (DMSO) δ: 2.69 (3H, s), 3.45-3.73 (6H, m), 4.80 (1H, d, J=10.2 Hz), 7.86 (2H, d, J=7.2 Hz), 8.10 (2H, d, J=7.2 Hz), 10.12(4H, br).

Reference Example 12

Synthesis of morpholin-4-yl-((2S)-4-morpholin-2-yl-phenyl)-methanone

4-[(2S)-4-((1R)-1-phenylethyl)-morpholin-2-yl]-benzoic acid

To a suspension of (2S)-2-(4-bromophenyl)-4-((1R)-1-phenylethyl)morpholine (3.46 g, 10.0 mmol) in tetrahydrofuran (80 ml) was added n-butyllithium (7.7 ml, 12.0 mmol, 1.56 M in hexane) at −78° C. After stirring for 10 minutes, excess of dry ice was added to the mixture and the reaction mixture was maintained at −78° C. for 1.5 hours and then partitioned between diethyl ether and 0.2 N aqueous sodium hydroxide. The aqueous layer was washed with diethyl ether and neutralized with 1N hydrochloric acid. The resulting aqueous layer was extracted with ethyl acetate. The organic layer was washed with brine, dried over sodium sulfate and concentrated in vacuo. Filtration of the precipitate gave 4-[(2S)-4-((1R)-1-phenyl-ethyl)-morpholin-2-yl]-benzoic acid (3.05 g, 98%) as white crystals.

$^1$H-NMR (CDCl$_3$) δ: 1.39(3H, d, J=6.9 Hz), 2.10-2.18(2H, m), 2.63(1H,m), 3.15(1H,m), 3.41(1H, q, J=6.9 Hz), 3.78

(1H, m), 3.93(1H, m), 4.55(1H, dd, J=10.2, 2.1 Hz), 7.25-7.39 (5H,m), 7.47(2H, d, J=8.4 Hz), 8.07(2H, d, J=8.4 Hz).

Morpholin-4-yl-{4-[(2S)-4-((1R)-1-phenyl-ethyl)-morpholin-2-yl]-phenyl}-methanone 1,1'-Carbonyldiimidazole (357 mg, 2.20 mmol) was added to a solution of 4-[(2S)-4-((1R)-1-phenylethyl)-morpholin-2-yl]-benzoic acid (623 mg, 2.00 mmol) in dichloromethane at 0° C. After stirring for 2 hours, morpholine (0.35 ml, 4.0 mmol) was added to the reaction mixture. After stirring over night, the resulting suspension was concentrated in vacuo. The residue was purified by silica gel column chromatography (hexane/ethyl acetate) to afford morpholin-4-yl-{4-[(2S)-4-((1R)-1-phenylethyl)-morpholin-2-yl]-phenyl}-methanone (465 mg, 60%.) as a colorless oil.

$^1$H-NMR (CDCl$_3$) δ: 1.36(3H, d, J=6.9 Hz), 2.01-2.14(2H, m), 2.59-2.63(1H, m), 3.07-3.12(1H,m), 3.36(1H, q, J=6.9 Hz), 3.37-3.78(9H, m), 3.90-3.91(1H, m), 4.62(1H, dd, J=10.2, 2.4 Hz), 7.24-7.44(9H, m).

Morpholin-4-yl-((2S)-4-morpholin-2-yl-phenyl)-methanone

A solution of morpholin-4-yl-{4-[(2S)-4-((1R)-1-phenylethyl)-morpholin-2-yl]-phenyl}-methanone (465 mg, 1.20 mmol) and 20% palladium hydroxide on carbon (0.50 g) in ethanol (6.0 ml) was stirred under hydrogen atmosphere at room temperature for 10 hours. The mixture was passed through Celite column and the organic layer was concentrated under reduced pressure to yield morpholin-4-yl-((2S)-4-morpholin-2-yl-phenyl)-methanone (331 mg, 100%) as a clear oil.

MS (M+1): 277

Reference Example 13

Synthesis of N$^2$,N$^2$-Dimethyl-N$^1$-(4-((2S)-morpholin-2-yl)phenyl)glycinamide 2-Chloro-N-[(2S)-4-{((1R)-1-phenylethyl)morpholin-2-yl}phenyl]acetamide To a solution of (2S)-2-(4-aminophenyl)-4-((1R)-1-phenylethyl)morpholine (2.93 g, 10 mmol) and triethylamine (3.0 g, 30 mmol) in tetrahydrofuran (50 ml) was added chloroacetyl chloride (2.26 g, 20 mmol). The mixture was stirred at room temperature for 2 hours and partitioned between water and dichloromethane. The organic extract was washed with brine and dried over anhydrous sodium sulfate. The solvent was removed under reduced pressure and the precipitated crystals were collected by filtration, washed with isopropyl ether to give 2-chloro-N-((2S)-4-(((1R)-1-phenylethyl) morpholin-2-yl)phenyl)acetamide (3.5 g, 97%) as yellow crystals.

$^1$H-NMR (CDCl$_3$) δ 1.35 (3H, d, J=6.6 Hz), 2.02-2.17 (2H, m), 2.60 (1H, d, J=11.1 Hz), 3.08 (1H, d, J=11.1 Hz), 3.36 (1H, q, J=6.9 Hz), 3.75 (1H, td, J=11.4 Hz and 2.4 Hz), 3.91 (1H, dd, J=9.9 Hz and 1.5 Hz), 4.19 (2H, s), 4.57 (1H, dd, J=10.2 Hz and 2.1 Hz), 7.23-7.32 (5H, m), 7.36 (2H, d, J=8.4 Hz), 7.51 (2H, d, J=8.1 Hz), 8.21 (1H, br.s).

N$^2$,N$^2$-Dimethyl-N$^1$-(4-((2S)-4-((1R)-1-phenylethyl) morpholin-2-yl)phenyl)glycinamide A solution of 2-chloro-N-((2S)-4-(((1R)-1-phenylethyl) morpholin-2-yl)phenyl)acetamide (0.9 g, 2.5 mmol), potassium carbonate (1.72 g, 12.5 mmol), and dimethylamine hydrochloride (1.00 g, 12.5 mmol) in tetrahydrofuran (40 ml) and acetonitrile (80 ml) was stirred at 95° C. for 10 hours. After filtration, the solvent was removed in vacuo and the residue was partitioned between water and dichloromethane. The organic layer was dried over anhydrous sodium sulfate and the solvent was evaporated under reduced pressure give N$^2$,N$^2$-dimethyl-N$^1$-(4-((2S)-4-((1R)-1-phenylethyl)morpholin-2-yl)phenyl)glycinamide (1.15 g, quant.) as an yellow oil.

$^1$H-NMR (CDCl$_3$) δ: 1.35 (3H, d, J=6.6 Hz), 2.05-2.13 (2H, m), 2.38 (6H, s), 2.57 (1H, m), 3.07 (2H, s), 3.10 (1H, m), 3.35 (1H, q, J=6.6 Hz), 3.72 (1H, m), 3.90 (1H, m), 4.56 (1H, dd, J=10.2 Hz and 2.1 Hz), 7.20-7.39 (7H, m), 7.56 (2H, d, J=8.4 Hz), 9.90 (1H, br.s).

N$^2$,N$^2$-Dimethyl-N$^1$-(4-((2S)-morpholin-2-yl)phenyl)glycinamide

To a solution of N$^2$,N$^2$-dimethyl-N$^1$-(4-((2S)-4-((1R)-1-phenylethyl)morpholin-2-yl)phenyl)glycinamide (0.91 g, 2.5 mmol) and ammonium formate (0.79 g, 12.5 mmol) in mixture of tetrahydrofuran (20 ml), methanol (40 ml) and water (7 ml) was added 10% palladium on carbon (wet, 300 mg) and stirred at 95° C. for 3 hours. After filtration, the solvent was removed in vacuo and the residue was partitioned between water and dichloromethane. The organic layer was dried over anhydrous sodium sulfate and the solvent was evaporated under reduced pressure to give N$^2$,N$^2$-dimethyl-N$^1$-(4-((2S)-morpholin-2-yl)phenyl)glycinamide (0.63 g, 96%) as a colorless oil.

$^1$H-NMR (CDCl$_3$) δ: 2.05-2.13 (2H, m), 2.38 (6H, s), 2.57 (1H, m), 3.07 (2H, s), 3.10 (1H, m), 3.72 (1H, m), 3.90 (1H, m), 4.56 (1H, dd, J=10.2 Hz and 2.1 Hz), 7.35 (2H, d, J=8.4 Hz), 7.56 (2H, d, J=8.4 Hz), 9.90 (1H, br.s).

Reference Example 14

Synthesis of 2-Trimethyl-N-(4-((2S)-morpholin-2-yl)phenyl)acetamide

2-Trimethyl-N-(4-((2S)-4-((1R)-1-phenylethyl)morpholin-2-yl)phenyl)acetamide

To a solution of (2S)-2-(4-aminophenyl)-4-((1R)-1-phenylethyl)morpholine (0.68 g, 2.4 mmol) and triethylamine (0.73 g, 7.2 mmol) in tetrahydrofuran (50 ml) was added trimethylacetyl chloride (0.44 g, 3.6 mmol). The mixture was stirred at room temperature for 2 hours and partitioned between water and ethyl acetate. The organic extract was washed with brine and dried over anhydrous sodium sulfate. The solvent was removed under reduced pressure and the precipitated crystals were collected by filtration, washed with isopropyl ether to give 2-trimethyl-N-(4-((2S)-4-((1R)-1-phenylethyl)morpholin-2-yl)phenyl)acetamide (0.88 g, quant.) as yellow crystals.

$^1$H-NMR (CDCl$_3$) δ: 1.30 (9H, s), 1.34 (3H, d, J=6.3 Hz), 2.01-2.12 (2H, m), 2.58 (1H, dd, J=11.4 Hz, 1.2 Hz), 3.06 (1H, d, J=11.4 Hz), 3.34 (1H, q, J=6.9 Hz), 3.72 (1H, m), 3.88 (1H, m), 4.57 (1H, dd, J=10.2 Hz and 2.1 Hz), 6.98-7.56 (10H, m).

2-Trimethyl-N-(4-((2S)-morpholin-2-yl)phenyl)acetamide

To a solution of N$^2$,N$^2$-dimethyl-N$^1$-(4-((2S)-4-((1R)-1-phenylethyl)morpholin-2-yl)phenyl)glycinamide (0.88 g, 3.2 mmol) and ammonium formate (1.00 g, 16 mmol) in mixture of tetrahydrofuran (500 ml), methanol (100 ml) and water (50 ml) was added 10% palladium on carbon (wet, 300 mg) and the solution was stirred at 95° C. for 3 hours. After filtration, the solvent was removed in vacuo and the residue was partitioned between water and dichloromethane. The organic layer was dried over anhydrous sodium sulfate and the solvent was evaporated under reduced pressure to give 2-trimethyl-N-(4-((2S)-morpholin-2-yl)phenyl)acetamide (0.63 g, 96%) as a colorless oil.

Reference Example 15

Synthesis of (3R)-3-(4-Bromophenyl)piperidine

N-Acetyl-(3R)-3-(4-bromophenyl)piperidine

Chiral resolution of the racemate of N-acetyl-3-(4-bromophenyl)piperidine by HPLC (column: CHIRALPAK AS-H, eluent: n-hexanelethanol=80/20 (v/v)) afforded N-acetyl-(3R)-3-(4-bromophenyl)piperidine as colorless crystals.
$^1$H-NMR (CDCl$_3$) δ: 1.58-1.71 (3H, m), 1.34 (1H, d, J=11.4 Hz), 2.11 (3H, s), 2.49 (2H, m), 3.06 (1H, td, J=11.7 Hz, 4.8 Hz), 3.86 (1H, m), 4.69 (1H, m), 7.11 (2H, d, J=8.4 Hz), 7.45 (2H, d, J=8.4 Hz, 10.5 Hz).

(3R)-3-(4-Bromophenyl)piperidine

To a solution of N-acetyl-(3R)-3-(4-bromophenyl)piperidine (2.88 g, 13.2 mmol) in mixture of tetrahydrofuran (24 ml), methanol (24 ml) and water (12 ml) was added lithium hydroxide monohydrate (3.8 g, 92.4 mmol) and stirred at 95° C. for 2 hours. After filtration, the solvent was removed in vacuo and the residue was partitioned between water and dichloromethane. The organic layer was dried over anhydrous sodium sulfate and the solvent was evaporated under reduced pressure to give (3R)-3-(4-bromophenyl)piperidine (2.3 g, 87%) as colorless crystals that was used in the next step without further purification.

Example 1

6-(3-Fluoro-pyridin-4-yl)-3-methyl-2-((3S)-3-(4-morpholin-4-yl-phenyl)-piperazin-1-yl)-3H-pyrimidin-4-one (Compound No. 7)

(3R)-3-(4-(morpholin-4-yl)phenyl)piperazine trihydrochloride was prepared from di-tert-butyl (2R)-2-(4-bromophenyl)-piperazine-1,4-dicarboxylate by the same route as that in Reference Example 10.
To a solution of the above prepared (3R)-3-(4-(morpholin-4-yl)phenyl)piperazine trihydrochloride (0.5 g, 1.40 mmol) and triethylamine (0.8 g, 7.91 mmol) in tetrahydrofuran (10 ml) was added 2-chloro-6-(3-fluoropyridin-4-yl)-3-methyl-(3H)-pyrimidin-4-one (0.3 g, 1.25 mmol) which was prepared by Reference Example 2 portionwise. After stirring for 12 hours, the resulting suspension was partitioned between chloroform and 1N sodium hydroxide and the aqueous layer was extracted with chloroform. The combined organic layer was washed with brine, dried over magnesium sulfate, and concentrated in vacuo. The residue was purified by silica gel column chromatography eluting 5-10% methanol in chloroform to furnish 6-(3-fluoro-pyridin-4-yl)-3-methyl-2-((3S)-3-(4-morpholin-4-yl-phenyl)-piperazin-1-yl)-3H-pyrimidin-4-one (0.41 g, 0.91 mmol, 73%) as white crystals.

Example 2

6-(3-Fluoro-pyridin-4-yl)-3-methyl-2-((3S)-3-(4-piperidin-1-yl-phenyl)-piperazin-1-yl)-3H-pyrimidin-4-one (Compound No. 14)

A solution of (2S)-2-(4-piperidin-1-yl-phenyl)-piperazine trihydrochloride obtained in Reference Example 3 (199 mg, 0.561 mmol) and triethylamine (427 µl, 306 mmol) in tetrahydrofuran was refluxed for 15 minutes. After cooling to room temperature, 2-chloro-6-(3-fluoropyridin-4-yl)-3-methyl-3H-pyrimidin-4-one (122 mg, 0.510 mmol) was added portionwise and the mixture was stirred overnight. The reaction mixture was concentrated in vacuo and the residue was dissolved in dichloromethane and aqueous sodium bicarbonate, and the solution was passed through CHEM ELUT CE1010 (manufactured by VARIAN). The filtrate was concentrated, and the resulting residue was washed with diethyl ether. Hydrogen chloride in ethyl acetate (4N) was added to a solution of the resulting solids in ethyl acetate, and the precipitate was collected by the filtration and dried to furnish 6-(3-fluoro-pyridin-4-yl)-3-methyl-2-((3S)-3-(4-piperidin-1-yl-phenyl)-piperazin-1-yl)-3H-pyrimidin-4-one trihydrochloride (267 mg, 0.479 mmol, 94%) as pale yellow powder.

Example 3

2-((2S)-2-(4-(Dimethylamino)phenyl)morpholin-4-yl)-6-(3-fluoropyridin-4-yl)-3-methyl-3H-pyrimidin-4-one (Compound No. 36)

A solution of (2S)-2-(4-(dimethylamino)phenyl)morpholine hydrochloride (0.20 g, 0.64 mmol), 2-chloro-1-methyl-6-oxo-4-(3-fluoropyridin-4-yl)-1,6-dihydropyrimidine (0.12 g, 0.53 mmol), and triethylamine (0.19 g, 1.92 mmol) in tetrahydrofuran (10 ml) was stirred at 95° C. for 3 hours. The solvent was evaporated off in vacuo and the residue treated with water and dichloromethane. The organic layer was dried over anhydrous sodium sulfate and the solvent was evaporated under reduced pressure. The obtained residue was purified by column chromatography on silica gel (chloroform-methanol, 10:1) to afford 2-((2S)-2-(4-(dimethylamino)phenyl)morpholin-4-yl)-6-(3-fluoropyridin-4-yl)-3-methyl-3H-pyrimidin-4-one (0.10 g, 50%) as yellow crystals Example 4

N-(4-((2S)-4-((4-(3-Fluoro-pyridin-4-yl)-1-methyl-6-oxo-1,6-dihydro-pyrimidin-2-yl)-morpholin-2-yl)-phenyl)-acetamide (Compound No. 143)

A solution of N-(4-((2S)-morpholin-2-yl)phenyl)acetamide obtained in Reference Example 4 (0.20 g, 0.91 mmol), 2-chloro-1-methyl-6-oxo-4-(3-fluoropyridin-4-yl)-1,6-dihydropyrimidine (0.19 g, 0.82 mmol), and triethylamine (0.41 g, 4.05 mmol) in tetrahydrofuran (10 ml) was stirred at 95° C. for 3 hours. The solvent was evaporated off in vacuo and the residue was treated with water and dichloromethane. The organic layer was dried over anhydrous sodium sulfate and the solvent was evaporated under reduced pressure. The obtained residue was purified by column chromatography on silica gel (chloroform-methanol, 10:1) to afford N-(4-((2S)-4-((4-(3-fluoro-pyridin-4-yl)-1-methyl-6-oxo-1,6-dihydro-pyrimidin-2-yl)-morpholin-2-yl)-phenyl)-acetamide (0.05 g, 14%) as a yellow oil.

Example 5

6-(2,3-Dichloropyridin-4-yl)-2-((2S)-2-(4-fluorophenyl)morpholin-4-yl)-3-methyl-3H-pyrimidin-4-one (Compound No. 254)

To a solution of (2S)-2-(4-fluorophenyl)morpholine hydrochloride (0.8 g, 3.68 mmol) and triethylamine (2.1 g, 20.8 mmol) in tetrahydrofuran (20 ml) was added 2-chloro-6-(2,3-dichloropyridin-4-yl)-3-methyl-3H-pyrimidin-4-one (2.0 g, 6.88 mmol) portionwise and the mixture was stirred for 12 hours. The resulting suspension was partitioned between chloroform and 1N sodium hydroxide and the aqueous layer was extracted with chloroform. The combined organic layer was washed with brine, dried over magnesium sulfate, and concentrated in vacuo. The residue was purified by silica gel chromatography eluting 5-10% methanol in chloroform to furnish 6-(2,3-dichloropyridin-4-yl)-2-((2S)-2-(4-fluorophenyl)morpholin-4-yl)-3-methyl-3H-pyrimidin-4-one (1.1 g, 2.53 mmol, 69%) as white crystals.

Example 6-1

6-(3-Fluoropyridin-4-yl)-3-methyl-2-(morpholin-4-yl)-3H-pyrimidin-4-one (Compound No. 2)

To a solution of morpholine (3.2 g, 36.7 mmol) and triethylamine (10.2 g, 101 mmol) in tetrahydrofuran (80 ml) was added 2-chloro-6-(3-fluoropyridin-4-yl)-3-methyl-3H-pyrimidin-4-one (8.0 g, 32.4 mmol) portionwise and stirred for 12 hours. The resulting suspension was partitioned between chloroform and 1N sodium hydroxide and the aqueous layer was extracted with chloroform. The combined organic layer was washed with brine, dried over magnesium sulfate, and concentrated in vacuo. The residue was purified by silica gel chromatography eluting 5-10% methanol in chloroform to furnish 6-(3-fluoropyridin-4-yl)-3-methyl-2-(morpholin-4-yl)-3H-pyrimidin-4-one (8.9 g, 30.7 mmol, 92%) as white crystals.

Example 6-2

6-(3-Methoxypyridin-4-yl)-3-methyl-2-(morpholin-4-yl)-3H-pyrimidin-4-one (Compound No. 172)

A suspension of 6-(3-fluoropyridin-4-yl)-3-methyl-2-(morpholin-4-yl)-3H-pyrimidin-4-one obtained in Example 6-1 (0.60 g, 2.07 mmol), and sodium methoxide (1.37 g, 25.4 mmol) in tetrahydrofuran (15 ml) was heated at 60° C. for 3 hours. The resulting suspension was partitioned between chloroform and brine and the aqueous layer was extracted with chloroform. The combined organic layer was washed with brine, dried over magnesium sulfate, and concentrated in vacuo. The residue was purified by silica gel chromatography eluting 5-10% methanol in chloroform to furnish 6-(3-methoxypyridin-4-yl)-3-methyl-2-(morpholin-4-yl)-3H-pyrimidin-4-one (0.40 g, 1.32 mmol, 64%) as white crystals.

Example 7

6-(3-Chloro-2-methoxypyridin-4-yl)-2-((2S)-2-(4-fluorophenyl)morpholin-4-yl)-3-methyl-3H-pyrimidin-4-one (Compound No. 174)

A suspension of 6-(2,3-dichloropyridin-4-yl)-2-((2S)-2-(4-fluorophenyl)morpholin-4-yl)-3-methyl-3H-pyrimidin-4-one (0.50 g, 1.15 mmol), and sodium methoxide (1.1 g, 20.4 mmol) in tetrahydrofuran (10 ml) was heated at 60° C. for 5 hours. The resulting suspension was partitioned between chloroform and brine and the aqueous layer was extracted with chloroform. The combined organic layer was washed with brine, dried over magnesium sulfate, and concentrated in vacuo. The residue was purified by silica gel chromatography eluting 5-10% methanol in chloroform to furnish 6-(3-chloro-2-methoxypyridin-4-yl)-2-((2S)-2-(4-fluorophenyl) morpholin-4-yl)-3-methyl-3H-pyrimidin-4-one (0.27 g, 0.58 mmol, 50%) as white crystals.

Example 8

6-(3-(4-Fluorobenzyloxy)pyridin-4-yl)-3-methyl-2-(morpholin-4-yl)-3H-pyrimidin-4-one (Compound No. 176)

To a solution of 2-(morpholin-4-yl)-3-methyl-6-(3-fluoropyridin-4-yl)-3H-pyrimidin-4-one (0.60 g, 2.07 mmol), and 4-fluorobenzyl alcohol (3.3 g, 26.2 mmol) in tetrahydrofuran (15 ml) was added sodium hydride (1.03 g, 2.58 mmol) at 0° C. After stirring at 60° C. for 5 hours, the resulting suspension was partitioned between chloroform and brine and the aqueous layer was extracted with chloroform. The combined organic layer was washed with brine, dried over magnesium sulfate, and concentrated in vacuo. The residue was purified by silica gel chromatography eluting 5-10% methanol in chloroform to furnish colorless oil. The methanol (10 ml) solution of resulting oil was treated with 4N hydrochloric acid (5 ml). The residue obtained by evaporation was washed by ethyl acetate to furnish 6-(3-(4-fluorobenzyloxy)pyridin-4-yl)-3-methyl-2-(morpholin-4-yl)-3H-pyrimidin-4-one hydrochloride (0.23 g, 0.53 mmol, 31%) as white crystals.

Example 9

6-(3-(2-(4-Fluorophenyl)ethylamino)pyridin-4-yl)-3-methyl-2-(morpholin-4-yl)-3H-pyrimidin-4-one (Compound No. 192)

A suspension of 6-(3-fluoropyridin-4-yl)-3-methyl-2-(morpholin-4-yl)-3H-pyrimidin-4-one (0.60 g, 2.07 mmol), and 2-(4-fluorophenyl)ethylamine (2.9 g, 20.8 mmol) was heated at 120° C. for 8 hours. The resulting suspension was partitioned between chloroform and brine and the aqueous layer was extracted with chloroform. The combined organic layer was washed with brine, dried over magnesium sulfate, and concentrated in vacuo. The residue was purified by silica gel chromatography eluting 5-10% methanol in chloroform to furnish a colorless oil. The methanol (10 ml) solution of resulting oil was treated with 4N hydrochloric acid (5 ml). The residue obtained by evaporation was washed by ethyl acetate to furnish 6-(3-(2-(4-fluorophenyl)ethylamino)pyridin-4-yl)-3-methyl-2-(morpholin-4-yl)-3H-pyrimidin-4-one hydrochloride (0.45 g, 1.01 mmol, 49%) as white crystals.

Example 10-1

6-(2-chloropyridin-4-yl)-2-((2S)-2-(5-cyano-2-methoxyphenyl)morpholin-4-yl)-3-methyl-3H-pyrimidin-4-one (Compound No. 270)

(2S)-2-(5-Cyano-2-methoxyphenyl)-morpholine hydrochloride obtained in Reference Example 5 and 2-chloro-6-(2-chloropyridin-4-yl)-3-methyl-3H-pyrimidin-4-one were reacted as the same manner as Example 1 to afford 6-(2- chloropyridin-4-yl)-2-((2S)-2-(5-cyano-2-methoxyphenyl) morpholin-4-yl)-3-methyl-3H-pyrimidin-4-one.

Example 10-2

2-((2S)-2-(5-Cyano-2-methoxyphenyl)morpholin-4-yl)-3-methyl-6-(2-methylaminopyridin-4-yl)-3H-pyrimidin-4-one (Compound No. 279)

A suspension of 6-(2-chloropyridin-4-yl)-2-((2S)-2-(5-cyano-2-methoxyphenyl) morpholin-4-yl)-3-methyl-3H-pyrimidin-4-one obtained in Example 10-1 (0.80 g, 1.83 mmol), and diethanolamine (1.0 g, 9.51 mmol) in N-methylformamide (8 ml) was heated at 150° C. for 48 hours. The resulting suspension was partitioned between chloroform and brine and the aqueous layer was extracted with chloroform. The combined organic layer was washed with brine, dried over magnesium sulfate, and concentrated in vacuo. The residue was purified by silica gel chromatography eluting 5-10% methanol in chloroform to furnish 2-((2S)-2-(5-cyano-2-methoxyphenyl)-morpholin-4-yl)-3-methyl-6-(2-methylaminopyridin-4-yl)-3H-pyrimidin-4-one (0.036 g, 0.084 mmol, 5.0%) as white crystals.

Example 11

6-(3-Fluoropyridin-4-yl)-2-((2S)-2-(4-(N-methyl-N-((3R)-tetrahydrofuran-3yl)amino)phenyl)morpholin-4-yl)-3-methyl-3H-pyrimidin-4-one (Compound No. 221)

2-Chloro-3-methyl-6-(3-fluoropyridin-4-yl)-3H-pyrimidin-4-one (0.26 g, 1.09 mmol) was added to a solution of (2S)-2-(4-(N-methyl-N-((3R)-tetrahydrofuran-3yl)amino) phenyl)morpholine hydrochloride obtained in Reference Example 6 (0.4 g, 1.19 mmol) and triethylamine (0.6 g, 5.93 mmol) in tetrahydrofuran (20 ml) at room temperature for 15 hours. The mixture was partitioned between water and chloroform. The organic layer was washed with brine, dried over magnesium sulfate, and concentrated in vacuo. The residue was purified by silica gel column chromatography eluting 5-10% methanol in chloroform to furnish 6-(3-fluoropyridin-4-yl)-2-((2S)-2-(4-(N-methyl-N-((3R)-tetrahydrofuran-3-yl)amino)-phenyl)morpholin-4-yl)-3-methyl-3H-pyrimidin-4-one (0.20 g, 39%) as white crystals.

Example 12

2-((2S)-2-(4-(1-Acetylpiperidin-4-yloxy)phenyl) morpholin-4-yl)-6-(3-fluoropyridin-4-yl)-3-methyl-pyrimidin-4-one (Compound No. 238)

2-Chloro-3-methyl-6-(3-fluoropyrimidin-4-yl)-3H-pyrimidin-4-one (0.21 g, 0.88 mmol) was added to a solution of (2S)-2-(4-(1-acetylpiperidin-4-yloxy)phenyl)-morpholine hydrochloride obtained in Reference Example 8 (0.30 g, 0.88 mmol) and triethylamine (0.45 g, 4.15 mmol) in tetrahydrofuran (20 ml) and the solution was stirred at room temperature for 15 hours. The mixture was partitioned between water and chloroform. The organic layer was washed with brine, dried over magnesium sulfate, and concentrated in vacuo. The residue was purified by silica gel column chromatography eluting 5-10% methanol in chloroform to furnish 2-((2S)-2-(4-(1-acetylpiperidin-4-yloxy)phenyl)morpholin-4-yl)-6-(3-fluoropyridin-4-yl)-3-methyl-pyrimidin-4-one (0.26 g, 58%) as white crystals.

Example 13

2-((2S)-2-(4-Aminophenyl)morpholin-4-yl)-6-(3-fluoropyridin-4-yl)-3-methyl-3H-pyrimidin-4-one (Compound No. 158)

2-Chloro-3-methyl-6-(3-fluoropyrimidin-4-yl)-3H-pyrimidin-4-one (1.1 g, 4.59 mmol) was added to a solution of (2S)-2-(4-aminophenyl)morpholine hydrochloride (1.0 g, 4.66 mmol) and triethylamine (1.4 g, 13.8 mmol) in tetrahydrofuran (20 ml) at room temperature and the solution was stirred for 15 hours. The solvent was removed in vacuo and the residue was partitioned between water and chloroform. The organic layer was dried over anhydrous sodium sulfate and the solvent was removed under reduced pressure. The resulting residue was purified by silica gel column chromatography eluting 5-10% methanol in chloroform to furnish 2-((2S)-2-(4-aminophenyl)morpholin-4-yl)-6-(3-fluoropyridin-4-yl)-3-methyl-3H-pyrimidin-4-one (0.80 g, 46%) as white crystals.

Example 14

Methyl (4-((2S)-4-(6-(3-fluoropyridin-4-yl)-3-methyl-4-oxo-3H-pyrimidin-2-yl)morpholin-2-yl)phenyl)carbamate (Compound No. 295)

Methyl chloroformate (0.13 g, 1.38 mmol) was added to a solution of 2-((2S)-2-(4-aminophenyl)morpholine-4-yl)-6-(3-fluoropyridin-4-yl)-3-methyl-3H-pyrimidin-4-one obtained in Example 13 (0.35 g, 0.92 mmol) and triethylamine (0.25 g, 2.47 mmol) in tetrahydrofuran (20 ml) and the solution was stirred at room temperature for one hour. The mixture was partitioned between water and chloroform. The organic layer was washed with brine, dried over magnesium sulfate, and concentrated in vacuo. The residue was purified by silica gel column chromatography eluting 5-10% methanol in chloroform to furnish methyl (4-((2S)-4-(6-(3-fluoropyridin-4-yl)-3-methyl-4-oxo-3H-pyrimidin-2-yl)morpholin-2-yl)phenyl)carbamate (0.17 g, 42%) as white crystals.

Example 15

N'-(4-((2S)-4-(6-(3-Fluoropyridin-4-yl)-3-methyl-4-oxo-3H-pyrimidin-2-yl)morpholin-2-yl)phenyl)-N, N-dimethylurea (Compound No. 298)

N,N-Dimethylcarbamoyl chloride (0.26 g, 2.41 mmol) was added to a solution of 2-((2S)-2-(4-aminophenyl)morpholine-4-yl)-3-methyl-6-(3-fluoropyridin-4-yl)-3H-pyrimidin-4-one (0.45 g, 1.18 mmol) and triethylamine (1.2 g, 11.9 mmol) in tetrahydrofuran (20 ml) and the solution was stirred at 50° C. for 48 hours. The mixture was partitioned between water and chloroform. The organic layer was washed with brine, dried over magnesium sulfate, and concentrated in vacuo. The residue was purified by silica gel column chromatography eluting 5-10% methanol in chloroform to furnish N'-(4-((2S)-4-(6-(3-fluoropyridin-4-yl)-3-methyl-4-oxo-3H-pyrimidin-2-yl)morpholin-2-yl)phenyl)-N,N-dimethylurea (0.35 g, 67%) as white crystals.

Example 16

6-(3-Fluoropyridin-4-yl)-3-methyl-2-((3S)-3-(4-([1, 2,4]oxadiazol-3-yl)phenyl)piperazin-1-yl)-3H-pyrimidin-4-one (Compound No. 322)

2-Chloro-3-methyl-6-(3-fluoropyrimidin-4-yl)-3H-pyrimidin-4-one (0.31 g, 1.29 mmol) was added to a solution of (2S)-2-(4-([1,2,4]oxadiazol-3-yl)phenyl)-piperazine dihydrochloride obtained in Reference Example 10 (0.40 g, 1.32 mmol) and triethylamine (0.70 g, 6.92 mmol) in tetrahydrofuran (20 ml) at room temperature and the solution was stirred for 15 hours. The mixture was partitioned between water and chloroform. The organic layer was washed with brine, dried over magnesium sulfate, and concentrated in vacuo. The residue was purified by silica gel column chromatography eluting 5-10% methanol in chloroform to furnish 6-(3-fluoropyridin-4-yl)-3-methyl-2-((3S)-3-(4-([1,2,4]oxadiazol-3-yl)phenyl)piperazin-1-yl)-3H-pyrimidin-4-one (0.46 g, 82%) as white crystals.

Example 17

6-(3-Fluoropyridin-4-yl)-3-methyl-2-((3S)-3-(4-(5-methyl-[1,2,4]oxadiazol-3-yl)phenyl)piperazin-1-yl)-3H-pyrimidin-4-one (Compound No. 334)

2-Chloro-3-methyl-6-(3-fluoropyrimidin-4-yl)-3H-pyrimidin-4-one (0.17 g, 0.71 mmol) was added to a solution of (2S)-2-(4-(5-methyl-[1,2,4]oxadiazol-3-yl)phenyl)piperazine dihydrochloride obtained in Reference Example 11 (0.20 g, 0.71 mmol) and triethylamine (0.35 g, 3.46 mmol) in tetrahydrofuran (10 ml) at room temperature and the solution was stirred for 15 hours. The mixture was partitioned between water and chloroform. The organic layer was washed with brine, dried over magnesium sulfate, and concentrated in vacuo. The residue was purified by silica gel column chromatography eluting 5-10% methanol in chloroform to furnish 6-(3-fluoropyridin-4-yl)-3-methyl-2-((3S)-3-(4-(5-methyl-[1,2,4]oxadiazol-3-yl)phenyl)piperazin-1-yl)-3H-pyrimidin-4-one (0.16 g, 51%) as white crystals.

Example 18

6-(3-Fluoro-pyridin-4-yl)-3-methyl-2-{(2S)-2-[4-morpholine-4-carbonyl]-phenyl}-morpholin-4-yl)-3H-pyrimidin-4-one (Compound No. 310)

A solution of morpholin-4-yl-((2S)-4-morpholin-2-yl-phenyl)-methanone obtained in Reference Example 12 (110 mg, 0.40 mmol), 2-chloro-3-methyl-6-(3-fluoro-4-pyridyl)-pyrimidine-4-one (71 mg, 0.30 mmol) and triethylamine (0.20 ml) in tetrahydrofuran (4.0 ml) was stirred at room temperature for 6 hours. The reaction mixture was evaporated in vacuo and the residue was washed with water and diethyl ether. Filtrating the precipitate gave 6-(3-fluoro-pyridin-4-yl)-3-methyl-2-{(2S)-2-[4-morpholine-4-carbonyl]-phenyl}-morpholin-4-yl}-3H-pyrimidin-4-one (99.6 mg, 69%) as white crystals.

Example 19

2-((2S)-2-(4-(N-((3R)-Tetrahydrofuran-3-yl)amino)phenyl)morpholin-4-yl)-3-methyl-6-(3-fluoropyridin-4-yl)-3H-pyrimidin-4-one (Compound No. 220)

A solution of 2-chloro-6-(3-fluoropyridin-4-yl)-3-methyl-3H-pyrimidin-4-one (0.08 g, 0.35 mmol), (2S)-2-(4-(N-((3R)-tetrahydrofuran-3-yl)amino)phenyl)morpholine obtained in Reference Example 7 (0.11 g, 0.44 mmol) and triethylamine (0.22 g, 2.2 mmol) in tetrahydrofuran (10 ml) was stirred at 95° C. for 3 hours. The mixture was partitioned between water and dichloromethane, and the organic layer was washed with brine, dried over anhydrous sodium sulfate, and concentrated in vacuo. The residue was purified by silica gel column chromatography eluting 5-10% methanol in chloroform to furnish 2-((2S)-2-(4-(N-((3R)-tetrahydrofuran-3-yl)amino)phenyl)-morpholin-4-yl)-3-methyl-6-(3-fluoropyridin-4-yl)-3H-pyrimidin-4-one (0.07 g, 47%) as pale yellow crystals.

Example 20

$N^2,N^2$-Dimethyl-$N^1$-(4-((2S)-4-(3-methyl-4-oxo-3,4-dihydro-6-(3-fluoropyridin-4-yl)pyrimidin-2-yl)morpholin-2-yl)phenyl)glycinamide (Compound No. 288)

A solution of $N^2,N^2$-dimethyl-$N^1$-(4-((2S)-morpholin-2-yl)phenyl)glycinamide obtained in Reference Example 13 (0.21 g, 0.8 mmol), 2-chloro-6-(3-fluoropyridin-4-yl)-3-methyl-3H-pyrimidin-4-one (0.15 g, 0.64 mmol), and triethylamine (0.40 g, 4 mmol) in tetrahydrofuran (10 ml) was stirred at 95° C. for one hour. The solvent was removed in vacuo and the residue was partitioned between water and dichloromethane. The organic layer was dried over anhydrous sodium sulfate and the solvent was removed under reduced pressure. The resulting residue was purified by silica gel column chromatography (chloroform/methanol=10/1) to afford $N^2,N^2$-dimethyl-$N^1$-(4-((2S)-4-(3-methyl-4-oxo-3,4-dihydro-6-(3-fluoropyridin-4-yl)pyrimidin-2-yl)-morpholin-2-yl)phenyl)glycinamide (0.15 g, 50%) as colorless crystals.

Example 21

2-Trimethyl-N-(4-((2S)-4-(3-methyl-4-oxo-3,4-dihydro-6-(3-fluoropyridin-4-yl))pyrimidin-2-yl)morpholin-2-yl)phenyl)acetamide (Compound No. 215)

A solution of 2-trimethyl-N-(4-((2S)-morpholin-2-yl)phenyl)acetamide obtained in Reference Example 14 (0.13 g, 0.5 mmol), 2-chloro-6-(3-fluoropyridin-4-yl)-3-methyl-3H-pyrimidine-4-one (0.08 g, 0.4 mmol), and triethylamine (0.25 g, 2.5 mmol) in tetrahydrofuran (10 ml) was stirred at 95° C. for one hour. The solvent was removed in vacuo and the residue was partitioned between water and dichloromethane. The organic layer was dried over anhydrous sodium sulfate and the solvent was removed under reduced pressure. The resulting residue was purified by silica gel column chromatography (chloroform/methanol=10/1) to afford 2-trimethyl-N-(4-((2S)-4-(3-methyl-4-oxo-3,4-dihydro-6-(3-fluoropyridin-4-yl))pyrimidin-2-yl)morpholin-2-yl)phenyl)acetamide (0.17 g, 47%) as colorless crystals.

Example 22

2-((3R)-3-(4-Bromophenyl)piperidin-1-yl)-6-(3-fluoropyridin-4-yl)-3-methyl-3H-pyrimidine-4-one (Compound No. 303)

A solution of (3R)-3-(4-bromophenyl)piperidine obtained in Reference Example 15 (0.21 g, 0.9 mmol), 2-chloro-6-(3-fluoropyridin-4-yl)-3-methyl-3H-pyrimidine-4-one (0.21 g, 0.9 mmol), and triethylamine (0.30 g, 3.0 mmol) in tetrahydrofuran (10 ml) was stirred at 95° C. for 3 hours. The solvent was removed in vacuo and the residue was partitioned between water and dichloromethane. The organic layer was dried over anhydrous sodium sulfate and the solvent was removed under reduced pressure. The resulting residue was purified by silica gel column chromatography (chloroform/methanol=10/1) to afford 2-((3R)-3-(4-bromophenyl)piperidin-1-yl)-6-(3-fluoropyridin-4-yl)-3-methyl-3H-pyrimidine-4-one (0.24 g, 62%) as colorless crystals.

The compounds in the following table were prepared in the same manner as the methods described above. The compound numbers in the following table correspond to those shown in the above-described table of preferred compounds.

TABLE 2

| Compound No. | 1H-NMR δ: | [M + 1] |
|---|---|---|
| 1 | 2.97-3.00 (1H, m), 3.14-3.17 (1H, m), 3.47 (3H, s), 3.66-3.74 (2H, m), 3.85-3.89 (1H, m), 4.03-4.07 (1H, m), 4.74 (1H, dd, J = 1.2, 10.2 Hz), 6.60 (1H, s), 7.20 (2H, dd, J = 6.8, 7.3 Hz), 7.48 (2H, dd, J = 6.8, 7.3 Hz), 7.98 (1H, dd, J = 1.2, 4.2 Hz), 8.56 (1H, d, J = 4.2 Hz), 8.68 (1H, d, J = 1.2 Hz) (DMSO-d6) | 385 |
| 2 | 3.29-3.32 (4H, m), 3.41 (3H, s), 3.73-3.77 (4H, m), 6.59 (1H, s), 8.00 (1H, dd, J = 1.2, 4.2 Hz), 8.56 (1H, d, J = 4.2 Hz), 8.71 (1H, d, J = 1.2 Hz) (DMSO-d6) | 291 |
| 3 | 2.71-2.78 (1H, m), 3.14-3.18 (1H, m), 3.47 (3H, s), 3.62-3.66 (1H, m), 3.78-3.91 (5H, m), 4.06-4.10 (1H, m), 4.95 (1H, dd, J = 1.2, 10.2 Hz), 6.60 (1H, s), 7.05 (1H, d, =7.3 Hz), 7.12 (1H, s), 7.42 (1H, d, J = 7.3 Hz), 8.00 (1H, dd, J = 1.2, 4.2 Hz), 8.56 (1H, d, J = 4.2 Hz), 8.69 (1H, d, J = 1.2 Hz) (DMSO-d6) | 431 |
| 4 | 3.23-3.27 (1H, m), 3.32-3.35 (1H, m), 3.47 (3H, s), 3.62-3.66 (1H, m), 3.88-4.05 (3H, m), 5.00 (1H, dd, J = 1.2, 10.2 Hz), 6.62 (1H, s), 6.98 (1H, s), 7.23-7.35 (2H, m), 7.58-7.66 (2H, m), 8.01 (1H, dd, J = 1.2, 4.2 Hz), 8.57 (1H, d, J = 4.2 Hz), 8.71 (1H, d, J = 1.2 Hz) (DMSO-d6) | 407 |
| 5 | 3.22-3.27 (1H, m), 3.48 (3H, s), 3.49-3.51 (1H, m), 3.64-3.88 (3H, m), 4.00-4.04 (1H, m), 5.27 (1H, dd, J = 1.2, 10.2 Hz), 6.61 (1H, s), 7.25-7.50 (3H, m), 8.55 (1H, d, J = 4.2 Hz), 8.70 (1H, d, J = 1.2 Hz) (DMSO-d6) | 419 |
| 6 | 2.76-2.84 (1H, m), 3.18-3.23 (1H, m), 3.48 (3H, s), 3.63-3.67 (1H, m), 3.83-3.93 (5H, m), 4.09-4.14 (1H, m), 5.00 (1H, dd, J = 1.2, 10.2 Hz), 6.61 (1H, s), 7.24 (1H, d, J = 7.3 Hz), 7.76 (1H, s), 7.85 (1H, d, J = 7.3 Hz), 7.99-8.03 (1H, m), 8.57 (1H, d, J = 4.2 Hz), 8.70 (1H, d, J = 1.2 Hz) (DMSO-d6) | 422 |
| 7 | 2.81-2.86 (1H, m), 2.98-3.10 (7H, m), 3.43 (3H, s), 3.55-3.75 (6H, m), 3.87-3.90 (1H, m), 6.56 (1H, s), 6.93 (2H, d, J = 7.3 Hz), 7.32 (2H, d, J = 7.3 Hz), 7.94-7.98 (1H, m), 8.32 (1H, s), 8.56 (1H, d, J = 4.2 Hz), 8.69 (1H, d, J = 1.2 Hz) (DMSO-d6) | 451 |
| 8 | 3.07-3.19 (5H, m), 3.28 (1H, m), 3.50-3.63 (2H, m), 3.56 (3H, s), 3.86 (4H, m), 3.97 (1H, m), 4.13 (1H, m), 4.65 (1H, dd, J = 1.9, 10.4 Hz), 6.88 (1H, s), 6.93 (2H, d, J = 8.7 Hz), 7.31 (2H, d, J = 8.7 Hz), 7.95 (1H, dd, J = 5.4, 6.9 Hz), 8.51 (1H, d, J = 5.4 Hz), 8.55 (1H, d, J = 3.3 Hz) (CDCl$_3$) | 452 |
| 9 | 2.05 (6H, m), 2.22 (1H, m), 2.84 (1H, m), 3.98 (1H, m), 3.00-3.60 (8H, m), 3.56 (3H, s), 3.97 (1H, m), 4.12 (1H, m), 4.60 (1H, d, J = 10.4 Hz), 6.56 (2H, d, J = 8.7 Hz), 6.88 (1H, s), 7.29 (2H, d, J = 8.7 Hz), 7.96 (1H, dd, J = 5.4, 6.9 Hz), 8.50 (1H, d, J = 5.4 Hz), 8.55 (1H, d, J = 3.3 Hz) (CDCl$_3$) | 480 |
| 10 | 3.05 (1H, dd, J = 10.5, 12.9 Hz), 3.27 (1H, m), 3.50-3.63 (2H, m), 3.58 (3H, s), 4.00 (1H, m), 4.15 (1H, m), 4.70 (1H, dd, J = 1.9, 10.4 Hz), 6.89 (1H, s), 7.29 (2H, d, J = 9.0 Hz), 7.54 (2H, d, J = 9.0 Hz), 7.92 (1H, dd, J = 5.4, 6.9 Hz), 8.51 (1H, d, J = 5.4 Hz), 8.56 (1H, d, J = 3.3 Hz) (CDCl$_3$) | 446 |
| 11 | 2.29 (3H, s), 3.02-3.04 (5H, m), 3.21-3.23 (5H, m), 3.58 (3H, s), 3.52-3.61 (2H, m), 3.98 (1H, m), 4.14 (1H, m), 4.63 (1H, dd, J = 1.2, 9.6 Hz), 5.73 (1H, m), 6.88 (1H, s), 6.93 (2H, d, J = 8.7 Hz), 7.23 (3H, m), 7.41 (2H, dd, J = 7.5, 8.1 Hz), 7.79 (2H, d, J = 9.3 Hz), 7.94 (1H, dd, J = 5.4, 6.9 Hz), 8.51 (1H, d, J = 5.4 Hz), 8.56 (1H, d, J = 3.3 Hz) (CDCl$_3$) | 607 |
| 12 | 2.86-2.89 (1H, m), 3.08-3.12 (1H, m), 3.52-3.62 (5H, m), 3.86-4.06 (2H, m), 4.73 (1H, dd, J = 1.2, 10.2 Hz), 7.22 (2H, dd, J = 6.8 Hz, 7.3 Hz), 7.46 (2H, dd, J = 6.8 Hz, 7.3 Hz), 7.71-7.75 (1H, m), 8.60 (1H, d, J = 4.2 Hz), 8.75 (1H, s) (DMSO-d6) | 403 |
| 13 | 1.96 (4H, m), 3.24 (4H, m), 3.38 (2H, m), 3.43 (3H, s), 3.50 (2H, m), 3.77 (1H, d, J = 14.0 Hz), 3.88 (1H, d, J = 13.6 Hz), 4.48 (1H, t, J = 10.4 Hz), 6.61 (2H, d, J = 8.8 Hz), 6.65 (1H, s), 7.44 (2H, d, J = 8.8 Hz), 7.98 (1H, dd, J = 4.8, 2.8 Hz), 8.60 (1H, d, J = 4.8 Hz), 8.73 (1H, d, J = 2.8 Hz), 9.55 (1H, d, J = 7.6 Hz), 9.78 (1H, br s) (DMSO-d6) | 435 |
| 14 | 1.63 (2H, m), 1.86 (4H, m), 3.42 (5H, m), 3.44 (3H, m), 3.56 (3H, m), 3.88 (2H, m), 4.64 (1H, br s), 6.66 (1H, s), 7.72 (4H, br s), 8.00 (1H, dd, J = 5.2, 3.2 Hz), 8.60 (1H, d, J = 5.2 Hz), 8.73 (1H, d, J = 3.2 Hz), 9.83 (1H, br s), 10.10 (1H, br s) (DMSO-d6) | 449 |
| 15 | 2.30 (1H, m), 2.41 (1H, m), 2.80 (3H, d, J = 5.2 Hz), 2.81 (3H, d, J = 5.2 Hz), 3.27 (1H, m), 3.42 (2H, m), 3.43 (3H, m), 3.52 (4H, m), 3.65 (1H, m), 3.76 (1H, d, J = 13.3 Hz), 3.89 (1H, d, J = 13.6 Hz), 4.00 (1H, m), 4.51 (1H, t, J = 11.6 Hz), 6.65 (1H, s), 6.68 (2H, d, J = 8.4 Hz), 7.50 (2H, d, J = 8.4 Hz), 7.99 (1H, dd, J = 4.8, 2.8 Hz), 8.59 (1H, d, J = 4.8 Hz), 8.73 (1H, d, J = 2.8 Hz), 9.64 (1H, d, J = 8.4 Hz), 9.94 (1H, s), 11.24 (1H, s) (DMSO-d6) | 478 |
| 16 | 2.28 (1H, m), 2.41 (1H, m), 2.81 (3H, d, J = 5.0 Hz), 2.82 (d, J = 5.0 Hz), 3.27 (1H, m), 3.39 (2H, m), 3.43 (3H, s), 3.63 (4H, m), 3.80 (4H, m), 4.51 (1H, t, J = 11.2 Hz), 6.65 (1H, s), 6.69 (2H, d, J = 6.4 Hz), 7.49 (2H, d, J = 6.4 Hz), 7.98 (1H, dd, J = 4.8, 2.8 Hz), 8.59 (1H, d, J = 4.8 Hz), 8.73 (1H, d, J = 2.8 Hz), 9.60 (1H, br s), 9.82 (1H, br s), 11.09 (1H, br s) (DMSO-d6) | 478 |
| 17 | 1.67-2.14 (9H, m), 2.60-2.83 (6H, m), 3.06-3.14 (1H, m), 3.26-3.33 (1H, m), 3.50-3.73 (7H, m), 3.93-4.00 (1H, m), 4.13-4.17 (1H, m), 4.62 (1H, dd, | 519 |

TABLE 2-continued

| Compound No. | 1H-NMR δ: | [M + 1] |
|---|---|---|
| | J = 1.2, 10.2 Hz), 6.87 (1H, s), 6.93 (2H, d, J = 7.3 Hz), 7.26 (2H, d, J = 7.3 Hz), 7.94 (1H, dd, J = 1.2, 4.2 Hz), 8.50-8.55 (2H, m) (CDCl$_3$) | |
| 18 | 1.44-1.92 (10H, m), 2.32-2.55 (5H, m), 2.72-2.76 (2H, m), 3.07-3.14 (1H, m), 3.26-3.32 (1H, m), 3.50-3.60 (5H, m), 3.75-3.79 (2H, m), 3.92-4.00 (1H, m), 4.12-4.16 (1H, m), 4.63 (1H, dd, J = 1.2, 10.2 Hz), 6.87 (1H, s), 6.93 (2H, d, J = 7.3 Hz), 7.28 (2H, d, J = 7.3 Hz), 7.95 (1H, dd, J = 1.2, 4.2 Hz), 8.49-8.55 (2H, m) (CDCl$_3$) | 533 |
| 19 | 1.62-1.69 (3H, m), 1.98-2.06 (2H, m), 2.92-2.98 (2H, m), 3.07-3.15 (1H, m), 3.25-3.32 (1H, m), 3.51-3.60 (7H, m), 3.87-3.92 (2H, m), 4.12-4.16 (1H, m), 4.63 (1H, dd, J = 1.2, 10.2 Hz), 6.87 (1H, s), 6.95 (2H, d, J = 7.3 Hz), 7.28 (2H, d, J = 7.3 Hz), 7.94 (1H, dd, J = 1.2, 4.2 Hz), 8.50-8.55 (2H, m) (CDCl$_3$) | 466 |
| 20 | 1.61-1.66 (2H, m), 1.91-1.96 (2H, m), 2.30-2.31 (1H, m), 2.32 (6H, s), 2.69-2.74 (2H, m), 3.08-3.15 (1H, m), 3.20-3.28 (1H, m), 3.50-3.61 (5H, m), 3.74-3.77 (2H, m), 3.94-4.00 (1H, m), 4.12-4.16 (1H, m), 4.62 (1H, dd, J = 1.2, 10.2 Hz), 6.88 (1H, s), 6.96 (2H, d, J = 7.3 Hz), 7.28 (2H, d, J = 7.3 Hz), 7.94 (1H, dd, J = 1.2, 4.2 Hz), 8.50-8.56 (2H, m) (CDCl$_3$) | 493 |
| 21 | 2.81 (3H, d, J = 4.4 Hz), 3.11 (4H, m), 3.39 (3H, s), 3.95-3.35 (10H, m), 4.55 (1H, t, J = 10.8 Hz), 6.65 (1H, s), 7.10 (2H, d, J = 8.8 Hz), 7.56 (2H, d, J = 8.8 Hz), 7.98 (1H, dd, J = 4.8, 2.8 Hz), 8.59 (1H, d, J = 4.8 Hz), 8.73 (1H, d, J = 2.8 Hz), 9.70 (1H, br s), 10.03 (1H, br s), 10.81 (1H, br s) (DMSO-d6) | 464 |
| 22 | 3.44 (3H, s), 3.57 (12H, m), 3.82 (1H, d, J = 13.2 Hz), 3.90 (1H, d, J = 13.2 Hz), 4.56 (1H, t, J = 10.8 Hz), 6.66 (1H, s), 7.07 (1H, br s), 7.18 (2H, d, J = 8.4 Hz), 7.36 (4H, br s), 7.60 (2H, d, J = 8.4 Hz), 8.01 (1H, dd, J = 5.2, 2.8 Hz), 8.74 (1H, d, J = 2.8 Hz), 9.74 (1H, br s), 10.12 (1H, br s) (DMSO-d6) | 526 |
| 23 | 1.86 (4H, m), 1.99 (2H, m), 2.14 (2H, m), 2.79 (2H, t, J = 11.6 Hz), 3.02 (2H, m), 3.28 (1H, m), 3.39 (2H, m), 3.43 (3H, s), 3.52 (3H, m), 3.61 (1H, m), 3.81 (1H, d, J = 12.6 Hz), 3.91 (3H, m), 4.54 (1H, t, J = 9.6 Hz), 6.56 (1H, s), 7.15 (2H, d, J = 8.0 Hz), 7.57 (2H, d, J = 8.0 Hz), 8.00 (qH, dd, J = 5.2, 2.8 Hz), 8.60 (1H, d, J = 5.2 Hz), 8.74 (1H, d, J = 2.8 Hz), 9.76 (1H, d, J = 8.8 Hz), 10.15 (1H, br s), 11.10 (1H, br s) (DMSO-d6) | 518 |
| 24 | 1.40 (1H, m), 1.86 (8H, m), 2.20 (2H, d, J = 12.0 Hz), 2.80 (2H, m), 2.90 (2H, m), 3.43 (3H, s), 3.70-3.30 (6H, m), 3.80 (1H, d, J = 10.0 Hz), 3.90 (3H, m), 4.65 (1H, t, J = 8.8 Hz), 6.65 (1H, s), 7.15 (2H, d, J = 8.4 Hz), 7.57 (2H, d, J = 8.4 Hz), 8.00 (1H, dd, J = 5.2, 2.8 Hz), 8.60 (1H, d, J = 5.2 Hz), 8.74 (1H, d, J = 2.8 Hz), 9.78 (1H, d, J = 8.8 Hz), 10.19 (1H, br s), 10.54 (1H, br s) (DMSO-d6) | 532 |
| 25 | 1.71 (2H, m), 2.12 (2H, m), 2.73 (6H, d, J = 5.1 Hz), 2.74-2.81 (3H, m), 3.30-3.95 (8H, m), 3.39 (3H, s), 4.54 (1H, m), 6.65 (1H, s), 7.10 (2H, d, J = 8.7 Hz), 7.53 (2H, d, J = 8.7 Hz), 7.99 (1H, dd, J = 6.6, 5.1 Hz), 8.59 (1H, d, J = 4.5 Hz), 8.74 (1H, d, J = 3.3 Hz), 9.71 (1H, m), 10.02 (1H, m), 10.66 (1H, m), (DMSO-d6) | 492 |
| 26 | 1.64 (2H, m), 1.91 (2H, m), 3.13-3.90 (11H, m), 3.48 (3H, s), 4.59 (1H, m), 6.65 (1H, s), 7.36 (2H, d, J = 8.4 Hz), 7.61 (2H, d, J = 8.4 Hz), 7.99 (1H, dd, J = 6.9, 5.1 Hz), 8.59 (1H, d, J = 5.1 Hz), 8.72 (1H, d, J = 3.0 Hz), 9.67 (1H, m), 9.91 (1H, m) (DMSO-d6) | 465 |
| 27 | 1.91-2.05 (2H, m), 3.09 (1H, m), 3.28-3.57 (7H, m), 3.41 (3H, s), 3.74-3.86 (2H, m), 4.41-4.73 (2H, m), 6.58 (2H, d, J = 8.4 Hz), 6.65 (1H, s), 7.44 (2H, d, J = 8.4 Hz), 7.99 (1H, dd, J = 6.6, 5.1 Hz), 8.60 (1H, d, J = 5.1 Hz), 8.74 (1H, d, J = 3.0 Hz), 9.59 (1H, m), 9.86 (1H, m) | 451 |
| 28 | 1.89-2.01 (2H, m), 2.93-3.29 (6H, m), 3.44 (3H, s), 3.58-3.66 (2H, m), 3.80-3.86 (1H, m), 3.90-4.00 (1H, m), 4.37-4.40 (1H, m), 4.55-4.58 (1H, m), 4.94 (1H, d, =10.2 Hz), 6.48 (2H, d, J = 7.2 Hz), 6.59 (1H, s), 7.20 (2H, d, J = 7.2 Hz), 7.96 (1H, dd, J = 1.2, 4.2 Hz), 8.56 (1H, d, J = 4.2 Hz), 8.70 (1H, d, J = 1.2 Hz) (CDCl$_3$) | 452 |
| 29 | 1.76-2.02 (2H, m), 2.97-3.29 (6H, m), 3.46 (3H, s), 3.60-3.69 (2H, m), 3.82-3.89 (1H, m), 4.01-4.05 (1H, m), 4.37-4.40 (1H, m), 4.55-4.58 (1H, m), 4.95 (1H, d, =10.2 Hz), 6.50 (2H, d, J = 7.2 Hz), 6.99 (1H, s), 7.23 (2H, d, J = 7.2 Hz), 8.18 (1H, dd, J = 1.2, 4.2 Hz), 8.99 (1H, d, J = 4.2 Hz), 9.29 (1H, d, J = 1.2 Hz) (CDCl$_3$) | 452 |
| 30 | 1.17 (1H, m), 1.33-1.43 (4H, m), 1.61-1.64 (3H, m), 1.75 (2H, d, J = 12.0 Hz), 2.70 (3H, s), 2.98 (2H, dd, J = 10.6, 12.8 Hz), 3.44 (3H, s), 3.58 (3H, m), 3.84 (1H, m), 4.00 (1H, m), 4.56 (1H, dd, J = 1.4, 10.4 Hz), 7.20 (2H, d, J = 8.6 Hz), 7.97 (1H, dd, J = 5.2, 6.7 Hz), 8.56 (1H, d, J = 5.2 Hz), 8.69 (1H, d, J = 3.1 Hz) (DMSO-d6) | 477 |
| 31 | 1.31 (6H, d, J = 6.5 Hz), 2.74 (2H, dd, J = 11.7, 12.4 Hz), 2.94 (1H, dd, J = 10.7, 12.5 Hz), 3.15 (1H, m), 3.30-3.39 (2H, m), 3.46 (3H, s), 3.65 (2H, d, J = 12.8 Hz), 3.81-3.89 (3H, m), 4.03 (1H, d, J = 7.9 Hz), 4.63 (1H, d, J = 9.4 Hz), 6.60 (1H, s), 7.02 (2H, d, J = 8.6 Hz), 7.30 (1H, d, J = 8.6 Hz), 7.97 (1H, dd, J = 5.2, 6.7 Hz), 8.58 (1H, d, J = 5.2 Hz), 8.74 (1H, d, J = 3.1 Hz), 9.11 (1H, br), 9.71 (1H, br.d, J = 8.3 Hz) (DMSO-d6) | 478 |
| 32 | 1.58-1.70 (6H, m), 3.08-3.20 (6H, m), 3.50-3.61 (2H, m), 3.57 (3H, s), 4.10 (1H, m), 4.13 (1H, m), 4.64 (1H, dd, J = 2.4, 10.8 Hz), 6.88 (1H, s), 6.95 (2H, d, J = 8.7 Hz), 7.30 (2H, d, J = 8.7 Hz), 7.98 (1H, dd, J = 5.1, 5.1 Hz), 8.51 (1H, d, J = 5.4 Hz), 8.57 (1H, d, J = 3.3 Hz) (CDCl$_3$) | 450 |

TABLE 2-continued

| Compound No. | 1H-NMR δ: | [M + 1] |
|---|---|---|
| 33 | | |
| 34 | 1.58-1.70 (4H, m), 3.08-3.20 (6H, m), 3.50-3.61 (2H, m), 3.57 (3H, s), 4.10 (1H, m), 4.13 (1H, m), 4.64 (1H, dd, J = 2.4, 10.8 Hz), 6.88 (1H, s), 6.95 (2H, d, J = 8.7 Hz), 7.30 (2H, d, J = 8.7 Hz), 7.98 (1H, dd, J = 5.1, 5.1 Hz), 8.51 (1H, d, J = 5.4 Hz), 8.57 (1H, d, J = 3.3 Hz) (CDCl$_3$) | 436 |
| 35 | 2.05 (6H, m), 2.22 (1H, m), 2.84 (1H, m), 3.98 (1H, m), 3.00-3.60 (8H, m), 3.56 (3H, s), 3.97 (1H, m), 4.12 (1H, m), 4.60 (1H, d, J = 10.4 Hz), 6.56 (2H, d, J = 8.7 Hz), 6.88 (1H, s), 7.29 (2H, d, J = 8.7 Hz), 7.96 (1H, dd, J = 5.4, 6.9 Hz), 8.50 (1H, d, J = 5.4 Hz), 8.55 (1H, d, J = 3.3 Hz) (CDCl$_3$) | 479 |
| 36 | 2.97 (6H, s), 3.13 (1H, dd, J = 10.5, 12.9 Hz), 3.29 (1H, m), 3.50-3.60 (2H, m), 3.56 (3H, s), 3.98 (1H, m), 4.15 (1H, dd, J = 2.1, 9.9 Hz), 4.61 (1H, dd, J = 2.1, 10.5 Hz), 6.74 (2H, d, J = 8.7 Hz), 6.88 (1H, s), 7.29 (2H, d, J = 8.7 Hz), 7.96 (1H, dd, J = 5.1, 5.1 Hz), 8.51 (1H, d, J = 5.4 Hz), 8.55 (1H, d, J = 3.3 Hz) (CDCl$_3$) | 410 |
| 37 | 1.10 (6H, d, J = 6.3 Hz), 2.69 (5H, m), 3.11 (1H, dd, J = 10.5, 12.9 Hz), 3.24-3.31 (5H, m), 3.50-3.57 (2H, m), 3.56 (3H, m), 3.96 (1H, m), 4.14 (1H, dd, J = 2.1, 9.9 Hz), 4.63 (1H, dd, J = 2.1, 10.5 Hz), 6.87-6.95 (4H, m), 7.30 (2H, m), 8.50 (1H, d, J = 5.1 Hz), 8.55 (1H, d, J = 3.0 Hz) (CDCl$_3$) | 493 |
| 38 | 1.66 (1H, br.s), 2.62 (2H, t, J = 5.4 Hz), 2.68 (4H, t, J = 4.9 Hz), 3.10 (1H, dd, J = 10.8, 12.9 Hz), 3.23 (4H, t, J = 4.8 Hz), 3.30 (1H, m), 3.61-3.68 (2H, m), 3.67 (3H, s), 3.67 (2H, dd, J = 5.1, 5.4 Hz), 3.97 (1H, m), 4.13 (1H, m), 4.63 (1H, dd, J = 2.4, 10.8 Hz), 6.88 (1H, s), 6.93 (2H, d, J = 8.7 Hz), 7.30 (2H, d, J = 8.7 Hz), 7.95 (1H, dd, J = 5.1, 5.1 Hz), 8.50 (1H, d, J = 5.4 Hz), 8.55 (1H, d, J = 3.3 Hz) (CDCl$_3$) | 495 |
| 39 | 1.98-2.13 (4H, m), 355-3.66 (3H, s), 3.84-3.94 (4H, m), 6.68 (1H, s), 6.94 (1H, d, J = 7.5 Hz), 7.06 (1H, dd, J = 7.5, 7.5 Hz), 7.26 (1H, d, J = 7.5, 7.8 Hz), 7.38 (1H, m), 8.08 (1H, dd, J = 5.1, 5.1 Hz), 8.49 (1H, d, J = 5.1 Hz), 8.54 (1H, d, J = 3.0 Hz) (CD3OD-CDCl$_3$) | 406 |
| 40 | 1.09 (1H, m), 1.33 (2H, m), 1.45 (2H, m), 1.61 (2H, m), 1.79 (3H, m), 2.80 (4H, m), 3.44 (3H, m), 3.50 (2H, m), 3.52 (3H, s), 3.85 (2H, m), 4.57 (1H, m), 6.65 (1H, s), 7.50 (2H, m), 7.99 (1H, dd, J = 4.8, 2.8 Hz), 8.60 (1H, d, J = 4.8 Hz), 8.73 (1H, d, J = 2.8 Hz), 9.53 (1H, br s) (DMSO-d6) | 477 |
| 41 | 3.46 (3H, s), 3.52 (4H, m), 3.81 (3H, m), 3.92 (2H, d, J = 13.3 Hz), 4.69 (1H, t, J = 11.0 Hz), 6.66 (1H, s), 7.05 (2H, d, J = 8.7 Hz), 7.71 (6H, m), 8.01 (1H, dd, J = 4.9, 2.7 Hz), 8.60 (1H, d, J = 4.9 Hz), 8.73 (1H, d, J = 2.7 Hz), 9.71 (1H, br s), 9.89 (1H, br s) (DMSO-d6) | 472 |
| 42 | 2.98 (6H, s), 3.43 (1H, m), 3.44 (3H, s), 3.55 (2H, m), 4.40-3.80 (3H, m), 4.55 (1H, t, J = 10.0 Hz), 6.65 (1H, s), 7.04 (2H, br s), 7.57 (2H, br s), 8.00 (1H, dd, J = 5.2, 2.8 Hz), 8.60 (1H, d, J = 5.2 Hz), 8.73 (1H, d, J = 2.8 Hz), 9.69 (1H, br s), 10.00 (1H, br s) (DMZO-d6) | 409 |
| 43 | 3.18-3.22 (4H, m), 3.44-3.92 (15H, m), 4.52-4.55 (1H, m), 5.11 (2H, s), 6.64 (1H, s), 7.04 (2H, d, J = 7.2 Hz), 7.36-7.39 (5H, m), 7.48 (2H, d, J = 7.2 Hz), 7.96-8.00 (1H, m), 8.58 (1H, d, J = 4.2 Hz), 8.72 (1H, d, J = 4.2 Hz), 9.42-9.65 (2H, br) (DMSO-d6) | 584 |
| 44 | 3.16-3.20 (4H, m), 3.39-3.91 (13H, m), 4.51-4.58 (1H, m), 6.65 (1H, s), 7.06-7.10 (2H, m), 7.43-7.66 (4H, m), 7.97-8.01 (1H, m), 8.60 (1H, d, J = 4.2 Hz), 8.73 (1H, s), 9.20 (1H, brs), 9.70-9.72 (1H, br), 10.02-10.05 (1H, br) (DMSO-d6) | 450 |
| 45 | 1.32 (6H, d, J = 6.8 Hz), 3.26-3.88 (18H, m), 4.60-4.65 (2H, m), 6.65 (1H, s), 7.10 (2H, d, J = 7.2 Hz), 7.60 (2H, d, J = 7.2 Hz), 7.99-8.03 (1H, m), 8.61 (1H, d, J = 4.2 Hz), 8.75 (1H, d, J = 1.2 Hz), 9.75-9.85 (1H, br), 10.30-10.33 (1H, br), 11.05-11.10 (1H, br) (DMSO-d6) | 492 |
| 46 | 3.18-3.24 (8H, m), 3.43-3.60 (13H, m), 4.51-4.55 (1H, m), 6.65 (1H, s), 7.09 (2H, d, J = 7.2 Hz), 7.60 (2H, d, J = 7.2 Hz), 7.99 (1H, dd, J = 1.2 Hz, 4.2 Hz), 8.59 (1H, d, J = 4.2 Hz), 8.72 (1H, d, J = 1.2 Hz), 9.81-9.84 (1H, br), 10.18-10.32 (3H, br), 10.62-10.66 (1H, br) (DMSO-d6) | 494 |
| 47 | 2.09 (3H, s), 3.18-3.24 (5H, m), 3.40-3.91 (15H, m), 4.42-4.50 (3H, m), 6.65 (1H, s), 7.10 (2H, d, J = 7.2 Hz), 7.56 (2H, d, J = 7.2 Hz), 7.98 (1H, dd, J = 1.2 Hz, 4.2 Hz), 8.60 (1H, d, J = 4.2 Hz), 8.72 (1H, d, J = 1.2 Hz), 9.70-9.74 (1H, br), 9.89-9.97 (1H, br), 11.13-11.16 (1H, br) (DMSO-d6) | 536 |
| 48 | 2.69-2.76 (1H, m), 3.10-3.14 (1H, m), 3.51-3.52 (1H, m), 3.53 (3H, s), 3.68-3.73 (1H, m), 3.80-3.93 (4H, m), 4.06-4.10 (1H, m), 4.99 (1H, dd, J = 1.2 Hz, 10.2 Hz), 7.21 (1H, d, J = 7.3 Hz), 7.70-7.74 (2H, m), 7.82 (1H, dd, J = 4.2 Hz), 8.60 (1H, d, J = 4.2 Hz), 8.75 (1H, d, J = 1.2 Hz) (DMSO-d6) | 440 |
| 49 | 3.28-3.61 (7H, m), 3.81-3.88 (1H, m), 3.98-4.02 (1H, m), 5.27 (1H, dd, J = 1.2 Hz, 10.2 Hz), 7.23-7.47 (3H, m), 7.72-7.76 (1H, m), 8.58 (1H, d, J = 4.2 Hz), 8.75 (1H, s) (DMSO-d6) | 437 |
| 50 | 1.91-2.03 (2H, m), 3.09 (1H, m), 3.30-3.52 (6H, m), 3.41 (3H, s), 3.75-3.87 (2H, m), 4.40-4.52 (3H, m), 6.58 (2H, d, J = 8.7 Hz), 6.65 (1H, s), 7.40 (2H, d, J = 8.7 Hz), 7.97 (1H, dd, J = 6.6, 5.1 Hz), 8.59 (1H, d, J = 5.1 Hz), 8.72 (1H, d, J = 3.0 Hz), 9.48-9.58 (2H, m) (DMSO-d6) | 451 |
| 51 | 1.15 (6H, d, J = 6.0 Hz), 2.31 (2H, dd, J = 11.1 Hz), 2.97-3.21 (6H, m), 3.52-3.62 (4H, m), 3.55 (3H, s), 3.95 (1H, dd, J = 10.5, 2.4 Hz), 6.85 (1H, s), 6.93 (2H, d, J = 9.0 Hz), 7.32 (2H, d, J = 9.0 Hz), 7.97 (1H, dd, J = 6.9, 5.4 Hz), 8.50 (1H, d, J = 4.5 Hz), 8.54 (1H, d, J = 3.3 Hz) (CDCl$_3$) | 478 |
| 52 | 1.27 (6H, d, J = 6.3 Hz), 2.42 (2H, dd, J = 11.1, 11.1 Hz), 3.00 (1H, dd, J = 12.3, 10.8 Hz), 3.16-3.22 (3H, m), 3.45-3.60 (4H, m), 3.55 (3H, s), | 479 |

TABLE 2-continued

| Compound No. | 1H-NMR δ: | [M + 1] |
|---|---|---|
| | 3.81 (1H, m), 3.95 (1H, m), 6.85 (1H, s), 6.92 (2H, d, J = 8.4 Hz), 7.33 (2H, d, J = 8.4 Hz), 7.97 (1H, m), 8.50 (1H, d, J = 5.1 Hz), 8.54 (1H, d, J = 3.0 Hz) (CDCl₃) | |
| 53 | 175-1.86 (4H, m), 2.80 (1H, m), 2.97-3.04 (2H, m), 3.45 (3H, s), 3.79-3.83 (2H, m), 6.57 (1H, s), 7.28 (2H, d, J = 8.1 Hz), 7.51 (2H, d, J = 8.1 Hz), 8.01 (1H, dd, J = 6.0, 6.0 Hz), 8.58 (1H, d, J = 4.5 Hz), 8.71 (1H, d, J = 3.0 Hz) (DMSO-d6) | 443 |
| 54 | 1.78-1.99 (4H, m), 2.82 (1H, m), 2.95-3.04 (2H, m), 3.46 (3H, s), 3.78-3.83 (2H, m), 6.57 (1H, s), 7.26-7.44 (3H, m), 7.53 (1H, s), 8.01 (1H, dd, J = 6.6, 5.1 Hz), 8.58 (1H, d, J = 4.8 Hz), 8.71 (1H, d, J = 3.0 Hz) (DMSO-d6) | 443 |
| 55 | 2.98 (1H, m), 3.15 (1H, m), 3.23-3.30 (6H, m), 3.45 (3H, s), 3.63-3.68 (2H, m), 3.86 (1H, m), 4.03 (1H, m), 4.64 (1H, m), 6.59 (1H, s), 6.81 (1H, dd, J = 7.2, 7.2 Hz), 6.98-7.01 (4H, m), 7.21-7.32 (4H, m), 7.98 (1H, dd, J = 6.9, 5.1 Hz), 8.57 (1H, d, J = 4.8 Hz), 8.69 (1H, d, J = 3.0 Hz) (DMSO-d6) | 527 |
| 56 | 1.74-1.99 (8H, m), 2.65 (1H, m), 2.95-3.03 (2H, m), 3.16-3.20 (4H, m), 3.44 (3H, s), 3.76-3.80 (2H, m), 6.49 (2H, d, J = 8.7 Hz), 6.56 (1H, s), 7.08 (2H, d, J = 8.7 Hz), 8.00 (1H, dd, J = 6.9, 4.8 Hz), 8.57 (1H, dd, J = 4.8, 0.9 Hz), 8.70 (1H, d, J = 3.3 Hz) (DMSO-d6) | 433 |
| 57 | 2.83-3.09 (5H, m), 3.26 (3H, s), 3.46 (3H, s), 3.67-3.76 (2H, m), 4.01-4.04 (1H, m), 6.57 (1H, s), 7.62 (2H, d, J = 7.2 Hz), 7.76 (2H, d, J = 7.2 Hz), 7.95-8.05 (5H, m), 8.56 (1H, d, J = 4.2 Hz), 8.69 (1H, d, J = 1.2 Hz) (DMSO-d6) | 520 |
| 58 | 2.82-3.10 (5H, m), 3.46 (3H, s), 3.66-3.69 (2H, m), 4.00-4.03 (1H, m), 6.56 (1H, s), 7.60 (2H, d, J = 7.2 Hz), 7.75 (2H, d, J = 7.2 Hz), 7.90-7.98 (5H, m), 8.56 (1H, d, J = 4.2 Hz), 8.69 (1H, d, J = 1.2 Hz) (DMSO-d6) | 467 |
| 59 | 1.82-1.99 (8H, m), 2.69 (1H, m), 2.96-3.00 (2H, m), 3.19-3.23 (4H, m), 3.45 (3H, s), 3.77-3.82 (2H, m), 6.39 (1H, d, J = 7.8 Hz) 6.44 (1H, s), 6.52 (1H, d, J = 7.8 Hz), 7.09 (1H, dd, J = 7.8, 7.8 Hz), 8.01 (1H, dd, J = 6.6, 5.1 Hz), 8.57 (1H, d, J = 4.8 Hz), 8.70 (1H, d, J = 3.0 Hz) (DMSO-d6) | 434 |
| 60 | | |
| 61 | 1.61 (1H, br.s), 1.95 (2H, d, J = 14.0 Hz), 2.21 (2H, ddd, J = 4.0, 13.5, 13.8 Hz), 2.74 (2H, s), 3.19 (2H, td, J = 2.1, 13.0 Hz), 3.52 (4H, m), 3.59 (3H, s), 6.88 (1H, s), 7.05 (1H, d, J = 7.2 Hz), 7.16 (1H, dd, J = 0.9, 6.6 Hz), 7.22 (1H, s), 7.41 (1H, d, J = 6.0 Hz), 8.01 (1H, dd, J = 5.1, 5.1 Hz), 8.52 (1H, d, J = 5.4 Hz), 8.56 (1H, d, J = 3.3 Hz) (CDCl₃) | 406 |
| 62 | 1.95 (2H, d, J = 14.0 Hz), 2.21 (2H, ddd, J = 4.0, 13.5, 13.8 Hz), 2.46 (3H, s), 2.74 (2H, s), 3.19 (2H, td, J = 2.1, 13.0 Hz), 3.52 (4H, m), 3.59 (3H, s), 6.88 (1H, s), 7.05 (1H, d, J = 7.2 Hz), 7.16 (1H, dd, J = 0.9, 6.6 Hz), 7.22 (1H, s), 7.41 (1H, d, J = 6.0 Hz), 8.01 (1H, dd, J = 5.1, 5.1 Hz), 8.52 (1H, d, J = 5.4 Hz), 8.56 (1H, d, J = 3.3 Hz) (CDCl₃) | 420 |
| 63 | 1.61 (1H, br.s), 1.85-1.94 (2H, m), 2.07 (2H, td, J = 4.2, 13.5 Hz), 3.10 (2H, td, J = 2.5, 13.5 Hz), 3.51-3.65 (2H, m), 3.55 (3H, s), 3.59 (3H, s), 6.68 (1H, d, J = 7.8 Hz), 6.78 (1H, dd, J = 6.6, 7.5 Hz), 6.88 (1H, s), 7.07-7.12 (2H, m), 8.00 (1H, dd, J = 5.1, 5.1 Hz), 8.52 (1H, d, J = 3.0 Hz), 8.58 (1H, d, J = 3.0 Hz) (CDCl₃) | 392 |
| 64 | 1.48-1.49 (2H, m), 1.61-1.67 (4H, m), 1.92-2.00 (1H, m), 2.20-2.30 (1H, m), 2.48-2.95 (4H, m), 3.12-3.32 (9H, m), 3.66 (3H, s), 3.96 (1H, m), 4.11 (1H, m), 4.60 (1H, dd, J = 2.4, 10.8 Hz), 6.48-6.56 (2H, m), 6.87 (1H, s), 7.18-7.23 (2H, m), 7.96 (1H, dd, J = 5.1, 5.1 Hz), 8.50 (1H, d, J = 5.4 Hz), 8.54 (1H, d, J = 3.3 Hz) (CDCl₃) | 519 |
| 65 | 1.90 (2H, d, J = 13.8 Hz), 2.05 (2H, td, J = 3.9, 13.5 Hz), 2.80 (3H, s), 3.12 (2H, td, J = 2.5, 14.4 Hz), 3.17 (2H, s), 3.58 (3H, s), 3.56-3.64 (2H, m), 6.53 (1H, d, J = 7.8 Hz), 6.74 (1H, dd, J = 7.5, 7.8 Hz), 6.88 (1H, s), 7.08-7.20 (2H, m), 8.00 (1H, dd, J = 5.1, 5.1 Hz), 8.52 (1H, d, J = 3.0 Hz), 8.58 (1H, d, J = 3.0 Hz) (CDCl₃) | 406 |
| 66 | 3.06 (1H, dd, J = 12.0, 10.4 Hz), 3.25 (3H, m), 3.58 (3H, s), 3.65 (2H, m), 4.09 (1H, dd, J = 10.4, 2.4 Hz), 6.86 (1H, s), 7.29 (2H, d, J = 8.4 Hz), 7.53 (2H, d, J = 8.4 Hz), 7.56 (2H, d, J = 8.4 Hz), 7.60 (2H, d, J = 8.4 Hz), 7.97 (1H, dd, J = 4.8, 2.8 Hz), 8.50 (1H, d, J = 4.8 Hz), 8.55 (1H, d, J = 2.8 Hz) (CDCl₃) | 526 |
| 67 | 3.06 (1H, dd, J = 12.4, 10.4 Hz), 3.25 (3H, m), 3.58 (3H, s), 3.66 (2H, m), 4.10 (1H, dd, J = 10.4, 2.2 Hz), 6.86 (1H, s), 7.56 (2H, d, J = 8.4 Hz), 7.62 (2H, d, J = 8.4 Hz), 7.70 (4H, s), 7.97 (1H, dd, J = 4.8, 3.1 Hz), 8.51 (1H, d, J = 4.8 Hz), 8.55 (1H, d, J = 3.1 Hz) (CDCl₃) | 510 |
| 68 | 1.44 (3H, t, J = 6.8 Hz), 3.06 (1H, dd, J = 12.4, 10.8 Hz), 3.21 (3H, m), 3.57 (3H, s), 3.62 (2H, m), 4.05 (1H, m), 4.08 (2H, q, J = 6.8 Hz), 6.86 (1H, s), 6.97 (2H, d, J = 8.8 Hz), 7.53 (6H, m), 7.98 (1H, dd, J = 4.8, 3.2 Hz), 8.51 (1H, d, J = 4.8 Hz), 8.55 (1H, d, J = 3.2 Hz) (CDCl₃) | 486 |
| 69 | 1.90 (3H, m), 2.01 (1H, m), 2.50 (3H, s), 2.84 (1H, m), 3.16 (1H, m), 3.38 (3H, m), 3.44 (3H, s), 3.70 (9H, m), 4.59 (1H, br s), 6.65 (1H, s), 7.39 (2H, br s), 7.66 (2H, br s), 8.00 (1H, dd, J = 5.2, 2.4 Hz), 8.59 (1H, d, J = 5.2 Hz), 8.73 (1H, d, J = 2.4 Hz), 9.79 (1H, br s), 10.24 (1H, br s), 11.15 (1H, br s) (DMSO-d6) | 518 |
| 70 | 1.83 (4H, m), 1.99 (1H, m), 2.21 (1H, m), 2.61 (4H, m), 2.86 (1H, m), 3.01 (1H, dd, J = 12.4, 10.4 Hz), 3.20 (4H, m), 3.33 (1H, q, J = 6.8 Hz), 3.47 (2H, m), 3.54 (3H, s), 3.59 (2H, m), 3.88 (1H, dd, J = 10.4, 2.4 Hz), 6.55 (2H, d, J = 8.4 Hz), 6.85 (1H, s), 7.29 (2H, d, J = 8.4 Hz), 7.98 (1H, | 504 |

TABLE 2-continued

| Compound No. | 1H-NMR δ: | [M + 1] |
|---|---|---|
| | dd, J = 5.2, 3.2 Hz), 8.49 (1H, d, J = 5.2 Hz), 8.54 (1H, d, J = 3.2 Hz) (CDCl₃) | |
| 71 | 1.60 (6H, s), 2.82 (1H, dd, J = 12.8, 10.0 Hz), 3.34 (1H, td, J = 11.9, 2.8 Hz), 3.55 (1H, d, J = 11.9 Hz), 3.62 (3H, s), 3.81 (1H, d, J = 12.8 Hz), 3.85 (3H, s), 4.00 (1H, td, J = 11.9, 2.8 Hz), 4.23 (1H, dd, J = 11.9, 2.2 Hz), 5.06 (1H, dd, J = 10.0, 2.2 Hz), 6.87 (1H, d, J = 9.2 Hz), 6.88 (1H, s), 7.43 (1H, dd, J = 9.2, 2.4 Hz), 7.66 (1H, d, J = 2.4 Hz), 8.01 (1H, dd, J = 5.2, 3.2 Hz), 8.51 (1H, d, J = 5.2 Hz), 8.55 (1H, d, J = 3.2 Hz) (CDCl₃) | 455 |
| 72 | 1.79-1.90 (4H, m), 2.81 (1H, m), 2.96-3.06 (2H, m), 3.44 (3H, s), 3.78-3.83 (2H, m), 6.57 (1H, s), 7.14 (2H, dd, J = 8.7, 8.7 Hz), 7.34 (2H, m), 8.01 (1H, dd, J = 6.9, 5.1 Hz), 8.57 (1H, m), 8.71 (1H, d, J = 3.0 Hz) (DMSO-d6) | 383 |
| 73 | 1.94 (1H, m), 2.20 (1H, m), 2.54 (4H, m), 3.00 (1H, m), 3.16-3.62 (8H, m), 3.56 (3H, s), 3.75 (4H, t, J = 4.6 Hz), 3.96 (1H, m), 4.12 (1H, m), 4.60 (1H, dd, J = 1.9, 10.4 Hz), 6.55 (2H, d, J = 8.7 Hz), 6.87 (1H, s), 7.25 (2H, d, J = 8.6 Hz), 7.96 (1H, dd, J = 5.1, 5.1 Hz), 8.50 (1H, d, J = 5.4 Hz), 8.55 (1H, d, J = 3.3 Hz) (CDCl₃) | 521 |
| 74 | 1.60 (9H, s), 1.85 (2H, d, J = 13.8 Hz), 2.06 (2H, td, J = 3.9, 13.5 Hz), 3.10 (2H, t, J = 13.2 Hz), 3.59 (3H, s), 3.59-3.62 (2H, m), 3.94 (2H, s), 6.82-6.95 (4H, m), 7.98 (1H, dd, J = 5.1, 5.1 Hz), 8.53 (1H, d, J = 3.0 Hz), 8.57 (1H, d, J = 3.0 Hz) (CDCl₃) | 510 |
| 75 | 1.83-2.05 (5H, m), 2.20 (1H, m), 2.55 (4H, m), 3.00 (1H, m), 3.15-3.63 (8H, m), 3.56 (3H, s), 3.97 (1H, m), 4.16 (1H, m), 4.61 (1H, dd, J = 1.9, 10.4 Hz), 6.56 (2H, d, J = 8.7 Hz), 6.69 (1H, s), 8.71 (2H, d, J = 6.0 Hz), 7.30 (2H, d, J = 8.7 Hz), 7.98 (1H, dd, J = 5.1, 5.1 Hz), 8.50 (1H, d, J = 5.4 Hz), 8.55 (1H, d, J = 3.3 Hz) (CDCl₃) | MS |
| 76 | 2.29 (3H, s), 3.06 (4H, t, J = 4.8 Hz), 3.38 (4H, t, J = 4.8 Hz), 3.51 (3H, s), 5.70 (1H, s), 7.24-7.29 (5H, m), 7.96 (1H, dd, J = 5.1, 5.1 Hz), 8.50 (1H, d, J = 5.4 Hz), 8.55 (1H, d, J = 3.3 Hz) (CDCl₃) | 446 |
| 77 | 2.31 (2H, q, d, J = 5.1 Hz), 3.01 (1H, t, J = 10.0 Hz), 3.10 (1H, m), 3.20 (3H, m), 3.35 (1H, q, J = 6.9 Hz), 3.53 (3H, s), 3.54 (5H, m), 3.91 (1H, dd, J = 10.8, 2.8 Hz), 5.34 (1H, br s), 5.65 (1H, br s), 6.60 (2H, d, J = 8.8 Hz), 6.85 (1H, s), 7.28 (2H, d, J = 8.8 Hz), 7.98 (1H, dd, J = 5.2, 3.2 Hz), 8.50 (1H, d, J = 5.2 Hz), 8.54 (1H, d, J = 3.2 Hz) (CDCl₃) | 478 |
| 78 | 2.41 (2H, m), 3.00 (1H, t, J = 10.0 Hz), 3.18 (3H, m), 3.24 (1H, m), 3.43 (1H, m), 3.55 (3H, s), 3.59 (6H, m), 3.90 (1H, dd, J = 10.8, 2.8 Hz), 6.58 (2H, d, J = 8.4 Hz), 6.85 (1H, s), 7.32 (2H, d, J = 8.4 Hz), 7.97 (1H, dd, J = 5.2, 3.2 Hz), 8.50 (1H, d, J = 5.2 Hz), 8.54 (1H, d, J = 3.2 Hz) (CDCl₃) | 460 |
| 79 | 1.48-2.05 (7H, m), 2.20 (1H, m), 2.55 (4H, m), 3.00 (1H, m), 3.09-3.60 (8H, m), 3.56 (3H, s), 3.97 (1H, m), 4.16 (1H, m), 4.60 (1H, dd, J = 1.9, 10.4 Hz), 6.57 (2H, d, J = 8.7 Hz), 6.88 (1H, s), 7.24 (2H, d, J = 8.7 Hz), 7.96 (1H, dd, J = 5.1, 5.1 Hz), 8.50 (1H, d, J = 5.4 Hz), 8.55 (1H, d, J = 3.3 Hz) (CDCl₃) | MS |
| 80 | 1.94 (1H, m), 2.20 (1H, m), 2.54 (4H, m), 3.00 (1H, m), 3.16-3.62 (8H, m), 3.56 (3H, s), 3.75 (4H, t, J = 4.6 Hz), 3.96 (1H, m), 4.16 (1H, m), 4.60 (1H, dd, J = 1.9, 10.4 Hz), 6.55 (2H, d, J = 8.7 Hz), 6.87 (1H, s), 7.25 (2H, d, J = 8.6 Hz), 7.96 (1H, dd, J = 5.1, 5.1 Hz), 8.50 (1H, d, J = 5.4 Hz), 8.55 (1H, d, J = 3.3 Hz) (CDCl₃) | MS |
| 81 | 1.11 (1H, m), 1.41 (4H, m), 1.63 (3H, m), 1.75 (2H, m), 2.70 (3H, s), 2.85-3.98 (11H, m), 6.56 (1H, s), 6.59 (2H, s), 6.74 (2H, d, J = 8.6 Hz), 7.26 (2H, d, J = 8.6 Hz), 7.96 (1H, dd, J = 5.3, 3.1 Hz), 8.57 (1H, d, J = 5.3 Hz), 8.69 (1H, d, J = 3.1 Hz) (DMSO-d6) | 477 |
| 82 | 1.68-1.70 (4H, m), 1.87-1.90 (1H, m), 2.06-2.10 (1H, m), 3.01-3.16 (10H, m), 3.40 (3H, s), 3.53-3.58 (3H, m), 3.83-3.98 (2H, m), 4.56 (1H, dd, J = 1.2 Hz, 10.2 Hz), 6.51 (2H, d, J = 7.2 Hz), 6.59 (1H, s), 7.20 (2H, d, J = 7.2 Hz), 7.96 (1H, dd, J = 1.2 Hz, 4.2 Hz), 8.56 (1H, d, J = 4.2 Hz), 8.69 (1H, d, J = 1.2 Hz) (DMSO-d6) | 505 |
| 83 | 3.02 (4H, t, J = 4.7 Hz), 3.22 (4H, t, J = 4.2 Hz), 3.48 (3H, s), 6.83 (1H, s), 6.91-6.83 (2H, m), 7.33-7.26 (4H, m), 7.41 (1H, dd, J = 6.9, 7.8 Hz), 7.65 (2H, d, J = 8.3 Hz), 7.94 (1H, dd, J = 5.4, 6.9 Hz), 8.51 (1H, d, J = 5.4 Hz), 8.54 (1H, d, J = 3.3 Hz) (CDCl₃) | 442 |
| 84 | 1.26 (6H, d, J = 6.0 Hz), 2.42 (2H, t, J = 10.8 Hz), 3.11 (1H, dd, J = 11.7, 13.8 Hz), 3.16-3.61 (5H, m), 3.57 (3H, s), 3.79 (2H, m), 3.97 (1H, m), 4.12 (1H, m), 4.64 (1H, dd, J = 1.9, 10.4 Hz), 6.87 (1H, s), 6.91 (2H, d, J = 8.6 Hz), 7.25 (2H, d, J = 8.6 Hz), 7.94 (1H, dd, J = 5.1, 5.1 Hz), 8.50 (1H, d, J = 5.4 Hz), 8.55 (1H, d, J = 3.3 Hz) (CDCl₃) | MS |
| 85 | 3.07 (1H, dd, J = 12.4, 11.2 Hz), 3.22 (3H, m), 3.57 (3H, s), 3.65 (2H, m), 3.82 (3H, s), 3.86 (3H, s), 4.05 (1H, dd, J = 10.4, 2.4 Hz), 6.58 (2H, m), 6.87 (1H, s), 7.24 (2H, m), 7.46 (2H, d, J = 8.0 Hz), 7.53 (2H, d, J = 8.0 Hz), 8.00 (1H, dd, J = 4.8, 2.8 Hz), 8.52 (1H, d, J = 4.8 Hz), 8.55 (1H, d, J = 2.8 Hz) (CDCl₃) | 502 |
| 86 | 3.06 (1H, dd, J = 12.4, 10.4 Hz), 3.23 (3H, m), 3.57 (3H, s), 3.65 (2H, m), 3.93 (3H, s), 3.96 (3H, s), 4.07 (1H, dd, J = 10.0, 2.0 Hz), 6.86 (1H, s), 6.95 (1H, d, J = 8.0 Hz), 7.11 (1H, d, J = 2.0 Hz), 7.15 (1H, dd, J = 8.0, 2.0 Hz), 7.50 (1H, d, J = 8.4 Hz), 7.57 (1H, d, J = 8.4 Hz), 7.98 (1H, dd, J = 4.8, 3.2 Hz), 8.50 (1H, d, J = 4.8 Hz), 8.55 (1H, d, J = 3.2 Hz) (CDCl₃) | 502 |

TABLE 2-continued

| Compound No. | 1H-NMR δ: | [M + 1] |
|---|---|---|
| 87 | 3.05 (1H, dd, J = 12.4, 10.4 Hz), 3.25 (3H, m), 3.57 (3H, s), 3.64 (2H, m), 4.08 (1H, dd, J = 10.4, 2.4 Hz), 6.86 (1H, s), 7.41 (2H, d, J = 8.4 Hz), 7.52 (4H, d, J = 8.4 Hz), 7.57 (2H, d, J = 8.4 Hz), 7.97 (1H, dd, J = 5.2, 2.8 Hz), 8.50 (1H, d, J = 5.2 Hz), 8.55 (1H, d, J = 2.8 Hz) (CDCl₃) | 476 |
| 88 | 3.43 (2H, m), 3.46 (3H, s), 3.62 (2H, m), 3.93 (2H, d, J = 13.6 Hz), 4.74 (1H, t, J = 10.6 Hz), 6.66 (1H, s), 7.46 (2H, d, J = 8.4 Hz), 7.54 (3H, m), 7.77 (1H, d, J = 2.0 Hz), 7.83 (2H, d, J = 8.4 Hz), 8.03 (1H, dd, J = 4.8, 2.8 Hz), 8.61 (1H, d, J = 4.8 Hz), 8.74 (1H, d, J = 2.8 Hz), 9.90 (1H, d, J = 8.8 Hz), 10.40 (1H, br s) (DMSO-d6) | 510 |
| 89 | 3.05 (1H, dd, J = 12.4, 10.8 Hz), 3.25 (3H, m), 3.57 (3H, s), 3.63 (2H, m), 4.09 (1H, dd, J = 10.4, 2.4 Hz), 6.86 (1H, s), 7.42 (1H, dd, J = 8.0, 2.0 Hz), 7.54 (5H, m), 7.67 (1H, d, J = 2.0 Hz), 7.96 (1H, dd, J = 5.2, 3.2 Hz), 8.50 (1H, d, J = 5.2 HZ), 8.55 (1H, d, J = 3.2 Hz) (CDCl₃) | 510 |
| 90 | 3.04 (1H, dd, J = 12.4, 10.8 Hz), 3.24 (3H, m), 3.58 (3H, s), 3.64 (2H, m), 4.13 (1H, dd, J = 10.0, 2.0 Hz), 6.87 (1H, s), 7.61 (2H, d, J = 8.0 Hz), 7.95 (1H, dd, J = 4.8, 2.8 Hz), 8.14 (1H, d, J = 8.0 Hz), 8.50 (1H, d, J = 4.8 Hz), 8.55 (1H, d, J = 2.8 Hz), 8.77 (1H, s) (CDCl₃) | 434 |
| 91 | 0.37 (2H, m), 0.66 (2H, m), 1.30 (1H, m), 3.05 (1H, dd, J = 12.6, 10.8 Hz), 3.19-3.25 (3H, m), 3.57 (3H, s), 3.62-3.70 (2H, m), 3.85 (2H, d, J = 6.9 Hz), 4.06 (1H, m), 6.86 (1H, s), 6.98 (2H, d, J = 8.7 Hz), 7.46-7.58 (6H, m), 7.92 (1H, m), 8.50 (1H, d, J = 5.1 Hz), 8.54 (1H, d, J = 3.0 Hz) (CDCl₃) | 512 |
| 92 | 1.37 (6H, d, J = 6.0 Hz), 3.05 (1H, dd, J = 12.3, 10.8 Hz), 3.19-3.25 (3H, m), 3.57 (3H, s), 3.62-3.67 (2H, m), 4.06 (1H, dd, J = 10.2, 2.7 Hz), 4.59 (1H, m), 6.86 (1H, s), 6.96 (2H, d, J = 9.0 Hz), 7.49-7.58 (6H, m), 7.98 (1H, m), 8.51 (1H, d, J = 5.1 Hz), 8.55 (1H, d, J = 3.3 Hz) (CDCl₃) | 500 |
| 93 | 0.99 (3H, t, J = 7.5 Hz), 1.47-1.82 (4H, m), 3.06 (1H, dd, J = 12.6, 10.8 Hz), 3.19-3.26 (3H, m), 3.57 (3H, s), 3.62-3.67 (2H, m), 4.01 (2H, t, J = 6.3 Hz), 4.04 (1H, m), 6.86 (1H, s), 6.97 (2H, d, J = 8.4 Hz), 7.50-7.58 (6H, m), 7.98 (1H, m), 8.51 (1H, d, J = 5.1 Hz), 8.55 (1H, d, J = 3.0 Hz) (CDCl₃) | 514 |
| 94 | 2.93 (6H, m), 3.12 (1H, m), 3.39 (3H, s), 3.44-3.60 (4H, m), 4.03-4.13 (2H, m), 6.69 (2H, d, J = 8.7 Hz), 6.83 (1H, s), 7.14-7.45 (7H, m), 7.85 (1H, m), 8.49 (1H, d, J = 5.1 Hz), 8.55 (1H, d, J = 3.0 Hz) (CDCl₃) | 513 |
| 95 | 2.90 (3H, s), 2.94 (3H, s), 3.25-3.72 (8H, m), 3.99-4.24 (2H, m), 4.73-4.84 (2H, m), 6.16 (0.5H, s), 6.62 (1H, d, J = 8.7 Hz), 6.71 (1H, d, J = 8.4 Hz), 6.78-7.42 (8.5H, m), 7.90 (1H, m), 8.51-8.56 (2H, m) (CDCl₃) | 547 |
| 96 | 2.94 (6H, s), 3.12 (1H, m), 3.40 (3H, s), 3.53-3.61 (4H, m), 4.03-4.15 (2H, m), 6.69 (2H, d, J = 9.0 Hz), 6.83 (1H, s), 7.13-7.42 (6H, m), 7.86 (1H, m), 8.50 (1H, d, J = 4.8 Hz), 8.55 (1H, d, J = 3.0 Hz) (CDCl₃) | 547 |
| 97 | 2.93 (6H, s), 3.13 (1H, m), 3.39 (3H, s), 3.53-3.60 (4H, m), 4.03-4.15 (2H, m), 6.69 (2H, d, J = 8.7 Hz), 6.82 (1H, s), 7.15-7.39 (6H, m), 7.84 (1H, m), 8.49 (1H, d, J = 4.8 Hz), 8.55 (1H, d, J = 3.0 Hz) (CDCl₃) | 547 |
| 98 | 3.02 (4H, t, J = 4.7 Hz), 3.22 (4H, t, J = 4.2 Hz), 3.48 (3H, s), 6.83 (1H, s), 6.91-6.83 (2H, m), 7.33-7.26 (4H, m), 7.41 (1H, dd, J = 6.9, 7.8 Hz), 7.65 (2H, d, J = 8.3 Hz), 7.94 (1H, dd, J = 5.4, 6.9 Hz), 8.51 (1H, d, J = 5.4 Hz), 8.54 (1H, d, J = 3.3 Hz) (CDCl₃) | 424 |
| 99 | 3.02 (4H, t, J = 4.7 Hz), 3.22 (4H, t, J = 4.2 Hz), 3.48 (3H, s), 6.83 (1H, s), 6.91-6.83 (2H, m), 7.33-7.26 (4H, m), 7.41 (1H, dd, J = 6.9, 7.8 Hz), 7.65 (2H, d, J = 8.3 Hz), 7.94 (1H, dd, J = 5.4, 6.9 Hz), 8.51 (1H, d, J = 5.4 Hz), 8.54 (1H, d, J = 3.3 Hz) (CDCl₃) | 488 |
| 100 | 3.02 (4H, t, J = 4.7 Hz), 3.22 (4H, t, J = 4.2 Hz), 3.48 (3H, s), 6.83 (1H, s), 6.91-6.83 (2H, m), 7.33-7.26 (4H, m), 7.41 (1H, dd, J = 6.9, 7.8 Hz), 7.65 (2H, d, J = 8.3 Hz), 7.94 (1H, dd, J = 5.4, 6.9 Hz), 8.51 (1H, d, J = 5.4 Hz), 8.54 (1H, d, J = 3.3 Hz) (CDCl₃) | 438 |
| 101 | 3.02 (4H, t, J = 4.7 Hz), 3.22 (4H, t, J = 4.2 Hz), 3.48 (3H, s), 6.83 (1H, s), 6.91-6.83 (2H, m), 7.33-7.26 (4H, m), 7.41 (1H, dd, J = 6.9, 7.8 Hz), 7.65 (2H, d, J = 8.3 Hz), 7.94 (1H, dd, J = 5.4, 6.9 Hz), 8.51 (1H, d, J = 5.4 Hz), 8.54 (1H, d, J = 3.3 Hz) (CDCl₃) | 456 |
| 102 | 3.02 (4H, t, J = 4.7 Hz), 3.22 (4H, t, J = 4.2 Hz), 3.48 (3H, s), 6.83 (1H, s), 6.91-6.83 (2H, m), 7.33-7.26 (4H, m), 7.41 (1H, dd, J = 6.9, 7.8 Hz), 7.65 (2H, d, J = 8.3 Hz), 7.94 (1H, dd, J = 5.4, 6.9 Hz), 8.51 (1H, d, J = 5.4 Hz), 8.54 (1H, d, J = 3.3 Hz) (CDCl₃) | 498 |
| 103 | 3.02 (4H, t, J = 4.7 Hz), 3.22 (4H, t, J = 4.2 Hz), 3.48 (3H, s), 6.83 (1H, s), 6.91-6.83 (2H, m), 7.33-7.26 (4H, m), 7.41 (1H, dd, J = 6.9, 7.8 Hz), 7.65 (2H, d, J = 8.3 Hz), 7.94 (1H, dd, J = 5.4, 6.9 Hz), 8.51 (1H, d, J = 5.4 Hz), 8.54 (1H, d, J = 3.3 Hz) (CDCl₃) | 484 |
| 104 | 1.80-1.87 (2H, m), 2.06-2.12 (2H, m), 3.01-3.10 (3H, m), 3.51 (3H, s), 3.78-3.82 (2H, m), 6.57 (1H, s), 6.80-6.87 (1H, m), 7.09-7.16 (2H, m), 7.58-7.62 (1H, m), 8.00-8.04 (1H, m), 8.57 (1H, d, J = 4.2 Hz), 8.70 (1H, d, J = 1.2 Hz), 10.90 (1H, brs) (DMSO-d6) | 422 |
| 105 | 1.52-1.59 (2H, m), 2.01-2.09 (2H, m), 3.09-3.17 (2H, m), 3.42 (3H, s), 3.59-3.71 (3H, m), 6.11 (1H, d, J = 8.2 Hz), 6.57 (1H, s), 6.79 (1H, d, J = 7.2 Hz), 6.87-6.90 (2H, m), 7.25-7.30 (1H, m), 8.00-8.03 (1H, m), 8.57 (1H, d, J = 4.2 Hz), 8.69 (1H, d, J = 1.2 Hz) (DMSO-d6) | 448 |
| 106 | 1.56-1.67 (2H, m), 2.02-2.06 (2H, m), 3.04-3.11 (2H, m), 3.41 (3H, s), 3.50-3.67 (3H, m), 3.77 (3H, s), 4.57 (1H, d, J = 8.2 Hz), 6.49-6.58 (2H, m), 6.67 (1H, d, J = 7.2 Hz), 6.76-6.82 (2H, m), 8.00-8.04 (1H, m), 8.57 (1H, d, J = 4.2 Hz), 8.70 (1H, d, J = 1.2 Hz) (DMSO-d6) | 410 |

TABLE 2-continued

| Compound No. | 1H-NMR δ: | [M + 1] |
|---|---|---|
| 107 | 1.46-1.56 (2H, m), 1.99-2.03 (2H, m), 2.71 (6H, s), 3.03-3.11 (2H, m), 3.38-3.40 (1H, m), 3.41 (3H, s), 3.65-3.70 (2H, m), 4.85-4.88 (1H, m), 6.56-6.65 (5H, m), 8.00 (1H, dd, J = 1.2 Hz, 4.2 Hz), 8.57 (1H, d, J = 4.2 Hz), 8.70 (1H, d, J = 1.2 Hz) (DMSO-d6) | 423 |
| 108 | 1.49-1.59 (2H, m), 2.00-2.07 (2H, m), 3.06-3.14 (2H, m), 3.41 (3H, s), 3.46-3.48 (1H, m), 3.67 (3H, s), 3.69-3.72 (2H, m), 5.55 (1H, d, J = 8.2 Hz), 6.09-6.24 (3H, m), 6.56 (1H, s), 6.96 (1H, dd, J = 7.2, 7.3 Hz), 8.01 (1H, dd, J = 1.2, 4.2 Hz), 8.57 (1H, d, J = 4.2 Hz), 8.70 (1H, d, J = 1.2 Hz) (DMSO-d6) | 410 |
| 109 | 1.47-1.57 (2H, m), 1.99-2.07 (2H, m), 3.03-3.14 (2H, m), 3.40 (3H, s), 3.41-3.44 (1H, m), 3.63-3.65 (5H, m), 5.08 (1H, d, J = 8.2 Hz), 6.56-6.60 (3H, m), 6.72 (2H, d, J = 7.2 Hz), 8.00 (1H, dd, J = 1.2, 4.2 Hz), 8.57 (1H, d, J = 4.2 Hz), 8.70 (1H, d, J = 1.2 Hz) (DMSO-d6) | 410 |
| 110 | 1.59 (6H, s), 3.12 (1H, dd, J = 12.8, 10.4 Hz), 3.31 (1H, td, J = 11.8, 2.0 Hz), 3.54 (1H, d, J = 11.8 Hz), 3.58 (3H, s), 3.64 (1H, d, J = 12.8 Hz), 3.99 (1H, td, J = 11.6, 2.0 Hz), 4.18 (1H, dd, J = 11.8, 2.0 Hz), 4.73 (1H, dd, J = 10.4, 2.0 Hz), 6.89 (1H, s), 7.39 (2H, d, J = 8.4 Hz), 7.53 (2H, d, J = 8.4 Hz), 7.95 (1H, dd, J = 4.8, 3.2 Hz), 8.51 (1H, d, J = 4.8 Hz), 8.55 (1H, d, J = 3.2 Hz) (CDCl$_3$) | 424 |
| 111 | 1.77 (2H, m), 2.20 (2H, m), 2.37 (3H, s), 2.45 (2H, t, J = 11.2 Hz), 2.78 (3H, m), 3.30 (1H, td, J = 11.4, 2.0 Hz), 3.55 (1H, d, J = 13.2 Hz), 3.62 (3H, s), 3.80 (1H, d, J = 12.8 Hz), 3.85 (3H, s), 3.99 (1H, td, J = 11.4, 2.0 Hz), 4.20 (1H, dd, J = 11.4, 2.0 Hz), 5.05 (1H, dd, J = 10.0, 2.0 Hz), 6.87 (1H, d, J = 8.8 Hz), 6.89 (1H, s), 7.44 (1H, dd, J = 8.8, 2.4 Hz), 7.71 (1H, d, J = 2.4 Hz), 8.00 (1H, dd, J = 4.8, 3.2 Hz), 8.51 (1H, d, J = 4.8 Hz), 8.55 (1H, d, J = 3.2 Hz) (CDCl$_3$) | 510 |
| 112 | 3.11 (1H, dd, J = 10.8, 12.9 Hz), 3.32 (1H, td, J = 3.2, 12.0 Hz), 3.52-3.66 (2H, m), 3.58 (3H, s), 3.99 (1H, m), 4.16 (1H, m), 4.74 (1H, dd, J = 3.3, 11.1 Hz), 6.89 (1H, m), 7.33-7.42 (5H, m), 7.94 (1H, dd, J = 5.4, 6.9 Hz), 8.51 (1H, d, J = 5.4 Hz), 8.55 (1H, d, J = 3.3 Hz) (CDCl$_3$) | 367 |
| 113 | 2.84 (3H, s), 3.12 (1H, dd, J = 10.5, 12.6 Hz), 3.33 (1H, td, J = 3.2, 12.0 Hz), 3.50-3.60 (2H, m), 3.56 (3H, s), 3.96 (1H, m), 4.15 (1H, m), 4.59 (1H, d, J = 9.0 Hz), 6.61 (2H, d, J = 8.4 Hz), 6.88 (1H, s), 7.22 (2H, d, J = 8.4 Hz), 7.32 (1H, m), 7.96 (1H, dd, J = 5.0, 6.7 Hz), 8.50 (1H, d, J = 5.0 Hz), 8.55 (1H, d, J = 3.0 Hz) (CDCl$_3$) | 395 |
| 114 | 1.48 (6H, s), 2.98 (1H, dd, J = 10.5, 12.6 Hz), 3.17 (1H, td, J = 3.2, 12.0 Hz), 3.41 (3H, s), 3.69 (2H, m), 3.88 (1H, m), 4.04 (1H, dd, J = 3.3, 11.1 Hz), 4.71 (1H, d, J = 9.0 Hz), 5.40 (1H, s), 6.60 (1H, s), 7.35 (2H, d, J = 8.4 Hz), 7.46 (2H, d, J = 8.4 Hz), 7.98 (1H, dd, J = 5.4, 6.9 Hz), 8.58 (1H, d, J = 5.4 Hz), 8.70 (1H, d, J = 3.3 Hz) (DMSO-d6) | 424 |
| 115 | 2.98 (1H, dd, J = 10.5, 12.6 Hz), 3.17 (1H, td, J = 3.2, 12.0 Hz), 3.41 (3H, s), 3.69 (2H, m), 3.88 (1H, m), 4.04 (1H, dd, J = 3.3, 11.1 Hz), 4.71 (1H, d, J = 9.0 Hz), 5.40 (1H, s), 6.21 (2H, br.s), 6.57 (1H, s), 6.63 (2H, d, J = 8.4 Hz), 7.33-7.55 (6H, m), 7.97 (1H, dd, J = 5.0, 6.7 Hz), 8.56 (1H, d, J = 5.0 Hz), 8.69 (1H, d, J = 3.0 Hz) (DMSO-d6) | 456 |
| 116 | 2.67 (3H, s), 3.03 (1H, dd, J = 12.4, 10.4 Hz), 3.23 (3H, m), 3.57 (3H, s), 3.63 (2H, m), 4.11 (1H, dd, J = 10.0, 2.0 Hz), 6.87 (1H, s), 8.58 (2H, d, J = 8.4 Hz), 7.96 (1H, dd, J = 5.2, 3.2 Hz), 8.08 (2H, d, J = 8.4 Hz), 8.50 (1H, d, J = 5.2 Hz), 8.55 (1H, d, J = 3.2 Hz) (CDCl$_3$) | 448 |
| 117 | 1.66-1.84 (3H, m), 1.89-1.97 (1H, m), 2.91-3.04 (3H, m), 3.42 (3H, s), 3.62-3.77 (2H, m), 6.55 (1H, s), 7.31 (2H, d, J = 5.1 Hz), 7.53 (2H, d, J = 5.4 Hz), 7.96 (1H, dd, J = 6.6, 4.8 Hz), 8.56 (1H, d, J = 4.8 Hz), 8.69 (1H, d, J = 3.0 Hz) (DMSO) | 443 |
| 118 | | |
| 119 | 3.13 (1H, dd, J = 10.5, 12.9 Hz), 3.29 (1H, m), 3.50-3.60 (2H, m), 3.57 (3H, s), 3.82 (3H, s), 3.98 (1H, m), 4.14 (1H, dd, J = 2.1, 9.9 Hz), 4.67 (1H, dd, J = 2.1, 10.5 Hz), 6.88 (1H, s), 6.94 (2H, d, J = 8.7 Hz), 7.33 (2H, d, J = 8.7 Hz), 7.94 (1H, dd, J = 5.1, 5.1 Hz), 8.51 (1H, d, J = 5.4 Hz), 8.55 (1H, d, J = 3.3 Hz) (CDCl$_3$) | 396 |
| 120 | 3.05 (1H, dd, J = 10.5, 12.9 Hz), 3.23 (1H, m), 3.50 (2H, t, J = 11.1, 12.6 Hz), 3.62 (3H, s), 3.80 (3H, s), 3.98 (1H, m), 4.14 (1H, dd, J = 2.1, 9.9 Hz), 4.67 (1H, dd, J = 2.1, 10.5 Hz), 6.89 (2H, d, J = 8.7 Hz), 7.21 (2H, d, J = 8.7 Hz), 7.37 (1H, dd, J = 5.1, 5.1 Hz), 8.51 (1H, d, J = 5.4 Hz), 8.55 (1H, d, J = 3.3 Hz) (CDCl$_3$) | 474 |
| 121 | 1.97 (1H, m), 1.98 (3H, s), 2.30 (1H, m), 3.11-3.61 (9H, m), 3.56 (3H, s), 3.97 (1H, m), 4.59-4.63 (2H, m), 5.62 (1H, m), 6.58 (2H, d, J = 8.7 Hz), 6.87 (1H, s), 7.28 (2H, d, J = 9.0 Hz), 7.94 (1H, m), 8.49 (1H, d, J = 4.5 Hz), 8.55 (1H, d, J = 3.0 Hz) (CDCl$_3$) | 493 |
| 122 | 2.51-2.59 (4H, m), 3.48 (3H, s), 3.63-3.70 (4H, m), 6.60 (1H, s), 7.98 (1H, dd, J = 1.2, 4.2 Hz), 8.57 (1H, d, J = 4.2 Hz), 8.69 (1H, d, J = 1.2 Hz) (DMSO-d6) | 303 |
| 123 | 1.70-1.93 (4H, m), 2.40-2.45 (2H, m), 2.50-2.54 (4H, m), 2.56-2.96 (3H, m), 3.06-3.10 (4H, m), 3.41 (3H, s), 3.50-3.74 (4H, m), 4.43-4.47 (1H, m), 6.54 (1H, s), 6.89 (2H, d, J = 7.2 Hz), 7.16 (2H, d, J = 7.2 Hz), 7.95 (1H, dd, J = 1.2, 4.2 Hz), 8.56 (1H, s), 8.69 (1H, d, J = 1.2 Hz) (DMSO-d6) | 493 |

TABLE 2-continued

| Compound No. | 1H-NMR δ: | [M + 1] |
|---|---|---|
| 124 | 1.71-1.82 (4H, m), 2.86 (6H, s), 2.91-2.96 (3H, m), 3.42 (3H, s), 3.63-3.70 (2H, m), 6.54 (1H, s), 6.70 (2H, d, J = 7.2 Hz), 7.13 (2H, d, J = 7.2 Hz), 7.95 (1H, dd, J = 1.2, 4.2 Hz), 8.56 (1H, d, J = 4.2 Hz), 8.69 (1H, d, J = 1.2 Hz) (DMSO-d6) | 408 |
| 125 | 1.70-1.94 (4H, m), 2.90-2.97 (3H, m), 3.05-3.08 (4H, m), 3.42 (3H, s), 3.65-3.74 (6H, m), 6.54 (1H, s), 6.90 (2H, d, J = 7.2 Hz), 7.19 (2H, d, J = 7.2 Hz), 7.95 (1H, dd, J = 1.2, 4.2 Hz), 8.56 (1H, d, J = 4.2 Hz), 8.69 (1H, d, J = 1.2 Hz) (DMSO-d6) | 450 |
| 126 | 1.52-1.90 (10H, m), 2.89-2.96 (2H, m), 3.07-3.10 (4H, m), 3.41 (3H, s), 3.64-3.74 (3H, m), 6.54 (1H, s), 6.88 (2H, d, J = 7.2 Hz), 7.15 (2H, d, J = 7.2 Hz), 7.95 (1H, dd, J = 1.2, 4.2 Hz), 8.56 (1H, d, J = 4.2 Hz), 8.69 (1H, d, J = 1.2 Hz) (DMSO-d6) | 448 |
| 127 | 1.70-1.81 (4H, m), 2.21 (3H, s), 2.42-2.45 (4H, m), 2.88-2.94 (3H, m), 3.07-3.11 (4H, m), 3.43 (3H, s), 3.63-3.70 (2H, m), 6.54 (1H, s), 6.89 (2H, d, J = 7.2 Hz), 7.16 (2H, d, J = 7.2 Hz), 7.95 (1H, dd, J = 1.2, 4.2 Hz), 8.56 (1H, d, J = 4.2 Hz), 8.69 (1H, d, J = 1.2 Hz) (DMSO-d6) | 463 |
| 128 | 1.66-1.82 (6H, m), 2.05-2.10 (2H, m), 2.61-2.64 (2H, m), 2.73 (6H, s), 2.90-2.94 (3H, m), 3.26-3.30 (1H, m), 3.41 (3H, s), 3.64-3.82 (4H, m), 6.54 (1H, s), 6.93 (2H, d, J = 7.2 Hz), 7.18 (2H, d, J = 7.2 Hz), 7.95 (1H, dd, J = 1.2, 4.2 Hz), 8.56 (1H, d, J = 4.2 Hz), 8.69 (1H, d, J = 1.2 Hz) (DMSO-d6) | 491 |
| 129 | 1.71-1.82 (4H, m), 2.90-2.97 (3H, m), 3.07-3.11 (4H, m), 3.42 (3H, s), 3.51-3.55 (4H, m), 3.64-3.74 (2H, m), 5.11 (2H, s), 6.54 (1H, s), 6.92 (2H, d, J = 7.2 Hz), 7.19 (2H, d, J = 7.2 Hz), 7.30-7.45 (5H, m), 7.95 (1H, dd, J = 1.2, 4.2 Hz), 8.56 (1H, d, J = 4.2 Hz), 8.69 (1H, d, J = 1.2 Hz) (DMSO-d6) | 583 |
| 130 | 1.98-2.10 (4H, m), 3.08-3.16 (2H, m), 3.28 (3H, s), 3.67-3.72 (2H, m), 3.79 (2H, s), 6.53 (1H, s), 7.24 (2H, d, J = 7.2 Hz), 7.41-7.56 (3H, m), 7.77 (1H, dd, J = 1.2, 4.2 Hz), 8.56 (1H, d, J = 4.2 Hz), 8.69 (1H, d, J = 1.2 Hz) (DMSO-d6) | 452 |
| 131 | 1.55-1.62 (2H, m), 1.84-1.88 (2H, m), 2.36-2.44 (11H, m), 2.85-2.92 (2H, m), 3.39 (3H, s), 3.47-3.51 (2H, m), 3.69-3.73 (2H, m), 4.40-4.43 (1H, m), 6.55 (1H, s), 7.98 (1H, dd, J = 1.2, 4.2 Hz), 8.57 (1H, d, J = 4.2 Hz), 8.70 (1H, d, J = 1.2 Hz) (DMSO-d6) | 417 |
| 132 | 1.71-1.94 (4H, m), 2.90-3.00 (7H, m), 3.11-3.12 (4H, m), 3.28-3.30 (1H, m), 3.42 (3H, s), 3.64-3.75 (2H, m), 6.55 (1H, s), 6.90 (2H, d, J = 7.2 Hz), 7.19 (2H, d, J = 7.2 Hz), 7.95 (1H, dd, J = 1.2, 4.2 Hz), 8.56 (1H, d, J = 4.2 Hz), 8.68 (1H, d, J = 1.2 Hz) (DMSO-d6) | 449 |
| 133 | 1.60 (4H, m), 1.73 (2H, m), 1.88 (2H, m), 2.80 (3H, s), 3.14 (1H, dd, J = 12.8, 10.4 Hz), 3.28 (1H, td, J = 11.4, 2.0 Hz), 3.55 (2H, m), 3.56 (3H, s), 3.96 (1H, td, J = 11.4, 2.4 Hz), 4.16 (2H, m), 4.60 (1H, dd, J = 10.4, 2.4 Hz), 6.81 (1H, d, J = 8.8 Hz), 6.87 (1H, s), 7.24 (1H, d, J = 8.8 Hz), 7.96 (1H, dd, J = 5.2, 3.2 Hz), 8.51 (1H, d, J = 5.2 Hz), 8.55 (1H, d, J = 3.2 Hz) (CDCl$_3$) | 464 |
| 134 | 1.50 (4H, m), 1.64 (4H, m), 1.72 (2H, m), 1.83 (2H, m), 2.76 (3H, s), 3..14 (1H, dd, J = 12.8, 10.4 Hz), 3.28 (1H, td, J = 11.4, 2.0 Hz), 3.56 (2H, m), 3.57 (3H, s), 3.77 (1H, m), 3.96 (1H, td, J = 11.4, 1.6 Hz), 4.14 (1H, dd, J = 11.4, 1.6 Hz), 4.59 (1H, dd, J = 10.4, 2.0 Hz), 6.74 (2H, d, J = 8.8 Hz), 7.24 (2H, d, J = 8.8 Hz), 7.96 (1H, dd, J = 4.8, 3.2 Hz), 8.51 (1H, d, J = 4.8 Hz), 8.55 (1H, d, J = 3.2 Hz) (CDCl$_3$) | 492 |
| 135 | 1.18 (3H, m), 1.37 (2H, m), 1.62 (1H, m), 1.77 (2H, m), 2.05 (2H, m), 3.12 (1H, dd, J = 12.9, 11.4 Hz), 3.27 (2H, m), 3.55 (3H, m), 3.56 (3H, s), 3.95 (1H, td, J = 11.4, 1.8 Hz), 4.13 (1H, dd, J = 11.4, 1.8 Hz), 4.57 (1H, dd, J = 10.5, 2.1 Hz), 6.58 (2H, d, J = 8.4 Hz), 6.88 (1H, s), 7.18 (2H, d, J = 8.4 Hz), 7.96 (1H, dd, J = 4.5, 3.3 Hz), 8.51 (1H, d, J = 4.5 Hz), 8.55 (1H, d, J = 3.3 Hz) (CDCl$_3$) | 464 |
| 136 | 1.44 (2H, m), 1.62 (2H, m), 1.71 (2H, m), 2.02 (2H, m), 3.12 (1H, dd, J = 12.8, 10.8 Hz), 3.28 (1H, td, J = 11.4, 2.0 Hz), 3.54 (2H, m), 3.56 (3H, s), 3.69 (1H, br s), 3.77 (1H, m), 3.96 (1H, td, J = 11.4, 2.0 Hz), 4.13 (1H, dd, J = 11.4, 2.0 Hz), 4.58 (1H, dd, J = 10.8, 2.4 Hz), 6.60 (2H, d, J = 8.4 Hz), 6.87 (1H, s), 7.19 (2H, d, J = 8.4 Hz), 7.96 (1H, dd, J = 4.8, 2.1 Hz), 8.51 (1H, d, J = 4.8 Hz), 8.55 (1H, d, J = 2.1 Hz) (CDCl$_3$) | 450 |
| 137 | 1.26 (6H, d, J = 7.2 Hz), 2.92 (1H, m), 3.12 (1H, dd, J = 10.8, 12.9 Hz), 3.31 (1H, td, J = 3.2, 12.0 Hz), 3.51-3.66 (2H, m), 3.57 (3H, s), 3.97 (1H, m), 4.14 (1H, m), 4.71 (1H, dd, J = 2.5, 10.1 Hz), 6.88 (1H, s), 7.26 (2H, d, J = 8.4 Hz), 7.33 (2H, d, J = 8.4 Hz), 7.95 (1H, dd, J = 5.1, 6.6 Hz), 8.51 (1H, d, J = 4.5 Hz), 8.55 (1H, d, J = 3.0 Hz) (CDCl$_3$) | 409 |
| 138 | 2.28 (1H, br.s), 3.13 (1H, dd, J = 10.8, 12.9 Hz), 3.30 (1H, m), 3.56 (3H, s), 3.50-3.72 (4H, m), 3.97-4.22 (4H, m), 4.59 (1H, dd, J = 1.9, 10.4 Hz), 4.76 (1H, m), 6.49 (2H, d, J = 8.6 Hz), 6.88 (1H, s), 7.24 (2H, d, J = 8.6 Hz), 7.96 (1H, dd, J = 5.1, 6.6 Hz), 8.50 (1H, d, J = 4.5 Hz), 8.55 (1H, d, J = 3.0 Hz) (CDCl$_3$) | 438 |
| 139 | 3.10 (1H, dd, J = 10.8, 12.9 Hz), 3.31 (1H, td, J = 3.2, 12.0 Hz), 3.51-3.62 (2H, m), 3.57 (3H, s), 3.96-4.17 (6H, m), 4.65 (1H, dd, J = 2.5, 10.1 Hz), 6.88 (1H, s), 6.93 (2H, d, J = 8.4 Hz), 7.33 (2H, d, J = 8.4 Hz), 7.95 (1H, dd, J = 5.1, 6.6 Hz), 8.51 (1H, d, J = 4.8 Hz), 8.55 (1H, d, J = 3.0 Hz) (CDCl$_3$) | 546 |
| 140 | 2.28 (3H, s), 3.07 (4H, m), 3.59 (4H, m), 3.73 (3H, s), 5.78 (1H, s), 6.88 (1H, s), 6.98 (1H, m), 7.27 (1H, s), 7.61 (1H, dd, J = 8.7, 15.0 Hz), 7.94-7.98 (2H, m), 8.52 (1H, d, J = 4.8 Hz), 8.56 (1H, d, J = 3.0 Hz) (CDCl$_3$) | 464 |

TABLE 2-continued

| Compound No. | 1H-NMR δ: | [M + 1] |
|---|---|---|
| 141 | 2.04 (2H, d, J = 13.1 Hz), 2.34 (3H, s), 2.53 (2H, m), 2.91 (2H, m), 3.55 (3H, s), 3.70 (2H, d, J = 13.1 Hz), 4.27 (1H, m), 6.07 (1H, s), 6.86 (1H, s), 7.36-7.48 (5H, m), 7.96 (1H, dd, J = 8.7, 15.0 Hz), 8.48 (1H, d, J = 4.8 Hz), 8.54 (1H, d, J = 3.0 Hz) (CDCl$_3$) | 445 |
| 142 | 2.06 (2H, d, J = 13.1 Hz), 2.22 (2H, m), 2.99 (2H, m), 3.13 (1H, m), 3.54 (3H, s), 3.70 (2H, d, J = 13.1 Hz), 6.86 (1H, s), 7.43-7.66 (6H, m), 7.96 (1H, dd, J = 8.7, 15.0 Hz), 8.48 (1H, d, J = 4.8 Hz), 8.54 (1H, d, J = 3.0 Hz) (CDCl$_3$) | 432 |
| 143 | 2.19 (3H, s), 3.07 (1H, dd, J = 10.8, 12.9 Hz), 3.29 (1H, m), 3.52-3.65 (2H, m), 3.57 (3H, s), 3.98 (1H, m), 4.16 (1H, m), 4.70 (1H, dd, J = 1.9, 10.4 Hz), 6.89 (1H, s), 6.91 (1H, s), 7.36 (2H, d, J = 8.5 Hz), 7.54 (2H, d, J = 8.5 Hz), 7.94 (1H, dd, J = 5.1, 6.6 Hz), 8.51 (1H, d, J = 4.8 Hz), 8.55 (1H, d, J = 3.0 Hz) (CDCl$_3$) | 424 |
| 144 | 1.58-1.65 (2H, m), 1.81-1.92 (6H, m), 3.11 (1H, dd, J = 13.2, 10.8 Hz), 3.30 (1H, m), 3.51-3.63 (2H, m), 3.58 (3H, s), 3.98 (1H, m), 4.15 (1H, m), 4.66 (1H, dd, J = 10.5, 2.1 Hz), 4.77 (1H, m), 6.90 (2H, d, J = 8.1 Hz), 6.91 (1H, s), 7.31 (2H, d, J = 8.1 Hz), 7.96 (1H, dd, J = 6.6, 5.1 Hz), 8.52 (1H, d, J = 4.8 Hz), 8.57 (1H, d, J = 3.0 Hz) (CDCl$_3$) | 451 |
| 145 | 1.33 (6H, d, J = 6.0 Hz), 1.81-1.92 (6H, m), 3.11 (1H, m), 3.29 (1H, m), 3.50-3.62 (2H, m), 3.57 (3H, s), 3.98 (1H, m), 4.15 (1H, m), 4.63 (1H, m), 4.65 (1H, m), 6.87 (1H, s), 6.91 (2H, d, J = 8.4 Hz), 7.31 (2H, d, J = 8.4 Hz), 7.95 (1H, dd, J = 6.3, 5.1 Hz), 8.51 (1H, d, J = 5.1 Hz), 8.55 (1H, d, J = 3.0 Hz) (CDCl$_3$) | 425 |
| 146 | 0.36 (2H, m), 0.66 (2H, m), 1.27 (1H, m), 3.11 (1H, dd, J = 13.2, 10.5 Hz), 3.29 (1H, m), 3.57-3.61 (2H, m), 3.58 (3H, s), 3.82 (2H, d, J = 6.9 Hz), 3.98 (1H, m), 4.15 (1H, m), 4.67 (1H, dd, J = 10.5, 2.1 Hz), 6.89 (1H, s), 6.93 (2H, d, J = 8.7 Hz), 7.32 (2H, d, J = 8.7 Hz), 7.95 (1H, dd, J = 6.6, 5.1 Hz), 8.52 (1H, d, J = 5.1 Hz), 8.56 (1H, d, J = 3.0 Hz) (CDCl$_3$) | 437 |
| 147 | 3.11 (1H, m), 3.29 (1H, m), 3.57-3.66 (2H, m), 3.58 (3H, s), 3.99 (1H, m), 4.16 (1H, m), 4.75 (1H, dd, J = 10.5, 2.1 Hz), 6.89 (1H, s), 7.25 (2H, d, J = 8.7 Hz), 7.45 (2H, d, J = 8.7 Hz), 7.92 (1H, dd, J = 6.6, 5.1 Hz), 8.52 (1H, d, J = 5.1 Hz), 8.56 (1H, d, J = 3.0 Hz) (CDCl$_3$) | 451 |
| 148 | 1.25-1.65 (4H, m), 1.80-1.97 (6H, m), 3.11 (1H, dd, J = 13.2, 10.5 Hz), 3.29 (1H, m), 3.51-3.63 (2H, m), 3.57 (3H, s), 3.98 (1H, m), 4.14 (1H, m), 4.25 (1H, m), 4.65 (1H, dd, J = 10.5, 2.1 Hz), 6.88 (1H, s), 6.92 (2H, d, J = 9.0 Hz), 7.31 (2H, d, J = 9.0 Hz), 7.95 (1H, dd, J = 6.6, 5.1 Hz), 8.51 (1H, d, J = 5.1 Hz), 8.56 (1H, d, J = 3.0 Hz) (CDCl$_3$) | 465 |
| 149 | 1.69 (2H, dd, J = 11.2, 4.4 Hz), 1.88 (2H, qd, J = 11.4, 4.4 Hz), 2.81 (3H, s), 3.13 (1H, dd, J = 12.8, 10.8 Hz), 3.28 (1H, td, J = 11.4, 2.8 Hz), 3.49 (3H, m), 3.56 (3H, m), 3.82 (1H, m), 3.96 (1H, td, J = 11.4, 2.4 Hz), 4.07 (2H, dd, J = 11.2, 4.0 Hz), 4.15 (1H, dd, J = 11.4, 2.4 Hz), 4.61 (1H, dd, J = 10.4, 2.0 Hz), 6.82 (2H, d, J = 8.4 Hz), 6.87 (1H, s), 7.27 (2H, d, J = 8.4 Hz), 7.95 (1H, dd, J = 5.2, 3.2 Hz), 8.50 (1H, d, J = 5.2 Hz), 8.55 (1H, d, J = 3.2 Hz) (CDCl$_3$) | 480 |
| 150 | 2.38 (2H, t, J = 7.3 Hz), 3.13 (1H, dd, J = 10.8, 12.9 Hz), 3.28 (1H, m), 3.56 (3H, s), 3.50-3.59 (2H, m), 3.88 (4H, t, J = 7.3 Hz), 3.96 (1H, td, J = 2.2, 11.6 Hz), 4.14 (1H, d, J = 11.8 Hz), 4.60 (1H, dd, J = 2.1, 10.4 Hz), 6.45 (2H, d, J = 8.6 Hz), 6.88 (1H, s), 7.24 (2H, d, J = 8.6 Hz), 7.96 (1H, dd, J = 5.1, 6.6 Hz), 8.51 (1H, d, J = 4.5 Hz), 8.55 (1H, d, J = 3.0 Hz) (CDCl$_3$) | 422 |
| 151 | 1.18 (6H, t, J = 6.9 Hz), 2.89 (1H, dd, J = 10.8, 12.9 Hz), 3.28 (1H, m), 3.36 (4H, q, J = 6.9 Hz), 3.57 (3H, s), 3.50-3.60 (2H, m), 3.73 (3H, s), 3.98 (1H, td, J = 2.2, 11.6 Hz), 4.14 (1H, d, J = 11.8 Hz), 4.96 (1H, dd, J = 2.1, 10.4 Hz), 6.19 (1H, d, J = 2.1 Hz), 6.31 (1H, dd, J = 2.4, 8.4 Hz), 6.88 (1H, s), 7.26 (1H, d, J = 1.8 Hz), 8.02 (1H, dd, J = 5.1, 6.6 Hz), 8.51 (1H, d, J = 4.5 Hz), 8.55 (1H, d, J = 3.0 Hz) (CDCl$_3$) | 468 |
| 152 | 1.09-1.34 (5H, m), 1.57-1.91 (9H, m), 2.77-2.91 (3H, m), 3.03-3.12 (1H, m), 3.41 (3H, s), 3.61-3.73 (2H, m), 5.24-5.27 (1H, m), 6.50-6.54 (3H, m), 7.00 (2H, d, J = 7.2 Hz), 7.95 (1H, dd, J = 1.2, 4.2 Hz), 8.56 (1H, d, J = 4.2 Hz), 8.69 (1H, d, J = 1.2 Hz) (DMSO-d6) | 462 |
| 153 | 1.73-1.90 (4H, m), 2.95-3.10 (5H, m), 3.45 (3H, s), 3.70-3.76 (2H, m), 3.87-3.93 (2H, m), 6.55 (1H, s), 6.70 (1H, dd, J = 7.2 Hz, 7.3 Hz), 7.00-7.32 (7H, m), 7.97 (1H, dd, J = 1.2, 4.2 Hz), 8.57 (1H, d, J = 4.2 Hz), 8.69 (1H, d, J = 1.2 Hz) (DMSO-d6) | 482 |
| 154 | 1.10-1.15 (1H, m), 1.32-1.46 (4H, m), 1.64-1.89 (9H, m), 2.67 (3H, s), 2.86-2.94 (3H, m), 3.46 (3H, s), 3.63-3.69 (3H, m), 6.54 (2H, d, J = 7.2 Hz), 7.10 (2H, d, J = 7.2 Hz), 7.95 (1H, dd, J = 1.2, 4.2 Hz), 8.56 (1H, d, J = 4.2 Hz), 8.68 (1H, d, J = 1.2 Hz) (DMSO-d6) | 476 |
| 155 | 0.88 (1H, m), 1.02 (4H, m), 1.40 (2H, m), 1.59 (1H, m), 1.71 (2H, m), 1.73 (3H, s), 1.81 (2H, m), 3.12 (1H, dd, J = 12.8, 10.6 Hz), 3.33 (1H, td, J = 12.4, 4.4 Hz), 3.55 (1H, d, J = 12.4 Hz), 3.60 (3H, m), 3.68 (1H, d, J = 12.8, 1H), 4.01 (1H, td, J = 12.4, 2.4 Hz), 4.20 (1H, d, J = 12.4, 2.0 Hz), 4.60 (1H, m), 4.78 (1H, dd, J = 10.6, 2.0 Hz), 6.87 (1H, s), 7.13 (2H, d, J = 8.4 Hz), 7.45 (2H, d, J = 8.4 Hz), 7.93 (1H, dd, J = 4.8, 3.2 Hz), 8.52 (1H, d, J = 4.8 Hz), 8.56 (1H, d, J = 3.2 Hz) (CDCl$_3$) | 506 |
| 156 | 1.13 (m, 1H), 1.16 (3H, t, J = 6.9 Hz), 1.37 (m, 4H), 1.70 (m, 1H), 1.84 (m, 4H), 3.16 (1H, dd, J = 12.9, 10.5 Hz), 3.28 (3H, m), 3.55 (3H, m), 3.56 (s, 3H), 3.96 (1H, t, J = 11.4 Hz), 4.13 (1H, d, J = 11.4 Hz), 4.58 (1H, d, J = 8.1 Hz), 6.72 (2H, d, J = 9.0 Hz), 6.88 (1H, s), 7.23 (2H, d, J = 9.0 Hz), | 492 |

TABLE 2-continued

| Compound No. | 1H-NMR δ: | [M + 1] |
|---|---|---|
| | 7.97 (1H, dd, J = 5.1, 3.3 Hz), 8.51 (1H, d, J = 5.1 Hz), 8.55 (1H, d, J = 3.3 Hz) (CDCl₃) | |
| 157 | 2.34 (6H, s), 2.72-2.76 (2H, m), 3.11 (1H, dd, J = 12.6, 10.8 Hz), 3.29 (1H, m), 3.51-3.61 (2H, m), 3.57 (3H, s), 3.94-4.18 (4H, m), 4.66 (1H, dd, J = 11.4, 2.1 Hz), 6.84 (1H, s), 6.95 (2H, d, J = 8.7 Hz), 7.32 (2H, d, J = 8.7 Hz), 7.95 (1H, m), 8.51 (1H, d, J = 5.1 Hz), 8.55 (1H, d, J = 3.0 Hz) (CDCl₃) | 454 |
| 158 | 3.15 (1H, dd, J = 10.8, 12.9 Hz), 3.29 (1H, m), 3.52-3.65 (2H, m), 3.61 (3H, s), 3.76 (2H, br.s), 3.98 (1H, m), 4.16 (1H, m), 4.62 (1H, dd, J = 1.9, 10.4 Hz), 6.68 (2H, d, J = 8.7 Hz), 6.88 (1H, s), 7.24 (2H, d, J = 8.7 Hz), 7.96 (1H, dd, J = 5.4, 6.9 Hz), 8.51 (1H, d, J = 5.4 Hz), 8.55 (1H, d, J = 3.3 Hz) (CDCl₃) | 382 |
| 159 | 3.15 (1H, dd, J = 10.8, 12.9 Hz), 3.29 (1H, m), 3.52-3.65 (2H, m), 3.61 (3H, s), 3.99 (1H, m), 4.16 (1H, m), 4.71 (1H, d, J = 10.1 Hz), 6.90-7.01 (5H, m), 7.17-7.59 (8H, m), 7.94 (1H, dd, J = 5.4, 6.9 Hz), 8.33 (2H, d, J = 4.6 Hz), 8.56 (2H, m) (CDCl₃) | 536 |
| 160 | 3.15 (1H, dd, J = 10.8, 12.9 Hz), 2.97 (6H, s), 3.30 (1H, m), 3.54 (1H, m), 3.60 (3H, s), 3.72 (1H, m), 3.85 (3H, s), 3.98 (1H, m), 4.16 (1H, m), 4.98 (1H, dd, J = 1.9, 10.4 Hz), 6.24 (1H, d, J = 2.4 Hz), 6.36 (1H, dd, J = 2.4, 8.3 Hz), 6.68 (1H, s), 7.34 (1H, d, J = 4.2 Hz), 7.81 (2H, d, J = 6.0 Hz), 8.70 (2H, d, J = 6.0 Hz) (CDCl₃) | 440 |
| 161 | 3.15 (1H, dd, J = 10.8, 12.9 Hz), 3.29 (1H, m), 3.52-3.65 (2H, m), 3.61 (3H, s), 3.99 (1H, m), 4.16 (1H, m), 4.69 (1H, dd, J = 1.9, 10.4 Hz), 6.58 (1H, br.s), 6.74-6.77 (1H, m), 6.85 (1H, d, J = 8.4 Hz), 6.89 (1H, s), 7.38 (4H, m), 7.49-7.51 (1H, m), 7.96 (1H, dd, J = 5.4, 6.9 Hz), 8.21 (1H, d, J = 6.0 Hz), 8.52 (1H, d, J = 5.4 Hz), 8.56 (1H, d, J = 3.3 Hz) (CDCl₃) | 459 |
| 162 | 3.14 (1H, dd, J = 10.8, 12.9 Hz), 3.30 (1H, m), 3.58-3.67 (2H, m), 3.59 (3H, s), 4.00 (1H, m), 4.16 (1H, m), 4.70 (1H, dd, J = 1.9, 10.4 Hz),, 6.78 (1H, s), 6.88 (1H, s), 7.23 (1H, s), 7.38 (2H, d, J = 8.3 Hz), 7.55 (2H, d, J = 8.3 Hz), 8.72 (2H, m), 8.40 (1H, d, J = 2.7 Hz), 8.52 (2H, m), 8.56 (1H, d, J = 3.3 Hz) (CDCl₃) | 459 |
| 163 | 3.12 (1H, dd, J = 10.8, 12.9 Hz), 3.29 (1H, m), 3.52-3.64 (2H, m), 3.59 (3H, s), 3.99 (1H, m), 4.16 (1H, m), 4.68 (1H, dd, J = 1.9, 10.4 Hz), 5.81 (1H, br.s), 6.88 (1H, s), 7.10 (2H, d, J = 8.4 Hz), 7.19 (1H, dd, J = 4.8, 8.4 Hz), 7.33 (2H, d, J = 8.4 Hz), 7.40 (1H, m), 7.96 (1H, dd, J = 5.4, 6.9 Hz), 8.21 (1H, d, J = 6.0 Hz), 8.40 (1H, d, J = 2.7 Hz), 8.52 (1H, d, J = 5.4 Hz), 8.56 (1H, d, J = 3.3 Hz) (CDCl₃) | 459 |
| 164 | 2.65-2.69 (1H, m), 3.08-3.12 (1H, m), 3.48 (3H, s), 3.60-3.64 (1H, m), 3.79 (3H, s), 3.80-3.90 (2H, m), 4.05-4.08 (1H, m), 4.93 (1H, dd, J = 1.2, 10.2 Hz), 5.12-5.16 (1H, br), 6.45 (1H, s), 7.03 (1H, d, J = 7.3 Hz), 7.10 (1H, s), 7.40 (1H, d, J = 7.3 Hz), 7.69 (1H, d, J = 4.2 Hz), 8.64 (1H, d, J = 4.2 Hz), 8.76 (1H, s) (DMSO-d6) | 448 |
| 165 | 2.88-2.96 (1H, m), 3.13-3.19 (1H, m), 3.63-3.70 (2H, m), 3.82-3.90 (1H, m), 4.01-4.06 (1H, m), 4.74 (1H, dd, J = 1.2, 10.2 Hz), 6.06-6.10 (1H, br), 6.46 (1H, s), 7.21 (2H, dd, J = 6.8, 7.3 Hz), 7.45 (2H, dd, J = 6.8, 7.3 Hz), 7.70 (1H, d, J = 4.2 Hz), 8.63 (1H, d, J = 4.2 Hz), 8.76 (1H, s) (DMSO-d6) | 401 |
| 166 | 2.93-2.97 (1H, m), 3.14-3.17 (1H, m), 3.45 (3H, s), 3.64-3.72 (2H, m), 3.92 (3H, s), 3.92-3.94 (1H, m), 4.04-4.08 (1H, m), 4.75 (1H, dd, J = 1.2, 10.2 Hz), 5.96-5.99 (1H, br), 6.83 (1H, s), 7.23 (2H, dd, J = 6.8, 7.3 Hz), 7.41 (1H, s), 7.43-58 (3H, m), 8.26 (1H, d, J = 4.2 Hz) (DMSO-d6) | 397 |
| 167 | 2.51 (3H, s), 2.88-2.93 (1H, m), 3.09-3.16 (1H, m), 3.49 (3H, s), 3.61-3.68 (2H, m), 3.84-3.90 (1H, m), 3.99-4.06 (1H, m), 4.73 (1H, dd, J = 1.2, 10.2 Hz), 5.94-5.96 (1H, br), 6.49 (1H, s), 7.20 (2H, dd, J = 6.8, 7.3 Hz), 7.45 (2H, dd, J = 6.8, 7.3 Hz), 8.09 (1H, d, J = 4.2 Hz), 8.84 (1H, d, J = 4.2 Hz), 8.91 (1H, s) | 381 |
| 168 | 3.00-3.08 (1H, m), 3.37-3.40 (1H, m), 3.48 (3H, s), 3.70-3.74 (1H, m), 3.84-3.92 (2H, m), 4.05-4.09 (1H, m), 4.86 (1H, dd, J = 1.2, 10.2 Hz), 7.16-7.22 (3H, m), 7.49-7.58 (8H, m), 8.28-8.31 (4H, m), 8.47-8.50 (2H, m) (DMSO-d6) | 519 |
| 169 | 2.90-2.97 (1H, m), 3.12-3.20 (1H, m), 3.53 (3H, s), 3.64-3.72 (2H, m), 3.85-3.92 (1H, m), 4.01-4.05 (1H, m), 4.75 (1H, dd, J = 1.2, 10.2 Hz), 4.85-4.90 (1H, br), 6.51 (1H, s), 7.17 (2H, dd, J = 6.8, 7.3 Hz), 7.42 (2H, dd, J = 6.8, 7.3 Hz), 7.81-7.86 (1H, m), 7.97-8.06 (2H, m), 8.30 (1H, d, J = 7.3 Hz), 8.50 (1H, d, J = 7.3 Hz), 9.22 (1H, d, J = 4.2 Hz) (DMSO-d6) | 417 |
| 170 | 2.94-3.02 (1H, m), 3.17-3.20 (1H, m), 3.46 (3H, s), 3.66-4.05 (4H, m), 4.46-4.50 (1H, br), 4.76 (1H, dd, J = 1.2, 10.2 Hz), 6.93 (1H, s), 7.22 (2H, dd, J = 6.8, 7.3 Hz), 7.50 (2H, dd, J = 6.8, 7.3 Hz), 8.00-8.03 (1H, m), 8.09 (1H, s), 8.52 (1H, d, J = 4.2 Hz) (DMSO-d6) | 401 |
| 171 | 2.88-2.96 (1H, m), 3.06-3.10 (1H, m), 3.47 (3H, s), 3.62-3.68 (2H, m), 3.84-3.86 (1H, m), 4.00-4.05 (1H, m), 4.72 (1H, dd, J = 1.2, 10.2 Hz), 6.41 (1H, s), 7.18 (2H, dd, J = 6.8, 7.3 Hz), 7.46 (2H, dd, J = 6.8, 7.3 Hz), 7.65 (1H, d, J = 4.2 Hz), 8.46 (1H, d, J = 4.2 Hz) (DMSO-d6) | 436 |
| 172 | 3.20-3.27 (4H, m), 3.41 (3H, s), 3.73-76 (4H, m), 4.00 (3H, s), 6.80 (1H, s), 7.90 (1H, d, J = 4.2 Hz), 8.33 (1H, d, J = 4.2 Hz), 8.54 (1H, s) (DMSO-d6) | 303 |

TABLE 2-continued

| Compound No. | 1H-NMR δ: | [M + 1] |
|---|---|---|
| 173 | 2.54 (3H, s), 2.69-2.73 (1H, m), 3.09-3.16 (1H, m), 3.50 (3H, s), 3.58-3.62 (1H, m), 3.74-3.90 (5H, m), 4.06-4.09 (1H, m), 4.92 (1H, dd, J = 1.2, 10.2 Hz), 6.48 (1H, s), 7.05 (1H, d, J = 7.3 Hz), 7.11 (1H, s), 7.40 (1H, d, =7.3 Hz), 8.07 (1H, d, J = 4.2 Hz), 8.84 (1H, d, J = 4.2 Hz), 8.92 (1H, s) (DMSO-d6) | 427 |
| 174 | 2.87-2.91 (1H, m), 3.08-3.12 (1H, m), 3.46 (3H, s), 3.61-3.68 (2H, m), 3.86-4.06 (6H, m), 4.72 (1H, dd, J = 1.2, 10.2 Hz), 6.33 (1H, s), 7.16-7.22 (3H, m), 7.42-7.47 (2H, m), 8.18 (1H, d, J = 1.2 Hz) (DMSO-d6) | 431 |
| 175 | 2.89-2.99 (1H, m), 3.15-3.19 (1H, m), 3.47 (3H, s), 3.65-3.73 (2H, m), 3.89-3.92 (1H, m), 4.05-4.07 (1H, m), 4.11 (3H, s), 4.75 (1H, dd, J = 1.2, 10.2 Hz), 6.21-6.27 (1H, br), 6.91 (1H, s), 7.23 (2H, dd, J = 6.8, 7.3 Hz), 7.49 (2H, dd, J = 6.8, 7.3 Hz), 8.39 (1H, d, J = 4.2 Hz), 8.59 (1H, d, J = 4.2 Hz), 8.80 (1H, s) (DMSO-d6) | 397 |
| 176 | 3.24-3.27 (4H, m), 3.39 (3H, s), 3.71-3.74 (4H, m), 3.92-3.96 (1H, br), 5.40 (2H, s), 6.80 (1H, s), 7.30 (2H, dd, J = 6.8, 7.3 Hz), 7.55 (2H, dd, J = 6.8, 7.3 Hz), 8.16 (1H, d, J = 4.2 Hz), 8.48 (1H, d, J = 4.2 Hz), 8.76 (1H, s) (DMSO-d6) | 397 |
| 177 | 2.72-2.77 (1H, m), 3.25-3.29 (1H, m), 3.46 (3H, s), 3.62-3.67 (1H, m), 3.81-3.85 (5H, m), 4.07-4.10 (1H, m), 4.96 (1H, dd, J = 1.2, 10.2 Hz), 6.92 (1H, s), 7.07 (1H, d, J = 7.3 Hz), 7.18 (1H, s), 7.54 (1H, d, J = 7.3 Hz), 8.03 (1H, d, J = 4.2 Hz), 8.08 (1H, s), 8.52 (1H, d, J = 4.2 Hz) (DMSO-d6) | 448 |
| 178 | 2.65-2.70 (1H, m), 3.04-3.10 (1H, m), 3.55 (3H, s), 3.68-3.72 (1H, m), 3.77-4.00 (3H, m), 4.57-4.61 (1H, br), 4.92 (1H, dd, J = 1.2, 10.2 Hz), 6.51 (1H, s), 7.01-7.04 (1H, m), 7.38 (1H, d, J = 7.3 Hz), 7.83-7.88 (1H, m), 8.01-8.10 (2H, m), 8.38 (1H, d, J = 7.3 Hz), 8.50 (1H, d, J = 7.3 Hz), 9.27 (1H, d, J = 4.2 Hz) (DMSO-d6) | 463 |
| 179 | 2.64-2.68 (1H, m), 3.10-3.12 (1H, m), 3.48 (3H, s), 3.56-3.63 (1H, m), 3.74-3.89 (5H, m), 3.89-4.07 (1H, m), 4.91 (1H, dd, J = 1.2, 10.2 Hz), 6.40 (1H, s), 7.03 (1H, d, J = 7.3 Hz), 7.10 (1H, s), 7.39 (1H, d, J = 7.3 Hz), 7.64 (1H, d, J = 4.2 Hz), 8.48 (1H, d, J = 4.2 Hz) (DMSO-d6) | 482 |
| 180 | 2.74-2.82 (1H, m), 3.30-3.33 (1H, m), 3.50 (3H, s), 3.69-3.72 (4H, m), 3.87-3.91 (2H, m), 4.12-4.15 (1H, m), 5.00 (1H, dd, J = 1.2, 10.2 Hz), 7.05-7.09 (2H, m), 7.17 (1H, s), 7.43-7.57 (7H, m), 8.27-8.30 (4H, m), 8.46-8.47 (2H, m) (DMSO-d6) | 566 |
| 181 | 3.26-3.32 (2H, m), 3.46 (3H, s), 3.62-3.67 (1H, m), 3.91-4.06 (3H, m), 5.03 (1H, dd, J = 1.2, 10.2 Hz), 6.44-6.46 (1H, br), 6.96 (1H, s), 6.98 (1H, s), 7.23-7.36 (2H, m), 7.58-7.67 (2H, m), 8.05 (1H, d, J = 4.2 Hz), 8.11 (1H, s), 8.53 (1H, d, J = 4.2 Hz) (DMSO-d6) | 423 |
| 182 | 2.71-2.77 (1H, m), 3.10-3.18 (1H, m), 3.48 (3H, s), 3.61-4.10 (11H, m), 4.93 (1H, dd, J = 1.2, 10.2 Hz), 6.88 (1H, s), 7.05 (1H, d, J = 7.3 Hz), 7.12 (1H, s), 7.42 (1H, d, J = 7.3 Hz), 8.22 (1H, d, J = 4.2 Hz), 8.49 (1H, d, J = 4.2 Hz), 8.71 (1H, s) (DMSO-d6) | 443 |
| 183 | 3.18-3.26 (1H, m), 3.35-3.42 (1H, m), 3.48 (3H, s), 3.62-3.66 (1H, m), 3.88-4.01 (3H, m), 4.13 (3H, s), 5.01 (1H, dd, J = 1.2, 10.2 Hz), 6.94 (1H, s), 6.98 (1H, s), 7.23-7.35 (2H, m), 7.57-7.66 (2H, m), 8.46 (1H, d, J = 4.2 Hz), 8.61 (1H, d, J = 4.2 Hz), 8.83 (1H, s) (DMSO-d6) | 419 |
| 184 | 3.16-3.20 (1H, m), 3.51 (3H, s), 3.62-3.84 (3H, m), 3.88-4.08 (5H, m), 4.48-4.52 (1H, br), 5.27 (1H, dd, J = 1.2, 10.2 Hz), 6.89 (1H, s), 7.25-7.48 (3H, m), 8.30 (1H, d, J = 4.2 Hz), 8.51 (1H, d, J = 4.2 Hz), 8.74 (1H, s) (DMSO-d6) | 431 |
| 185 | 2.72-2.77 (1H, m), 3.16-3.20 (1H, m), 3.47 (3H, s), 3.59-3.63 (1H, m), 3.78-3.85 (5H, m), 4.00 (3H, s), 4.04-4.08 (1H, m), 5.00 (1H, dd, J = 1.2, 10.2 Hz), 6.81 (1H, s), 7.24 (1H, d, J = 7.3 Hz), 7.75 (1H, s), 7.83 (1H, d, J = 7.3 Hz), 7.92 (1H, d, J = 4.2 Hz), 8.33 (1H, d, J = 4.2 Hz), 8.53 (1H, s) (DMSO-d6) | 434 |
| 186 | 3.27-3.30 (1H, m), 3.43 (3H, s), 3.62-3.84 (4H, m), 3.99-4.03 (1H, m), 5.30 (1H, dd, J = 1.2, 10.2 Hz), 6.92 (1H, s), 7.26-7.50 (3H, m), 8.02 (1H, d, J = 4.2 Hz), 8.10 (1H, s), 8.51 (1H, d, J = 4.2 Hz) (DMSO-d6) | 436 |
| 187 | 2.73-2.82 (1H, m), 3.20-3.24 (1H, m), 3.47 (3H, s), 3.63-3.68 (1H, m), 3.85-3.89 (2H, m), 3.92 (3H, s), 4.09-4.12 (1H, m), 5.02 (1H, dd, J = 1.2, 10.2 Hz), 6.80 (1H, s), 7.23 (1H, d, J = 7.3 Hz), 7.77 (1H, s), 7.85 (1H, d, J = 7.3 Hz), 8.03 (1H, d, J = 4.2 Hz), 8.32 (1H, s), 8.53 (1H, d, J = 4.2 Hz) (DMSO-d6) | 438 |
| 188 | 2.71-2.75 (1H, m), 3.16-3.20 (1H, m), 3.45 (3H, s), 3.60-3.64 (1H, m), 3.85-3.88 (8H, m), 4.05-4.09 (1H, m), 4.96 (1H, dd, J = 1.2, 10.2 Hz), 6.68 (1H, s), 7.06 (1H, d, J = 7.3 Hz), 7.13 (1H, s), 7.42 (1H, s), 7.44 (1H, s), 7.58 (1H, d, J = 4.2 Hz), 8.52 (1H, d, J = 4.2 Hz) (DMSO-d6) | 443 |
| 189 | 3.24-3.27 (4H, m), 3.43 (3H, s), 3.71-3.76 (4H, m), 3.85 (3H, s), 4.01-4.04 (1H, br), 5.41 (2H, s), 6.92-7.01 (2H, m), 7.11 (1H, d, J = 7.3 Hz), 7.38-7.47 (2H, m), 8.33 (1H, d, J = 4.2 Hz), 8.56 (1H, d, J = 4.2 Hz), 8.91 (1H, s) (DMSO-d6) | 409 |
| 190 | 3.10-3.14 (2H, m), 3.25-3.28 (4H, m), 3.43 (3H, s), 3.73-3.76 (4H, m), 4.51-4.55 (2H, m), 6.75 (1H, s), 7.12 (2H, dd, J = 6.8, 7.3 Hz), 7.36 (2H, dd, J = 6.8, 7.3 Hz), 8.21 (1H, d, J = 4.2 Hz), 8.49 (1H, d, J = 4.2 Hz), 8.73 (1H, s) (DMSO-d6) | 411 |
| 191 | 3.10-3.14 (2H, m), 3.27-3.30 (4H, m), 3.44 (3H, s), 3.74-3.76 (4H, m), 3.82 (3H, s), 4.52-4.56 (2H, m), 6.86-7.00 (4H, m), 7.21-7.27 (2H, m), | 423 |

TABLE 2-continued

| Compound No. | 1H-NMR δ: | [M + 1] |
|---|---|---|
| | 8.42 (1H, d, J = 4.2 Hz), 8.58 (1H, d, J = 4.2 Hz), 8.84 (1H, s) (DMSO-d6) | |
| 192 | 2.88-2.92 (2H, m), 3.07-3.10 (4H, m), 3.42 (3H, s), 3.56-3.58 (2H, m), 3.66-3.68 (4H, m), 4.88-4.92 (1H, br), 6.61 (1H, s), 7.04-7.32 (4H, m), 7.85-7.87 (1H, br), 8.00 (1H, d, J = 4.2 Hz), 8.07 (1H, d, J = 4.2 Hz), 8.31 (1H, s) (DMSO-d6) | 410 |
| 193 | 1.99-2.10 (2H, m), 2.72-2.77 (2H, m), 3.28-3.30 (4H, m), 3.43 (3H, s), 3.74-3.76 (8H, m), 4.31-4.38 (2H, m), 6.82-6.94 (2H, m), 7.00 (1H, s), 7.14-7.20 (2H, m), 8.41 (1H, d, J = 4.2 Hz), 8.57 (1H, d, J = 4.2 Hz), 8.77 (1H, s) (DMSO-d6) | 437 |
| 194 | 2.07-2.12 (2H, m), 2.49-2.53 (1H, (1H, dd, br), 2.74-2.79 (2H, m), 3.28-3.31 (4H, m), 3.43 (3H, s), 3.74-3.76 (4H, m), 4.30-4.33 (2H, m), 6.97 (1H, s), 7.09 (2H, dd, J = 6.8 Hz, 7.3 Hz), 7.27 (2H, dd, J = 6.8 Hz, 7.3 Hz), 8.29 (1H, d, J = 4.2 Hz), 8.50 (1H, d, J = 4.2 Hz), 8.71 (1H, s) (DMSO-d6) | 425 |
| 195 | 2.84-2.89 (2H, m), 3.08-3.12 (4H, m), 3.35-3.42 (5H, m), 3.68-3.79 (7H, m), 4.32-4.37 (1H, br), 6.64 (1H, s), 6.81-7.21 (5H, m), 7.98-8.09 (2H, m), 8.21 (1H, s) (DMSO-d6) | 422 |
| 196 | 2.74-2.81 (4H, m), 3.14-3.21 (1H, m), 3.46 (3H, s), 3.60-3.64 (1H, m), 3.78-3.82 (1H, m), 3.91-3.96 (4H, m), 4.10-4.13 (1H, m), 4.99 (1H, dd, J = 1.2 Hz, 10.2 Hz), 6.60-6.62 (2H, m), 7.01-7.03 (2H, m), 7.25 (1H, d, J = 7.3 Hz), 7.77 (1H, d, J = 1.2 Hz), 7.83 (1H, dd, J = 1.2 Hz, 4.2 Hz), 8.52 (1H, d, J = 4.2 Hz) (DMSO-d6) | 433 |
| 197 | 1.16 (3H, t, J = 6.9 Hz), 1.13 (1H, m), 1.37 (4H, m), 1.70 (1H, m), 1.84 (4H, m), 3.16 (1H, dd, J = 12.9, 10.5 Hz), 3.28 (3H, m), 3.55 (m, 3H), 3.56 (3H, s), 3.96 (1H, t, J = 11.4 Hz), 4.13 (1H, d, J = 11.4 Hz), 4.58 (1H, d, J = 8.1 Hz), 6.72 (2H, d, J = 9.0 Hz), 6.88 (1H, s), 7.23 (2H, d, J = 9.0 Hz), 7.97 (1H, dd, J = 5.1, 3.3 Hz), 8.51 (1H, d, J = 5.1 Hz), 8.55 (1H, d, J = 3.3 Hz) (CDCl3) | 492 |
| 198 | 0.88 (1H, m), 1.14 (2H, m), 1.38 (2H, m), 1.57 (1H, m), 1.76 (2H, m), 1.93 (2H, m), 2.97 (3H, s), 3.11 (1H, dd, J = 12.8, 10.8 Hz), 3.28 (1H, td, J = 11.2, 2.2 Hz), 3.53 (1H, d, J = 11.2 Hz), 3.58 (3H, s), 3.68 (1H, d, J = 12.8 Hz), 3.99 (1H, td, J = 11.2, 2.2 Hz), 4.06 (1H, m), 4.19 (1H, dd, J = 11.2, 2.2 Hz), 4.77 (1H, dd, J = 10.8, 2.0 Hz), 6.88 (1H, s), 7.29 (2H, d, J = 8.4 Hz), 7.45 (2H, d, J = 8.4 Hz), 7.95 (1H, dd, J = 5.2, 3.2 Hz), 8.53 (1H, d, J = 5.2 Hz), 8.56 (1H, d, J = 3.2 Hz) (CDCl3) | 542 |
| 199 | 0.97 (1H, m), 1.21 (2H, m), 1.41 (2H, m), 1.61 (1H, m), 1.89 (2H, m), 1.97 (2H, m), 2.99 (1H, dd, J = 12.4, 10.4 Hz), 3.26 (1H, td, J = 11.2, 2.4 Hz), 3.50 (1H, d, J = 11.2 Hz), 3.56 (1H, d, J = 11.2 Hz), 3.97 (1H, td, J = 11.2, 2.4 Hz), 4.15 (1H, d, J = 11.2 Hz), 4.65 (1H, m), 4.66 (1H, dd, J = 10.4, 2.0 Hz), 6.86 (1H, s), 7.05 (2H, d, J = 8.4 Hz), 7.14 (1H, t, J = 8.4 Hz), 7.24 (2H, t, J = 8.4 Hz), 7.90 (1H, dd, J = 5.2, 3.2 Hz), 8.52 (1H, d, J = 5.2 Hz), 8.56 (1H, d, J = 3.2 Hz) (CDCl3) | 568 |
| 200 | 0.50 (2H, m), 0.90 (1H, m), 0.98 (2H, m), 1.04 (2H, m), 1.39 (2H, m), 1.58 (1H, m), 1.73 (1H, m), 1.82 (2H, m), 3.13 (1H, dd, J = 12.8, 10.4 Hz), 3.33 (1H, td, J = 13.2 Hz), 3.55 (1H, d, J = 13.2 Hz), 3.60 (3H, s), 3.68 (1H, d, J = 12.8 Hz), 4.00 (1H, td, J = 13.2, 2.4 Hz), 4.20 (1H, dd, J = 13.2, 2.4 Hz), 4.60 (1H, m), 4.78 (1H, dd, J = 10.4, 2.0 Hz), 6.87 (1H, s), 7.22 (2H, d, J = 8.0 Hz), 7.46 (2H, d, J = 8.0 Hz), 7.94 (1H, dd, J = 4.8, 2.8 Hz), 8.53 (1H, d, J = 4.8 Hz), 8.57 (1H, d, J = 2.8 Hz) (CDCl3) | 532 |
| 201 | 0.80 (1H, m), 1.02 (2H, m), 1.32 (2H, m), 1.49 (1H, m), 1.70 (2H, m), 1.80 (2H, m), 3.11 (1H, dd, J = 12.5, 11.0 Hz), 3.30 (1H, t, J = 12.6 Hz), 3.53 (1H, d, J = 12.6 Hz), 3.59 (3H, s), 3.67 (1H, d, J = 12.5 Hz), 3.99 (1H, t, J = 12.6 Hz), 4.16 (2H, m), 4.74 (1H, d, J = 11.0 Hz), 6.88 (1H, s), 7.06 (2H, d, J = 8.2 Hz), 7.37 (2H, d, J = 8.2 Hz), 7.47 (2H, t, J = 7.6 Hz), 7.56 (1H, t, J = 7.6 Hz), 7.76 (2H, d, J = 7.6 Hz), 7.96 (1H, dd, J = 4.9, 2.8 Hz), 8.54 (1H, d, J = 4.9 Hz), 8.56 (1H, d, J = 2.8 Hz) (CDCl3) | 604 |
| 202 | 1.13 (1H, m), 1.39 (4H, m), 1.70 (1H, m), 1.82 (4H, m), 3.13 (1H, dd, J = 12.8, 10.4 Hz), 3.28 (1H, m), 3.89 (1H, t, J = 4.8 Hz), 3.52 (2H, m), 3.56 (3H, s), 3.59 (1H, m), 3.69 (1H, q, J = 4.8 Hz), 3.96 (1H, td, J = 11.4, 2.0 Hz), 4.15 (1H, d, J = 11.4 Hz), 4.61 (1H, dd, J = 10.4, 2.0 Hz), 6.86 (2H, d, J = 8.8 Hz), 6.87 (1H, s), 7.24 (2H, d, J = 8.8 Hz), 7.95 (1H, dd, J = 4.8, 2.4 Hz), 8.51 (1H, d, J = 4.8 Hz), 8.55 (1H, d, J = 2.4 Hz) (CDCl3) | 508 |
| 203 | | |
| 204 | 3.03-3.33 (4H, m), 3.59 (3H, s), 3.67-3.73 (2H, m), 3.88-3.95 (3H, m), 4.03-4.08 (1H, m), 4.44 (2H, br), 4.70 (1H, dd, J = 1.2 Hz), 6.61-6.70 (2H, m), 7.16-7.25 (2H, m), 7.41 (2H, d, J = 7.2 Hz), 7.89-8.00 (2H, m), 8.58-8.61 (2H, m), 8.72-8.77 (1H, m) (DMSO-d6). | 484 (M + 1) |
| 205 | 0.86-1.24 (6H, m), 1.52-1.63 (7H, m), 2.32-2.36 (1H, m), 2.64-2.70 (1H, m), 2.95-3.16 (3H, m), 3.46 (3H, s), 3.64-3.73 (2H, m), 3.84-3.88 (1H, m), 4.00-4.03 (1H, m), 4.68 (1H, dd, J = 1.2 Hz, 10.2 Hz), 6.59 (1H, s), 7.10 (2H, d, J = 7.2 Hz), 7.34 (2H, d, J = 7.2 Hz), 7.98 (1H, dd, J = 1.2 Hz, 4.2 Hz), 8.57 (1H, d, J = 4.2 Hz), 8.70 (1H, d, J = 1.2 Hz) (DMSO-d6). | 504 (M + 1) |
| 206 | | |
| 207 | 2.46-2.62 (3H, m), 2.75-2.79 (1H, m), 2.91-2.98 (3H, m), 3.14-3.18 (1H, m), 3.42-3.45 (1H, m), 3.50 (3H, s), 3.70-3.72 (1H, m), 3.72 (3H, s), 3.74 (3H, s), 4.26 (1H, dd, J = 1.2 Hz, 12.6 Hz), 6.60 (1H, s), 6.70 (1H, s), 6.82 (1H, s), 8.02 (1H, dd, J = 1.2 Hz, 4.2 Hz), 8.56 (1H, d, J = 4.2 Hz), 8.70 (1H, d, J = 1.2 Hz) (DMSO-d6). | 452 (M + 1) |

TABLE 2-continued

| Compound No. | 1H-NMR δ: | [M + 1] |
|---|---|---|
| 208 | 2.56-2.83 (4H, m), 2.97-3.16 (4H, m), 3.51 (3H, s), 3.52-3.54 (1H, m), 3.67-3.70 (1H, m), 4.24 (1H, dd, J = 1.2, 12.6 Hz), 6.60 (1H, s), 7.12-7.19 (3H, m), 7.35 (1H, dd, J = 7.2 Hz, 7.3 Hz), 8.01 (1H, dd, J = 1.2 Hz, 4.2 Hz), 8.57 (1H, d, J = 4.2 Hz), 8.71 (1H, d, J = 1.2 Hz) (DMSO-d6). | 392 (M + 1) |
| 209 | 1.25-2.04 (10H, m), 2.23 (1H, m), 3.07 (1H, dd, J = 10.8, 13.2 Hz), 3.27 (1H, td, J = 3.0, 12.0 Hz), 3.50-3.61 (2H, m), 3.57 (3H, s), 3.98 (1H, td, J = 2.1, 11.4 Hz), 4.14 (1H, dd, J = 1.2, 11.1 Hz), 4.70 (1H, dd, J = 2.1, 10.5 Hz), 6.88 (1H, s), 7.20 (1H, br.s), 7.37 (2H, d, J = 8.4 Hz), 7.56 (2H, d, J = 8.4 Hz), 7.93 (1H, dd, J = 5.1, 6.6 Hz), 8.51 (1H, d, J = 5.4 Hz), 8.55 (1H, d, J = 3.3 Hz) (CDCl$_3$) | 492 |
| 210 | 2.42 (3H, s), 3.05 (1H, dd, J = 10.5, 12.9 Hz), 3.29 (1H, td, J = 3.3, 12.3 Hz), 3.51-3.63 (2H, m), 3.62 (3H, s), 3.98 (1H, td, J = 2.3, 11.6 Hz), 4.15 (1H, dd, J = 2.1, 13.2 Hz), 4.66 (1H, dd, J = 2.1, 10.5 Hz), 6.88 (1H, s), 7.07 (1H, dd, J = 2.1, 8.4 Hz), 7.29 (1H, d, J = 1.5 Hz), 7.55 (1H, d, J = 8.1 Hz), 7.93 (1H, dd, J = 5.1, 6.6 Hz), 8.51 (1H, d, J = 5.1 Hz), 8.56 (1H, d, J = 3.3 Hz) (CDCl$_3$) | 460 |
| 211 | 3.10 (1H, dd, J = 10.8, 13.2 Hz), 3.29 (1H, td, J = 3.0, 12.0 Hz), 4.16 (1H, dd, 3.52-3.65 (2H, m), 3.58 (3H, s), 4.00 (1H, td, J = 2.1, 11.4 Hz), 4.16 (1H, dd, J = 1.2, 11.1 Hz), 4.73 (1H, dd, J = 2.1, 10.5 Hz), 6.89 (1H, s), 7.43 (2H, d, J = 8.4 Hz), 7.50-7.57 (2H, m), 7.69 (2H, d, J = 8.4 Hz), 7.85-7.96 (5H, m), 8.52 (1H, d, J = 5.4 Hz), 8.56 (1H, d, J = 3.3 Hz) (CDCl$_3$) | 486 |
| 212 | 3.14 (1H, dd, J = 10.8, 13.2 Hz), 3.35 (1H, td, J = 3.0, 12.0 Hz), 3.48 (3H, s), 3.52-3.69 (2H, m), 3.59 (3H, s), 4.00 (1H, td, J = 2.1, 11.4 Hz), 4.17 (1H, dd, J = 1.2, 11.1 Hz), 4.72 (1H, dd, J = 2.1, 10.5 Hz), 6.58 (2H, m), 6.87 (1H, s), 7.26-7.29 (1H, m), 7.31 (2H, d, J = 8.3 Hz), 7.43 (2H, d, J = 8.3 Hz), 7.06 (1H, m), 8.24 (1H, d, J = 3.6 Hz), 8.52 (1H, d, J = 5.0 Hz), 8.55 (1H, d, J = 3.0 Hz) (CDCl$_3$) | 473 |
| 213 | 0.77-0.88 (2H, m), 1.03-1.11 (2H, m), 1.49 (1H, m), 3.07 (1H, dd, J = 10.6, 13.0 Hz), 3.27 (1H, d, J = 13.0 Hz), 3.50-3.62 (2H, m), 3.57 (3H, s), 3.97 (1H, t, J = 11.7 Hz), 4.16 (1H, dd, J = 2.1, 11.1 Hz), 4.69 (1H, dd, J = 10.2 Hz), 6.88 (1H, s), 7.35 (2H, d, J = 8.4 Hz), 7.46 (1H, br.s), 7.55 (2H, d, J = 8.1 Hz), 7.93 (1H, m), 8.50 (1H, d, J = 5.1 Hz), 8.54 (1H, d, J = 2.7 Hz) (CDCl$_3$) | 450 |
| 214 | 1.05 (6H, d, J = 6.9 Hz), 1.74 (3H, s), 3.12 (1H, dd, J = 10.5, 12.9 Hz), 3.34 (1H, td, J = 2.9, 13.0 Hz), 3.53-3.70 (2H, m), 3.60 (3H, s), 4.02 (1H, dd, J = 9.3, 11.7 Hz), 4.20 (1H, d, J = 11.9 Hz), 4.79 (1H, d, J = 8.1 Hz), 5.07 (1H, q, J = 6.9 Hz), 6.72 (1H, s), 7.15 (2H, d, J = 8.4 Hz), 7.48 (2H, d, J = 8.4 Hz), 7.94 (1H, dd, J = 5.1, 6.6 Hz), 8.53 (1H, d, J = 4.8 Hz), 8.57 (1H, d, J = 3.0 Hz) (CDCl$_3$) | 466 |
| 215 | 1.32 (9H, s), 3.07 (1H, dd, J = 9.3, 11.7 Hz), 3.27 (1H, td, J = 2.9, 13.0 Hz), 3.50-3.62 (2H, m), 3.57 (3H, s), 4.00 (1H, td, J = 2.4, 12.4 Hz), 4.17 (1H, dd, J = 2.4, 12.0 Hz), 4.69 (1H, dd, J = 2.4, 10.8 Hz), 6.88 (1H, s), 7.33 (2H, d, J = 8.4 Hz), 7.55 (2H, d, J = 6.0 Hz), 7.93 (2H, d, J = 8.4 Hz), 8.50 (1H, d, J = 5.4 Hz), 8.55 (1H, d, J = 3.3 Hz) (CDCl$_3$) | 466 |
| 216 | 1.62-1.68 (5H, m), 1.89 (6H, m), 2.04-2.11 (3H, m), 3.12 (1H, dd, J = 10.8, 12.9 Hz), 3.28 (1H, m), 3.30 (1H, m), 3.54 (3H, s), 3.50-3.73 (2H, m), 3.96 (1H, m), 4.12 (1H, dd, J = 9.9, 11.7 Hz), 4.59 (1H, dd, J = 8.7, 10.5 Hz), 6.78 (2H, d, J = 8.4 Hz), 6.87 (1H, s), 7.17 (2H, d, J = 8.4 Hz), 7.96 (1H, dd, J = 5.1, 6.3 Hz), 8.51 (1H, d, J = 5.1 Hz), 8.55 (1H, d, J = 3.3 Hz) (CDCl$_3$) | 516 |
| 217 | 1.35-1.67 (11H, m), 2.07 (3H, m), 2.79 (3H, s), 3.14 (1H, dd, J = 10.5, 12.9 Hz), 3.29 (1H, td, J = 3.0, 12.0 Hz), 3.54-3.69 (1H, td, J = 3.0, 12.0 Hz), 3.54-3.69 (2H, m), 3.58 (3H, s), 3.99 (1H, td, J = 2.4, 11.8 Hz), 4.17 (1H, dd, J = 2.4, 11.7 Hz), 4.70 (1H, dd, J = 2.1, 10.5 Hz), 6.87 (1H, s), 7.15 (2H, d, J = 8.4 Hz), 7.30 (2H, d, J = 8.4 Hz), 7.96 (1H, dd, J = 5.1, 6.3 Hz), 8.52 (1H, d, J = 4.8 Hz), 8.56 (1H, d, J = 3.0 Hz) (CDCl$_3$) | 530 |
| 218 | 1.57-2.01 (13H, m), 3.12 (1H, dd, J = 10.6, 12.7 Hz), 3.30 (1H, td, J = 3.3, 12.0 Hz), 3.51-3.64 (4H, m), 3.57 (3H, s), 3.96 (1H, td, J = 2.1, 11.8 Hz), 4.12 (1H, dd, J = 2.1, 4.4 Hz), 4.58 (1H, dd, J = 8.4, 10.8 Hz), 6.60 (2H, d, J = 8.4 Hz), 6.87 (1H, s), 7.17 (2H, d, J = 8.4 Hz), 7.96 (1H, dd, J = 4.8, 6.6 Hz), 8.51 (1H, d, J = 4.8 Hz), 8.55 (1H, d, J = 3.0 Hz) (CDCl$_3$) | 516 |
| 219 | 1.43 (2H, d, J = 11.4 Hz), 1.71-1.65 (8H, m), 2.04-2.10 (4H, m), 2.77 (3H, s), 3.14-3.20 (2H, m), 3.30 (1H, td, J = 3.3, 12.0 Hz), 3.51-3.64 (2H, m), 3.57 (3H, s), 3.96 (1H, td, J = 2.1, 11.8 Hz), 4.12 (1H, dd, J = 2.1, 4.4 Hz), 4.65 (1H, dd, J = 8.4, 10.8 Hz), 6.87 (1H, s), 7.06 (2H, d, J = 8.4 Hz), 7.29 (2H, d, J = 8.4 Hz), 7.96 (1H, dd, J = 4.8, 6.6 Hz), 8.52 (1H, d, J = 4.8 Hz), 8.55 (1H, d, J = 3.0 Hz) (CDCl$_3$) | 530 |
| 220 | 1.90 (1H, m), 2.27 (1H, m), 3.14 (1H, dd, J = 10.5, 12.9 Hz), 3.30 (1H, td, J = 3.0, 12.0 Hz), 3.55-3.58 (2H, m), 3.55 (3H, s), 3.70-4.12 (7H, m), 4.59 (1H, dd, J = 2.1, 10.5 Hz), 6.21 (2H, d, J = 8.7 Hz), 6.87 (1H, s), 7.21 (2H, d, J = 8.7 Hz), 7.95 (1H, dd, J = 5.1, 6.6 Hz), 8.56 (1H, d, J = 5.1 Hz), 8.54 (1H, d, J = 3.3 Hz) (CDCl$_3$) | 452 |
| 221 | 1.92-1.97 (1H, m), 2.22-2.24 (1H, m), 2.87 (3H, s), 3.13 (1H, dd, J = 10.8, 12.9 Hz), 3.29 (1H, td, J = 3.0, 12.0 Hz), 3.50-3.61 (2H, m), 3.59 (3H, s), 3.75-4.49 (6H, m), 4.50 (1H, m), 4.62 (1H, dd, J = 10.5 Hz), 6.83 (2H, d, J = 8.7 Hz), 6.87 (1H, s), 7.28 (2H, d, J = 8.7 Hz), 7.75 (1H, d, J = 6.3 Hz), 8.50 (1H, d, J = 5.1 Hz), 8.55 (1H, d, J = 3.3 Hz) (CDCl$_3$) | 466 |

TABLE 2-continued

| Compound No. | 1H-NMR δ: | [M + 1] |
|---|---|---|
| 222 | 1.79-1.83 (4H, m), 2.60-2.63 (4H, m), 2.90 (2H, dd, J = 6.0, 6.0 Hz), 3.10 (1H, dd, J = 12.9, 10.8 Hz), 3.29 (1H, m), 3.50-3.62 (2H, m), 3.57 (3H, s), 3.98 (1H, m), 4.10-4.14 (3H, m), 4.66 (1H, dd, J = 10.5, 2.1 Hz), 6.88 (1H, s), 6.94 (1H, d, J = 8.7 Hz), 7.32 (1H, d, J = 8.7 Hz), 7.94 (1H, dd, J = 6.6, 5.4 Hz), 8.51 (1H, d, J = 5.1 Hz), 8.55 (1H, d, J = 3.0 Hz) (CDCl$_3$) | 480 (M + 1) |
| 223 | 1.88 (3H, s), 3.11 (1H, dd, J = 10.6, 12.9 Hz), 3.26 (3H, s), 3.32 (1H, td, J = 10.5, 12.9 Hz), 3.48-3.60 (2H, m), 3.59 (3H, s), 4.01 (1H, td, J = 2.7, 11.4 Hz), 4.20 (1H, dd, J = 9.6, 11.5 Hz), 4.77 (1H, dd, J = 8.7, 10.1 Hz), 6.87 (1H, s), 7.20 (2H, d, J = 8.4 Hz), 7.47 (2H, d, J = 8.2 Hz), 7.93 (1H, dd, J = 5.1, 6.4 Hz), 8.51 (1H, d, J = 5.1 Hz), 8.55 (1H, d, J = 3.0 Hz) (CDCl$_3$) | 438 |
| 224 | 2.86-3.20 (4H, m), 3.20-4.06 (16H, m), 4.42-4.46 (2H, m), 4.70 (1H, dd, J = 1.2 Hz, 10.2 Hz), 6.60 (1H, s), 7.02 (2H, d, J = 7.2 Hz), 7.39 (2H, d, J = 7.2 Hz), 7.98 (1H, dd, J = 1.2 Hz, 4.2 Hz), 8.57 (1H, d, J = 4.2 Hz), 8.71 (1H, d, J = 1.2 Hz), 11.31 (1H, br) (DMSO-d6). | 496 (M + 1) |
| 225 | 2.92-3.00 (1H, m), 3.06-3.13 (1H, m), 3.45 (3H, s), 3.62-3.67 (2H, m), 5.84-5.88 (1H, m), 3.99-4.03 (1H, m), 4.60 (1H, dd, J = 1.2 Hz, 10.2 Hz), 6.59 (1H, s), 6.72 (2H, d, J = 7.2 Hz), 7.22 (2H, d, J = 7.2 Hz), 7.97 (1H, dd, J = 1.2 Hz, 4.2 Hz), 8.56 (1H, d, J = 4.2 Hz), 8.69 (1H, d, J = 1.2 Hz), 9.40 (1H, brs) (DMSO-d6). | 383 (M + 1) |
| 226 | 1.27 (6H, t, J = 7.2 Hz), 2.88-3.22 (6H, m), 3.46-3.49 (5H, m), 3.66-3.70 (2H, m), 3.88-3.96 (1H, m), 4.02-4.07 (1H, m), 4.40-4.71 (4H, m), 6.61 (1H, s), 6.70 (2H, d, J = 7.2 Hz), 7.40 (2H, d, J = 7.2 Hz), 8.03 (1H, dd, J = 1.2 Hz, 4.2 Hz), 8.60 (1H, d, J = 4.2 Hz), 8.78 (1H, d, J = 1.2 Hz), 10.91 (1H, br) (DMSO-d6). | 482 (M + 1) |
| 227 | 1.36-1.41 (1H, m), 1.68-1.91 (5H, m), 2.95-3.18 (4H, m), 3.47-3.50 (7H, m), 3.67-3.71 (2H, m), 3.88-4.07 (2H, m), 4.46-4.50 (2H, m), 4.70 (1H, dd, J = 1.2 Hz, 10.2 Hz), 6.63 (1H, s), 6.88 (1H, br), 7.01 (2H, d, J = 7.2 Hz), 7.43 (2H, d, J = 7.2 Hz), 8.12 (1H, dd, J = 1.2 Hz, 4.2 Hz), 8.65 (1H, d, J = 4.2 Hz), 8.86 (1H, d, J = 1.2 Hz), 11.25 (1H, br) (DMSO-d6). | 494 (M + 1) |
| 228 | 2.94-3.20 (2H, m), 3.41-4.06 (17H, m), 4.44-4.47 (2H, m), 4.70 (1H, dd, J = 1.2 Hz, 10.2 Hz), 6.01 (2H, br), 8.61 (1H, s), 7.03 (2H, d, J = 7.2 Hz), 7.41 (2H, d, J = 7.2 Hz), 8.06 (1H, dd, J = 1.2 Hz, 4.2 Hz), 8.62 (1H, d, J = 4.2 Hz), 8.80 (1H, d, J = 4.2 Hz), 10.14 (1H, br) (DMSO-d6). | 495 (M + 1) |
| 229 | 2.85-3.17 (5H, m), 3.48 (3H, s), 3.60-4.03 (14H, m), 4.46-4.48 (2H, m), 4.70 (1H, dd, J = 1.2 Hz, 10.2 Hz), 5.54 (2H, br), 6.63 (1H, s), 7.00 (2H, d, J = 7.2 Hz), 7.40 (2H, d, J = 7.2 Hz), 8.10 (1H, dd, J = 1.2 Hz, 4.2 Hz), 8.64 (1H, d, J = 4.2 Hz), 8.85 (1H, d, J = 1.2 Hz), 12.28 (1H, br) (DMSO-d6). | 509 |
| 230 | 2.06 (3H, s), 2.98-3.20 (4H, m), 3.45 (3H, s), 3.50-4.03 (12H, m), 4.46-4.50 (2H, m), 4.70 (1H, dd, J = 1.2 Hz, 10.2 Hz), 5.43 (1H, br), 6.30 (1H, s), 7.01 (2H, d, J = 7.2 Hz), 7.40 (2H, d, J = 7.2 Hz), 8.10 (1H, dd, J = 1.2 Hz, 4.2 Hz), 8.64 (1H, d, J = 4.2 Hz), 8.84 (1H, d, J = 1.2 Hz), 11.92 (1H, br) (DMSO-d6). | 537 (M + 1) |
| 231 | 2.94-2.98 (1H, m), 3.16-4.07 (18H, m), 4.41-4.50 (2H, m), 4.70 (1H, dd, J = 1.2 Hz, 10.2 Hz), 6.21 (1H, br), 6.63 (1H, s), 7.02 (2H, d, J = 7.2 Hz), 7.38 (2H, d, J = 7.2 Hz), 7.46-7.50 (5H, m), 8.10 (1H, dd, J = 1.2 Hz, 4.2 Hz), 8.64 (1H, d, J = 4.2 Hz), 8.85 (1H, d, J = 1.2 Hz), 12.07 (1H, br) (DMSO-d6). | 599 (M + 1) |
| 232 | 2.16-2.21 (2H, m), 2.78 (6H, m), 2.96-3.02 (1H, m), 3.18-3.23 (3H, m), 3.47 (3H, s), 3.66-3.70 (2H, m), 3.81-3.85 (1H, m), 4.03-4.11 (3H, m), 4.69 (1H, dd, J = 1.2 Hz, 10.2 Hz), 6.63 (1H, s), 6.97 (2H, d, J = 7.2 Hz), 7.36-7.45 (3H, m), 8.14 (1H, dd, J = 1.2 Hz, 4.2 Hz), 8.66 (1H, d, J = 4.2 Hz), 8.89 (1H, d, J = 1.2 Hz) (DMSO-d6). | 468 (M + 1) |
| 233 | 1.25 (6H, t, J = 7.3 Hz), 2.16-2.18 (2H, m), 2.86-3.20 (8H, m), 3.47 (3H, s), 3.66-3.70 (2H, m), 3.80-4.11 (4H, m), 4.68 (1H, dd, J = 1.2 Hz, 10.2 Hz), 6.40 (1H, br), 6.23 (1H, s), 6.96 (2H, d, J = 7.2 Hz), 7.38 (2H, d, J = 7.2 Hz), 8.08 (1H, dd, J = 1.2 Hz, 4.2 Hz), 8.63 (1H, d, J = 4.2 Hz), 8.82 (1H, d, J = 1.2 Hz), 10.98 (1H, br) (DMSO-d6). | 496 (M + 1) |
| 234 | 2.24-2.30 (2H, m), 3.12-3.27 (6H, m), 3.43-3.47 (5H, m), 3.66-3.70 (2H, m), 3.87-4.10 (8H, m), 4.69 (1H, dd, J = 1.2 Hz, 10.2 Hz), 6.21 (1H, br), 6.63 (1H, s), 6.96 (2H, d, J = 7.2 Hz), 7.37 (2H, d, J = 7.2 Hz), 8.13 (1H, dd, J = 1.2 Hz, 4.2 Hz), 8.65 (1H, d, J = 4.2 Hz), 8.87 (1H, d, J = 1.2 Hz), 11.77 (1H, br) (DMSO-d6). | 510 (M + 1) |
| 235 | 1.90 (1H, m), 2.60 (1H, m), 2.90-3.01 (2H, m), 3.14 (1H, dd, J = 10.8, 12.9 Hz), 3.29 (1H, td, J = 3.2, 12.3 Hz), 3.51-3.62 (2H, m), 3.57 (3H, s), 4.00 (2H, td, J = 2.1, 11.8 Hz), 4.14 (1H, dd, J = 2.1, 10.5 Hz), 4.62 (1H, dd, J = 2.1, 10.5 Hz), 5.00 (1H, m), 6.70 (2H, d, J = 8.4 Hz), 6.88 (1H, s), 7.18-7.37 (6H, m), 7.96 (1H, dd, J = 5.1, 6.4 Hz), 8.51 (1H, d, J = 5.1 Hz), 8.55 (1H, d, J = 3.0 Hz) (CDCl$_3$) | 498 |
| 236 | 1.66-1.70 (2H, m), 1.93-1.97 (2H, m), 2.28-2.38 (5H, m), 2.72-2.76 (2H, m), 2.93-3.00 (1H, m), 3.15-3.20 (1H, m), 3.46 (3H, s), 3.64-3.68 (2H, m), 3.86-4.05 (2H, m), 4.38-4.42 (1H, m), 4.66 (1H, dd, J = 1.2 Hz, 10.2 Hz), 6.58 (1H, s), 6.95 (2H, d, J = 7.2 Hz), 7.33 (2H, d, J = 7.2 Hz), 7.97 (1H, dd, J = 1.2 Hz, 4.2 Hz), 8.56 (1H, d, J = 4.2 Hz), 8.69 (1H, d, J = 1.2 Hz) (DMSO-d6). | 480 (M + 1) |

TABLE 2-continued

| Compound No. | 1H-NMR δ: | [M + 1] |
|---|---|---|
| 237 | 1.60-1.64 (2H, m), 1.97-2.00 (2H, m), 2.94-3.00 (1H, m), 3.14-3.17 (1H, m), 3.25-3.50 (6H, m), 3.64-3.68 (2H, m), 3.85-4.10 (3H, m), 4.65-4.68 (2H, m), 6.59 (1H, s), 6.98 (2H, d, J = 7.2 Hz), 7.33-7.46 (7H, m), 7.98 (1H, dd, J = 1.2 Hz, 4.2 Hz), 8.56 (1H, d, J = 4.2 Hz), 8.70 (1H, d, J = 1.2 Hz) (DMSO-d6). | 570 (M + 1) |
| 238 | 1.46-1.62 (2H, m), 1.92-2.02 (2H, m), 2.02 (3H, s), 2.94-3.00 (1H, m), 3.15-3.23 (3H, m), 3.46 (3H, s), 3.65-3.69 (3H, m), 3.83-3.87 (2H, m), 4.02-4.06 (1H, m)4.60-4.68 (2H, m), 6.59 (1H, s), 6.99 (2H, d, J = 7.2 Hz), 7.35 (2H, d, J = 7.2 Hz), 7.97 (1H, dd, J = 1.2 Hz, 4.2 Hz), 8.56 (1H, d, J = 4.2 Hz), 8.69 (1H, d, J = 1.2 Hz) (DMSO-d6). | 508 (M + 1) |
| 239 | 2.04-2.26 (2H, m), 2.13 (3H, s), 2.94 (3H, s), 3.13-3.60 (7H, m), 3.56 (3H, s), 3.97-4.16 (2H, m), 4.61-4.64 (1H, m), 5.43 (1H, m), 6.59 (2H, m), 6.87 (1H, s), 7.28 (2H, m), 7.95 (1H, m), 8.51 (1H, d, J = 4.5 Hz), 8.55 (1H, d, J = 3.3 Hz) (CDCl3) | 507 (M + 1) |
| 240 | 2.66 (4H, t, J = 4.5 Hz), 3.08 (1H, dd, J = 10.6, 13.0 Hz), 3.12 (2H, s), 3.30 (1H, t, J = 12.3 Hz), 3.51-3.66 (2H, m), 3.57 (3H, s), 3.78 (4H, t, J = 4.8 Hz), 3.99 (1H, td, J = 2.1, 11.7 Hz), 4.15 (1H, dd, J = 9.0 Hz), 4.71 (1H, d, J = 10.2 Hz), 6.89 (1H, s), 7.39 (2H, d, J = 8.4 Hz), 7.61 (2H, d, J = 8.4 Hz), 7.94 (1H, dd, J = 5.1, 6.6 Hz), 8.51 (1H, d, J = 4.8 Hz), 8.55 (1H, d, J = 5.1 Hz), 9.11 (1H, s) (CDCl3) | 509 |
| 241 | 3.06 (1H, dd, J = 10.8, 13.2 Hz), 3.29 (1H, td, J = 3.0, 12.0 Hz), 3.53 (1H, d, J = 12.6 Hz), 3.57 (3H, s), 3.64 (1H, d, J = 13.2 Hz), 3.99 (1H, m), 4.17 (1H, dd, J = 2.1, 12.1 Hz), 4.66 (2H, d, J = 5.7 Hz), 4.79 (1H, dd, J = 2.1, 10.5 Hz), 6.41 (1H, br.t), 7.69 (1H, s), 7.31-7.38 (5H, m), 7.48 (2H, d, J = 8.1 Hz), 7.84 (2H, d, J = 8.1 Hz), 7.91 (1H, dd, J = 5.1, 6.6 Hz), 8.50 (1H, d, J = 5.1 Hz), 8.55 (1H, d, J = 3.3 Hz) (CDCl3) | 500 |
| 242 | 2.33 (3H, s), 2.51-2.67 (8H, s), 3.08 (1H, dd, J = 10.2, 12.9 Hz), 3.15 (2H, s), 3.28 (1H, m), 3.47-3.63 (2H, m), 3.57 (3H, s), 3.98 (1H, td, J = 2.1, 11.8 Hz), 4.15 (1H, dd, J = 2.1, 10.5 Hz), 4.71 (1H, dd, J = 8.4, 10.5 Hz), 6.88 (1H, s), 7.38 (2H, d, J = 8.4 Hz), 7.61 (2H, d, J = 8.4 Hz), 7.93 (1H, dd, J = 4.8, 6.3 Hz), 8.50 (1H, d, J = 4.8 Hz), 8.55 (1H, d, J = 3.0 Hz), 9.17 (1H, s) (CDCl3) | 522 |
| 243 | 2.80 (4H, t, J = 4.5 Hz), 3.08 (1H, dd, J = 10.2, 12.9 Hz), 3.22 (2H, s), 3.27 (4H, t, J = 4.5 Hz), 3.30 (1H, m), 3.50-3.63 (2H, m), 3.57 (3H, s), 3.62 (1H, td, J = 2.1, 11.8 Hz), 4.15 (1H, dd, J = 8.4, 10.5 Hz), 4.71 (1H, dd, J = 8.4, 10.5 Hz), 6.88 (1H, s), 6.89-6.97 (3H, m), 7.26-7.29 (2H, m), 7.39 (2H, d, J = 8.4 Hz), 7.60 (2H, d, J = 8.4 Hz), 7.93 (1H, dd, J = 4.8, 6.3 Hz), 8.50 (1H, d, J = 5.4 Hz), 8.55 (1H, d, J = 3.0 Hz), 9.19 (1H, br.s) (CDCl3) | 584 |
| 244 | 1.86-2.04 (6H, m), 2.93-3.19 (8H, m), 3.46 (3H, s), 3.64-3.68 (2H, m), 3.87-3.90 (1H, m), 4.03-4.07 (3H, m), 4.67 (1H, dd, J = 1.2 Hz, 10.2 Hz), 6.60 (1H, s), 6.94 (2H, d, J = 7.2 Hz), 7.36 (2H, d, J = 7.2 Hz), 7.97 (1H, dd, J = 1.2 Hz, 4.2 Hz), 8.56 (1H, d, J = 4.2 Hz), 8.70 (1H, d, J = 1.2 Hz) (DMSO-d6). | 494 (M + 1) |
| 245 | 1.72-1.86 (6H, m), 2.14-2.20 (2H, m), 2.88-3.00 (3H, m), 3.10-3.17 (3H, m), 3.30-3.34 (2H, m), 3.46 (3H, s), 3.64-3.69 (2H, m), 3.83-3.90 (1H, m), 4.03-4.08 (3H, m), 4.68 (1H, dd, J = 1.2 Hz, 10.2 Hz), 6.60 (1H, s), 6.95 (2H, d, J = 7.2 Hz), 7.36 (2H, d, J = 7.2 Hz), 7.97 (1H, dd, J = 1.2 Hz, 4.2 Hz), 8.56 (1H, d, J = 4.2 Hz), 8.70 (1H, d, J = 1.2 Hz) (DMSO-d6). | 508 (M + 1) |
| 246 | 1.83-1.89 (2H, m), 2.16 (3H, s), 2.35-2.43 (9Hm), 2.93-3.00 (1H, m), 3.11-3.17 (1H, m), 3.31-3.33 (1H, m), 3.46 (3H, s), 3.64-3.68 (2H, m), 3.83-4.05 (4H, m), 4.66 (1H, dd, J = 1.2 Hz, 10.2 Hz), 6.59 (1H, s), 6.92 (2H, d, J = 7.2 Hz), 7.33 (2H, d, J = 7.2 Hz), 7.98 (1H, dd, J = 1.2 Hz, 4.2 Hz), 8.56 (1H, d, J = 4.2 Hz), 8.69 (1H, d, J = 1.2 Hz) (DMSO-d6). | 523 (M + 1) |
| 247 | 2.65-2.69 (1H, m), 3.08-3.12 (1H, m), 3.48 (3H, s), 3.60-3.64 (1H, m), 3.79 (3H, s), 3.80-3.90 (2H, m), 4.05-4.08 (1H, m), 4.93 (1H, dd, J = 1.2, 10.2 Hz), 5.12-5.16 (1H, br), 6.45 (1H, s), 7.03 (1H, d, J = 7.3 Hz), 7.10 (1H, s), 7.40 (1H, d, J = 7.3 Hz), 7.69 (1H, d, J = 4.2 Hz), 8.64 (1H, d, J = 4.2 Hz), 8.76 (1H, s) (DMSO-d6) | 448 |
| 248 | 2.88-2.96 (1H, m), 3.13-3.19 (1H, m), 3.63-3.70 (2H, m), 3.82-3.90 (1H, m), 4.01-4.06 (1H, m), 4.74 (1H, dd, J = 1.2, 10.2 Hz), 6.06-6.10 (1H, br), 6.46 (1H, s), 7.21 (2H, dd, J = 6.8, 7.3 Hz), 7.45 (2H, dd, J = 6.8, 7.3 Hz), 7.70 (1H, d, J = 4.2 Hz), 8.63 (1H, d, J = 4.2 Hz), 8.76 (1H, s) (DMSO-d6) | 401 |
| 249 | 2.93-2.97 (1H, m), 3.14-3.17 (1H, m), 3.45 (3H, s), 3.64-3.72 (2H, m), 3.92 (3H, s), 3.92-3.94 (1H, m), 4.04-4.08 (1H, m), 4.75 (1H, dd, J = 1.2, 10.2 Hz), 5.96-5.99 (1H, br), 6.83 (1H, s), 7.23 (2H, dd, J = 6.8, 7.3 Hz), 7.41 (1H, s), 7.43-58 (3H, m), 8.26 (1H, d, J = 4.2 Hz) (DMSO-d6) | 397 |
| 250 | 2.51 (3H, s), 2.88-2.93 (1H, m), 3.09-3.16 (1H, m), 3.49 (3H, s), 3.61-3.68 (2H, m), 3.84-3.90 (1H, m), 3.99-4.06 (1H, m), 4.73 (1H, dd, J = 1.2, 10.2 Hz), 5.94-5.96 (1H, br), 6.49 (1H, s), 7.20 (2H, dd, J = 6.8, 7.3 Hz), 7.45 (2H, dd, J = 6.8, 7.3 Hz), 8.09 (1H, d, J = 4.2 Hz), 8.84 (1H, d, J = 4.2 Hz), 8.91 (1H, s) (DMSO-d6) | 381 |
| 251 | 3.00-3.08 (1H, m), 3.37-3.40 (1H, m), 3.48 (3H, s), 3.70-3.74 (1H, m), 3.84-3.92 (2H, m), 4.05-4.09 (1H, m), 4.86 (1H, dd, J = 1.2, 10.2 Hz), 7.16-7.22 (3H, m), 7.49-7.58 (8H, m), 8.28-8.31 (4H, m), 8.47-8.50 (2H, m) (DMSO-d6) | 519 |
| 252 | 2.90-2.97 (1H, m), 3.12-3.20 (1H, m), 3.53 (3H, s), 3.64-3.72 (2H, m), 3.85-3.92 (1H, m), 4.01-4.05 (1H, m), 4.75 (1H, dd, J = 1.2, 10.2 Hz), | 417 |

TABLE 2-continued

| Compound No. | 1H-NMR δ: | [M + 1] |
|---|---|---|
| | 4.85-4.90 (1H, br), 6.51 (1H, s), 7.17 (2H, dd, J = 6.8, 7.3 Hz), 7.42 (2H, dd, J = 6.8, 7.3 Hz), 7.81-7.86 (1H, m), 7.97-8.06 (2H, m), 8.30 (1H, d, =7.3 Hz), 8.50 (1H, d, J = 7.3 Hz), 9.22 (1H, d, J = 4.2 Hz) (DMSO-d6) | |
| 253 | 2.94-3.02 (1H, m), 3.17-3.20 (1H, m), 3.46 (3H, s), 3.66-4.05 (4H, m), 4.46-4.50 (1H, br), 4.76 (1H, dd, J = 1.2, 10.2 Hz), 6.93 (1H, s), 7.22 (2H, dd, J = 6.8, 7.3 Hz), 7.50 (2H, dd, J = 6.8, 7.3 Hz), 8.00-8.03 (1H, m), 8.09 (1H, s), 8.52 (1H, d, J = 4.2 Hz) (DMSO-d6) | 401 |
| 254 | 2.88-2.96 (1H, m), 3.06-3.10 (1H, m), 3.47 (3H, s), 3.62-3.68 (2H, m), 3.84-3.86 (1H, m), 4.00-4.05 (1H, m), 4.72 (1H, dd, J = 1.2, 10.2 Hz), 6.41 (1H, s), 7.18 (2H, dd, J = 6.8, 7.3 Hz), 7.46 (2H, dd, J = 6.8, 7.3 Hz), 7.65 (1H, d, J = 4.2 Hz), 8.46 (1H, d, J = 4.2 Hz) (DMSO-d6) | 436 |
| 255 | 3.20-3.27 (4H, m), 3.41 (3H, s), 3.73-76 (4H, m), 4.00 (3H, s), 6.80 (1H, s), 7.90 (1H, d, J = 4.2 Hz), 8.33 (1H, d, J = 4.2 Hz), 8.54 (1H, s) (DMSO-d6) | 303 |
| 256 | 2.54 (3H, s), 2.69-2.73 (1H, m), 3.09-3.16 (1H, m), 3.50 (3H, s), 3.58-3.62 (1H, m), 3.74-3.90 (5H, m), 4.06-4.09 (1H, m), 4.92 (1H, dd, J = 1.2, 10.2 Hz), 6.48 (1H, s), 7.05 (1H, d, J = 7.3 Hz), 7.11 (1H, s), 7.40 (1H, d, =7.3 Hz), 8.07 (1H, d, J = 4.2 Hz), 8.84 (1H, d, J = 4.2 Hz), 8.92 (1H, s) (DMSO-d6) | 427 |
| 257 | 2.87-2.91 (1H, m), 3.08-3.12 (1H, m), 3.46 (3H, s), 3.61-3.68 (2H, m), 3.86-4.06 (6H, m), 4.72 (1H, dd, J = 1.2, 10.2 Hz), 6.33 (1H, s), 7.16-7.22 (3H, m), 7.42-7.47 (2H, m), 8.18 (1H, d, J = 1.2 Hz) (DMSO-d6) | 431 |
| 258 | 2.89-2.99 (1H, m), 3.15-3.19 (1H, m), 3.47 (3H, s), 3.65-3.73 (2H, m), 3.89-3.92 (1H, m), 4.05-4.07 (1H, m), 4.11 (3H, s), 4.75 (1H, dd, J = 1.2, 10.2 Hz), 6.21-6.27 (1H, br), 6.91 (1H, s), 7.23 (2H, dd, J = 6.8, 7.3 Hz), 7.49 (2H, dd, J = 6.8, 7.3 Hz), 8.39 (1H, d, J = 4.2 Hz), 8.59 (1H, d, J = 4.2 Hz), 8.80 (1H, s) (DMSO-d6) | 397 |
| 259 | 3.24-3.27 (4H, m), 3.39 (3H, s), 3.71-3.74 (4H, m), 3.92-3.96 (1H, br), 5.40 (2H, s), 6.80 (1H, s), 7.30 (2H, dd, J = 6.8, 7.3 Hz), 7.55 (2H, dd, J = 6.8, 7.3 Hz), 8.16 (1H, d, J = 4.2 Hz), 8.48 (1H, d, J = 4.2 Hz), 8.76 (1H, s) (DMSO-d6) | 397 |
| 260 | 2.72-2.77 (1H, m), 3.25-3.29 (1H, m), 3.46 (3H, s), 3.62-3.67 (1H, m), 3.81-3.85 (5H, m), 4.07-4.10 (1H, m), 4.96 (1H, dd, J = 1.2, 10.2 Hz), 6.92 (1H, s), 7.07 (1H, d, J = 7.3 Hz), 7.18 (1H, s), 7.54 (1H, d, J = 7.3 Hz), 8.03 (1H, d, J = 4.2 Hz), 8.08 (1H, s), 8.52 (1H, d, J = 4.2 Hz) (DMSO-d6) | 448 |
| 261 | 2.65-2.70 (1H, m), 3.04-3.10 (1H, m), 3.55 (3H, s), 3.68-3.72 (4H, m), 3.77-4.00 (3H, m), 4.57-4.61 (1H, br), 4.92 (1H, dd, J = 1.2, 10.2 Hz), 6.51 (1H, s), 7.01-7.04 (1H, m), 7.38 (1H, d, J = 7.3 Hz), 7.83-7.88 (1H, m), 8.01-8.10 (2H, m), 8.38 (1H, d, J = 7.3 Hz), 8.50 (1H, d, J = 7.3 Hz), 9.27 (1H, d, J = 4.2 Hz) (DMSO-d6) | 463 |
| 262 | 2.64-2.68 (1H, m), 3.10-3.12 (1H, m), 3.48 (3H, s), 3.56-3.63 (1H, m), 3.74-3.89 (5H, m), 3.89-4.07 (1H, m), 4.91 (1H, dd, J = 1.2, 10.2 Hz), 6.40 (1H, s), 7.03 (1H, d, J = 7.3 Hz), 7.10 (1H, s), 7.39 (1H, d, J = 7.3 Hz), 7.64 (1H, d, J = 4.2 Hz), 8.48 (1H, d, J = 4.2 Hz) (DMSO-d6) | 482 |
| 263 | 2.74-2.82 (1H, m), 3.30-3.33 (1H, m), 3.50 (3H, s), 3.69-3.72 (4H, m), 3.87-3.91 (2H, m), 4.12-4.15 (1H, m), 5.00 (1H, dd, J = 1.2, 10.2 Hz), 7.05-7.09 (2H, m), 7.17 (1H, s), 7.43-7.57 (7H, m), 8.27-8.30 (4H, m), 8.46-8.47 (2H, m) (DMSO-d6) | 566 |
| 264 | 3.26-3.32 (2H, m), 3.46 (3H, s), 3.62-3.67 (1H, m), 3.91-4.06 (3H, m), 5.03 (1H, dd, J = 1.2, 10.2 Hz), 6.44-6.46 (1H, br), 6.96 (1H, s), 6.98 (1H, s), 7.23-7.36 (2H, m), 7.58-7.67 (2H, m), 8.05 (1H, d, J = 4.2 Hz), 8.11 (1H, s), 8.53 (1H, d, J = 4.2 Hz) (DMSO-d6) | 423 |
| 265 | 2.71-2.77 (1H, m), 3.10-3.18 (1H, m), 3.48 (3H, s), 3.61-4.10 (11H, m), 4.93 (1H, dd, J = 1.2, 10.2 Hz), 6.88 (1H, s), 7.05 (1H, d, J = 7.3 Hz), 7.12 (1H, s), 7.42 (1H, d, J = 7.3 Hz), 8.22 (1H, d, J = 4.2 Hz), 8.49 (1H, d, J = 4.2 Hz), 8.71 (1H, s) (DMSO-d6) | 443 |
| 266 | 3.18-3.26 (1H, m), 3.35-3.42 (1H, m), 3.48 (3H, s), 3.62-3.66 (1H, m), 3.88-4.01 (3H, m), 4.13 (3H, s), 5.01 (1H, dd, J = 1.2, 10.2 Hz), 6.94 (1H, s), 6.98 (1H, s), 7.23-7.35 (2H, m), 7.57-7.66 (2H, m), 8.46 (1H, d, J = 4.2 Hz), 8.61 (1H, d, J = 4.2 Hz), 8.83 (1H, s) (DMSO-d6) | 419 |
| 267 | 3.16-3.20 (1H, m), 3.51 (3H, s), 3.62-3.84 (3H, m), 3.88-4.08 (5H, m), 4.48-4.52 (1H, br), 5.27 (1H, dd, J = 1.2, 10.2 Hz), 6.89 (1H, s), 7.25-7.48 (3H, m), 8.30 (1H, d, J = 4.2 Hz), 8.51 (1H, d, J = 4.2 Hz), 8.74 (1H, s) (DMSO-d6) | 431 |
| 268 | 2.72-2.77 (1H, m), 3.16-3.20 (1H, m), 3.47 (3H, s), 3.59-3.63 (1H, m), 3.78-3.85 (5H, m), 4.00 (3H, s), 4.04-4.08 (1H, m), 5.00 (1H, dd, J = 1.2, 10.2 Hz), 6.81 (1H, s), 7.24 (1H, d, J = 7.3 Hz), 7.75 (1H, s), 7.83 (1H, d, J = 7.3 Hz), 7.92 (1H, d, J = 4.2 Hz), 8.33 (1H, d, J = 4.2 Hz), 8.53 (1H, s) (DMSO-d6) | 434 |
| 269 | 3.27-3.30 (1H, m), 3.43 (3H, s), 3.62-3.84 (4H, m), 3.99-4.03 (1H, m), 5.30 (1H, dd, J = 1.2, 10.2 Hz), 6.92 (1H, s), 7.26-7.50 (3H, m), 8.02 (1H, d, J = 4.2 Hz), 8.10 (1H, s), 8.51 (1H, d, J = 4.2 Hz) (DMSO-d6) | 436 |
| 270 | 2.73-2.82 (1H, m), 3.20-3.24 (1H, m), 3.47 (3H, s), 3.63-3.68 (1H, m), 3.85-3.89 (2H, m), 3.92 (3H, s), 4.09-4.12 (1H, m), 5.02 (1H, dd, J = 1.2, 10.2 Hz), 6.80 (1H, s), 7.23 (1H, d, J = 7.3 Hz), 7.77 (1H, s), 7.85 (1H, d, J = 7.3 Hz), 8.03 (1H, d, J = 4.2 Hz), 8.32 (1H, s), 8.53 (1H, d, J = 4.2 Hz) (DMSO-d6) | 438 |

TABLE 2-continued

| Compound No. | 1H-NMR δ: | [M + 1] |
|---|---|---|
| 271 | 2.71-2.75 (1H, m), 3.16-3.20 (1H, m), 3.45 (3H, s), 3.60-3.64 (1H, m), 3.85-3.88 (8H, m), 4.05-4.09 (1H, m), 4.96 (1H, dd, J = 1.2, 10.2 Hz), 6.68 (1H, s), 7.06 (1H, d, J = 7.3 Hz), 7.13 (1H, s), 7.42 (1H, s), 7.44 (1H, s), 7.58 (1H, d, J = 4.2 Hz), 8.52 (1H, d, J = 4.2 Hz) (DMSO-d6) | 443 |
| 272 | 3.24-3.27 (4H, m), 3.43 (3H, s), 3.71-3.76 (4H, m), 3.85 (3H, s), 4.01-4.04 (1H, br), 5.41 (2H, s), 6.92-7.01 (2H, m), 7.11 (1H, d, J = 7.3 Hz), 7.38-7.47 (2H, m), 8.33 (1H, d, J = 4.2 Hz), 8.56 (1H, d, J = 4.2 Hz), 8.91 (1H, s) (DMSO-d6) | 409 |
| 273 | 3.10-3.14 (2H, m), 3.25-3.28 (4H, m), 3.43 (3H, s), 3.73-3.76 (4H, m), 4.51-4.55 (2H, m), 6.75 (1H, s), 7.12 (2H, dd, J = 6.8 Hz, 7.3 Hz), 7.36 (2H, dd, J = 6.8 Hz, 7.3 Hz), 8.21 (1H, d, J = 4.2 Hz), 8.49 (1H, d, J = 4.2 Hz), 8.73 (1H, s) (DMSO-d6) | 411 |
| 274 | 3.10-3.14 (2H, m), 3.27-3.30 (4H, m), 3.44 (3H, s), 3.74-3.76 (4H, m), 3.82 (3H, s), 4.52-4.56 (2H, m), 6.86-7.00 (4H, m), 7.21-7.27 (2H, m), 8.42 (1H, d, J = 4.2 Hz), 8.58 (1H, d, J = 4.2 Hz), 8.84 (1H, s) (DMSO-d6) | 423 |
| 275 | 2.88-2.92 (2H, m), 3.07-3.10 (4H, m), 3.42 (3H, s), 3.56-3.58 (2H, m), 3.66-3.68 (4H, m), 4.88-4.92 (1H, br), 6.61 (1H, s), 7.04-7.32 (4H, m), 7.85-7.87 (1H, br), 8.00 (1H, d, J = 4.2 Hz), 8.07 (1H, d, J = 4.2 Hz), 8.31 (1H, s) (DMSO-d6) | 410 |
| 276 | 1.99-2.10 (2H, m), 2.72-2.77 (2H, m), 3.28-3.30 (4H, m), 3.43 (3H, s), 3.74-3.76 (8H, m), 4.31-4.38 (2H, m), 6.82-6.94 (2H, m), 7.00 (1H, s), 7.14-7.20 (2H, m), 8.41 (1H, d, J = 4.2 Hz), 8.57 (1H, d, J = 4.2 Hz), 8.77 (1H, s) (DMSO-d6) | 437 |
| 277 | 2.07-2.12 (2H, m), 2.49-2.53 (1H, (1H, dd, br), 2.74-2.79 (2H, m), 3.28-3.31 (4H, m), 3.43 (3H, s), 3.74-3.76 (4H, m), 4.30-4.33 (2H, m), 6.97 (1H, s), 7.09 (2H, dd, J = 6.8 Hz, 7.3 Hz), 7.27 (2H, dd, J = 6.8 Hz, 7.3 Hz), 8.29 (1H, d, J = 4.2 Hz), 8.50 (1H, d, J = 4.2 Hz), 8.71 (1H, s) (DMSO-d6) | 425 |
| 278 | 2.84-2.89 (2H, m), 3.08-3.12 (4H, m), 3.35-3.42 (5H, m), 3.68-3.78 (7H, m), 4.32-4.37 (1H, br), 6.64 (1H, s), 6.81-7.21 (5H, m), 7.98-8.09 (2H, m), 8.21 (1H, s) (DMSO-d6) | 422 |
| 279 | 2.74-2.81 (4H, m), 3.14-3.21 (1H, m), 3.46 (3H, s), 3.60-3.64 (1H, m), 3.78-3.82 (1H, m), 3.91-3.96 (4H, m), 4.10-4.13 (1H, m), 4.99 (1H, dd, J = 1.2 Hz, 10.2 Hz), 6.60-6.62 (1H, m), 7.01-7.03 (2H, m), 7.25 (1H, d, J = 7.3 Hz), 7.77 (1H, d, J = 1.2 Hz), 7.83 (1H, dd, J = 1.2 Hz, 4.2 Hz), 8.52 (1H, d, J = 4.2 Hz) (DMSO-d6) | 433 |
| 280 | 1.19-1.47 (5H, m), 1.56-1.79 (3H, m), 2.03-2.06 (2H, m), 3.06 (1H, dd, J = 12.9 Hz, 10.5 Hz), 3.29 (1H, m), 3.51-3.56 (1H, m), 3.58 (3H, s), 3.62-3.67 (1H, m), 3.96-4.01 (2H, m), 4.18-4.21 (1H, m), 4.79 (1H, d, J = 8.7 Hz), 5.94 (1H, d, J = 7.8 Hz), 6.78 (1H, s), 7.47 (2H, d, J = 8.1 Hz), 7.79 (2H, d, J = 8.4 Hz), 7.92 (1H, dd, J = 6.6 Hz, 6.6 Hz), 8.51 (1H, d, J = 4.8 Hz), 8.57 (1H, d, J = 3.0 Hz). (CDCl₃) | 492 |
| 281 | 1.60-1.81 (3H, m), 1.88-1.96 (5H, m), 2.76-2.97 (3H, m), 3.19 (4H, t, J = 6.3 Hz), 3.42 (3H, s), 3.62-3.75 (2H, m), 6.50 (2H, d, J = 8.7 Hz), 6.54 (1H, s), 7.11 (2H, d, J = 8.4 Hz), 7.95 (1H, dd, J = 5.1, 6.6 Hz), 8.56 (1H, d, J = 5.1 Hz), 8.69 (1H, d, J = 3.3 Hz) (DMSO-d6) | 434 |
| 282 | 1.74-1.88 (3H, m), 1.92-2.01 (1H, m), 2.94-3.07 (3H, m), 3.44 (3H, s), 3.70-3.76 (2H, m), 3.79 (3H, s), 6.56 (1H, d, J = 0.9 Hz), 7.02 (2H, dd, J = 1.8 Hz, 6.9 Hz), 7.39 (2H, d, J = 8.1 Hz), 7.56-7.61 (4H, m), 7.97 (1H, dd, J = 4.8 Hz, 6.6 Hz), 8.57 (1H, d, J = 5.1 Hz), 8.69 (1H, d, J = 3.0 Hz) (DMSO-d6) | 471 |
| 283 | 3.06 (1H, dd, J = 12.9 Hz, 10.5 Hz), 3.29 (1H, m), 3.51-3.56 (1H, m), 3.58 (3H, s), 3.63-3.68 (3H, m), 3.83-3.88 (2H, m), 4.01 (1H, m), 4.17-4.22 (1H, m), 4.80 (1H, dd, J = 10.8 Hz, 2.4 Hz), 6.59 (1H, m), 6.89 (1H, s), 7.48 (2H, d, J = 8.4 Hz), 7.83 (2H, d, J = 8.4 Hz), 7.92 (1H, dd, J = 6.6 Hz, 5.4 Hz), 8.51 (1H, d, J = 5.1 Hz), 8.56 (1H, d, J = 3.0 Hz) (CDCl₃) | 454 |
| 284 | 2.99-3.11 (7H, m), 3.28 (1H, m), 3.51-3.56 (1H, m), 3.58 (3H, s), 3.60-3.66 (1H, m), 4.00 (1H, m), 4.17-4.10 (1H, m), 4.77 (1H, d, J = 10.5 Hz, 2.4 Hz), 6.89 (1H, s), 7.45 (4H, s), 7.93 (1H, dd, J = 6.6 Hz, 5.1 Hz), 8.52 (1H, d, J = 5.1 Hz), 8.56 (1H, d, J = 3.0 Hz). (CDCl₃) | 438 |
| 285 | 2.03 (3H, s), 3.08 (1H, t, J = 11.9 Hz), 3.28 (1H, m), 3.58 (3H, s), 3.51-3.64 (2H, m), 3.99 (1H, t, J = 11.7 Hz), 4.16 (1H, d, J = 11.7 Hz), 4.74 (1H, dd, J = 10.8 Hz, 2.1 Hz), 6.68 (1H, br.s), 6.88 (1H, s), 7.26 (2H, d, J = 8.4 Hz), 7.41 (2H, d, J = 8.4 Hz), 7.93 (1H, dd, J = 4.8 Hz, 6.6 Hz), 8.51 (1H, d, J = 5.1 Hz), 8.56 (1H, d, J = 3.0 Hz) (CDCl₃) | 460 |
| 286 | 1.51 (2H, m), 1.60 (4H, m), 2.55 (4H, m), 3.08 (2H, s), 3.11 (1H, dd, J = 2.4 Hz, 13.2 Hz), 3.29 (1H, td, J = 3.0 Hz, 11.9 Hz), 3.51-3.63 (2H, m), 358 (3H, s), 3.99 (1H, td, J = 2.4 Hz, 11.6 Hz), 4.17 (1H, dd, J = 1.5 Hz, 11.7 Hz), 4.71 (1H, dd, J = 1.8 Hz, 10.2 Hz), 6.89 (1H, s), 7.38 (2H, d, J = 8.7 Hz), 7.61 (2H, d, J = 8.7 Hz), 7.95 (1H, d, J = 5.1 Hz), 8.51 (1H, d, J = 4.8 Hz), 8.55 (1H, d, J = 3.0 Hz), 9.34 (1H, br.s) (CDCl₃) | 507 |
| 287 | 1.85 (4H, m), 2.70 (4H, m), 3.10 (1H, dd, J = 10.8 Hz, 12.9 Hz), 3.29 (2H, s), 3.31-3.32 (1H, m), 3.51-3.64 (2H, m), 3.58 (3H, s), 3.99 (1H, td, J = 2.1 Hz, 11.7 Hz), 4.18 (1H, dd, J = 2.4 Hz, 12.0 Hz), 4.68 (1H, dd, J = 2.1 Hz, 10.5 Hz), 6.89 (1H, s), 7.37 (2H, d, J = 8.7 Hz), 7.61 (2H, d, J = 8.7 Hz), 7.94 (1H, d, J = 5.1 Hz), 8.51 (1H, d, J = 4.8 Hz), 8.55 (1H, d, J = 3.0 Hz), 9.15 (1H, br.s) (CDCl₃) | 493 |

TABLE 2-continued

| Compound No. | 1H-NMR δ: | [M + 1] |
|---|---|---|
| 288 | 2.39 (6H, s), 3.05-3.12 (1H, m), 3.08 (2H, s), 3.28 (1H, td, J = 3.0 Hz, 12.0 Hz), 3.50-3.63 (2H, m), 3.58 (3H, s), 3.98 (1H, td, J = 2.0 Hz, 11.3 Hz), 4.17 (1H, dd, J = 12.0 Hz, 2.4 Hz), 4.71 (1H, dd, J = 2.6 Hz, 10.5 Hz), 6.89 (1H, s), 7.38 (2H, d, J = 8.7 Hz), 7.63 (2H, d, J = 8.7 Hz), 7.94 (1H, d, J = 5.1 Hz), 8.51 (1H, d, J = 4.8 Hz), 8.55 (1H, d, J = 3.0 Hz), 9.16 (1H, br.s) (CDCl$_3$) | 467 |
| 289 | 1.25 (6H, t, J = 7.3 Hz), 3.07-3.14 (5H, m), 3.26-3.30 (3H, m), 3.50-3.56 (5H, m), 3.98-4.02 (1H, m), 4.12-4.15 (1H, m), 4.33-4.37 (2H, m), 4.65 (1H, dd, J = 1.2 Hz, 10.2 Hz), 6.88 (1H, s), 6.98 (2H, d, J = 7.2 Hz), 7.32 (2H, d, J = 7.2 Hz), 7.93 (1H, dd, J = 1.2 Hz, 4.2 Hz), 8.51 (1H, d, J = 4.2 Hz), 8.56 (1H, d, J = 1.2 Hz) (DMSO-d6) | 482 |
| 290 | 1.60-1.69 (6H, m), 3.10 (1H, m), 3.28-3.38 (3H, m), 3.51-3.58 (1H, m), 3.58 (3H, s), 3.61-3.71 (3H, m), 4.00 (1H, m), 4.17-4.20 (1H, m), 4.76 (1H, d, J = 9.9 Hz), 6.89 (1H, s), 7.45 (4H, m), 7.93 (1H, dd, J = 5.7 Hz, 5.7 Hz), 8.52 (1H, d, J = 4.8 Hz), 8.56 (1H, d, J = 2.4 Hz) (CDCl$_3$) | 478 |
| 291 | 2.27 (3H, s), 3.07 (1H, dd, J = 10.8 Hz, 12.9 Hz), 3.32 (1H, td, J = 3.0 Hz, 12.0 Hz), 3.52-3.69 (2H, m), 3.58 (3H, s), 4.01 (1H, td, J = 2.0 Hz, 11.3 Hz), 4.20 (1H, dd, J = 12.0 Hz, 2.4 Hz), 4.82 (1H, dd, J = 2.1 Hz, 10.5 Hz), 6.89 (1H, s), 7.40 (2H, d, J = 8.7 Hz), 7.91 (1H, dd, J = 6.3 Hz, 1.2 Hz), 8.00 (2H, d, J = 8.7 Hz), 8.50 (1H, d, J = 3.08 Hz), 8.55 (1H, d, J = 3.0 Hz) (CDCl$_3$) | 409 |
| 292 | 1.50 (3H, d, J = 6.6 Hz), 1.96 (1H, m), 3.10 (1H, dd, J = 10.8 Hz, 12.9 Hz), 3.30 (1H, td, J = 3.0 Hz, 12.0 Hz), 3.52-3.66 (2H, m), 3.58 (3H, s), 3.99 (1H, td, J = 2.0 Hz, 11.3 Hz), 4.18 (1H, dd, J = 12.0 Hz, 2.4 Hz), 4.73 (1H, dd, J = 2.1 Hz, 10.5 Hz), 4.93 (1H, m), 6.88 (1H, s), 7.40 (2H, d, J = 8.7 Hz), 7.91 (1H, dd, J = 6.3 Hz, 1.2 Hz), 8.00 (2H, d, J = 8.7 Hz), 8.50 (1H, d, J = 3.1 Hz), 8.55 (1H, d, J = 3.0 Hz) (CDCl$_3$) | 411 |
| 293 | 1.69-1.73 (1H, m), 1.84-1.98 (2H, m), 2.10 (1H, d, J = 14.3 Hz), 2.92-3.01 (3H, m), 3.54 (3H, s), 3.65-3.72 (2H, m), 6.85 (1H, s), 7.15 (2H, d, J = 8.4 Hz), 7.48 (2H, d, J = 8.4 Hz), 7.94 (1H, dd, J = 6.6 Hz, 1.3 Hz), 8.50 (1H, d, J = 5.0 Hz), 8.54 (1H, d, J = 3.1 Hz) (CDCl$_3$) | 444 |
| 294 | 3.11 (1H, dd, J = 12.9 Hz, 10.5 Hz), 3.14 (3H, d, J = 4.5 Hz), 3.30 (1H, td, J = 12..0 Hz, 3.0 Hz), 3.48-3.67 (2H, m), 3.59 (3H, s), 4.01 (1H, td, J = 2.4 Hz, 12.0 Hz), 4.18 (1H, dd, J = 2.1 Hz, 11.7 Hz), 4.75 (1H, dd, J = 2.1 Hz, 10.5 Hz), 6.07 (1H, m), 6.88 (1H, s), 7.26 (2H, d, J = 8.4 Hz), 7.47 (2H, d, J = 8.4 Hz), 7.91 (1H, dd, J = 6.6 Hz, 1.7 Hz), 8.51 (1H, d, J = 5.0 Hz), 8.56 (1H, d, J = 3.1 Hz) (CDCl$_3$) | 454 |
| 295 | 3.04-3.09 (1H, m), 3.26-3.31 (1H, m), 3.50-3.62 (5H, m), 3.79 (3H, s), 3.95-4.01 (1H, m), 4.14-4.17 (1H, m), 4.69 (1H, dd, J = 1.2 Hz, 10.2 Hz), 6.71 (1H, br), 6.88 (1H, s), 7.30-7.43 (4H, m), 7.94 (1H, dd, J = 1.2 Hz, 4.2 Hz), 8.51 (1H, d, J = 4.2 Hz), 8.56 (1H, d, J = 1.2 Hz) (DMSO-d6) | 440 |
| 296 | 1.78-1.82 (4H, m), 2.49-2.55 (3H, m), 2.69-2.85 (3H, m), 3.09-3.13 (1H, m), 3.21-3.26 (1H, m), 3.55-3.61 (5H, m), 3.97-4.16 (5H, m), 4.66 (1H, dd, J = 1.2 Hz, 10.2 Hz), 6.89 (1H, s), 6.95 (2H, d, J = 7.2 Hz), 7.32 (2H, d, J = 7.2 Hz), 7.94 (1H, dd, J = 1.2 Hz, 4.2 Hz), 8.51 (1H, d, J = 4.2 Hz), 8.55 (1H, d, J = 1.2 Hz) (CDCl$_3$) | 510 |
| 297 | 3.04-3.11 (1H, m), 3.21-3.28 (1H, m), 3.48-3.61 (9H, m), 3.74-3.77 (4H, m), 3.91-4.00 (1H, m), 4.08-4.11 (1H, m), 4.68 (1H, dd, J = 1.2 Hz, 10.2 Hz), 6.41 (1H, br.s), 7.35-7.42 (4H, m), 7.94 (1H, dd, J = 1.2 Hz, 4.2 Hz), 8.51 (1H, d, J = 1.2 Hz), 8.54 (1H, d, J = 4.2 Hz) (CDCl$_3$) | 495 |
| 298 | 3.04 (6H, s), 3.08-3.12 (1H, m), 3.26-3.30 (1H, m), 3.50-3.61 (5H, m), 3.94-4.01 (1H, m), 4.14-4.18 (1H, m), 4.66 (1H, dd, J = 1.2 Hz, 10.2 Hz), 6.39 (1H, br.s), 6.88 (1H, s), 7.28 (2H, d, J = 7.2 Hz), 7.42 (2H, d, J = 7.2 Hz), 7.95 (1H, dd, J = 1.2 Hz, 4.2 Hz), 8.50-8.55 (2H, m) (CDCl$_3$) | 453 |
| 299 | 3.02 (1H, dd, J = 10.6 Hz, 12.8 Hz), 3.26 (1H, td, J = 12.1 Hz, 3.0 Hz), 3.49-3.59 (2H, m), 3.56 (3H, s), 3.95 (1H, td, J = 11.7 Hz, 2.2 Hz), 4.12 (1H, m), 4.66 (1H, dd, J = 8.4 Hz, 10.4 Hz), 6.88 (1H, s), 7.00 (1H, br.s), 7.12 (2H, d, J = 8.5 Hz), 7.26-7.31 (2H, m), 7.42-7.47 (2H, m), 7.53 (1H, t, J = 7.4 Hz), 7.79 (2H, d, J = 7.2 Hz), 7.92 (1H, dd, J = 5.0 Hz, 6.5 Hz), 8.51 (1H, d, J = 5.0 Hz), 8.56 (1H, d, J = 3.0 Hz) (CDCl$_3$) | 522 |
| 300 | 3.10 (1H, dd, J = 10.8 Hz, 13.2 Hz), 3.30 (1H, td, J = 12.1 Hz, 3.0 Hz), 3.56 (3H, s), 3.58-3.66 (2H, m), 3.95 (1H, td, J = 11.7 Hz, 2.2 Hz), 4.16 (1H, m), 4.33 (2H, s), 4.75 (1H, dd, J = 2.1 Hz, 10.5 Hz), 6.87 (1H, s), 7.15 (1H, br.s), 7.19-7.411 (9H, m), 7.94 (1H, dd, J = 5.1 Hz, 6.6 Hz), 8.49 (1H, d, J = 5.4 Hz), 8.51 (1H, d, J = 3.3 Hz) (CDCl$_3$) | 536 |
| 301 | 2.87 (6H, s), 2.97 (1H, dd, J = 10.6 Hz, 13.3 Hz), 3.14 (1H, td, J = 12.1 Hz, 13.3 Hz), 3.46-3.60 (2H, m), 3.53 (3H, s), 3.90 (1H, m), 4.08-4.16 (1H, m), 4.57 (1H, dd, J = 10.4 Hz, 1.9 Hz), 6.87 (1H, s), 7.00 (2H, d, J = 8.5 Hz), 7.19 (2H, d, J = 8.5 Hz), 7.40-7.60 (4H, m), 7.90 (1H, d, J = 6.6 Hz), 8.19 (1H, d, J = 7.8 Hz), 8.34 (1H, d, J = 8.6 Hz), 849 (1H, s), 8.51 (1H, d, J = 2.4 Hz), 8.56 (1H, d, J = 3.0 Hz) (CDCl$_3$) | 615 |
| 302 | 3.09 (1H, dd, J = 10.8 Hz, 12.8 Hz), 3.28 (1H, td, J = 12.0 Hz, 3.0 Hz), 3.01-3.67 (2H, m), 3.58 (3H, s), 3.99 (1H, td, J = 2.4 Hz, 11 Hz), 4.10-4.19 (1H, m), 4.76 (1H, dd, J = 2.4 Hz, 10.8 Hz), 6.88 (1H, s), 7.27 (1H, m), 7.43 (2H, d, J = 8.7 Hz), 7.50 (2H, d, J = 8.7 Hz), 7.93 (2H, td, J = 6.6 Hz, 1.5 Hz), 8.04 (2H, m), 8.30 (1H, br.s), 8.46 (1H, dd, J = 1.3 Hz, 4.8 Hz), 8.50 (1H, d, J = 5.0 Hz), 8.55 (1H, d, J = 3.0 Hz) (CDCl$_3$) | 518 |

TABLE 2-continued

| Compound No. | 1H-NMR δ: | [M + 1] |
|---|---|---|
| 303 | 1.69-1.73 (1H, m), 1.84-1.98 (2H, m), 2.10 (1H, d, J = 14.3 Hz), 2.92-3.00 (3H, m), 3.54 (3H, s), 3.65-3.72 (2H, m), 6.84 (1H, s), 7.15 (2H, d, J = 8.4 Hz), 7.48 (2H, d, J = 8.4 Hz), 7.94 (1H, dd, J = 6.6 Hz, 1.3 Hz), 8.50 (1H, d, J = 5.0 Hz), 8.54 (1H, d, J = 3.1 Hz) (CDCl$_3$) | 444 |
| 304 | 3.04-3.08 (1H, m), 3.26-3.31 (1H, m), 3.50-3.61 (5H, m), 3.95-4.91 (1H, m), 4.14-4.18 (1H, m), 4.68 (1H, dd, J = 1.2 Hz, 10.2 Hz), 5.21 (2H, s), 6.78 (1H, br.s), 6.89 (1H, s), 7.33-7.45 (9H, m), 7.95 (1H, dd, J = 1.2 Hz, 4.2 Hz), 8.50-8.56 (2H, m) (CDCl$_3$) | 516 |
| 305 | 2.62-2.67 (2H, m), 2.97-3.10 (3H, m), 3.24-3.34 (1H, m), 3.52-3.62 (5H, m), 3.96-4.00 (1H, m), 4.12-4.16 (1H, m), 4.68 (1H, dd, J = 1.2 Hz, 10.2 Hz), 6.78 (1H, d, J = 7.2 Hz), 6.88 (1H, dd, J = 1.2 Hz, 10.2 Hz), 7.19-7.26 (2H, m), 7.93 (1H, dd, J = 1.2 Hz, 4.2 Hz), 8.09 (1H, br.s), 8.51 (1H, d, J = 4.2 Hz), 8.57 (1H, d, J = 1.2 Hz) (CDCl$_3$) | 436 |
| 306 | 1.36 (6H, s), 2.50 (2H, s), 3.07-3.14 (1H, m), 3.32-3.38 (1H, m), 3.53-3.64 (5H, m), 3.96-4.02 (1H, m), 4.15-4.20 (1H, m), 4.71 (1H, dd, J = 1.2 Hz, 10.2 Hz), 6.81 (1H, d, J = 7.2 Hz), 6.88 (1H, s), 7.21 (1H, dd, J = 1.2 Hz, 7.2 Hz), 7.33 (1H, d, J = 1.2 Hz), 7.93 (1H, dd, J = 1.2 Hz, 4.2 Hz), 8.09 (1H, br), 8.51 (1H, d, J = 4.2 Hz), 8.56 (1H, d, J = 1.2 Hz) (CDCl$_3$) | 464 |
| 307 | 1.30 (3H, t, J = 7.2 Hz), 3.04-3.12 (1H, m), 3.24-3.32 (1H, m), 3.50-3.62 (5H, m), 3.94-4.01 (1H, m), 4.15-4.24 (3H, m), 4.68 (1H, dd, J = 1.2 Hz, 10.2 Hz), 6.66 (1H, br.s), 6.89 (1H, s), 7.35 (2H, d, J = 7.2 Hz), 7.42 (2H, d, J = 7.2 Hz), 7.94 (1H, dd, J = 1.2 Hz, 4.2 Hz), 8.51 (1H, d, J = 4.2 Hz), 8.55 (1H, d, J = 1.2 Hz) (CDCl$_3$) | 454 |
| 308 | 1.51-1.47 (9H, m), 1.91 (1H, m), 2.89-2.98 (3H, m), 3.14 (4H, t, J = 5.1 Hz), 3.53 (3H, s), 3.69 (2H, d, J = 8.4 Hz), 6.84 (1H, s), 6.92 (2H, d, J = 11.1 Hz), 7.12 (2H, d, J = 11.1 Hz), 7.94 (1H, dd, J = 6.6 Hz, 5.4 Hz), 8.49 (1H, d, J = 4.8 Hz), 8.54 (1H, d, J = 7.7 Hz) (CDCl$_3$) | 448 |
| 309 | 1.51-1.47 (9H, m), 1.91 (1H, m), 2.89-2.98 (3H, m), 3.14 (4H, t, J = 5.1 Hz), 3.53 (3H, s), 3.69 (2H, d, J = 8.4 Hz), 6.84 (1H, s), 6.92 (2H, d, J = 11.1 Hz), 7.12 (2H, d, J = 11.1 Hz), 7.94 (1H, dd, J = 6.6 Hz, 5.4 Hz), 8.49 (1H, d, J = 4.8 Hz), 8.54 (1H, d, J = 7.7 Hz) | 448 |
| 310 | 3.07 (1H, dd, J = 12.9 Hz, 10.8 Hz), 3.28 (1H, m), 3.56-3.58 (1H, m), 3.58 (3H, s), 3.62-3.75 (9H, m), 4.00 (1H, m), 4.17 (1H, m), 4.78 (1H, dd, J = 10.5 Hz, 2.1 Hz), 6.89 (1H, s), 7.43-7.50 (4H, m), 7.93 (1H, dd, J = 6.6 Hz, 4.8 Hz), 8.52 (1H, d, J = 5.1 Hz), 8.56 (1H, d, J = 3.3 Hz). (CDCl$_3$) | 480 |
| 311 | 3.09 (1H, dd, J = 12.9 Hz, 10.8 Hz), 3.28 (1H, ddd, J = 12.3 Hz, 12.3 Hz, 3.0 Hz), 3.51-3.57 (1H, m), 3.57 (3H, s), 3.60-3.64 (1H, m), 3.94 (2H, m), 3.97 (1H, m), 4.14-4.17 (1H, m), 4.63 (1H, d, J = 10.2 Hz), 6.65-6.68 (1H, m), 6.75 (1H, s), 6.75-6.77 (1H, m), 6.89 (1H, s), 7.17 (1H, dd, J = 7.8 Hz, 7.8 Hz), 7.96 (1H, dd, J = 6.0 Hz, 5.4 Hz), 8.51 (1H, d, J = 5.4 Hz), 8.55 (1H, d, J = 3.3 Hz). (CDCl$_3$) | 382 |
| 312 | 2.77 (1H, dd, J = 12.6 Hz, 9.9 Hz), 3.29 (1H, ddd, J = 12.3 Hz, 12.3 Hz, 3.6 Hz), 3.52-3.61 (3H, m), 3.62 (3H, s), 3.77 (3H, s), 3.77-3.82 (1H, m), 3.99 (1H, ddd, J = 11.7 Hz, 11.7 Hz, 2.4 Hz), 4.18-4.21 (1H, m), 5.00 (1H, dd, J = 10.2 Hz, 2.1 Hz), 6.63 (1H, dd, J = 8.4 Hz, 2.4 Hz), 6.71 (1H, s), 6.88 (1H, s), 6.91 (1H, d, J = 2.7 Hz), 8.00 (1H, dd, J = 6.6 Hz, 5.1 Hz), 8.51 (1H, d, J = 4.5 Hz), 8.55 (1H, d, J = 3.3 Hz). (CDCl$_3$) | 412 |
| 313 | 2.16 (3H, s), 2.78 (1H, dd, J = 12.9 Hz, 10.2 Hz), 3.29 (1H, ddd, J = 12.0 Hz, 12.0 Hz, 3.0 Hz), 3.51-3.56 (1H, m), 3.62 (3H, s), 3.78-3.83 (1H, m), 3.84 (3H, s), 3.99 (1H, ddd, J = 11.7 Hz, 11.7 Hz, 2.4 Hz), 4.17-4.21 (1H, m), 5.02 (1H, dd, J = 10.2 Hz, 2.1 Hz), 6.86 (1H, d, J = 8.7 Hz), 6.89 (1H, s), 7.12 (1H, s), 7.46 (1H, d, J = 2.4 Hz), 7.59 (1H, dd, J = 8.7 Hz, 2.7 Hz), 8.00 (1H, dd, J = 6.6 Hz, 5.1 Hz), 8.51 (1H, d, J = 5.1 Hz), 8.55 (1H, d, J = 3.3 Hz). (CDCl$_3$) | 454 |
| 314 | 2.19 (3H, s), 3.09 (1H, dd, J = 12.9 Hz, 10.6 Hz), 3.29 (1H, ddd, J = 12.7 Hz, 12.7 Hz, 3.0 Hz), 3.50-3.54 (1H, m), 3.58 (3H, s), 3.64-3.68 (1H, m), 4.00 (1H, ddd, J = 11.8 Hz, 11.8 Hz, 2.2 Hz), 4.14-4.19 (1H, m), 4.74 (1H, dd, J = 10.5 Hz, 1.9 Hz), 6.89 (1H, s), 7.14-7.20 (2H, m), 7.32-7.41 (2H, m), 7.70 (1H, s), 7.96 (1H, dd, J = 5.4 Hz, 5.4 Hz), 8.53 (1H, d, J = 5.1 Hz), 8.55 (1H, d, J = 3.3 Hz) (CDCl$_3$) | 424 |
| 315 | 1.88-1.97 (2H, m), 2.83-2.91 (3H, m), 3.26-3.38 (1H, m), 3.54-3.65 (1H, m), 3.61 (3H, s), 3.69-3.74 (1H, m), 4.00-4.25 (4H, m), 5.02 (1H, dd, J = 1.8 Hz, 9.9 Hz), 6.88 (1H, s), 6.90 (1H, d, J = 8.4 Hz), 6.99-7.04 (1H, m), 7.24-7.31 (1H, m), 7.51-7.54 (1H, m), 7.98 (1H, dd, J = 5.1 Hz, 6.6 Hz), 8.53 (2H, m) (CDCl$_3$) | 440 |
| 316 | 1.24 (6H, t, J = 7.2 Hz), 3.04-3.11 (1H, m), 3.27-3.42 (5H, m), 3.50-3.61 (5H, m), 3.94-4.00 (1H, m), 4.14-4.18 (1H, m), 4.67 (1H, dd, J = 1.2 Hz, 10.2 Hz), 6.34 (1H, br), 6.90 (1H, s), 7.31 (2H, d, J = 7.2 Hz), 7.41 (2H, d, J = 7.2 Hz), 7.94 (1H, dd, J = 1.2 Hz, 4.2 Hz), 8.51-8.55 (2H, m) (CDCl$_3$) | 481 |
| 317 | 3.08-3.13 (1H, m), 3.24-3.32 (1H, m), 3.51-3.62 (7H, m), 3.96-4.02 (1H, m), 4.15-4.20 (1H, m), 4.68 (1H, dd, J = 1.2 Hz, 10.2 Hz), 6.86-6.88 (2H, m), 7.24-7.32 (2H, m), 7.68 (1H, br.s), 7.92 (1H, dd, J = 1.2 Hz, 4.2 Hz), 8.50 (1H, d, J = 4.2 Hz), 8.56 (1H, d, J = 1.2 Hz) (CDCl$_3$) | 422 |

TABLE 2-continued

| Compound No. | 1H-NMR δ: | [M + 1] |
|---|---|---|
| 318 | 3.13 (1H, dd, J = 10.5 Hz, 12.9 Hz), 3.37 (1H, m), 3.55-3.66 (2H, m), 3.59 (3H, s), 4.02 (1H, td, J = 11.7 Hz, 2.4 Hz), 4.18 (1H, dd, J = 11.7 Hz, 2.1 Hz), 4.50 (2H, s), 4.73 (1H, dd, J = 10.5 Hz, 1.8 Hz), 6.87 (1H, s), 7.33 (2H, d, J = 8.4 Hz), 7.41 (2H, d, J = 8.4 Hz), 7.99 (1H, dd, J = 6.6 Hz, 1.2 Hz), 8.49 (1H, d, J = 5.1 Hz), 8.53 (1H, d, J = 3.0 Hz) (CDCl$_3$) | 494 |
| 319 | 3.06 (1H, dd, J = 12.9 Hz, 10.5 Hz), 3.26 (1H, ddd, J = 12.0 Hz, 12.0 Hz, 3.0 Hz), 3.50-3.56 (1H, m), 3.57 (3H, s), 3.58-3.60 (1H, m), 3.78 (2H, m), 3.97 (1H, m), 4.14-4.17 (1H, m), 4.61 (1H, dd, J = 10.5 Hz, 2.1 Hz), 6.71 (1H, m), 6.85 (1H, dd, J = 8.7 Hz, 2.1 Hz), 6.88 (1H, s), 6.99 (1H, dd, J = 10.5 Hz, 8.7 Hz), 7.94 (1H, dd, J = 6.3 Hz, 5.1 Hz), 8.51 (1H, d, J = 5.4 Hz), 8.55 (1H, d, J = 3.3 Hz).(CDCl$_3$) | 400 |
| 320 | 3.03 (3H, s), 3.10 (1H, dd, J = 12.9 Hz, 10.8 Hz), 3.31 (1H, ddd, J = 12.0 Hz, 12.0 Hz, 3.0 Hz), 3.52-3.56 (1H, m), 3.58 (3H, s), 3.65-3.69 (1H, m), 3.99 (1H, ddd, J = 11.7 Hz, 11.7 Hz, 2.1 Hz), 4.18 (1H, m), 4.76 (1H, d, J = 10.2 Hz), 6.89 (1H, s), 6.80 (1H, s), 7.21-7.42 (4H, m), 7.94 (1H, dd, J = 6.0 Hz, 5.4 Hz), 8.53 (1H, d, J = 4.8 Hz), 8.56 (1H, d, J = 3.0 Hz). (CDCl$_3$) | 460 |
| 321 | 3.11-3.14 (1H, m), 3.32-3.37 (1H, m), 3.54-3.60 (4H, m), 3.69-3.73 (1H, m), 3.99-4.07 (1H, m), 4.20-4.24 (1H, m), 4.84 (1H, dd, J = 1.2 Hz, 10.2 Hz), 6.89 (1H, s), 7.48-7.58 (3H, m), 7.68 (1H, s), 7.92 (1H, dd, J = 1.2 Hz, 4.2 Hz), 8.50 (1H, d, J = 4.2 Hz), 8.55 (1H, d, J = 1.2 Hz), 8.98 (2H, s), 9.23 (1H, s) (CDCl$_3$) | 445 |
| 322 | 1.85 (1H, br.s), 3.00-3.08 (1H, m), 3.19-3.27 (3H, m), 3.56-3.67 (5H, m), 4.13 (1H, dd, J = 1.2 Hz, 10.2 Hz), 6.87 (1H, s), 7.61 (2H, d, J = 7.2 Hz), 7.96 (1H, dd, J = 1.2 Hz, 4.2 Hz), 8.14 (2H, d, J = 7.2 Hz), 8.50 (1H, d, J = 4.2 Hz), 8.55 (1H, d, J = 1.2 Hz), 8.78 (1H, s) (CDCl$_3$) | 434 |
| 323 | 1.69-1.73 (1H, m), 1.84-1.98 (2H, m), 2.10 (1H, d, J = 14.3 Hz), 2.86 (3H, m), 3.53 (3H, s), 3.64-3.69 (2H, m), 6.85 (2H, br.s), 6.67 (2H, d, J = 8.4 Hz), 6.83 (1H, s), 7.05 (2H, d, J = 8.4 Hz), 7.98 (1H, t, J = 6.6 Hz), 8.49 (1H, d, J = 5.1 Hz), 8.54 (1H, d, J = 3.0 Hz) (CDCl$_3$) | 380 |
| 324 | 1.70-2.12 (4H, m), 2.19 (3H, s), 2.92-3.00 (3H, m), 3.54 (3H, s), 3.63-3.72 (2H, m), 6.84 (1H, s), 7.27 (2H, d, J = 8.4 Hz), 7.46 (2H, d, J = 8.4 Hz), 7.96 (1H, dd, J = 6.6 Hz, 1.2 Hz), 8.50 (1H, d, J = 4.2 Hz), 8.54 (1H, d, J = 1.2 Hz) (CDCl$_3$) | 422 |
| 325 | 1.65-2.14 (4H, m), 2.92-3.00 (3H, m), 3.15 (3H, d, J = 4.8 Hz), 3.50 (3H, s), 3.66-3.70 (2H, m), 6.03 (1H, br.s), 6.84 (1H, s), 7.21 (2H, d, J = 8.3 Hz), 7.34 (2H, d, J = 8.3 Hz), 7.68 (1H, br.s), 7.95 (1H, dd, J = 6.6 Hz, 1.2 Hz), 7.95 (1H, dd, J = 6.6 Hz, 1.2 Hz), 8.50 (1H, d, J = 4.2 Hz), 8.54 (1H, d, J = 1.2 Hz) (CDCl$_3$) | 453 |
| 326 | 1.73-2.12 (4H, m), 2.92-3.00 (3H, m), 3.56 (3H, s), 3.65-3.70 (2H, m), 6.88 (1H, s), 6.99-7.17 (2H, m), 7.26 (2H, d, J = 8.4 Hz), 7.40 (2H, d, J = 8.4 Hz), 7.71 (1H, d, J = 2.7 Hz), 7.97-8.04 (3H, m), 8.22 (1H, dd, J = 6.6 Hz, 1.6 Hz), 8.50 (1H, d, J = 4.2 Hz), 8.54 (1H, d, J = 1.2 Hz) (CDCl$_3$) | 517 |
| 327 | 1.73-2.13 (4H, m), 2.94-3.01 (3H, m), 3.55 (3H, s), 3.64-3.70 (2H, m), 3.78 (3H, s), 6.60 (1H, br.s), 6.85 (1H, s), 7.21 (2H, d, J = 8.4 Hz), 7.38 (2H, d, J = 8.4 Hz), 7.96 (1H, dd, J = 6.6 Hz, 1.5 Hz), 8.50 (1H, d, J = 4.2 Hz), 8.54 (1H, d, J = 1.2 Hz) (CDCl$_3$) | 438 |
| 328 | 1.68-2.14 (4H, m), 2.93-2.99 (3H, m), 3.03 (3H, s), 3.55 (3H, s), 3.66-3.73 (2H, m), 6.66 (1H, br.s), 6.84 (1H, s), 7.20-7.30 (4H, m), 7.96 (1H, dd, J = 6.6 Hz, 1.5 Hz), 8.51 (1H, d, J = 4.2 Hz), 8.55 (1H, d, J = 1.2 Hz) (CDCl$_3$) | 458 |
| 329 | 1.26-2.23 (15H, m), 2.94-3.00 (3H, m), 3.54 (3H, s), 3.65 (2H, m), 6.85 (1H, s), 7.16 (1H, br.s), 7.22 (2H, d, J = 8.4 Hz), 7.51 (2H, d, J = 8.4 Hz), 7.96 (1H, dd, J = 6.6 Hz, 1.5 Hz), 8.50 (1H, d, J = 4.2 Hz), 8.55 (1H, d, J = 1.2 Hz) (CDCl$_3$) | 490 |
| 330 | 1.69-2.09 (4H, m), 2.38 (3H, m), 2.62 (4H, t, J = 4.8 Hz), 2.92 (3H, m), 3.23 (4H, t, J = 4.8 Hz), 3.54 (3H, s), 3.65-3.72 (2H, m), 6.84 (1H, s), 6.92 (2H, d, J = 8.7 Hz), 7.17 (2H, d, J = 8.7 Hz), 7.96 (1H, dd, J = 6.6 Hz, 1.5 Hz), 8.50 (1H, d, J = 4.2 Hz), 8.55 (1H, d, J = 1.2 Hz) (CDCl$_3$) | 463 |
| 331 | 3.10 (1H, dd, J = 10.6 Hz, 12.8 Hz), 3.33 (1H, td, J = 12.1 Hz, 3.0 Hz), 3.52-3.73 (2H, m), 3.59 (3H, s), 4.01 (1H, t, J = 10.7 Hz), 4.21 (1H, d, J = 11.3 Hz), 4.83 (1H, d, J = 9.8 Hz), 6.90 (1H, s), 7.27 (3H, m), 7.88-7.99 (3H, m), 8.07 (1H, s), 8.51 (1H, d, J = 6.5 Hz), 8.56 (1H, d, J = 3.0 Hz) (CDCl$_3$). | 450 |
| 332 | 2.73 (6H, s), 3.08 (1H, dd, J = 10.6 Hz, 12.9 Hz), 3.31 (1H, td, J = 12.6 Hz, 3.3 Hz), 3.52-3.71 (2H, m), 3.59 (3H, s), 4.03 (1H, td, J = 11.7 Hz, 2.1 Hz), 4.20 (1H, dd, J = 11.4 Hz, 2.1 Hz), 4.86 (1H, dd, J = 10.5 Hz, 1.8 Hz), 6.89 (1H, s), 7.60 (2H, d, J = 8.4 Hz), 7.81 (2H, d, J = 8.4 Hz), 7.94 (1H, s), 8.58 (2H, m) (CDCl$_3$) | 474 |
| 333 | 1.57-2.16 (4H, m), 2.94-3.05 (3H, m), 3.55 (3H, s), 3.72-3.76 (2H, m), 6.85 (1H, s), 7.26-7.39 (5H, m), 7.98 (1H, t, J = 6.6 Hz), 8.50 (1H, d, J = 5.1 Hz), 8.54 (1H, d, J = 3.0 Hz) (CDCl$_3$) | 365 |
| 334 | 2.00-2.04 (1H, m), 2.67 (3H, s), 3.00-3.11 (1H, m), 3.18-3.30 (3H, m), 3.57-3.66 (5H, m), 4.11 (1H, dd, J = 1.2 Hz, 10.2 Hz), 6.86 (1H, s), 7.57 (2H, d, J = 7.2 Hz), 7.97 (1H, dd, J = 1.2 Hz, 4.2 Hz), 8.08 (2H, d, J = 7.2 Hz), 8.50 (1H, d, J = 4.2 Hz), 8.55 (1H, d, J = 1.2 Hz) (CDCl$_3$) | 448 |
| 335 | 1.46 (3H, t, J = 7.3 Hz), 2.95-3.02 (3H, m), 3.19-3.25 (3H, m), 3.57-3.66 (5H, m), 4.11 (1H, dd, J = 1.2 Hz, 10.2 Hz), 6.86 (1H, s), 7.57 (2H, d, | 462 |

TABLE 2-continued

| Compound No. | 1H-NMR δ: | [M + 1] |
|---|---|---|
| | J = 7.2 Hz), 7.95 (1H, dd, J = 1.2 Hz, 4.2 Hz), 8.10 (2H, d, J = 7.2 Hz), 8.50 (1H, d, J = 4.2 Hz), 8.54 (1H, d, J = 1.2 Hz) (CDCl$_3$) | |
| 336 | 3.07-3.11 (1H, m), 3.31-3.36 (1H, m), 3.53-3.71 (5H, m), 4.00-4.05 (1H, m), 4.19-4.23 (1H, m), 4.82 (1H, dd, J = 1.2 Hz, 10.2 Hz), 6.89 (1H, s), 7.56 (2H, d, J = 7.2 Hz), 7.93 (1H, dd, J = 1.2 Hz, 4.2 Hz), 8.16 (2H, d, J = 7.2 Hz), 8.51 (1H, d, J = 4.2 Hz), 8.55 (1H, d, J = 1.2 Hz), 8.78 (1H, s) (CDCl$_3$) | 435 |
| 337 | 2.67 (3H, s), 3.07-3.14 (1H, m), 3.28-3.33 (1H, m), 3.53-3.70 (5H, m), 3.96-4.05 (1H, m), 4.18-4.22 (1H, m), 4.81 (1H, dd, J = 1.2 Hz, 10.2 Hz), 6.89 (1H, s), 7.53 (2H, d, J = 7.2 Hz), 7.93 (1H, dd, J = 1.2 Hz, 4.2 Hz), 8.10 (2H, d, J = 7.2 Hz), 8.51 (1H, d, J = 4.2 Hz), 8.56 (1H, d, J = 1.2 Hz) (CDCl$_3$) | 449 |
| 338 | 2.67 (3H, s), 3.10-3.14 (1H, m), 3.31-3.36 (1H, m), 3.53-3.71 (5H, m), 3.98-4.04 (1H, m), 4.19-4.23 (1H, m), 4.83 (1H, dd, J = 1.2 Hz, 10.2 Hz), 6.89 (1H, s), 7.60 (2H, d, J = 7.2 Hz), 7.93 (1H, dd, J = 1.2 Hz, 4.2 Hz), 8.06 (2H, d, J = 7.2 Hz), 8.51 (1H, d, J = 4.2 Hz), 8.55 (1H, d, J = 1.2 Hz) (CDCl$_3$). | 449 |
| 339 | 3.08 (1H, dd, J = 10.6 Hz, 12.9 Hz), 3.31 (1H, td, J = 12.6 Hz, 3.3 Hz), 3.52-3.71 (2H, m), 3.59 (3H, s), 4.01 (1H, td, J = 11.7 Hz, 2.1 Hz), 4.20 (1H, dd, J = 11.4 Hz, 2.1 Hz), 4.87 (1H, dd, J = 10.5 Hz, 1.8 Hz), 6.89 (1H, s), 7.60 (2H, d, J = 8.8 Hz), 7.90 (1H, dd, J = 6.2 Hz, 1.2 Hz), 8.27 (2H, d, J = 8.8 Hz), 8.51 (1H, d, J = 4.2 Hz), 8.57 (1H, d, J = 1.2 Hz) (CDCl$_3$) | 412 |
| 340 | 3.10-3.14 (1H, m), 3.31-3.36 (1H, m), 3.51-3.70 (5H, m), 3.96-4.02 (1H, m), 4.16-4.20 (1H, m), 4.87 (1H, dd, J = 1.2 Hz, 10.2 Hz), 6.62 (1H, s), 7.44 (1H, dd, J = 1.2 Hz, 4.2 Hz), 7.68 (2H, d, J = 7.2 Hz), 7.90-8.04 (3H, m), 8.57 (1H, d, J = 4.2 Hz), 8.71 (1H, d, J = 1.2 Hz) (CDCl$_3$). | 435 |
| 341 | 1.25 (6H, t, J = 7.3 Hz), 3.00-3.18 (6H, m), 3.48 (3H, s), 3.66-3.73 (3H, m), 3.76-3.80 (1H, m), 4.02-4.06 (1H, m), 4.28 (2H, d, J = 5.4 Hz), 4.80 (1H, dd, J = 1.2 Hz, 10.2 Hz), 6.61 (1H, s), 7.52 (2H, d, J = 7.2 Hz), 7.63 (2H, d, J = 7.2 Hz), 7.98 (1H, dd, J = 1.2 Hz, 4.2 Hz), 8.57 (1H, d, J = 4.2 Hz), 8.72 (1H, d, J = 1.2 Hz), 10.46 (1H, br.s) (DMSO-d6). | 452 |
| 342 | 1.82 (1H, br.s), 3.05-3.10 (1H, m), 3.30-3.38 (1H, m), 3.52-3.63 (5H, m), 3.96-4.02 (1H, m), 4.15-4.19 (1H, m), 4.72 (2H, s), 4.76 (1H, dd, J = 1.2 Hz, 10.2 Hz), 6.88 (1H, s), 7.41-7.44 (4H, m), 7.93 (1H, dd, J = 1.2 Hz, 4.2 Hz), 8.50 (1H, d, J = 4.2 Hz), 8.54 (1H, d, J = 1.2 Hz) (CDCl$_3$). | 397 |
| 343 | 2.43-2.46 (4H, m), 3.07-3.14 (1H, m), 3.30-3.34 (1H, m), 3.51 (2H, s), 3.58 (3H, s), 3.65-3.68 (2H, m), 3.68-3.72 (4H, m), 3.96-4.02 (1H, m), 4.15-4.18 (1H, m), 4.72 (1H, dd, J = 1.2 Hz, 10.2 Hz), 6.88 (1H, s), 7.34-7.37 (4H, m), 7.95 (1H, dd, J = 1.2 Hz, 4.2 Hz), 8.51 (1H, d, J = 4.2 Hz), 8.55 (1H, d, J = 1.2 Hz) (CDCl$_3$) | 466 |
| 344 | 0.70 (1H, m), 1.14 (3H, d, J = 6.0 Hz), 1.21-1.28 (2H, m), 1.50 (1H, m), 3.07 (1H, dd, J = 10.6 Hz, 12.9 Hz), 3.26 (1H, td, J = 12.6 Hz, 3.3 Hz), 3.50-3.62 (2H, m), 3.57 (3H, s), 4.01 (1H, td, J = 11.7 Hz, 2.1 Hz), 4.16 (1H, dd, J = 11.4 Hz, 2.1 Hz), 4.68 (1H, dd, J = 10.5 Hz, 1.8 Hz), 6.87 (1H, s), 7.35 (2H, d, J = 8.7 Hz), 7.46 (1H, br.s), 7.53 (2H, d, J = 8.8 Hz), 7.94 (1H, dd, J = 6.2 Hz, 1.2 Hz), 8.51 (1H, d, J = 4.2 Hz), 8.55 (1H, d, J = 3.3 Hz) (CDCl$_3$) | 464 |
| 345 | 1.61-1.94 (8H, m), 2.69 (1H, t, J = 8.1 Hz), 3.09 (1H, dd, J = 10.8 Hz, 12.8 Hz), 3.25 (1H, td, J = 3.0 Hz, 12.0 Hz), 3.52-3.64 (2H, m), 3.57 (3H, s), 3.98 (1H, td, J = 12.0 Hz, 2.1 Hz), 4.15 (1H, dd, J = 12.0 Hz, 1.5 Hz), 4.70 (1H, dd, J = 10.8 Hz, 2.1 Hz), 6.88 (1H, s), 7.21 (1H, br.s), 7.35 (2H, d, J = 8.7 Hz), 7.56 (2H, d, J = 8.8 Hz), 7.94 (1H, dd, J = 6.2 Hz, 1.2 Hz), 8.51 (1H, d, J = 4.2 Hz), 8.55 (1H, d, J = 3.3 Hz) (CDCl$_3$) | 478 |
| 346 | 0.69 (2H, m), 1.32 (2H, m), 1.47 (3H, s), 3.07 (1H, dd, J = 10.8 Hz, 13.4 Hz), 3.27 (1H, td, J = 7.0 Hz, 12.0 Hz), 3.52-3.64 (2H, m), 3.57 (3H, s), 4.01 (1H, td, J = 11.4 Hz, 2.1 Hz), 4.17 (1H, dd, J = 12.0 Hz, 1.5 Hz), 4.69 (1H, dd, J = 9.4 Hz, 2.1 Hz), 6.88 (1H, s), 7.35 (2H, d, J = 8.4 Hz), 7.48 (1H, br.s), 7.54 (2H, d, J = 8.4 Hz), 7.94 (1H, dd, J = 6.2 Hz, 1.2 Hz), 8.51 (1H, d, J = 4.2 Hz), 8.55 (1H, d, J = 3.3 Hz) (CDCl$_3$) | 464 |
| 347 | 1.56 (6H, s), 2.50 (1H, br.s), 3.10 (1H, dd, J = 10.7 Hz, 13.0 Hz), 3.30 (1H, td, J = 2.9 Hz, 12.2 Hz), 3.52-3.64 (2H, m), 3.57 (3H, s), 4.00 (1H, td, J = 11.4 Hz, 1.9 Hz), 4.16 (1H, dd, J = 11.5 Hz, 1.8 Hz), 4.70 (1H, dd, J = 10.4 Hz, 2.0 Hz), 6.88 (1H, s), 7.37 (2H, d, J = 8.4 Hz), 7.61 (2H, d, J = 8.4 Hz), 7.94 (1H, dd, J = 6.2 Hz, 1.2 Hz), 8.51 (1H, d, J = 4.2 Hz), 8.55 (1H, d, J = 3.3 Hz), 8.74 (1H, br.s) (CDCl$_3$) | 468 |
| 348 | 2.93-2.98 (1H, m), 3.14-3.28 (2H, m), 3.48 (3H, s), 3.67-3.75 (2H, m), 3.89-3.94 (1H, m), 4.06-4.10 (1H, m), 4.84 (1H, dd, J = 1.2 Hz, 10.2 Hz), 6.61 (1H, s), 7.57 (2H, d, J = 7.2 Hz), 7.95-8.00 (3H, m), 8.56 (1H, d, J = 4.2 Hz), 8.70 (1H, d, J = 1.2 Hz) (CDCl$_3$) | 411 |
| 349 | 1.98 (1H, br), 2.93-2.97 (1H, m), 3.19-3.25 (3H, m), 3.56 (3H, s), 3.58-3.62 (2H, m), 4.13 (1H, dd, J = 1.2 Hz, 10.2 Hz), 6.86 (1H, s), 7.60 (2H, d, J = 7.2 Hz), 7.69 (2H, d, J = 7.2 Hz), 7.92 (1H, dd, J = 1.2 Hz, 4.2 Hz), 8.50 (1H, d, J = 4.2 Hz), 8.55 (1H, d, J = 1.2 Hz) (CDCl$_3$) | 391 |
| 350 | 1.98 (1H, br), 2.93-2.97 (1H, m), 3.19-3.25 (3H, m), 3.56 (3H, s), 3.58-3.62 (2H, m), 4.13 (1H, dd, J = 1.2 Hz, 10.2 Hz), 6.86 (1H, s), 7.60 (2H, d, J = 7.2 Hz), 7.69 (2H, d, J = 7.2 Hz), 7.92 (1H, dd, J = 1.2 Hz, 4.2 Hz), 8.50 (1H, d, J = 4.2 Hz), 8.55 (1H, d, J = 1.2 Hz) (CDCl$_3$) | 391 |

TABLE 2-continued

| Compound No. | 1H-NMR δ: | [M + 1] |
|---|---|---|
| 351 | 1.68-2.14 (4H, m), 2.48 (6H, s), 2.93-2.99 (3H, m), 3.55 (3H, s), 3.66-3.73 (2H, m), 3.88 (2H, s), 6.85 (1H, s), 7.37 (2H, d, J = 8.1 Hz), 7.96 (2H, d, J = 8.1 Hz), 8.03 (1H, dd, J = 6.6 Hz, 1.5 Hz), 8.51 (1H, d, J = 4.2 Hz), 8.55 (1H, d, J = 1.2 Hz) (CDCl$_3$). | 450 |
| 352 | 1.45 (3H, s), 1.47 (3H, s), 3.08-3.37 (2H, m), 3.19 (3H, s), 3.48 (3H, s), 3.58-3.67 (2H, m), 3.58 (3H, s), 4.00 (1H, td, J = 11.5 Hz, 1.8 Hz), 4.16 (1H, dd, J = 11.5 Hz, 1.8 Hz), 4.73 (1H, dd, J = 10.5 Hz, 2.1 Hz), 6.89 (1H, s), 7.25 (2H, d, J = 8.4 Hz), 7.61 (2H, d, J = 8.4 Hz), 7.94 (1H, dd, J = 6.2 Hz, 1.2 Hz), 8.51 (1H, d, J = 4.2 Hz), 8.55 (1H, d, J = 3.3 Hz), 8.74 (1H, br.s) (CDCl$_3$) | 496 |
| 353 | 0.86-0.88 (2H, m), 1.10-1.11 (2H, m), 1.55 (1H, m), 3.09 (1H, m), 3.29 (1H, m), 3.49-3.57 (1H, m), 3.58 (3H, s), 3.65 (1H, m), 3.97 (1H, m), 4.16 (1H, m), 4.76 (1H, d, J = 8.7 Hz), 6.89 (1H, s), 7.13 (1H, m), 7.35-7.36 (4H, m), 7.79 (1H, s), 7.95 (1H, d, J = 5.4 Hz), 8.53 (1H, d, J = 6.0 Hz) (CDCl$_3$) | 450 |
| 354 | 0.84-0.85 (2H, m), 1.07-1.10 (2H, m), 1.47 (1H, m), 2.79 (1H, dd, J = 13.2 Hz, 9.6 Hz), 3.29 (1H, m), 3.51-3.56 (1H, m), 3.62 (3H, s), 3.83-3.95 (1H, m), 3.95 (3H, s), 4.02 (1H, m), 4.20 (1H, m), 5.03 (1H, d, J = 9.3 Hz), 6.86 (1H, m), 6.89 (1H, s), 7.32 (1H, m), 7.45-7.58 (2H, m), 8.00 (1H, d, J = 6.0 Hz), 8.51 (1H, d, J = 4.8 Hz), 8.55 (1H, d, J = 3.0 Hz) (CDCl$_3$) | 480 |
| 355 | 2.76 (1H, dd, J = 12.9, 10.5 Hz), 2.98 (3H, s), 3.32 (1H, ddd, J = 12.3 Hz, 12.3 Hz, 3.0 Hz), 3.53-3.57 (1H, m), 3.63 (3H, s), 3.81-3.86 (1H, m), 3.87 (3H, s), 4.00 (1H, ddd, J = 11.7 Hz, 11.7 Hz, 2.4 Hz), 4.22 (1H, dd, J = 12.0 Hz, 2.4 Hz), 5.04 (1H, dd, J = 10.2 Hz, 1.8 Hz), 6.55 (1H, s), 6.88-6.91 (2H, m), 7.26-7.30 (1H, m), 7.40 (1H, dd, J = 2.7 Hz), 8.00 (1H, dd, J = 6.6 Hz, 5.1 Hz). 8.53 (1H, d, J = 5.1 Hz). 8.56 (1H, d, J = 3.3 Hz) (CDCl$_3$) | 490 |
| 356 | 2.88-2.96 (1H, m), 3.15-3.20 (1H, m), 3.45 (3H, s), 3.64-3.70 (2H, m), 3.84-3.91 (1H, m), 4.01-4.05 (1H, m), 4.57 (2H, s), 4.68 (1H, dd, J = 1.2 Hz, 10.2 Hz), 6.60 (1H, s), 6.95-7.00 (3H, m), 7.96 (1H, dd, J = 1.2 Hz, 4.2 Hz), 8.57 (1H, d, J = 4.2 Hz), 8.75 (1H, d, J = 1.2 Hz), 10.74 (1H, br.s) (CDCl$_3$) | 438 |
| 357 | 3.06 (1H, dd, J = 12.9 Hz, 10.5 Hz), 3.26 (1H, ddd, J = 12.3 Hz, 12.3 Hz, 3.0 Hz), 3.48-3.53 (1H, m), 3.56 (3H, s), 3.58-3.60 (1H, m), 3.77 (2H, m), 3.97 (1H, m), 4.14-4.17 (1H, m), 4.60 (1H, dd, J = 10.5 Hz, 2.1 Hz), 6.78 (1H, m), 6.88 (1H, s), 6.95 (1H, m), 7.07 (1H, m), 7.94 (1H, dd, J = 6.6 Hz, 5.1 Hz), 8.51 (1H, d, J = 6.0 Hz), 8.55 (1H, d, J = 3.0 Hz) (CDCl$_3$) | 400 |
| 358 | 1.84-1.89 (1H, m), 2.02-2.10 (2H, m), 2.32-2.37 (1H, m), 3.13-3.20 (1H, m), 3.45-3.51 (3H, m), 3.54 (3H, s), 3.96 (1H, d, J = 10.2 Hz), 6.87 (1H, s), 7.15 (2H, dd, J = 6.8 Hz, 7.0 Hz), 7.95 (1H, dd, J = 1.2 Hz, 4.2 Hz), 8.06 (2H, dd, J = 1.2 Hz, 4.2 Hz), 8.51-8.55 (2H, m) (CDCl$_3$) | 451 |
| 359 | 1.86-1.91 (1H, m), 2.00-2.12 (2H, m), 2.31-2.35 (1H, m), 3.14-3.21 (1H, m), 3.48-3.60 (3H, m), 3.53 (3H, m), 2.98 (1H, d, J = 11.0 Hz), 6.88 (1H, s), 7.36-7.44 (2H, m), 7.74 (1H, d, J = 7.0 Hz), 7.82 (1H, d, J = 7.0 Hz), 7.98 (1H, dd, J = 1.2 Hz, 4.2 Hz), 8.52 (1H, d, J = 4.2 Hz), 8.54 (1H, d, J = 1.2 Hz) (CDCl$_3$) | 512 |
| 360 | 1.84-1.90 (1H, m), 2.01-2.10 (2H, m), 2.33-2.37 (1H, m), 3.13-3.21 (1H, m), 3.46-3.56 (3H, m), 3.54 (3H, m), 3.97 (1H, d, J = 10.2 Hz), 6.88 (1H, s), 7.37 (1H, dd, J = 7.0 Hz, 7.2 Hz), 7.64 (1H, d, J = 7.2 Hz), 7.96-8.01 (2H, m), 8.23 (1H, d, J = 1.2 Hz), 8.52-8.57 (2H, m) (CDCl$_3$) | 512 |
| 361 | 1.84-1.92 (1H, m), 2.00-2.09 (2H, m), 2.32-2.37 (1H, m), 3.13-3.20 (1H, m), 3.45-3.52 (3H, m), 3.54 (3H, s), 3.97 (1H, d, J = 10.2 Hz), 6.87 (1H, s), 7.63 (2H, d, J = 7.2 Hz), 7.93-7.99 (3H, m), 8.51-8.56 (2H, m) (CDCl$_3$) | 512 |
| 362 | 1.86-1.92 (1H, m), 2.01-2.10 (2H, m), 2.33-2.37 (1H, m), 3.12-3.20 (1H, m), 3.46-3.57 (3H, m), 3.54 (3H, s), 3.96-3.98 (4H, m), 6.88 (1H, s), 7.05-7.11 (2H, m), 7.47 (1H, dd, J = 6.8 Hz, 7.2 Hz), 7.97-8.02 (2H, m), 8.51-8.56 (2H, m) (CDCl$_3$) | 463 |
| 363 | 1.85-1.89 (1H, m), 2.04-2.10 (2H, m), 2.33-2.37 (1H, m), 3.46-3.54 (3H, m), 3.55 (3H, s), 3.88 (3H, s), 3.97 (1H, d, J = 10.2 Hz), 6.88 (1H, s), 7.06 (1H, dd, J = 1.2 Hz, 7.0 Hz), 7.40 (1H, dd, J = 7.0 Hz, 7.2 Hz), 7.60 (1H, d, J = 1.2 Hz), 7.67 (1H, d, J = 7.0 Hz), 7.98 (1H, dd, J = 1.2 Hz, 4.2 Hz), 8.52-8.56 (2H, m) (CDCl$_3$) | 463 |
| 364 | 1.82-1.88 (1H, m), 2.03-2.01 (2H, m), 2.32-2.36 (1H, m), 3.13-3.20 (1H, m), 3.45-3.51 (3H, m), 3.55 (3H, s), 3.88 (3H, s), 3.96 (1H, d, J = 10.2 Hz), 6.87 (1H, s), 6.99 (2H, d, J = 7.2 Hz), 7.96-8.02 (3H, m), 8.51-8.55 (2H, m) (CDCl$_3$) | 463 |
| 365 | 3.04-3.12 (1H, m), 3.21-3.28 (1H, m), 3.51-3.64 (2H, m), 3.58 (3H, s), 3.99-4.16 (4H, m), 4.51 (2H, t, J = 7.0 Hz), 4.72 (1H, J = 1.2 Hz, 10.2 Hz), 6.89 (1H, s), 7.43 (2H, d, J = 7.2 Hz), 7.58 (2H, d, J = 7.2 Hz), 7.94 (1H, dd, J = 1.2 Hz, 4.2 Hz), 8.51 (1H, d, J = 4.2 Hz), 8.55 (1H, d, J = 1.2 Hz) (CDCl$_3$) | 452 |
| 366 | 2.07-2.15 (2H, m), 3.06-3.14 (1H, m), 3.20-3.26 (1H, m), 3.38-3.72 (6H, m), 3.57 (3H, s), 3.95-4.00 (1H, m), 4.12-4.16 (1H, m), 4.70 (1H, dd, J = 1.2 Hz, 10.2 Hz), 5.05 (1H, br), 6.90 (1H, s), 7.32-7.49 (4H, m), 7.97 (1H, dd, J = 1.2 Hz, 4.2 Hz), 8.52-8.56 (2H, m) (CDCl$_3$) | 465 |

TABLE 2-continued

| Compound No. | 1H-NMR δ: | [M + 1] |
|---|---|---|
| 367 | 3.05-3.13 (1H, m), 3.25-3.29 (1H, m), 3.51-3.63 (4H, m), 3.57 (3H, s), 3.93-3.98 (3H, m), 4.15-4.19 (1H, m), 4.69 (1H, dd, J = 1.2 Hz, 10.2 Hz), 5.01 (1H, br), 6.89 (1H, s), 7.37 (2H, d, J = 7.2 Hz), 7.56 (2H, d, J = 7.2 Hz), 7.95 (1H, dd, J = 1.2 Hz, 10.2 Hz), 8.51 (1H, d, J = 4.2 Hz), 8.55 (1H, d, J = 1.2 Hz) (CDCl$_3$) | 451 |
| 368 | 1.94-1.98 (4H, m), 2.56-2.60 (2H, m), 3.02-3.11 (1H, m), 3.20-3.30 (1H, m), 3.50-3.67 (4H, m), 3.57 (3H, s), 3.95-4.01 (1H, m), 4.14-4.18 (1H, m), 4.72 (1H, dd, J = 1.2 Hz, 10.2 Hz), 6.90 (1H, s), 7.29 (2H, d, J = 7.2 Hz), 7.44 (2H, d, J = 7.2 Hz), 7.96 (1H, dd, J = 1.2 Hz, 4.2 Hz), 8.52-8.57 (2H, m) (CDCl$_3$) | 464 |
| 369 | 2.86 (1H, t, J = 7.0 Hz), 3.05-3.10 (1H, m), 3.23-3.29 (1H, m), 3.45-3.65 (6H, m), 3.57 (3H, s), 3.82-3.97 (5H, m), 4.12-4.18 (1H, m), 4.67 (1H, dd, J = 1.2 Hz, 10.2 Hz), 6.88 (1H, s), 7.36 (2H, d, J = 7.2 Hz), 7.94 (2H, d, J = 7.2 Hz), 7.94 (1H, dd, J = 1.2 Hz, 4.2 Hz), 8.49-8.56 (2H, m) (CDCl$_3$) | 495 |
| 370 | 2.50 (3H, s), 3.10 (1H, dd, J = 12.9 Hz, 10.5 Hz), 3.29 (1H, m), 3.53-3.66 (2H, m), 3.57 (3H, s), 3.98 (1H, td, J = 11.7 Hz, 2.4 Hz), 4.17 (1H, d, J = 10.8 Hz), 4.70 (1H, dd, J = 10.5 Hz, 2.1 Hz), 6.70 (1H, s), 7.27-7.34 (3H, m), 7.78-7.80 (2H, m), 8.71 (1H, d, J = 4.8 Hz), 8.72 (1H, d, J = 4.5 Hz). (CDCl$_3$) | 413 |

Experiment 1: Inhibitory Activity of the Medicament of the Present Invention Against P-GS1 Phosphorylation by Bovine Cerebral TPK1

A mixture containing 100 mM MES-sodium hydroxide (pH 6.5), 1 mM magnesium acetate, 0.5 mM EGTA, 5 mM β-mercaptoethanol, 0.02% Tween 20, 10% glycerol, 12 μg/ml P-GS1, 41.7 μM [γ$^{-32}$P] ATP (68 kBq/ml), bovine cerebral TPK1 and a compound shown in Table (a final mixture contained 1.7% DMSO deriving from a solution of a test compound prepared in the presence of 10% DMSO) was used as a reaction system. The phosphorylation was started by adding ATP, and the reaction was conducted at 25° C. for 2 hours, and then stopped by adding 21% perchloric acid on ice cooling. The reaction mixture was centrifuged at 12,000 rpm for 5 minutes and adsorbed on P81 paper (Whatmann), and then the paper was washed four times with 75 mM phosphoric acid, three times with water and once with acetone. The paper was dried, and the residual radioactivity was measured using a liquid scintillation counter. The results are shown in the table below. The test compound markedly inhibited the P-GS1 phosphorylation by TPK1. The results strongly suggest that the medicaments of the present invention inhibit the TPK1 activity, thereby suppress the Aβ neurotoxicity and the PHF formation, and that the medicaments of the present invention are effective for preventive and/or therapeutic treatment of Alzheimer disease and the above-mentioned diseases.

TABLE 3

| Compound No. | IC$_{50}$ (nM) |
|---|---|
| 4 | 7.9 |
| 5 | 1.4 |
| 14 | 3.7 |
| 17 | 1.7 |
| 22 | 0.53 |
| 41 | 0.73 |
| 56 | 6.4 |
| 92 | 1.2 |
| 105 | 8.2 |
| 196 | 13 |
| 209 | 2.2 |
| 210 | 0.51 |
| 212 | 5.4 |
| 224 | 1.1 |
| 247 | 13 |
| 221 | 3.9 |
| 238 | 6.4 |
| 158 | 2.9 |
| 295 | 1.2 |
| 298 | 11 |
| 322 | 4.8 |
| 334 | 2.9 |
| 310 | 7.4 |
| 220 | 2.7 |
| 288 | 0.27 |
| 215 | 4.2 |
| 303 | 6.2 |
| 305 | 1.2 |
| 313 | 0.48 |
| 314 | 4.1 |

Experiment 2: Inhibitory Activity on Tau Phosphorylation In Vivo

Test compound was administered to male CD-1 mice of 5-6 weeks weighing 25-35 g (Charles River Japan, inc.) at 1, 3, 10, 30 mg/kg p.o. (0.5% Tween/H$_2$O suspension) and after 1 hour, mice were decapitated and cortex was promptly removed, followed by being frozen in liquid N$_2$. Cortex was directly homogenized with 2.3% SDS homogenization buffer (62.5 mM Tris-HCl, 2.3% SDS, 1 mM each of EDTA, EGTA and DTT, protease inhibitor cocktail (sigma P2714) containing 0.2 μM 4-(2-Aminoethyl)benzenesulfonyl fluoride (AEBSF), 13 μM bestatin, 1.4 μM E-64, 0.1 mM leupeptin, 30 nM aprotinin, pH 6.8) and centrifuged at 15000×g for 15 min at 4° C. Protein concentrations were determined using DC protein assay kit (BIO-RAD). Supernatants were diluted with sample buffer (62.5 mM Tris-HCl, 25% glycerol, 2% SDS, 0.01% Bromophenol Blue, pH6.8) to adjust the protein concentrations around 0.5-2 mg/mg and then boiled for 5 min. 10 μg of samples were applied on 10% SDS-PAGE mini slab gels and transferred onto PVDF membranes. Membranes were incubated with PBS containing 5% non-fat milk for 1 h at room temperature and then probed with pS396 anti-body (BIOSOURCE) over night at 4° C. Anti-rabbit IgG HRP-conjugated anti-body (Promega) was used as secondary anti-body. Membranes were visualized by ECL kit (Amerasham Bioscience) and detected by LAS1000 (Fuji Photo Film).

Formulation Example

(1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

INDUSTRIAL APPLICABILITY

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:

1. A compound represented by the formula (I), an optically active isomer thereof, or a pharmaceutically acceptable salt thereof:

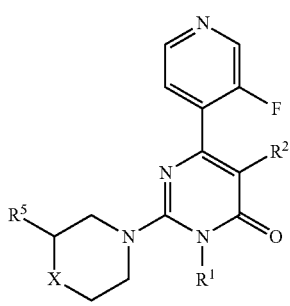

(I)

wherein each symbol is as defined below.
$R^1$ represents a $C_1$-$C_{12}$ alkyl which may be substituted;
$R^2$ represents hydrogen atom;
$R^5$ represents
a group represented by the following formula (II):

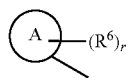

(II)

wherein A represents a $C_6$-$C_{10}$ aryl or heterocycle;
$R^6$ may be the same or different and represents
hydrogen atom,
hydroxyl,
a halogen,
nitro,
cyano
a $C_1$-$C_6$ alkyl which may be substituted,
a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocycle which may be substituted,
a $C_1$-$C_6$ alkyloxy which may be substituted,
a $C_3$-$C_6$ alkenyloxy which may be substituted,
a $C_3$-$C_6$ alkynyloxy which may be substituted,
a $C_3$-$C_7$ cycloalkyloxy which may be substituted,
a $C_3$-$C_7$ cycloalkenyloxy which may be substituted,
a $C_6$-$C_{10}$ aryloxy which may be substituted,
a heterocycle-oxy group which may be substituted,
mercapto,
a $C_1$-$C_6$ alkylthio which may be substituted,
a $C_3$-$C_6$ alkenylthio which may be substituted,
a $C_3$-$C_6$ alkynylthio which may be substituted,
a $C_3$-$C_7$ cycloalkylthio which may be substituted,
a $C_3$-$C_7$ cycloalkenylthio which may be substituted,
a $C_6$-$C_{10}$ arylthio which may be substituted,
a heterocycle-thio group which may be substituted,
amino,
a $C_1$-$C_6$ alkylamino which may be substituted,
a $C_3$-$C_6$ alkenylamino which may be substituted,
a $C_3$-$C_6$ alkynylamino which may be substituted,
a $C_3$-$C_7$ cycloalkylamino which may be substituted,
a $C_3$-$C_7$ cycloalkenylamino which may be substituted,
an $C_6$-$C_{10}$ arylamino which may be substituted,
a heterocycle-amino which may be substituted,
a N,N-di-$C_1$-$C_6$ alkylamino which may be substituted,
a N—$C_1$-$C_6$ alkyl-N—$C_3$-$C_6$ alkenylamino which may be substituted,
a N—$C_1$-$C_6$ alkyl-N—$C_3$-$C_6$ alkynylamino which may be substituted,
a N—$C_1$-$C_6$ alkyl-N—$C_3$-$C_7$ cycloalkylamino which may be substituted,
a N—$C_1$-$C_6$ alkyl-N—$C_3$-$C_7$ cycloalkenylamino which may be substituted,
a N—$C_1$-$C_6$ alkyl-N—$C_6$-$C_{10}$ arylamino which may be substituted,
a N—$C_1$-$C_6$ alkyl-N-heterocycle-amino which may be substituted,
a N,N-di-$C_3$-$C_6$ alkenylamino which may be substituted,
a N—$C_3$-$C_6$ alkenyl-N—$C_3$-$C_6$ alkynylamino which may be substituted,
a N—$C_3$-$C_6$ alkenyl-N—$C_3$-$C_7$ cycloalkylamino which may be substituted,
a N—$C_3$-$C_6$ alkenyl-N—$C_3$-$C_7$ cycloalkenylamino which may be substituted,
a N—$C_3$-$C_6$ alkenyl-N—$C_6$-$C_{10}$ arylamino which may be substituted,
a N—$C_3$-$C_6$ alkenyl-N-heterocycle-amino which may be substituted,
a N,N-di-$C_3$-$C_6$ alkynylamino which may be substituted,
a N—$C_3$-$C_6$ alkynyl-N—$C_3$-$C_7$ cycloalkylamino which may be substituted,
a N—$C_3$-$C_6$ alkynyl-N—$C_3$-$C_7$ cycloalkenylamino which may be substituted,
a N—$C_3$-$C_6$ alkynyl-N—$C_6$-$C_{10}$ arylamino which may be substituted, a N—C$_3$-C$_6$ alkynyl-N-heterocycle-amino which may be substituted,
a N,N-di-C$_3$-C$_7$ cycloalkylamino which may be substituted,
a N—C$_3$-C$_7$ cycloalkyl-N—C$_3$-C$_7$ cycloalkenylamino which may be substituted,
a N—C$_3$-C$_7$ cycloalkyl-N—C$_6$-C$_{10}$ arylamino which may be substituted,
a N—C$_3$-C$_7$ cycloalkyl-N-heterocycle-amino which may be substituted,
a N,N-di-C$_3$-C$_7$ cycloalkenylamino which may be substituted,
a N—C$_3$-C$_7$ cycloalkenyl-N—C$_6$-C$_{10}$arylamino which may be substituted,
a N—C$_3$-C$_7$ cycloalkenyl-N-heterocycle-amino which may be substituted,
a N,N-di-C$_6$-C$_{10}$ arylamino which may be substituted,
a N—C$_6$-C$_{10}$ aryl-N-heterocycle-amino which may be substituted,
a N.N-diheterocycle-amino which may be substituted,
a C$_3$-C$_6$ alkylcarbonyl which may be substituted,
a C$_2$-C$_6$ alkenylcarbonyl which may be substituted,
a C$_2$-C$_6$ alkynylcarbonyl which may be substituted,
a C$_3$-C$_7$ cycloalkylcarbonyl which may be substituted,
a C$_3$-C$_7$ cycloalkenylcarbonyl which may be substituted,
a C$_6$-C$_{10}$ arylcarbonyl which may be substituted,
a heterocycle-carbonyl which may be substituted,
a C$_1$-C$_6$ alkylsulfonyl which may be substituted,
a C$_3$-C$_6$ alkenylsulfonyl which may be substituted,
a C$_3$-C$_6$ alkynylsulfonyl which may be substituted,
a C$_3$-C$_7$ cycloalkylsulfonyl which may be substituted,
a C$_3$-C$_7$ cycloalkenylsulfonyl which may be substituted,
a C$_6$-C$_{10}$ arylsulfonyl which may be substituted,
a heterocycle-sulfonyl which may be substituted,
carboxyl,
a C$_1$-C$_6$ alkyloxycarbonyl which may be substituted,
a C$_3$-C$_6$ alkenyloxycarbonyl which may be substituted,
a C$_3$-C$_6$ alkynyloxycarbonyl which may be substituted,
a C$_3$-C$_7$ cycloalkyloxycarbonyl which may be substituted,
a C$_3$-C$_7$ cycloalkenyloxycarbonyl which may be substituted,
a C$_6$-C$_{10}$ aryloxycarbonyl which may be substituted,
a heterocycle-oxycarbonyl which may be substituted,
aminocarbonyl,
a C$_1$-C$_6$ alkylaminocarbonyl which may be substituted,
a C$_3$-C$_6$ alkenylaminocarbonyl which may be substituted,
a C$_3$-C$_6$ alkynylaminocarbonyl which may be substituted,
a C$_3$-C$_7$ cycloalkylaminocarbonyl which may be substituted,
a C$_3$-C$_7$ cycloalkenylaminocarbonyl which may be substituted,
a C$_6$-C$_{10}$ arylaminocarbonyl which may be substituted,
a heterocycle-aminocarbonyl which may be substituted,
a N,N-di-C$_1$-C$_6$ alkylaminocarbonyl which may be substituted,
a N—C$_1$-C$_6$ alkyl-N—C$_3$-C$_7$ alkenylaminocarbonyl which may be substituted,
a N—C$_1$-C$_6$ alkyl-N—C$_3$-C$_7$ alkynylaminocarbonyl which may be substituted,
a N—C$_1$-C$_6$ alkyl-N—C$_3$-C$_7$ cycloalkylaminocarbonyl which may be substituted,
a N—C$_1$-C$_6$ alkyl-N—C$_3$-C$_7$ cycloalkenylaminocarbonyl which may be substituted,
a N—C$_1$-C$_6$ alkyl-N—C$_6$-C$_{10}$ arylaminocarbonyl which may be substituted,
a N—C$_1$-C$_6$ alkyl-N-heterocycle-aminocarbonyl which may be substituted,
a N,N-di-C$_3$-C$_6$ alkenylaminocarbonyl which may be substituted,
a N—C$_3$-C$_6$ alkenyl-N—C$_3$-C$_6$ alkynylaminocarbonyl which may be substituted,
a N—C$_3$-C$_6$ alkenyl-N—C$_3$-C$_7$ cycloalkylaminocarbonyl which may be substituted,
a N—C$_3$-C$_6$ alkenyl-N—C$_3$-C$_7$ cycloalkenylaminocarbonyl which may be substituted,
a N—C$_3$-C$_6$ alkenyl- N—C$_6$-C$_{10}$ arylaminocarbonyl which may be substituted,
a N—C$_3$-C$_6$ alkenyl- N-heterocycle-aminocarbonyl which may be substituted,
a N,N-di-C$_3$-C$_6$ alkynylaminocarbonyl which may be substituted,
a N—C$_3$-C$_6$ alkynyl-N—C$_3$-C$_7$ cycloalkylaminocarbonyl which may be substituted,
a N—C$_3$-C$_6$ alkynyl-N—C$_3$-C$_7$ cycloalkenylaminocarbonyl which may be substituted,
a N—C$_3$-C$_6$ alkynyl-N—C$_6$-C$_{10}$ arylaminocarbonyl which may be substituted,
a N—C$_3$-C$_6$ alkynyl-N-heterocycle-aminocarbonyl which may be substituted,
a N,N-di-C$_3$-C$_7$ cycloalkylaminocarbonyl which may be substituted,
a N—C$_3$-C$_7$ cycloalkyl-N—C$_3$-C$_7$ cycloalkenylaminocarbonyl which may be substituted,
a N—C$_3$-C$_7$ cycloalkyl-N—C$_6$-C$_{10}$ arylaminocarbonyl which may be substituted,
a N—C$_3$-C$_7$ cycloalkyl-N-heterocycle-aminocarbonyl which may be substituted,
a N,N-di-C$_3$-C$_7$ cycloalkenylaminocarbonyl which may be substituted,
a N—C$_3$-C$_7$ cycloalkenyl-N—C$_6$-C$_{10}$ arylaminocarbonyl which may be substituted,
a N—C$_3$-C$_7$ cycloalkenyl-N-heterocycle-aminocarbonyl which may be substituted,
a N,N-di-C$_6$-C$_{10}$ arylaminocarbonyl which may be substituted,
a N—C$_6$-C$_{10}$ aryl-N-heterocycle-aminocarbonyl which may be substituted, or
a N,N-di-heterocycle-aminocarbonyl which may be substituted,
aminothiocarbonyl,
a C$_1$-C$_6$ alkylaminothiocarbonyl which may be substituted,
a C$_3$-C$_6$ alkenylaminothiocarbonyl which may be substituted,
a C$_3$-C$_6$ alkynylaminothiocarbonyl which may be substituted,
a C$_3$-C$_7$ cycloalkylaminothiocarbonyl which may be substituted,
a C$_3$-C$_7$ cycloalkenylaminothiocarbonyl which may be substituted,
a C$_6$-C$_{10}$ arylaminothiocarbonyl which may be substituted,
a heterocycle-aminothiocarbonyl which may be substituted,
a N,N-di-C$_1$-C$_6$ alkylaminothiocarbonyl which may be substituted,
a N—C$_1$-C$_6$ alkyl-N—C$_3$-C$_7$ alkenylaminothiocarbonyl which may be substituted,
a N—C$_1$-C$_6$ alkyl-N—C$_3$-C$_7$ alkynylaminothiocarbonyl which may be substituted,
a N—C$_1$-C$_6$ alkyl-N—C$_3$-C$_7$ cycloalkylaminothiocarbonyl which may be substituted,
a N—C$_1$-C$_6$ alkyl-N—C$_3$-C$_7$ cycloalkenylaminothiocarbonyl which may be substituted,
a N—C$_1$-C$_6$ alkyl-N—C$_6$-C$_{10}$ arylaminothiocarbonyl which may be substituted, a N—C₁-C₆ alkyl-N-heterocycle-aminothiocarbonyl which may be substituted, a N,N-di-C₃-C₆ alkenylaminothiocarbonyl which may be substituted, a N—C₃-C₆ alkenyl-N—C₃-C₆ alkynylaminothiocarbonyl which may be substituted, a N—C₃-C₆ alkenyl-N—C₃-C₇ cycloalkylaminothiocarbonyl which may be substituted, a N—C₃-C₆ alkenyl-N—C₃-C₇ cycloalkenylaminothiocarbonyl which may be substituted, a N—C₃-C₆ alkenyl- N—C₆-C₁₀ arylaminothiocarbonyl which may be substituted, a N—C₃-C₆ alkenyl- N-heterocycle-aminothiocarbonyl which may be substituted, a N,N-di-C₃-C₆ alkynylaminothiocarbonyl which may be substituted, a N—C₃-C₆ alkynyl-N—C₃-C₇ cycloalkylaminothiocarbonyl which may be substituted, a N—C₃-C₆ alkynyl-N—C₃-C₇ cycloalkenylaminothiocarbonyl which may be substituted, a N—C₃-C₆ alkynyl-N—C₆-C₁₀ arylaminothiocarbonyl which may be substituted, a N—C₃-C₆ alkynyl-N-heterocycle-aminothiocarbonyl which may be substituted, a N,N-di-C₃-C₇ cycloalkylaminothiocarbonyl which may be substituted, a N—C₃-C₇ cycloalkyl-N—C₃-C₇ cycloalkenylaminothiocarbonyl which may be substituted, a N—C₃-C₇ cycloalkyl-N—C₆-C₁₀ arylaminothiocarbonyl which may be substituted, a N—C₃-C₇ cycloalkyl-N-heterocycle-aminothiocarbonyl which may be substituted, a N,N-di-C₃-C₇ cycloalkenylaminothiocarbonyl which may be substituted, a N—C₃-C₇ cydoalkenyl-N—C₆-C₁₀ arylaminothiocarbonyl which may be substituted, a N—C₃-C₇ cycloalkenyl-N-heterocycle-aminothiocarbonyl which may be substituted, a N,N-di-C₆-C₁₀ arylaminothiocarbonyl which may be substituted, a N—C₆-C₁₀ aryl-N-heterocycle-aminothiocarbonyl which may be substituted, or a N,N-di-heterocycle-aminothiocarbonyl which may be substituted, r represents 0 or an integer of 1 to 5;

X represents oxygen atom.

2. The compound, an optically active isomer thereof, or a pharmaceutically acceptable salt thereof according to claim 1, wherein R¹ is a C₁-C₆ alkyl which may be substituted.

3. The compound, an optically active isomer thereof, or a pharmaceutically acceptable salt thereof according to claim 1, wherein R¹ is methyl group.

4. The compound, an optically active isomer thereof, or a pharmaceutically acceptable salt thereof according to claim 1, wherein A is phenyl group.

5. A compound according to claim 1 selected from the group consisting of:

2-((2S)-2-(4-((3R)-3-Dimethylamino-pyrrolidin-l-yl)-phenyl)-morpholin-4-yl)-6-(3-fluoro-pyridin-4-yl)-3-methyl-3H-primidin-4-one;

6-(3-Fluoro-pyridin-4-yl)-3-methyl-2-((2S)-2-(4-(4-pyrrolidin-1-yl-piperidin-1-yl)-phenyl (-morpholin-4-yl)-3H-pyrimidin-4-one;

2-((2S)-2-(4-(4-Dimethylamino-piperidin-1-yl)-phenyl)-morpholin-4-yl)-6-(3-fluoro-pyridin-4-yl)-3-methyl-3H-pyrimidin-4-one;

2-((2S)-2-(4-((3 S,5R)-3,5-Dimethyl-piperazin-1-yl)-phenyl)-morpholin-4-yl)-6-(3-fluoro-pyridin-4-yl)-3-methyl-3H-pyrimidin-4-one;

6-(3-Fluoro-pyridin-4-yl)-3-methyl-2(2S)-2-(4-(4-methyl-piperazin-1-yl)-phenyl)-morpholin-4-yl)-3H-pyrimidin-4-one;

2-((2S)-2-(4-((3S)-3-Dimethylamino-pyrrolidin-1-yl)-phenyl)-morpholin-4-yl)-6-(3-fluoro-pyridin-4-yl)-3-methyl-3H-pyrimidin-4-one;

6-(3-Fluoro-pyridin-4-yl)-2-((2S)-2-(4-(4-isopropyl-piperazin-1-yl)-phenyl)-morpholin-4-yl)-3-methyl-3H-pyrimidin-4-one;

6-(3-Fluoro-pyridin-4-yl)-2(2S)-2-(4-(4-(2-hydroxy-ethyl)-piperazin-1-yl)-phenyl)-morpholin-4-yl)-3-methyl-3H-pyrimidin-4-one, 2-((2S)-2-(4-Cyclopentylamino-phenyl)-morpholin-4-yl)-6-(3-fluoro-pyridin-4-yl)-3-methyl-3H-pyrimidin-4-one;

6-(3-Fluoro-pyridin-4-yl)-2-((2S)-2-(4-(3-hydroxy-azetidin-l-yl)-phenyl)-morpholin-4-yl)-3-methyl-3H-pyrimidin-4-one;

2-((2S)-2-(4-Cyclopentyloxy-phenyl)-morpholin-4-yl)-6-(3-fluoro-pyridin-4-yl)-3-methyl-3H-pyrimidin-4-one;

2-((2S)-2-(4-Cyclopropylmethoxy-phenyl)-morpholin-4-yl)-6-(3-fluoro-pyridin-4-yl)-3-methyl-3H-pyrimidin-4-one;

2-((2S)-2-(4-(2-Dimethylamino-ethoxy)-phenyl)-morpholin-4-yl)-6-(3-fluoro-pyridin-4-yl)-3-methyl-3H-pyrimidin-4-one;

2-((2S)-2-(4-Amino-phenyl)-morpholin-4-yl)-6-(3-fluoro-pyridin-4-yl)-3-methyl-3H-primidin-4-one;

6-(3-Fluoro-pyridin-4-yl)-3-methyl-2-42S)-2-(4-(methyl-((3R)-tetrahydro-furan-3-yl)-amino)-phenyl)-morpholin-4-yl)-3H-pyrimidin-4-one;

6-(3-Fluoro-pyridin-4-yl)-3-methyl-2-02S)-2-[4-(2-pyrrolidin-1-yl-ethoxy)-phenyl]-morpholin-4-yl)-3H-pyrimidin-4-one;

6-(3-Fluoro-pyridin-4-yl)-2-((2S)-2-(4-hydroxy-phenyl)-morpholin-4-yl)-3-methyl-3H-pyrimidin-4-one;

2-((2S)-2-(4-(2-Diethylamino-ethoxy)-phenyl)-morpholin-4-yl)-6-(3-fluoro-pyridin-4-yl)-3-methyl-3H-pyrimidin-4-one;

6-(3-Fluoro-pyridin-4-yl)-3-methyl-2-02S)-2-(4-(2-piperidin-l-yl-ethoxy)-phenyl)-morpholin-4-yl)-3H-pyrimidin-4-one;

6-(3-Fluoro-pyridin-4-yl)-3-methyl-2-02S)-2-(4-(2-(4-methyl-piperazin-1-₃4)-ethoxy)-phenyl)-morpholin-4-yl)-3H-pyrimidin-4-one;

6-(3-Fluoro-pyridin-4-yl)-3-methyl-2-{(2S)-2-[4-morpholine-4-carbonyl]-phenyl}-morpholin-4-yl}-3H-pyrimidin-4-one;

2-[(2 S)-2-(4-fluorophenyl)morpholin-4-yl]-6-(3-fluoro-pyridin-4-yl)-3-methyl-3H-pyrimidien-4-one;

(S)-6-(3-fluoropyridin-4-yl)-2-(2-(4-isopropoxyphenyl)morpholino)-3-methylpyrimidin-4(3H)-one;

(S)-2-(2-(4-(cyclopropylmethoxy)phenyl)morpholino-6-(3-fluoropyridin-4-yl)-3-methylpyrimidin-4(3H)-one;

(S)-2-(2-(4-(1,2,4-oxadiazol-3-yl)phenyl)morpholino)-6-(3-fluoropyridin-4-yl)-3-methylpyrimidin-4(3H)-one;

(S)-6-(3-fluoropyridin-4-yl)-3-methyl-2-(2-(4-(5-methyl-1,2,4-oxadiazol-3-yl phenyl)morpholino)pyrimidin-4(3H )-one;

2-[(2S)-2-(2-chloro-6-fluorophenyl)morpholin-4-yl]-6-(3-fluoropyridin-4-yl)-3-methylpyrimidin-4(3H)-one;

2-[(2S)-2-(4-bromo-3-methylphenyl)morpholin-4-yl]-6-(3-fluoropyridin-4-yl)-3-methylpyrimidin-4(3H)-one;

6-(3-fluoropyridin-4-yl)-3-methyl-2-((2S)-2-{4-[methyl(pyridin-2-yl) amino]phenyl}morpholin-4-yl)pyrimidin-4(3H)-one;

6-(3-fluoropyridin-4-yl)-3-methyl-2((2S)-2-{4-[(3R)-tetrahydrofuran-3-ylamino]phenyl}morpholin-4-yl)pyrimidin-4(3H)-one;

6-(3-fluoropyridin-4-yl)-3-methyl-2-{(2S)-2-[4-(2-morpholin-4-ylethoxy) phenyl]morpholin-4-yl}pyrimidin-4(3H)-one; and 2-((2S)-2-{4-[(1-acetylpiperidin-4-yl)oxy] phenyl}morpholin-4-yl)-6-(3-fluoropyridin-4-yl)-3-methylpyrimidin-4(3H)-one;

an optically active isomer thereof, or a pharmaceutically acceptable salt thereof.

6. A medicament comprising as an active ingredient a substance selected from the group consisting of the compound represented by the formula (I) and an optically active isomer thereof, or a pharmaceutically acceptable salt thereof according to claim 1.

7. A tau protein kinase 1 inhibitor selected from the group consisting of the compound represented by the formula (I) and an optically active isomer thereof, or a pharmaceutically acceptable salt thereof according to claim 1.

* * * * *